(12) United States Patent
Yasuma et al.

(10) Patent No.: US 8,673,942 B2
(45) Date of Patent: Mar. 18, 2014

(54) FUSED RING COMPOUNDS AND USE THEREOF

(75) Inventors: Tsuneo Yasuma, Osaka (JP); Nobuyuki Takakura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 233 days.

(21) Appl. No.: 12/936,785

(22) PCT Filed: Apr. 9, 2009

(86) PCT No.: PCT/JP2009/057625
§ 371 (c)(1),
(2), (4) Date: Oct. 7, 2010

(87) PCT Pub. No.: WO2009/125873
PCT Pub. Date: Oct. 15, 2009

(65) Prior Publication Data
US 2011/0098297 A1    Apr. 28, 2011

(30) Foreign Application Priority Data
Apr. 10, 2008 (JP) ................. 2008-102691

(51) Int. Cl.
*A61K 31/4436* (2006.01)
*C07D 417/14* (2006.01)

(52) U.S. Cl.
USPC ....................................... 514/342; 546/269.7

(58) Field of Classification Search
USPC ....................................... 546/269.7; 514/342
See application file for complete search history.

(56) References Cited

U.S. PATENT DOCUMENTS

| | | |
|---|---|---|
| 2002/0037907 A1 | 3/2002 | Steffan et al. |
| 2006/0111409 A1 | 5/2006 | Muto et al. |
| 2009/0118304 A1 | 5/2009 | Takahashi et al. |
| 2009/0247746 A1 | 10/2009 | Yasuma et al. |
| 2010/0197673 A1 | 8/2010 | Kim et al. |
| 2010/0210647 A1 | 8/2010 | Kim et al. |
| 2010/0267708 A1 | 10/2010 | Kim et al. |
| 2010/0291533 A1 | 11/2010 | Kim et al. |
| 2012/0035163 A1 | 2/2012 | Yasuma et al. |
| 2012/0252798 A1 | 10/2012 | Kim et al. |

FOREIGN PATENT DOCUMENTS

| | | |
|---|---|---|
| CN | 101801965 | 8/2010 |
| EP | 1 873 144 | 1/2008 |
| EP | 1 935 890 | 6/2008 |
| EP | 2 230 238 | 9/2010 |
| WO | 92/15301 | 9/1992 |
| WO | 02/06255 | 1/2002 |
| WO | 03/103648 | 12/2003 |
| WO | 2005/049019 | 6/2005 |
| WO | 2006/089397 | 8/2006 |
| WO | 2007/037534 | 4/2007 |
| WO | 2008/050821 | 5/2008 |
| WO | 2009/025477 | 2/2009 |
| WO | 2009/025478 | 2/2009 |
| WO | 2009/082152 | 7/2009 |
| WO | 2010/076884 | 7/2010 |

OTHER PUBLICATIONS

Opposition filed Dec. 10, 2010 in corresponding Costa Rican Patent Application No. 11730 (English translation).
International Search Report issued Jul. 6, 2009 in International (PCT) Application No. PCT/JP2009/057625.
English translation of Office Action issued Mar. 8, 2013 in corresponding Chinese application No. 200980121846.8.
Letter from Venezuelan associate (first page only), Oct. 21, 2013.
Máire E. Doyle et al.; "Pharmacological Agents that Directly Modulate Insulin Secretion"; Pharmacological Reviews; vol. 55, No. 1; pp. 105-131; 2003.
Daniel J. Drucker; "Dipeptidyl Peptidase-4 Inhibition and the Treatment of Type 2 Diabetes"; Diabetes Care; vol. 30, No. 6; pp. 1335-1343; 2007.
Nasser Mikhail; "Incretin Mimetics and Dipeptidyl Peptidase 4 Inhibitors in Clinical Trials for the Treatment of Type 2 Diabetes"; Expert Opinion Investig. Drugs; vol. 17(6); pp. 845-853; 2008.

*Primary Examiner* — Patricia L Morris
(74) *Attorney, Agent, or Firm* — Wenderoth, Lind & Ponack, L.L.P.

(57) ABSTRACT

The present invention aims to provide a glucokinase activator useful as a pharmaceutical agent such as an agent for the prophylaxis or treatment of diabetes, obesity and the like. The present invention provides a glucokinase activator containing a compound represented by the formula (I): wherein each symbol is defined in the specification, or a salt thereof or a prodrug thereof.

(I)

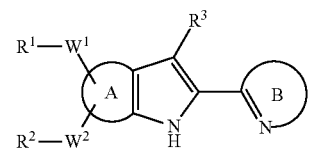

13 Claims, No Drawings

FUSED RING COMPOUNDS AND USE THEREOF

This application is a U.S. national stage of International Application No. PCT/JP2009/057625 filed Apr. 9, 2009.

TECHNICAL FIELD

The present invention relates to a fused ring compound having a glucokinase activating action and useful as a therapeutic agent for diabetes and the like.

BACKGROUND OF THE INVENTION

Glucokinase (sometimes to be abbreviated to as GK in the present specification) (EC2.7.1.1) is one of the four kinds of hexokinases found in mammals, and is also called hexokinase IV. GK is an enzyme that catalyzes the conversion of glucose to glucose-6-phosphate, which is the first step of glycolysis. GK is mainly present in the pancreatic β cell and the liver, and acts in the pancreatic β cell as a sensor of extracellular glucose concentration that defines the glucose-stimulated insulin secretion. In the liver, the enzyme reaction of GK becomes a rate determining factor and regulates glycogen synthesis and glycolysis. The three hexokinases (I, II, III) other than GK reach the maximum enzyme activity at a glucose concentration of 1 mM or below. In contrast, GK shows low affinity for glucose and has a Km value of 8-15 mM which is close to a physiological blood glucose level. Accordingly, GK-mediated promotion of intracellular glucose metabolism occurs, which corresponds to blood glucose changes from normal blood glucose (5 mM) to postprandial hyperglycemia (10-15 mM).

The hypothesis proposed by Matschinsky et al. in 1984 that GK acts as a glucose sensor in the pancreatic β cell and hepatocytes has been demonstrated by the analysis of glucokinase transgenic mouse in recent years (see J. Biol. Chem., 1995, vol. 270, page 30253-30256; J. Biol. Chem., 1997, vol. 272, page 22564-22569; J. Biol. Chem., 1997, vol. 272, page 22570-22575; NIPPON RINSHO, 2002, vol. 60, page 523-534; and Cell, 1995, vol. 83, page 69-78). That is, GK heterozygous deficient mouse showed a hyperglycemic condition, and further, a disordered glucose-stimulated insulin secretion response. GK homozygous deficient mouse dies shortly after birth with manifestations of marked hyperglycemia and urinary sugar. On the other hand, GK overexpressed mouse (hetero type) showed decreased blood glucose level, increased blood glucose clearance rate, increased liver glycogen content and the like. From these findings, it has been clarified that GK plays an important role in the systemic glucose homeostasis. In other words, decreased GK activity causes insulin secretion failure and lower liver glucose metabolism, which develops impaired glucose tolerance and diabetes. Conversely, GK activation or increased GK activity due to overexpression causes promoted insulin secretion and promoted liver glucose metabolism, which in turn increases the systemic use of glucose to improve glucose tolerance.

In addition, it has been clarified froth the analysis of a report on GK gene abnormality mainly in the family of MODY2 (Maturity Onset Diabetes of the Young) that GK also acts as a glucose sensor in human, and plays a key role in glucose homeostasis (see Nature, 1992, vol. 356, page 721-722). In GK gene abnormality, due to the decreased affinity of GK for glucose (increased Km value) and decreased Vmax, the blood glucose threshold value of insulin secretion increases and the insulin secretory capacity decreases. In the liver, due to the decreased GK activity, decreased glucose uptake, promoted gluconeogenesis, decreased glycogen synthesis and liver insulin resistance are observed. On the other hand, a family with a mutation increasing the GK activity has also been found. In such family, fasting hypoglycemia associated with increased plasma insulin concentration is observed (see New England Journal Medicine, 1998, vol. 338, page 226-230).

As mentioned above, GK acts as a glucose sensor in mammals including human, and plays an important role in blood glucose regulation. On the other hand, control of blood glucose utilizing the glucose sensor system of GK is considered to open a new way to treat diabetes in many type 2 diabetes patients. Particularly, since a GK activating substance is expected to show insulin secretagogue action in the pancreatic β cell and glucose uptake promotion and glucose release suppressive action in the liver, it will be useful as a prophylactic or therapeutic drug for type 2 diabetes.

In recent years, it has been clarified that pancreatic β cell type glucokinase expresses locally in the feeding center (Ventromedial Hypothalamus: VMH) of rat brain. A subset of nerve cell present in VMH is called glucose responsive neuron, and plays an important role in the body weight control. From electrophysiological experiments, the neuron is activated in response to physiological changes in the glucose concentration (5-20 mM). However, since the glucose concentration sensor system of VHM is assumed to have a mechanism mediated by glucokinase as in the case of insulin secretion in the pancreatic β cell, different from pancreatic β cell and the liver, a pharmaceutical agent-capable of activating glucokinase of VHM has a possibility of providing not only a blood glucose corrective effect but also improvement of obesity.

As mentioned above, a pharmaceutical agent capable of activating GK is useful as a prophylactic or therapeutic drug for diabetes, diabetic complications, obesity and the like.

As the indole compound, the following compound has been reported.

(1) It has been reported that a compound represented by the formula:

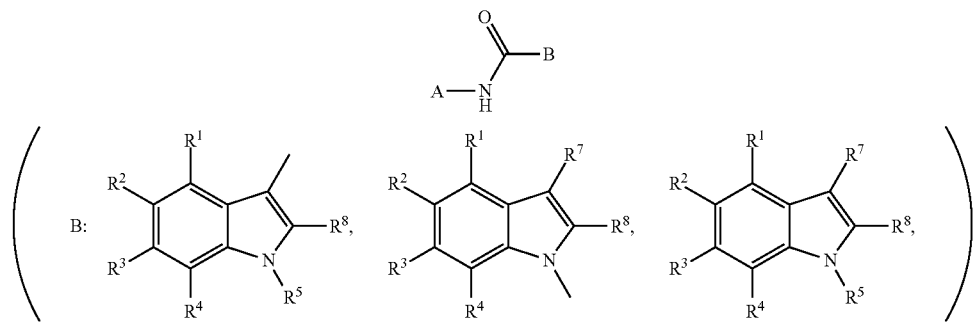

wherein $R^1, R^2, R^3, R^4, R^6$ and $R^7$ are independently a hydrogen atom, a halogen atom, nitro, —CN, —OH, —COOH, —CF$_3$, —NR$^{10}$R$^{11}$ wherein R$^{10}$ and R$^{11}$ are independently a hydrogen atom, a C$_{1-6}$ alkyl group, —CO—C$_{1-6}$ alkyl, carboxy-C$_{1-6}$ alkyl, —C—C$_{1-6}$ alkyl-COOH, —SO$_2$CH$_3$, aryl group and the like, a C$_{1-6}$ alkyl group, a C$_{3-8}$ cycloalkyl group, a heteroaryl group and the like;

$R^5$ is a C$_{1-6}$ alkyl group and the like; and

A is an optionally substituted thiazolyl and the like, is a glucokinase activator, which is useful for treatment of diabetes and the like (WO 2005/049019 (PTL 1)).

(2) It has been reported that a compound represented by the formula:

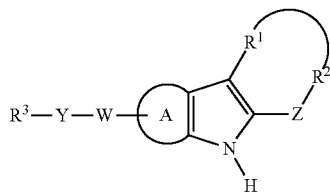

wherein ring A is an optionally substituted 6-membered ring,

W is O, S(O)$_m$ wherein m is 0, 1 or 2, CR$^5$R$^6$ wherein R$^5$ and R$^6$ are independently a hydrogen atom or a C$_{1-6}$ alkyl group, or NR$^7$ wherein R$^7$ is a hydrogen atom or R$^{3\prime}$—Y'— wherein R$^{3\prime}$ is an optionally substituted hydrocarbon group, an optionally substituted hydroxy group, an optionally substituted mercapto group, an optionally substituted amino group or an optionally substituted heterocyclic group, and Y' is a bond, CO, S(O)$_q$ wherein q is 0, 1 or 2 or CR$^{8\prime}$R$^{9\prime}$ wherein R$^{8\prime}$ and R$^{9\prime}$ are independently a hydrogen atom or a C$_{1-6}$ alkyl group, Y is a bond, CO, S(O)$_p$ wherein p is 0, 1 or 2, or CR$^8$R$^9$ wherein R$^8$ and R$^9$ are independently a hydrogen atom or a C$_{1-6}$ alkyl, R$^3$ is an optionally substituted hydrocarbon group, an optionally substituted hydroxy group, an optionally substituted mercapto group, an optionally substituted amino group or an optionally substituted heterocyclic group, Z is a bond, CO, O, S(O)$_n$ wherein n is 0 1 or 2, or NR$^{10}$ wherein R$^{10}$ is a hydrogen atom or a C$_{1-6}$ alkyl group, R$^1$ is a hydrogen atom, a halogen atom, an optionally substituted hydrocarbon group, an optionally substituted hydroxy group or an optionally substituted mercapto group, R$^2$ is a hydrogen atom, an optionally substituted hydrocarbon group, an optionally substituted hydroxy group, an optionally substituted mercapto group, an optionally substituted amino group or an optionally substituted heterocyclic group, or R$^1$ and R$^2$ are bond to each other to form an optionally substituted ring, is a glucokinase activator (WO 2006/112549 (PTL 2)).

(3) It has been reported that a compound represented by the formula:

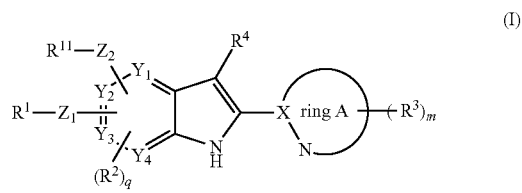

wherein

R$^1$ is an optionally substituted aryl group or an optionally substituted heteroaryl group;

R$^{11}$ is an optionally substituted aryl group, a 5- to 7-membered aliphatic heterocyclic group, or an optionally substituted 5- or 6-membered heteroaryl group;

R$^2$ is formyl, OH, a C$_{1-6}$ alkyl group, —CH$_{3-a}$F$_a$, —OCH$_{3-a}$F$_a$ wherein a is 1 to 3, amino, cyano, a halogen atom or —(CH$_2$)$_{1-4}$—OH;

R$^3$ is a C$_{1-6}$ alkyl group, —(CH$_2$)$_{1-6}$—OH, —C(O)—OC$_{1-6}$ alkyl, —(CH$_2$)$_{1-6}$—OC$_{1-6}$ alkyl, —(CH$_2$)$_{1-6}$—NH$_2$, cyano, —C(O)—C$_{1-6}$ alkyl, a halogen atom, a C$_{2-6}$ alkenyl group, —O—C$_{1-6}$ alkyl, —COOH or OH;

R$^4$ is a hydrogen atom or a C$_{1-6}$ alkyl group;

Y is a carbon atom or a nitrogen atom;

Z$_1$ is —O—, —S—, —S(O)— or S(O)$_2$—;

Z$_2$ is —O—, —S—, —S(O)—, S(O)$_2$— or —CH$_2$— which is optionally substituted by a halogen atom, a C$_{1-6}$ alkyl group and the like, or a single bond;

at least two of Y$_1$, Y$_2$, Y$_3$ and Y$_4$ are independently carbon atoms, and the others are a carbon atom or a nitrogen atom;

ring A is a heteroaryl group;

X is a carbon atom or a nitrogen atom;

m is 0 to 2; and q is 0 to 2, is a glucokinase activator, which is useful for treatment of diabetes, obesity and the like (WO 2007/037534 (PTL 3)).

However, none of the above-mentioned prior articles discloses the following formula (I).

CITATION LIST

Patent Literature

PTL 1: WO 2005/049019
PTL 2: WO 2006/112549
PTL 3: WO 2007/037534

SUMMARY OF THE INVENTION

The purpose of the present invention is to provide a glucokinase activator which is useful as a pharmaceutical agent such as agents for the prophylaxis or treatment of diabetes, obesity and the like, and the like.

The present inventors have conducted intensive studies and found that a compound represented by the formula (I):

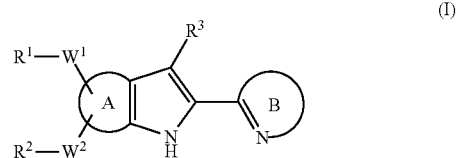

wherein
ring A is an optionally further substituted 6-membered ring;
ring B is an optionally substituted 5- to 7-membered nitrogen-containing heterocycle;
$W^1$ and $W^2$ are independently O, S, SO, $SO_2$ or $NR^4$ wherein $R^4$ is a hydrogen atom or a $C_{1-6}$ alkyl group;
$R^1$ is a substituted methyl group, an optionally substituted $C_{2-6}$ alkyl group, an optionally substituted $C_{3-10}$ cycloalkyl group, an optionally substituted $C_{6-14}$ aryl group or an optionally substituted heterocyclic group;
$R^2$ is an optionally substituted $C_{1-6}$ alkyl group or an optionally substituted $C_{3-10}$ cycloalkyl group; and
$R^3$ is a hydrogen atom or a halogen atom,
provided that N-methyl-4-[(1-methyl-1H-tetrazol-5-yl)thio]-2-(1,3-thiazol-2-yl)-1H-indol-7-amine is excluded,
or a salt thereof [hereinafter to be abbreviated as compound (I)] unexpectedly has a superior glucokinase activating action as well as superior properties as a pharmaceutical product such as stability and the like, and can be a safe and useful as a pharmaceutical agent, which resulted in the completion of the present invention.

Accordingly, the present invention relates to

[1] a compound represented by the formula (I):

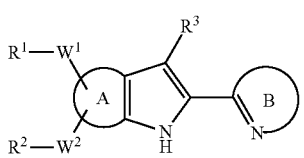

wherein
ring A is an optionally further substituted 6-membered ring;
ring B is an optionally substituted 5- to 7-membered nitrogen-containing heterocycle;
$W^1$ and $W^2$ are independently O, S, SO, $SO_2$ or $NR^4$ wherein $R^4$ is a hydrogen atom or a $C_{1-6}$ alkyl group;
$R^1$ is a substituted methyl group, an optionally substituted $C_{2-6}$ alkyl group, an optionally substituted $C_{3-10}$ cycloalkyl group, an optionally substituted $C_{6-14}$ aryl group or an optionally substituted heterocyclic group;
$R^2$ is an optionally substituted $C_{1-6}$ alkyl group or an optionally substituted $C_{3-10}$ cycloalkyl group; and
$R^3$ is a hydrogen atom or a halogen atom,
provided that N-methyl-4-[(1-methyl-1H-tetrazol-5-yl)thio]-2-(1,3-thiazol-2-yl)-1H-indol-7-amine is excluded,
or a salt thereof;

[2] a compound represented by the formula (I):

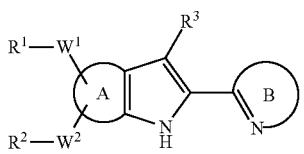

wherein
ring A is an optionally further substituted 6-membered ring;
ring B is an optionally substituted 5- to 7-membered nitrogen-containing heterocycle;
$W^1$ and $W^2$ are independently O, S, SO, $SO_2$ or $NR^4$ wherein $R^4$ is a hydrogen atom or a $C_{1-6}$ alkyl group;
$R^1$ is an optionally substituted $C_{3-10}$ cycloalkyl group, an optionally substituted $C_{6-14}$ aryl group or an optionally substituted heterocyclic group;
$R^2$ is an optionally substituted $C_{1-6}$ alkyl group or an optionally substituted $C_{3-10}$ cycloalkyl group; and
$R^3$ is a hydrogen atom or a halogen atom,
provided that N-methyl-4-[(1-methyl-1H-tetrazol-5-yl)thio]-2-(1,3-thiazol-2-yl)-1H-indol-7-amine is excluded, or a salt thereof;

[3] a compound represented by the formula (I):

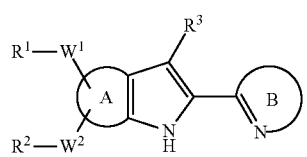

wherein
ring A is an optionally further substituted 6-membered ring;
ring B is an optionally substituted 5- to 7-membered nitrogen-containing heterocycle;
$W^1$ and $W^2$ are independently O, S, SO, $SO_2$ or $NR^4$ wherein $R^4$ is a $C_{1-6}$ alkyl group;
$R^1$ is an optionally substituted $C_{3-10}$ cycloalkyl group, an optionally substituted $C_{6-14}$ aryl group or an optionally substituted heterocyclic group;
$R^2$ is an optionally substituted $C_{1-6}$ alkyl group or an optionally substituted $C_{3-10}$ cycloalkyl group; and
$R^3$ is a hydrogen atom or a halogen atom,
or a salt thereof;

[4] a compound represented by the formula (I):

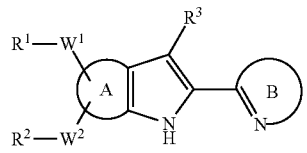

wherein
ring A is an optionally further substituted 6-membered ring;
ring B is an optionally substituted 5- to 7-membered nitrogen-containing heterocycle;
$W^1$ and $W^2$ are independently O, S, SO or $SO_2$;
$R^1$ is an optionally substituted $C_{3-10}$ cycloalkyl group, an optionally substituted $C_{6-14}$ aryl group or an optionally substituted heterocyclic group;
$R^2$ is an optionally substituted $C_{1-6}$ alkyl group or an optionally substituted $C_{3-10}$ cycloalkyl group; and
$R^3$ is a hydrogen atom or a halogen atom, a salt thereof;

[5] the compound of the above-mentioned [1], wherein ring A is benzene;

[6] the compound of the above-mentioned [1], wherein ring B is an optionally substituted 5-membered nitrogen-containing heterocycle;

[7] the compound of the above-mentioned [1], wherein $W^1$ and $W^2$ are both O;

[8] the compound of the above-mentioned [1], wherein $R^1$ is an optionally substituted $C_{6-14}$ aryl group or an optionally substituted heterocyclic group;

[9] the compound of the above-mentioned [1], wherein $R^2$ is an optionally substituted $C_{1-6}$ alkyl group;

[10] the compound of the above-mentioned [1], wherein $R^3$ is a hydrogen atom;

[11] the compound of the above-mentioned [1], wherein ring A is benzene,
ring B is an optionally substituted 5-membered nitrogen-containing heterocycle,
$W^1$ and $W^2$ are both O,
$R^1$ is an optionally substituted $C_{6-14}$ aryl group or an optionally substituted heterocyclic group,
$R^2$ is an optionally substituted $C_{1-6}$ alkyl group, and
$R^3$ is a hydrogen atom;

[12] a compound represented by the formula (II):

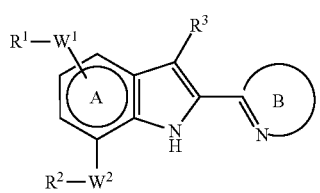

(II)

wherein
ring A is an optionally further substituted 6-membered ring;
ring B is an optionally substituted 5- to 7-membered nitrogen-containing heterocycle;
$W^1$ and $W^2$ are independently O, S, SO or $SO_2$;
$R^1$ is an optionally substituted $C_{3-10}$ cycloalkyl group, an optionally substituted $C_{6-14}$ aryl group or an optionally substituted heterocyclic group;
$R^2$ is an optionally substituted $C_{1-6}$ alkyl group or an optionally substituted $C_{3-10}$ cycloalkyl group; and
$R^3$ is a hydrogen atom or a halogen atom,
or a salt thereof [hereinafter to be abbreviated as compound (II)];

[13] 2-[2-(7-methoxy-5-{[6-(methylsulfonyl)pyridin-3-yl]oxy}-1H-indol-2-yl)-4,5-dihydro-1,3-thiazol-5-yl]-N-methylacetamide or a salt thereof;

[14] 2-(2-{7-(2-methoxy-1-methylethoxy)-5-[4-(methylsulfonyl)phenoxy]-1H-indol-2-yl}-4,5-dihydro-1,3-thiazol-5-yl)ethanol or a salt thereof;

[15] 2-methyl-1-{2-[7-(1-methylethoxy)-5-{[5-(methylsulfonyl)pyridin-2-yl]oxy}-1H-indol-2-yl]-4,5-dihydro-1,3-thiazol-5-yl}propan-2-ol or a salt thereof;

[16] N-(2-hydroxy-2-methylpropyl)-2-[2-(7-methoxy-5-{[6-(methylsulfonyl)pyridin-3-yl]oxy}-1H-indol-2-yl)-4,5-dihydro-1,3-thiazol-5-yl]acetamide or a salt thereof;

[17] 2-[2-(7-ethoxy-5-{[6-(methylsulfonyl)pyridin-3-yl]oxy}-1H-indol-2-yl)-4,5-dihydro-1,3-thiazol-5-yl]-N-methylacetamide or a salt thereof;

[18] N-[2-hydroxypropyl]-2-[2-(7-methoxy-5-{[6-(methylsulfonyl)pyridin-3-yl]oxy}-1H-indol-2-yl)-4,5-dihydro-1,3-thiazol-5-yl]acetamide or a salt thereof;

[19] a prodrug of the compound of the above-mentioned [I];

[20] a glucokinase activator comprising the compound of the above-mentioned [I] or a prodrug thereof;

[21] a pharmaceutical agent comprising the compound of the above-mentioned [I] or a prodrug thereof;

[22] the pharmaceutical agent of the above-mentioned [21], which is an agent for the prophylaxis or treatment of diabetes or obesity;

[23] a method for the prophylaxis or treatment of diabetes or obesity in a mammal, which comprises administering the compound of the above-mentioned [I] or a prodrug thereof to the mammal;

[24] use of the compound of the above-mentioned [I] or a prodrug thereof for the production of an agent for the prophylaxis or treatment of diabetes or obesity;
and the like.

EFFECT OF THE INVENTION

Since compound (I) has a superior glucokinase activating action, compound (I) is useful as a pharmaceutical agent such as agents for the prophylaxis or treatment of diabetes, obesity and the like, and the like.

DETAILED DESCRIPTION OF THE INVENTION

Unless otherwise specified, the "halogen atom" in the present specification means fluorine atom, chlorine atom, bromine atom or iodine atom.

Unless otherwise specified, the "$C_{1-3}$ alkylenedioxy group" in the present specification means methylenedioxy, ethylenedioxy or the like.

Unless otherwise specified, the "$C_{1-6}$ alkyl group" in the present specification means methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

Unless otherwise specified, the "$C_{2-6}$ alkyl group" in the present specification means ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

Unless otherwise specified, the "$C_{1-6}$ alkoxy group" in the present specification means methoxy, ethoxy, propoxy, isopropoxy, butoxy, isobutoxy, sec-butoxy, tert-butoxy or the like.

Unless otherwise specified, the "$C_{1-6}$ alkoxy-carbonyl group" in the present specification means methoxycarbonyl, ethoxycarbonyl, propoxycarbonyl, tert-butoxycarbonyl or the like.

Unless otherwise specified, the "$C_{1-6}$ alkyl-carbonyl group" in the present specification means acetyl, propanoyl, butanoyl, isobutanoyl, pentanoyl, isopentanoyl, hexanoyl or the like.

Each symbol in the formulas is described in detail in the following.

$R^1$ is a substituted methyl group, an optionally substituted $C_{2-6}$ alkyl group, an optionally substituted $C_{3-10}$ cycloalkyl group, an optionally substituted $C_{6-14}$ aryl group or an optionally substituted heterocyclic group.

The "$C_{2-6}$ alkyl group" of the "optionally substituted $C_{2-6}$ alkyl group" and "methyl" of the "substituted methyl group" for $R^1$ optionally have 1 to 3 substituents at substitutable positions.

Examples of the substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group, and
 (d) a halogen atom;
(3) an aromatic heterocyclic group (e.g., thienyl, furyl, pyridyl, pyrimidinyl, pyridazinyl, oxazolyl, thiazolyl, tetrazolyl, oxadiazolyl, pyrazinyl, quinolyl, indolyl) optionally substituted by 1 to 3 substituents selected from (a) a $C_{1-6}$ alkyl group optionally substituted by 1 to 3 halogen atoms,
(b) a hydroxy group,
(c) a $C_{1-6}$ alkoxy group, and
(d) a halogen atom;
(4) a non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl, thiazolinyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group,
(d) a $C_{1-6}$ alkyl-carbonyl group,
(e) a $C_{1-6}$ alkylsulfonyl group,
(f) an oxo group, and
(g) a halogen atom;
(5) an amino group optionally mono- or di-substituted by substituent(s) selected from
(a) a $C_{1-6}$ alkyl group optionally substituted by 1 to 3 substituents selected from a hydroxy group and a $C_{1-6}$ alkylsulfonyl group (e.g., methylsulfonyl),
(b) a $C_{1-6}$ alkyl-carbonyl group,
(c) a $C_{1-6}$ alkoxy-carbonyl group optionally substituted by 1 to 3 $C_{6-14}$ aryl groups (e.g., phenyl),
(d) a $C_{6-14}$ aryl-carbonyl group (e.g., benzoyl),
(e) a $C_{7-13}$ aralkyl-carbonyl group (e.g., benzylcarbonyl, phenethylcarbonyl),
(f) a carbamoyl group optionally mono- or di-substituted by substituent(s) selected from a $C_{1-6}$ alkyl group, a $C_{6-14}$ aryl group (e.g., phenyl) and a $C_{7-13}$ aralkyl group (e.g., benzyl),
(g) a $C_{1-6}$ alkylsulfonyl group (e.g., methylsulfonyl, ethylsulfonyl, isopropylsulfonyl),
(h) a $C_{6-14}$ arylsulfonyl group (e.g., benzenesulfonyl, 1-naphthalenesulfonyl, 2-naphthalenesulfonyl) optionally substituted by 1 to 3 $C_{1-6}$ alkyl groups,
(i) a $C_{7-13}$ aralkylsulfonyl group (e.g., benzylsulfonyl)
(j) a $C_{3-10}$ cycloalkyl group (e.g., cyclohexyl) optionally substituted by 1 to 3 substituents selected from a hydroxy group and a $C_{1-6}$ alkyl group,
(k) an aromatic heterocyclic group (e.g., triazolyl), and
(l) a non-aromatic heterocyclic group (e.g., tetrahydrothiopyranyl, 1-oxidotetrahydrothiopyranyl, 1,1-dioxidotetrahydrothiopyranyl);
(6) an amidino group;
(7) a $C_{1-6}$ alkyl-carbonyl group optionally substituted by 1 to 3 halogen atoms;
(8) a $C_{1-6}$ alkoxy-carbonyl group optionally substituted by 1 to 3 halogen atoms;
(9) an aromatic heterocyclyl-carbonyl group (e.g., thienylcarbonyl, indolylcarbonyl) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];
(10) a non-aromatic heterocyclyl-carbonyl group (e.g., piperidinylcarbonyl, piperazinylcarbonyl, morpholinylcarbonyl, thiomorpholinylcarbonyl, 1-oxidothiomorpholinylcarbonyl, 1,1-dioxidothiomorpholinylcarbonyl, pyrrolidinylcarbonyl, azetidinylcarbonyl) optionally substituted by 1 to 3 substituents selected from
(a) a hydroxy group,
(b) a $C_{1-6}$ alkyl group optionally substituted by 1 to 3 hydroxy groups,
(c) a halogen atom,
(d) a carboxy group,
(e) a $C_{1-6}$ alkoxy-carbonyl group,
(f) an amino group, and
(g) a $C_{1-6}$ alkylsulfonyl group;
(11) a $C_{1-6}$ alkylsulfonyl group (e.g., methylsulfonyl, ethylsulfonyl) optionally substituted by 1 to 3 halogen atoms;
(12) a carbamoyl group optionally mono- or di-substituted by substituent(s) selected from
(a) a $C_{1-6}$ alkyl group optionally substituted by 1 to 3 substituents selected from a hydroxy group, a $C_{1-6}$ alkoxy group, a $C_{1-6}$ alkylsulfonyl group (e.g., methylsulfonyl) and an aromatic heterocyclic group (e.g., furyl),
(b) a $C_{6-14}$ aryl group (e.g., phenyl),
(c) a $C_{7-13}$ aralkyl group (e.g., benzyl),
(d) a $C_{1-6}$ alkoxy group,
(e) a $C_{3-10}$ cycloalkyl group (e.g., cyclopropyl),
(f) a $C_{1-6}$ alkylsulfonyl group (e.g., methylsulfonyl),
(g) an aromatic heterocyclic group (e.g., triazolyl, tetrazolyl), and
(h) a non-aromatic heterocyclic group (e.g., tetrahydropyranyl);
(13) a thiocarbamoyl group optionally mono- or di-substituted by $C_{1-6}$ alkyl group(s) optionally substituted by 1 to 3 halogen atoms;
(14) a sulfamoyl group optionally mono- or di-substituted by $C_{1-6}$ alkyl group(s) optionally substituted by 1 to 3 halogen atoms;
(15) a carboxy group;
(16) a hydroxy group;
(17) a $C_{1-6}$ alkoxy group optionally substituted by 1 to 3 substituents selected from
(a) a halogen atom,
(b) a carboxy group,
(c) a $C_{1-6}$ alkoxy group, and
(d) a $C_{1-6}$ alkoxy-carbonyl group;
(18) a $C_{2-6}$ alkenyloxy group (e.g., ethenyloxy) optionally substituted by 1 to 3 halogen atoms;
(19) a $C_{3-10}$ cycloalkyloxy group (e.g., cyclohexyloxy);
(20) a $C_{7-13}$ aralkyloxy group (e.g., benzyloxy) optionally substituted by 1 to 3 halogen atoms;
(21) a $C_{6-14}$ aryloxy group (e.g., phenyloxy, naphthyloxy);
(22) a $C_{1-6}$ alkyl-carbonyloxy group (e.g., acetyloxy, tert-butylcarbonyloxy);
(23) a mercapto group;
(24) a $C_{1-6}$ alkylthio group (e.g., methylthio, ethylthio) optionally substituted by 1 to 3 substituents selected from
(a) a halogen atom,
(b) a $C_{6-14}$ aryl group, and
(c) a carboxy group;
(25) a $C_{6-14}$ arylthio group (e.g., phenylthio, naphthylthio);
(26) an aromatic heterocyclyl-thio group (e.g., tetrazolylthio) optionally substituted by 1 to 3 $C_{1-6}$ alkyl groups;
(27) a sulfo group;
(28) a cyano group;
(29) an azido group;
(30) a nitro group;
(31) a nitroso group;
(32) a halogen atom;
(33) a $C_{1-6}$ alkylsulfinyl group (e.g., methylsulfinyl);
(34) a $C_{3-10}$ cycloalkyl-$C_{1-6}$ alkyloxy group (e.g., cyclopropylmethyloxy);
(35) a $C_{1-3}$ alkylenedioxy group;
(36) an aromatic heterocyclyl-carbonylthio group (e.g., indolylcarbonylthio) optionally substituted by 1 to 3 amino groups [the amino groups are each optionally mono- or di-substituted by substituent(s) selected from a $C_{1-6}$ alkyl group and an aromatic heterocyclyl-sulfonyl group (e.g., thienylsulfonyl)];
(37) a formyl group;
(38) an aromatic heterocyclyl-oxy group (e.g., pyrimidyloxy, pyrazinyloxy);
(39) a $C_{1-6}$ alkylsulfonyloxy group (e.g., methylsulfonyloxy);
(40) a $C_{2-6}$ alkenyl-carbonyl group (e.g., vinylcarbonyl);
(41) a non-aromatic heterocyclyl-carbonyloxy group (e.g., morpholinylcarbonyloxy) optionally substituted by 1 to 3 $C_{1-6}$ alkyl groups;
(42) a di-tert-butylphenylsilyloxy group;
and the like. When two or more substituents are used, the substituents may be the same or different.

Examples of the "$C_{3-10}$ cycloalkyl group" of the "optionally substituted $C_{3-10}$ cycloalkyl group" for $R^1$ include cyclopropyl, cyclobutyl, cyclopentyl, cyclohexyl, cycloheptyl, cyclooctyl and the like.

The above-mentioned $C_{3-10}$ cycloalkyl group is optionally condensed with a benzene ring to form a fused ring group. Examples of the fused ring group include indanyl, dihydronaphthyl, tetrahydronaphthyl, fluorenyl and the like. In addition, the above-mentioned $C_{3-10}$ cycloalkyl group encompass a cross-liked hydrocarbon group such as bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl, norbornanyl and the like, and the like.

The "$C_{3-10}$ cycloalkyl group" of the "optionally substituted $C_{3-10}$ cycloalkyl group" for $R^1$ optionally has 1 to 3 substituents at substitutable positions.

Examples of the substituent include
(1) the groups exemplified as the substituents which "$C_{2-6}$ alkyl group" of the "optionally substituted $C_{2-6}$ alkyl group" for $R^1$ optionally has;
(2) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy group optionally substituted by 1 to 3 substituents selected from a carboxy group and a $C_{1-6}$ alkoxy-carbonyl group,
  (e) a $C_{1-6}$ alkyl-carbonyl group,
  (f) a $C_{1-6}$ alkoxy-carbonyl group,
  (g) a $C_{1-6}$ alkyl-carbonyloxy group (e.g., acetyloxy, tert-butylcarbonyloxy),
  (h) a carbamoyl group optionally mono- or di-substituted by substituent(s) selected from
    (i) a $C_{1-6}$ alkyl group optionally substituted by 1 to 3 substituents selected from a carboxy group, a hydroxy group, a $C_{1-6}$ alkoxy group, a $C_{1-6}$ alkoxy-carbonyl group, an amino group and a $C_{1-6}$ alkylsulfonyl group,
    (ii) a $C_{3-10}$ cycloalkyl group optionally substituted by 1 to 3 substituents selected from a $C_{1-6}$ alkyl group, a carboxy group, a hydroxy group, a $C_{1-6}$ alkoxy-carbonyl group, an amino group and a $C_{1-6}$ alkylsulfonyl group,
    (iii) a $C_{1-6}$ alkylsulfonyl group optionally substituted by 1 to 3 substituents selected from a $C_{1-6}$ alkyl group, a carboxy group, a hydroxy group, a $C_{1-6}$ alkoxy-carbonyl group and an amino group, and
    (iv) an amino group optionally mono- or di-substituted by substituent(s) selected from a $C_{1-6}$ alkyl group, a carboxy group, a hydroxy group, a $C_{1-6}$ alkoxy-carbonyl group and a $C_{1-6}$ alkylsulfonyl group,
  (i) an aromatic heterocyclic group (e.g., thienyl, tetrazolyl, imidazolyl, furyl, pyridyl) optionally substituted by 1 to 3 $C_{1-6}$ alkyl groups,
  (j) a non-aromatic heterocyclic group (e.g., tetrahydrofuranyl, piperidino, piperazinyl, morpholinyl, dihydrooxadiazolyl, hexahydropyrazinooxazinyl (e.g., hexahydropyrazino[2,1-c][1,4]oxazinyl), thiomorpholinyl, 1-oxidothiomorpholinyl) optionally substituted by 1 to 3 substituents selected from a $C_{1-6}$ alkyl-carbonyl group and an oxo group,
  (k) an amino group optionally mono- or di-substituted by substituent(s) selected from
    (i) a $C_{1-6}$ alkyl group optionally substituted by 1 to 3 substituents selected from a non-aromatic heterocyclic group (e.g., morpholinyl), a $C_{1-6}$ alkoxy group and a $C_{1-6}$ alkylsulfonyl group, and
    (ii) a $C_{3-10}$ cycloalkyl group (e.g., cyclopropyl, cyclohexyl),
  (l) a $C_{1-6}$ alkylsulfonyl group optionally substituted by 1 to 3 carboxy groups,
  (m) a $C_{1-6}$ alkylthio group optionally substituted by 1 to 3 substituents selected from a carboxy group, a $C_{1-6}$ alkoxy-carbonyl group, a hydroxy group and a carbamoyl group,
  (n) a phosphono group optionally mono- or di-substituted by $C_{1-6}$ alkyl group(s),
  (o) a non-aromatic heterocyclyl-carbonyl group (e.g., morpholinylcarbonyl),
  (p) an aromatic heterocyclyl-carbonyl group (e.g., thienylcarbonyl, indolylcarbonyl);
  (q) a cyano group, and
  (r) a $C_{6-14}$ aryloxy group optionally substituted by 1 to 3 substituents selected from a carboxy group and a $C_{1-6}$ alkoxy-carbonyl group;
(3) a $C_{2-6}$ alkenyl group (e.g., ethenyl, 1-propenyl) optionally substituted by 1 to 3 substituents selected from
  (a) a halogen atom,
  (b) a carboxy group,
  (c) a $C_{1-6}$ alkoxy-carbonyl group, and
  (d) a carbamoyl group;
(4) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;
and the like. When two or more substituents are used, the substituents may be the same or different.

Examples of the "$C_{6-14}$ aryl group" of the "optionally substituted $C_{6-14}$ aryl group." for $R^1$ include phenyl, naphthyl, anthryl, phenanthryl, acenaphthyl, biphenylyl and the like. Of these, phenyl, 1-naphthyl, 2-naphthyl and the like are preferable.

The "$C_{6-14}$ aryl group" of the "optionally substituted $C_{6-14}$ aryl group" for $R^1$ optionally has 1 to 3 substituents at substitutable positions. Examples of the substituent include those similar to the substituent which the "$C_{3-10}$ cycloalkyl group" of the "optionally substituted $C_{3-10}$ cycloalkyl group" for $R^1$ optionally has. When two or more substituents are used, the substituents may be the same or different.

Examples of the "heterocyclic group" of the "optionally substituted heterocyclic group" for $R^1$ include an aromatic heterocyclic group and a non-aromatic heterocyclic group.

Examples of the aromatic heterocyclic group include a 4 to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and the like.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;

fused heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), imidazothiazolyl (e.g., imidazo[2,1-b]thiazol-5-yl)pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like;

and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and a fused non-aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic or non-aromatic heterocycle containing 1 or 2 nitrogen atoms (e.g., pyrrole, imidazole, pyrazole, pyrazine, pyridine, pyrimidine, pyrrolidine, imidazolidine, pyrazolidine, piperidine, piperazine), a 5-membered aromatic or non-aromatic heterocycle containing one sulfur atom (e.g., thiophene, tetrahydrothiophene) and a benzene ring are condensed, a group wherein the above-mentioned group is partially saturated, and the like.

Preferable examples of the non-aromatic heterocyclic group include monocyclic non-aromatic heterocyclic groups such as tetrahydrofuranyl (e.g., 2-tetrahydrofuranyl), pyrrolidinyl (e.g., 1-pyrrolidinyl), piperidinyl (e.g., piperidino, 2-piperidinyl, 3-piperidinyl, 4-piperidinyl), morpholinyl (e.g., morpholino), thiomorpholinyl (e.g,thiomorpholino), 1-oxidothiomorpholinyl (e.g., 1-oxidothiomorpholin-4-yl), 1,1-dioxidothiomorpholinyl (e.g., 1,1-dioxidothiomorpholin-4-yl) piperaziny (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), thioxooxazolidinyl (e.g., 2-thioxo-1,3-oxazolidin-5-yl), pyranyl (e.g., 4-pyranyl), tetrahydropyranyl (e.g., 4-tetrahydropyranyl), thiopyranyl (e.g., 4-thiopyranyl), tetrahydrothiopyranyl (e.g., 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), pyrazolidinyl (e.g., pyrazolidin-1-yl), tetrahydropyrimidinyl, dioxanyl (e.g., 1,3-dioxan-2-yl, 1,3-dioxan-4-yl, 1,3-dioxan-5-yl, 1,4-dioxan-2-yl), dioxenyl (e.g., 4H-1,3-dioxen-2-yl, 4H-1,3-dioxen-4-yl, 4H-1,3-dioxen-5-yl, 4H-1,3-dioxen-6-yl, 2,3-dihydro-1,4-dioxin-5-yl) and the like;

fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl) dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrabydro-1-benzofuran-3-yl), chromenyl (e.g., 4H-chromen-2yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), hexahydropyrazinooxazinyl (e.g., hexahydropyazino[2,1-c][1,4]oxazinyl) and the like;

and the like.

The "heterocyclic group" of the "optionally substituted heterocyclic group" for $R^1$ optionally has 1 to 3 substituents at substitutable positions. Examples of the substituent include those similar to the substituent which the "$C_{3-10}$ cycloalkyl group" of the "optionally substituted $C_{3-10}$ cycloalkyl group" for $R^1$ optionally has. When two or more substituents are used, the substituents may be the same or different.

$R^1$ is preferably an optionally substituted $C_{6-14}$ aryl group (preferably phenyl) or an optionally substituted heterocyclic group (preferably an aromatic heterocyclic group (preferably pyridyl)).

Preferable examples of the substituent for the $C_{6-14}$ aryl group or heterocyclic group include (1) a $C_{1-6}$ alkylsulfonyl group (preferably methylsulfonyl), (2) a $C_{1-6}$ alkyl group (preferably methyl) optionally substituted by 1 to 3 $C_{1-6}$ alkoxy groups (preferably methoxy)

and the like, particularly preferably a $C_{1-6}$ alkylsulfonyl group (preferably methylsulfonyl).

$R^1$ is more preferably a $C_{6-14}$ aryl group (preferably phenyl) optionally substituted by 1 to 3 $C_{1-6}$ alkylsulfonyl groups (preferably methylsulfonyl).

In another embodiment, $R^1$ is more preferably a $C_{6-14}$ aryl group (preferably phenyl) or a heterocyclic group (preferably an aromatic heterocyclic group (preferably pyridyl)), each of which is optionally substituted by 1 to 3 substituents selected from
(1) a $C_{1-6}$ alkylsulfonyl group (preferably methylsulfonyl), and
(2) a $C_{1-6}$ alkyl group (preferably methyl) optionally substituted by 1 to 3 $C_{1-6}$ alkoxy groups (preferably methoxy).

In the embodiment, $R^1$ is particularly preferably a $C_{6-14}$ aryl group (preferably phenyl) or a heterocyclic group (preferably an aromatic heterocyclic group (preferably pyridyl)), each of which is optionally substituted by 1 to 3 $C_{1-6}$ alkylsulfonyl groups (preferably methylsulfonyl).

$R^2$ is an optionally substituted $C_{1-6}$ alkyl group or an optionally substituted $C_{3-10}$ cycloalkyl group.

The "$C_{1-6}$ alkyl group" of the "optionally substituted $C_{1-6}$ alkyl group" for $R^2$ optionally has 1 to 3 substituents at substitutable positions. Examples of the substituent include those similar to the substituent which the "$C_{2-6}$ alkyl group" of the "optionally substituted $C_{2-6}$ alkyl group" for $R^1$ optionally has. When two or more substituents are used, the substituents may be the same or different.

Examples of the "optionally substituted $C_{3-10}$ cycloalkyl group" for $R^2$ include those similar to the "optionally substituted $C_{3-10}$ cycloalkyl group" for $R^1$.

$R^2$ is preferably an optionally substituted $C_{1-6}$ alkyl group (preferably methyl, ethyl, isopropyl).

Preferable examples of the substituent for the $C_{1-6}$ alkyl group include
(1) a $C_{6-14}$ aryl group (preferably phenyl),
(2) an aromatic heterocyclic group (preferably pyridyl, imidazolyl) optionally substituted by 1 to 3 substituents selected from
    (a) a halogen atom (preferably chlorine atom), and
    (b) a $C_{1-6}$ alkyl group (preferably methyl),
(3) a non-aromatic heterocyclic group (preferably tetrahydropyranyl),
(4) a hydroxy group,
(5) a $C_{1-6}$ alkoxy group (preferably methoxy),
(6) a di-tert-butylphenylsilyloxy group
and the like.

$R^2$ is more preferably a $C_{1-6}$ alkyl group (preferably methyl, ethyl, isopropyl) optionally substituted by 1 to 3 substituents selected from
(1) a $C_{6-14}$ aryl group (preferably phenyl),
(2) an aromatic heterocyclic group (preferably pyridyl, imidazolyl) optionally substituted by 1 to 3 substituents selected from
    (a) a halogen atom (preferably chlorine atom), and
    (b) a $C_{1-6}$ alkyl group (preferably methyl),
(3) a non-aromatic heterocyclic group (preferably tetrahydropyranyl),
(4) a hydroxy group,
(5) a $C_{1-6}$ alkoxy group (preferably methoxy), and
(6) a di-tert-butylphenylsilyloxy group.

$R^3$ is a hydrogen atom or a halogen atom.
$R^3$ is preferably a hydrogen atom.

Ring A is an optionally further substituted 6-membered ring.

Examples of the "6-membered ring" of the "optionally further substituted 6-membered ring" for ring A include benzene, cyclohexene, cyclohexadiene, a 6-membered aromatic heterocycle and a 6-membered non-aromatic heterocycle.

Examples of the 6-membered aromatic heterocycle include a 6-membered ring, from among rings corresponding to the aromatic heterocyclic group exemplified as the "heterocyclic group" of the "optionally substituted heterocyclic group" for $R^1$, specifically, pyridine, pyridazine, pyrimidine, pyrazine, triazine and the like.

Examples of the 6-membered non-aromatic heterocycle include a 6-membered ring, from among rings corresponding to the non-aromatic heterocyclic group exemplified as the "heterocyclic group" of the "optionally substituted heterocyclic group" for $R^1$, specifically, piperidine, piperazine, morpholine, thiomorpholine, pyran, tetrahydropyran, thiopyran, tetrahydrothiopyran, 1-oxidotetrahydrothiopyran, 1,1-dioxidotetrahydrothiopyran, tetrahydropyrimidine, dioxane and the like.

The "6-membered ring" of the "optionally further substituted 6-membered ring" for ring A is preferably benzene.

The "6-membered ring" of the "optionally further substituted 6-membered ring" for ring A optionally has, besides —$W^1$—$R^1$ and —$W^2$—$R^2$, 1 or 2 substituents at substitutable positions. Examples of the substituent include those similar to the substituent which the "$C_{3-10}$ cycloalkyl group" of the "optionally substituted $C_{3-10}$ cycloalkyl group" for $R^1$ optionally has. When two or more substituents are used, the substituents may be the same or different.

Preferable examples of the substituent for the "6-membered ring" include a halogen atom (preferably fluorine atom) and the like.

Ring A is preferably a 6-membered ring (preferably benzene) optionally substituted by, besides —$W^1$—$R^1$ and —$W^2$—$R^2$, 1 to 3 halogen atoms (preferably fluorine atom).

Ring A is more preferably a 6-membered ring (preferably benzene) having no substituents except —$W^1$—$R^1$ and —$W^2$—$R^2$.

Ring B is an optionally substituted 5- to 7-membered nitrogen-containing heterocycle.

Examples of the "5- to 7-membered nitrogen-containing heterocycle" of the "optionally substituted 5- to 7-membered nitrogen-containing heterocycle" for ring B include a 5- to 7-membered ring containing at least one nitrogen atom, from among rings corresponding to the "heterocyclic group" of the "optionally substituted heterocyclic group" for $R^1$, specifically, pyridine, pyrimidine, pyridazine, pyrazine, pyrroline, imidazole, pyrazole, thiazole, isothiazole, oxazole, isoxazole, oxadiazole, thiadiazole, triazole, tetrazole, triazine, pyrrolidine, piperidine, morpholine, thiomorpholine, piperazine, hexamethylenimine, oxazolidine, thiazolidine, imidazolidine, oxazoline, thiazoline, imidazoline, dihydrooxadiazoline, pyrazolidine, tetrahydropyrimidine and the like.

The "5- to 7-membered nitrogen-containing heterocycle" of the "optionally substituted 5- to 7-membered nitrogen-containing heterocycle" for ring B is preferably a 5-membered nitrogen-containing heterocycle (preferably thiazoline, thiazole, thiadiazole), more preferably a 5-membered nitrogen-containing non-aromatic heterocycle (preferably thiazoline).

The "5- to 7-membered nitrogen-containing heterocycle" of the "optionally substituted 5- to 7-membered nitrogen-containing heterocycle" for ring B optionally has 1 to 5 (preferably 1 to 3) substituents at substitutable positions. Examples of the substituent include those similar to the substituent which the "$C_{3-10}$ cycloalkyl group" of the "optionally substituted $C_{3-10}$ cycloalkyl group" for $R^1$ optionally has. When two or more substituents are used, the substituents may be the same or different.

When two or more substituents are used, the two substituents bonded to the single atom or the adjacent atoms, in combination, from an "optionally substituted ring".

Examples of the "ring" of the "optionally substituted ring" include a $C_{3-10}$ cycloalkane, a $C_{3-10}$ cycloalkene, a $C_{4-10}$ cycloalkadiene, a $C_{6-14}$ aryl group, a heterocycle and the like.

Examples of the $C_{3-10}$ cycloalkane include a ring corresponding to the "$C_{3-10}$ cycloalkyl group" of the "optionally substituted $C_{3-10}$ cycloalkyl group" for $R^1$.

Examples of the $C_{6-14}$ arene include a ring corresponding to the "$C_{6-14}$ aryl group" of the "optionally substituted $C_{6-14}$ aryl group" for $R^1$.

Examples of the heterocycle include a ring corresponding to the aromatic heterocyclic group and non-aromatic heterocyclic group exemplified as the "heterocyclic group" of the "optionally substituted heterocyclic group" for $R^1$.

Examples of the $C_{3-10}$ cycloalkene include cyclopropene, cyclobutene, cyclopentene, cyclohexene, cycloheptene, cyclooctene and the like.

Examples of the $C_{4-10}$ cycloalkadiene include 1,3-cyclopentadiene, 1,3-cyclohexadiene, 1,4-cyclohexadiene, 1,3-cycloheptadiene and the like.

The "ring" of the "optionally substituted ring" optionally has 1 to 3 substituents at substitutable positions. Examples of the substituent include those similar to the substituent which the "$C_{3-10}$ cycloalkyl group" of the "optionally substituted $C_{3-10}$ cycloalkyl group" for $R^1$ optionally has. When two or more substituents are used, the substituents may be the same or different.

Preferable examples of the substituent include
(1) a $C_{1-6}$ alkyl group (preferably methyl, ethyl) optionally substituted by 1 to 3 substituents selected from
  (a) a hydroxy group,
  (b) a carbamoyl group,
  (c) a carboxy group,
  (d) a $C_{1-6}$ alkoxy-carbonyl group (preferably ethoxycarbonyl), and
  (e) a non-aromatic heterocyclic group (preferably thiomorpholinyl, 1-oxidothiomorpholinyl),
(2) a $C_{1-6}$ alkoxy-carbonyl group (preferably ethoxycarbonyl)
and the like.

In another embodiment, preferable examples of the substituent include
(1) a $C_{1-6}$ alkyl group (preferably methyl, ethyl, isobutyl) optionally substituted by 1 to 3 substituents selected from
  (a) a hydroxy group,
  (b) a carbamoyl group optionally mono- or di-substituted by substituent(s) selected from
    (i) a $C_{1-6}$ alkyl group (preferably methyl, ethyl, propyl, isobutyl) optionally substituted by 1 to 3 substituents selected from a hydroxy group and a $C_{1-6}$ alkoxy group (preferably methoxy), and
    (ii) a $C_{3-10}$ cycloalkyl group (preferably cyclopropyl),
  (c) a $C_{1-6}$ alkoxy group (preferably methoxy),
  (d) a carboxy group,
  (e) a $C_{1-6}$ alkoxy-carbonyl group (preferably ethoxycarbonyl),
  (f) a non-aromatic heterocyclic group (preferably thiomorpholinyl, 1-oxidothiomorpholinyl), and
  (g) a non-aromatic heterocyclyl-carbonyl group (preferably morpholinylcarbonyl),
(2) a $C_{1-6}$ alkoxy-carbonyl group (preferably ethoxycarbonyl)
and the like.

Ring B is preferably a 5- to 7-membered nitrogen-containing heterocycle (preferably a 5-membered nitrogen-containing heterocycle (preferably thiazoline, thiazole, thiadiazole), more preferably a 5-membered nitrogen-containing non-aromatic heterocycle (preferably thiazoline)) optionally substituted by 1 to 3 substituents selected from
(1) a $C_{1-6}$ alkyl group (preferably methyl, ethyl) optionally substituted by 1 to 3 substituents selected from
  (a) a hydroxy group,
  (b) a carbamoyl group,
  (c) a carboxy group,
  (d) a $C_{1-6}$ alkoxy-carbonyl group (preferably ethoxycarbonyl), and
  (e) a non-aromatic heterocyclic group (preferably thiomorpholinyl, 1-oxidothiomorpholinyl), and
(2) a $C_{1-6}$ alkoxy-carbonyl group (preferably ethoxycarbonyl).

In another embodiment, ring B is preferably a 5- to 7-membered nitrogen-containing heterocycle (preferably a 5-membered nitrogen-containing heterocycle (preferably thiazoline, thiazole, thiadiazole), more preferably a 5-membered nitrogen-containing non-aromatic heterocycle (preferably thiazoline)) optionally substituted by 1 to 3 substituents selected from
(1) a $C_{1-6}$ alkyl group (preferably methyl, ethyl, isobutyl) optionally substituted by 1 to 3 substituents selected from
  (a) a hydroxy group,
  (b) a carbamoyl group optionally mono- or di-substituted by substituent(s) selected from
    (i) a $C_{1-6}$ alkyl group (preferably methyl, ethyl, propyl, isobutyl) optionally substituted by 1 to 3 substituents selected from a hydroxy group and a $C_{1-6}$ alkoxy group (preferably methoxy), and
    (ii) a $C_{3-10}$ cycloalkyl group (preferably cyclopropyl),
  (c) a $C_{1-6}$ alkoxy group (preferably methoxy),
  (d) a carboxy group,
  (e) a $C_{1-6}$ alkoxy-carbonyl group (preferably ethoxycarbonyl),
  (f) a non-aromatic heterocyclic group (preferably thiomorpholinyl, 1-oxidothiomorpholinyl), and
  (g) a non-aromatic heterocyclyl-carbonyl group (preferably morpholinylcarbonyl), and
(2) a $C_{1-6}$ alkoxy-carbonyl group (preferably ethoxycarbonyl).

In the formula (I), the structure represented by

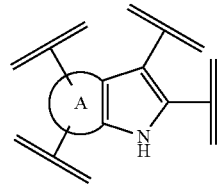

means a group derived from a bicycle formed by ring A and the pyrrole ring having one common bond (that is, they are condensed). The bond multiplicity for ring A and that for the pyrrole ring, involved in the bicycle formation, are the same. For example, when the structure represented by

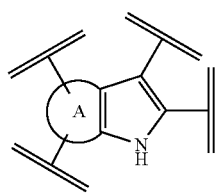

is the structure represented by

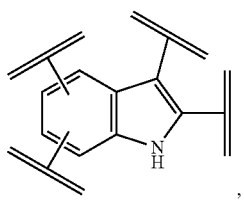

, ring A is "benzene".

$W^1$ and $W^2$ are independently O, S, SO, $SO_2$ or $NR^4$ wherein $R^4$ is a hydrogen atom or a $C_{1-6}$ alkyl group.

$W^1$ and $W^2$ is preferably independently O, S, SO or $SO_2$.

$W^1$ and $W^2$ is more preferably both O.

Compound (I) does not encompass N-methyl-4-[(1-methyl-1H-tetrazol-5-yl)thio]-2-(1,3-thiazol-2-yl)-1H-indol-7-amine.

Compound (I) is preferably the following compound.

[Compound (A'-I)]

Compound (I) wherein ring A is benzene;

ring B is an optionally substituted 5-membered nitrogen-containing heterocycle;

$W^1$ and $W^2$ are both O;

$R^1$ is an optionally substituted $C_{6-14}$ aryl group or an optionally substituted heterocyclic group;

$R^2$ is an optionally substituted $C_{1-6}$ alkyl group; and $R^3$ is a hydrogen atom.

[Compound (A-I)]

Compound (I) wherein ring A is a 6-membered ring (preferably benzene) having no substituents except $—W^1—R^1$ and $—W^2—R^2$;

ring B is a 5- to 7-membered nitrogen-containing heterocycle (preferably a 5-membered nitrogen-containing heterocycle (preferably thiazoline, thiazole, thiadiazole), more preferably a 5-membered nitrogen-containing non-aromatic heterocycle (preferably thiazoline)) optionally substituted by 1 to 3 substituents selected from (1) a $C_{1-6}$ alkyl group (preferably methyl, ethyl) optionally substituted by 1 to 3 substituents selected from
  (a) a hydroxy group,
  (b) a carbamoyl group,
  (c) a carboxy group,
  (d) a $C_{1-6}$ alkoxy-carbonyl group (preferably ethoxycarbonyl), and
  (e) a non-aromatic heterocyclic group (preferably thiomorpholinyl, 1-oxidothiomorpholinyl), and
(2) a $C_{1-6}$ alkoxy-carbonyl group (preferably ethoxycarbonyl);

$W^1$ and $W^2$ are both O;

$R^1$ is a $C_{6-14}$ aryl group (preferably phenyl) optionally substituted by 1 to 3 $C_{1-6}$ alkylsulfonyl groups (preferably methylsulfonyl);

$R^2$ is a $C_{1-6}$ alkyl group (preferably methyl, isopropyl) optionally substituted by 1 to 3 substituents selected from
(1) a $C_{6-14}$ aryl group (preferably phenyl),
(2) an aromatic heterocyclic group (preferably pyridyl, imidazolyl) optionally substituted by 1 to 3 substituents selected from
  (a) a halogen atom (preferably chlorine atom), and
  (b) a $C_{1-6}$ alkyl group (preferably methyl),
(3) a non-aromatic heterocyclic group (preferably tetrahydropyranyl),
(4) a hydroxy group,
(5) a $C_{1-6}$ alkoxy group (preferably methoxy), and
(6) a di-tert-butylphenylsilyloxy group; and $R^3$ is a hydrogen atom.

[Compound (B-I)]

Compound (I) wherein ring A is a 6-membered ring (preferably benzene) optionally substituted by, besides $—W^1—R^1$ and $—W^2—R^2$, 1 to 3 halogen atoms (preferably fluorine atom);

ring B is a 5- to 7-membered nitrogen-containing heterocycle (preferably a 5-membered nitrogen-containing heterocycle (preferably thiazoline, thiazole, thiadiazole), more preferably a 5-membered nitrogen-containing non-aromatic heterocycle (preferably thiazoline)) optionally substituted by 1 to 3 substituents selected from (1) a $C_{1-6}$ alkyl group (preferably methyl, ethyl, isobutyl) optionally substituted by 1 to 3 substituents selected from
  (a) a hydroxy group,
  (b) a carbamoyl group optionally mono- or di-substituted by substituent(s) selected from
    (i) a $C_{1-6}$ alkyl group (preferably methyl, ethyl, propyl, isobutyl) optionally substituted by 1 to 3 substituents selected from a hydroxy group and a $C_{1-6}$ alkoxy group (preferably methoxy), and
    (ii) a $C_{3-10}$ cycloalkyl group (preferably cyclopropyl),
  (c) a $C_{1-6}$ alkoxy group (preferably methoxy),
  (d) a carboxy group,
  (e) a $C_{1-6}$ alkoxy-carbonyl group (preferably ethoxycarbonyl),
  (f) a non-aromatic heterocyclic group (preferably thiomorpholinyl, 1-oxidothiomorpholinyl), and
  (g) a non-aromatic heterocyclyl-carbonyl group (preferably morpholinylcarbonyl), and
(2) a $C_{1-6}$ alkoxy-carbonyl group (preferably ethoxycarbonyl);

$W^1$ and $W^2$ are both 0;

$R^1$ is a $C_{6-14}$ aryl group (preferably phenyl) or a heterocyclic group (preferably an aromatic heterocyclic group (preferably pyridyl)), each of which is optionally substituted by 1 to 3 substituents selected from
(1) a $C_{1-6}$ alkylsulfonyl group (preferably methylsulfonyl), and
(2) a $C_{1-6}$ alkyl group (preferably methyl) optionally substituted by 1 to 3 $C_{1-6}$ alkoxy groups (preferably methoxy);

$R^2$ is a $C_{1-6}$ alkyl group (preferably methyl, ethyl, isopropyl) optionally substituted by 1 to 3 substituents selected from
(1) a $C_{6-14}$ aryl group (preferably phenyl),
(2) an aromatic heterocyclic group (preferably pyridyl, imidazolyl) optionally substituted by 1 to 3 substituents selected from
  (a) a halogen atom (preferably chlorine atom), and
  (b) a $C_{1-6}$ alkyl group (preferably methyl),
(3) a non-aromatic heterocyclic group (preferably tetrahydropyranyl),
(4) a hydroxy group,
(5) a $C_{1-6}$ alkoxy group (preferably methoxy), and
(6) a di-tert-butylphenylsilyloxy group; and $R^3$ is a hydrogen atom.

Of compound (I), compound (II) is preferable, more preferably the following compounds.

[Compound (A-II)]

Compound (1I) wherein ring A is benzene;

ring B is an optionally substituted 5-membered nitrogen-containing heterocycle;

$W^1$ and $W^2$ are both O;

$R^1$ is an optionally substituted $C_{6-14}$ aryl group or an optionally substituted heterocyclic group;

$R^2$ is an optionally substituted $C_{1-6}$ alkyl group; and $R^3$ is a hydrogen atom.

[Compound (B-II)]

Compound (1I) wherein ring A is a 6-membered ring (preferably benzene) optionally substituted by, besides —$W^1$—$R^1$ and —$W^2$—$R^2$, 1 to 3 halogen atoms (preferably fluorine atom);

ring B is a 5- to 7-membered nitrogen-containing heterocycle (preferably a 5-membered nitrogen-containing heterocycle (preferably thiazoline, thiazole, thiadiazole), more preferably a 5-membered nitrogen-containing non-aromatic heterocycle (preferably thiazoline)) optionally substituted by 1 to 3 substituents selected from (1) a $C_{1-6}$ alkyl group (preferably methyl, ethyl, isobutyl) optionally substituted by 1 to 3 substituents selected from
   (a) a hydroxy group,
   (b) a carbamoyl group optionally mono- or di-substituted by substituent(s) selected from
      (i) a $C_{1-6}$ alkyl group (preferably methyl, ethyl, propyl, isobutyl) optionally substituted by 1 to 3 substituents selected from a hydroxy group and a $C_{1-6}$ alkoxy group (preferably methoxy), and
      (ii) a $C_{3-10}$ cycloalkyl group (preferably cyclopropyl),
   (c) a $C_{1-6}$ alkoxy group (preferably methoxy),
   (d) a carboxy group,
   (e) a $C_{1-6}$ alkoxy-carbonyl group (preferably ethoxycarbonyl),
   (f) a non-aromatic heterocyclic group (preferably thiomorpholinyl, 1-oxidothiomorpholinyl), and
   (g) a non-aromatic heterocyclyl-carbonyl group (preferably morpholinylcarbonyl), and (2) a $C_{1-6}$ alkoxy-carbonyl group (preferably ethoxycarbonyl);

$W^1$ and $W^2$ are both O;

$R^1$ is a $C_{6-14}$ aryl group (preferably phenyl) or a heterocyclic group (preferably an aromatic heterocyclic group (preferably pyridyl)), each of which is optionally substituted by 1 to 3 substituents selected from (1) a $C_{1-6}$ alkylsulfonyl group (preferably methylsulfonyl), and (2) a $C_{1-6}$ alkyl group (preferably methyl) optionally substituted by 1 to 3 $C_{1-6}$ alkoxy groups (preferably methoxy);

$R^2$ is a $C_{1-6}$ alkyl group (preferably methyl, ethyl, isopropyl) optionally substituted by 1 to 3 substituents selected from (1) a $C_{6-14}$ aryl group (preferably phenyl), (2) an aromatic heterocyclic group (preferably pyridyl, imidazolyl) optionally substituted by 1 to 3 substituents selected from
   (a) a halogen atom (preferably chlorine atom), and
   (b) a $C_{1-6}$ alkyl group (preferably methyl), (3) a non-aromatic heterocyclic group (preferably tetrahydropyranyl), (4) a hydroxy group, (5) a $C_{1-6}$ alkoxy group (preferably methoxy), and (6) a di-tert-butylphenylsilyloxy group; and $R^3$ is a hydrogen atom.

When compound (I) or compound (II) [hereinafter to be correctively abbreviated as compound (I)] is in the form of a salt, as such salts, for example, a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like; alkaline earth metal salts such as calcium salt, magnesium salt and the like; aluminum salts; ammonium salts and the like.

Preferable examples of the salt with organic base include salts with trimethylamine, triethylamine, pyridine, picoline, ethanolamine, diethanolamine, triethanolamine, dicyclohexylamine, N,N-dibenzylethylenediamine and the like.

Preferable examples of the salt with inorganic acid include salt with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

A prodrug of the compound (I) means a compound which is converted to the compound (I) with a reaction due to an enzyme, an gastric acid, etc. under the physiological condition in the living body, that is, a compound which is converted to the compound (I) with enzymatic oxidation, reduction, hydrolysis and the like; a compound which is converted to the compound (I) by hydrolysis and the like due to gastric acid and the like. A prodrug of the compound (I) may be a compound obtained by subjecting an amino group in the compound (I) to an acylation, alkylation or phosphorylation (e.g., a compound obtained by subjecting an amino group in the compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in the compound (I) to an acylation, alkylation, phosphorylation or boration (e.g., a compound obtained by subjecting an hydroxy group in the compound (I) to an acetylation, palmitoylation, propanoylation, pivaloylation, succinylation, fumarylation, alanylation or dimethylaminomethylcarbonylation); a compound obtained by subjecting a carboxy group in the compound (I) to an esterification or amidation (e.g., a compound obtained by subjecting a carboxy group in the compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. These compounds can be produced from the compound (I) according to a method known per se.

A prodrug of the compound (I) may also be one which is converted into the compound (I) under a physiological condition, such as those described in IYAKUHIN NO KAIHATSU (Development of Pharmaceuticals), Vol. 7, Design of Molecules, p. 163-198, Published by HIROKAWA SHOTEN (1990).

Preferable specific examples of the prodrug of compound (I) include a compound wherein the amino group of the moiety pyrrole in the structure represented by the formula (I)

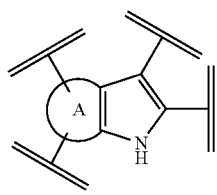

is acylated, alkylated, sulfonylated or phosphorylated.

The compound (I) may be labeled with an isotope (e.g., $^3$H, $^{14}$C, $^{35}$S, $^{125}$I etc.) and the like.

Furthermore, the compound (I) may be a non-hydrate or hydrate.

Deuterium-converted compound wherein $^1$H has been converted to $^2$H(D) are also encompassed in the compound (I).

The compound (I) or a prodrug thereof (hereinafter sometimes to be abbreviated as the compound of the present invention) shows low toxicity and can be used as an agent for the prophylaxis or treatment of various diseases to be mentioned later for mammals (e.g., humans, mice, rats, rabbits, dogs, cats, bovines, horses, pigs, monkeys) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; solvent, solubilizing agent, suspending agent, isotonicity agent, buffer and soothing agent for liquid preparations, and the like. Where necessary, an additive for pharmaceutical preparations such as preservative, antioxidant, colorant, sweetening agent and the like can be used.

Preferable examples of the excipient include lactose, sucrose, D-mannitol, D-sorbitol, starch, α-starch, dextrin, crystalline cellulose, low-substituted hydroxypropylcellulose, sodium carboxymethylcellulose, gum acacia, pullulan, light anhydrous silicic acid, synthetic aluminum silicate, magnesium aluminate metasilicate and the like.

Preferred examples of the lubricant include magnesium stearate, calcium stearate, talc, colloidal silica and the like.

Preferable examples of the binder include α-starch, saccharose, gelatin, gum acacia, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, calcium carboxymethylcellulose, sodium croscarmellose, sodium carboxymethylstarch, light anhydrous silicic acid, low-substituted hydroxypropylcellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferred examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferred examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferred examples of the isotonicity agent include sodium chloride, glycerol, D-mannitol, D-sorbitol, glucose and the like.

Preferred examples of the buffer include buffers such as phosphate, acetate, carbonate, citrate and the like.

Preferred examples of the soothing agent include benzyl alcohol and the like.

Preferred examples of the preservative include p-oxybenzoates, chlorobutanol, benzyl alcohol, phenethyl alcohol, dehydroacetic acid, sorbic acid and the like.

Preferred examples of the antioxidant include sulfite, ascorbate and the like.

Preferable examples of the colorant include water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment), natural pigments (e.g., beta carotene, chlorophyll, red iron oxide) and the like.

Preferable examples of the sweetening agent include saccharin sodium, dipotassium glycyrrhizinate, aspartame, stevia and the like.

The dosage form of the aforementioned pharmaceutical composition is, for example, an oral agent such as tablets (inclusive of sugar-coated tablets, film-coated tablets, sublingual tablets and orally disintegrable tablets), capsules (inclusive of soft capsules and microcapsules), granules, powders, troches, syrups, emulsions, suspensions, films (e.g., orally disintegrable film) and the like; a parenteral agent such as injections (e.g., subcutaneous injections, intravenous injections, intramuscular injections, intraperitoneal injections, drip infusions), external agents (e.g., transdermal preparations, ointments), suppositories (e.g., rectal suppositories, vaginal suppositories), pellets, nasal preparations, pulmonary preparations (inhalations), ophthalmic preparations and the like, and the like. These may be administered safely via an oral or parenteral (e.g., topical, rectal, intravenous administrations etc.) route.

These agents may be controlled-release preparations such as rapid-release preparations and sustained-release preparations (e.g., sustained-release microcapsules).

The pharmaceutical composition can be produced according to a method conventionally used in the field of pharmaceutical preparation, such as the method described in Japan Pharmacopoeia and the like. Concrete production methods of preparations are described in detail in the following.

While the content of the compound of the present invention in the pharmaceutical composition varies depending on the dosage form, dose of the compound of the present invention and the like, it is, for example, about 0.1 to 100 wt %.

The compound of the present invention has a superior GK activating action, and can be used as an agent for the prophylaxis or treatment of various diseases for mammals (e.g., human, bovine, horse, dog, cat, monkey, mouse, rat, specifically human). In addition, as the compound of the present invention has a selective GK activating action, it shows low toxicity (e.g., acute toxicity, chronic toxicity, cardiotoxicity, carcinogenic, genetic toxicity), which causes fewer side effects.

The compound of the present invention can be used as an agent for the prophylaxis or treatment of diabetes (e.g., type-1 diabetes, type-2 diabetes, gestational diabetes, obese diabetes etc.); an agent for the prophylaxis or treatment of obesity; an agent for the prophylaxis or treatment of hyperlipidemia (e.g., hypertriglyceridemia, hypercholesterolemia, hypo-HDL-emia, postprandial hyperlipidemia etc.); an agent for the prophylaxis or treatment of arteriosclerosis; an agent for the prophylaxis or treatment of impaired glucose tolerance (IGT); and an agent for preventing progression of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported new diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 100 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic foot lesion (e.g., gangrene, ulcer), xerostomia, hypacusis, cerebrovascular disorder, peripheral blood circulation disorder, diabetic diarrhea], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease, pyelonephritis, hydronephrosis), muscular dystrophy, myocardial infarction, angina pectoris, cerebrovascular accident (e.g., cerebral infarction, cerebral apoplexy), abnormal sugar metabolism, abnormal lipid metabolism, insulin resistance syndrome, Syndrome X, metabolic syndrome (according to the above-mentioned report by WHO, state concurrently associated with at least one of type 2 diabetes, impaired glucose tolerance and insulin resistance, and at least two from obesity, abnormal lipid metabolism, hypertension and trace albumin urine), Cushing's syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases (e.g., chronic rheumatoid arthritis, spondylitis deformans, osteoarthritis, lumbago, gout, postoperative or traumatic inflammation, swelling, neuralgia, pharyngolaryngitis, cystitis, hepatitis (inclusive of non-alcoholic steatohepatitis), pneumonia, pancreatitis, inflammatory bowel disease, ulcerative colitis, stomach mucous membrane injury (including stomach mucous membrane injury caused by aspirin)), visceral fat syndrome, Alzheimer's disease, cerebrovascular dementia, depression and the like.

The compound of the present invention can also be used for improvement of insulin resistance, promotion or increase of insulin secretion, decrease of visceral fat, suppression of accumulation of visceral fat, improvement of sugar metabolism, improvement of lipid metabolism (including suppression of oxidative LDL production, improvement of lipoprotein metabolism, lowering of blood remnant), improvement of coronary metabolism, prophylaxis or treatment of cardiovascular complication, prophylaxis or treatment of heart failure complication, prophylaxis or treatment of anovulation, prophylaxis or treatment of hirsutism, prophylaxis or treatment of hyperandrogenism, improvement of pancreatic ($\beta$ cell) function, regeneration of pancreas ($\beta$ cell), promotion of regeneration of pancreas ($\beta$ cell) and the like.

The compound of the present invention can also be used for the secondary prevention and suppression of progression of various diseases mentioned above (e.g., cardiovascular event such as myocardial infarction etc.).

The compound of the present invention is particularly useful as an agent for the prophylaxis or treatment of type-2 diabetes, obese diabetes and the like.

While the dose of the compound of the present invention varies depending on the administration subject, administration route, target disease, condition and the like, the compound of the present invention is generally given in a single dose of about 0.01-100 mg/kg body weight, preferably 0.05-30 mg/kg body weight, more preferably 0.1-10 mg/kg body weight, in the case of, for example, oral administration to adult diabetic patients. This dose is desirably given 1 to 3 times a day.

The compound of the present invention can be used in combination with drugs such as a therapeutic agent for diabetes, a therapeutic agent for diabetic complications, a therapeutic agent for hyperlipidemia, an antihypertensive agent, an antiobestic agent, a diuretic, a chemotherapeutic agent, an immunotherapeutic agent, an antithrombotic agent, a therapeutic agent for osteoporosis, a antidementia agent, an erectile dysfunction improver, a therapeutic agent for pollakiuria or urinary incontinence, a therapeutic agent for dysuria and the like (hereinafter to be referred to as a combination drug). In this case, the timing of administration of the compound of the present invention and a combination drug is not limited. These may be simultaneously administered an administration subject or administered in a staggered manner. Moreover, the compound of the present invention and a combination drug may be administered as two kinds of preparations each containing an active ingredient, or may be administered as a single preparation containing both active ingredients.

The dose of the combination drug can be determined as appropriate based on the dose clinically employed. The proportion of the compound of the present invention and the combination drug can be appropriately determined depending on the administration subject, administration route, target disease, condition, combination and the like. When, for example, the administration subject is human, the combination drug is used in an amount of 0.01-100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl-peptidase IV inhibitors (e.g., Alogliptin or a salt thereof (preferably benzoate), Vildagliptin, Sitagliptin, Saxagliptin, T-6666, TS-021), β3 agonists (e.g., AJ-9677), glucose-dependent insulin secretagogue (e.g., TAK-875), GPR40 agonists (e.g., compounds described in WO2006083781A1 and US 2007/0265332A1), GPR119 agonist (e.g., MBX-2982, PSN-821, APD-668), GLP-1 receptor agonists [e.g., GLP-1, GLP-1MR agent, N,N-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-hydroxysteroid dehydrogenase inhibitors (e.g., BVT-3498, dapagliflozin, remogliflozin), adiponectin or agonists thereof, IKK inhibitors (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agents for diabetic complications include aldose reductase inhibitors (e.g., Tolrestat, Epalrestat, Zenarestat, Zopolrestat, Minalrestat, Fidarestat, CT-112, ranirestat (AS-3201)), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), nerve regeneration-promoting agents (e.g., Y-128), PKC inhibitors (e.g., ruboxistaurin mesylate), AGE inhibitors (e.g., ALT-946, pimagedine, N-phenacylthiazolium bromide (ALT-766), ALT-711, EXO-226, Pyridorin, Pyridoxamine), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin and salts thereof (e.g., sodium salt, calcium salt)), squalene synthase inhibitors (lapaquistat or a salt thereof (preferably acetate), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agents include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonists), pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849), feeding deterrents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and derivatives thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agents include heparin (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agents include tacrine, donepezil, rivastigmine, galanthamine and the like.

Examples of the erectile dysfunction improvers include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

The combination drug is preferably insulin preparation, insulin sensitizer, α-glucosidase inhibitor, biguanide, insulin secretagogue (preferably sulfonylurea) and the like.

Two or more kinds of the above-mentioned combination drugs may be used in an appropriate combination.

When the compound of the present invention is used in combination with a combination drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent for diabetic complications, therapeutic agent for hyperlipidemia and antihypertensive agent can be reduced whereby an adverse effect which may be caused by these agents can be prevented effectively.

Compound (I) can be produced, for example, according to the method shown in the following Reaction Schemes 1, 2, 3 or 4.

Reaction Scheme 1

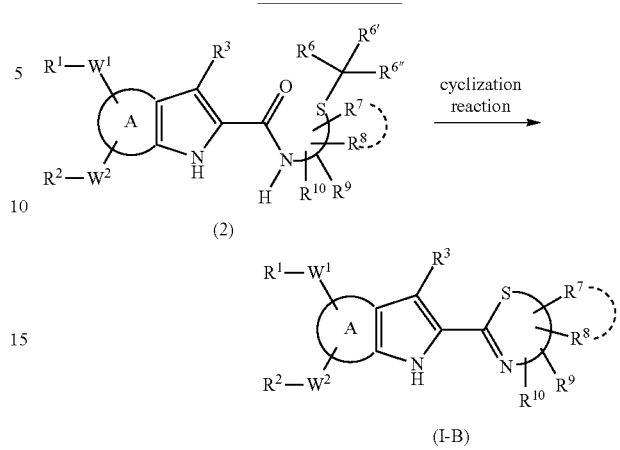

wherein $R^6$, $R^{6'}$ and $R^{6''}$ are independently a hydrogen atom, an optionally substituted $C_{1-6}$ alkyl group or an optionally substituted $C_{6-14}$ aryl group; $R^7$, $R^8$, $R^9$ and $R^{10}$ are independently a hydrogen atom or the aforementioned "substituent" for ring B; and the other symbols are as defined above.

Examples of the "optionally substituted $C_{1-6}$ alkyl group" for $R^6$, $R^{6'}$ or $R^{6''}$ include those similar to the "optionally substituted $C_{1-6}$ alkyl group" for $R^2$, and methyl group and ethyl group are preferable.

Examples of the "optionally substituted $C_{6-14}$ aryl group" for $R^6$, $R^{6'}$ or $R^{6''}$ include those similar to the "optionally substituted $C_{6-14}$ aryl group" for $R^2$, and a phenyl group and a 4-methoxyphenyl group are preferable.

Compound (I-B) can be produced from compound (2) according to a method described in Angew. Chem., Int. Ed., 2003, vol. 42, page 83; Tetrahedron, 1999, vol. 55, page 10271, or the like.

This reaction is carried out by reacting compound (2) with triphenylphosphine oxide and trifluoromethanesulfonic anhydride or phosphorus pentachloride.

This reaction is tarried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; nitriles such as acetonitrile, propionitrile and the like; aromatic hydrocarbons such as benzene, toluene and the like; saturated hydrocarbons such as cyclohexane, hexane and the like; halogenated hydrocarbons such as dichloromethane, chloroform, carbon tetrachloride, trichloroethylene and the like, and the like. These solvents may be used in a mixture at an appropriate ratio.

The amount of the triphenylphosphine oxide to be used is generally 1 to 10 mol, preferably 1 to 6 mol, per 1 mol of compound (2).

The amount of the trifluoromethanesulfonic anhydride or phosphorus pentachloride to be used is generally 1 to 10 mol, preferably 1 to 6 mol, per 1 mol of compound (2).

The reaction temperature is generally −70° C. to 100° C., preferably −30° C. to 60° C. The reaction time is generally 0.5 to 20 hr, preferably 0.5 to 6 hr.

Compound (2) used as a starting material for this reaction can be produced, for example, according to the method shown in the below-mentioned Reaction Scheme 5 or a method analogous thereto.

Reaction Scheme 2

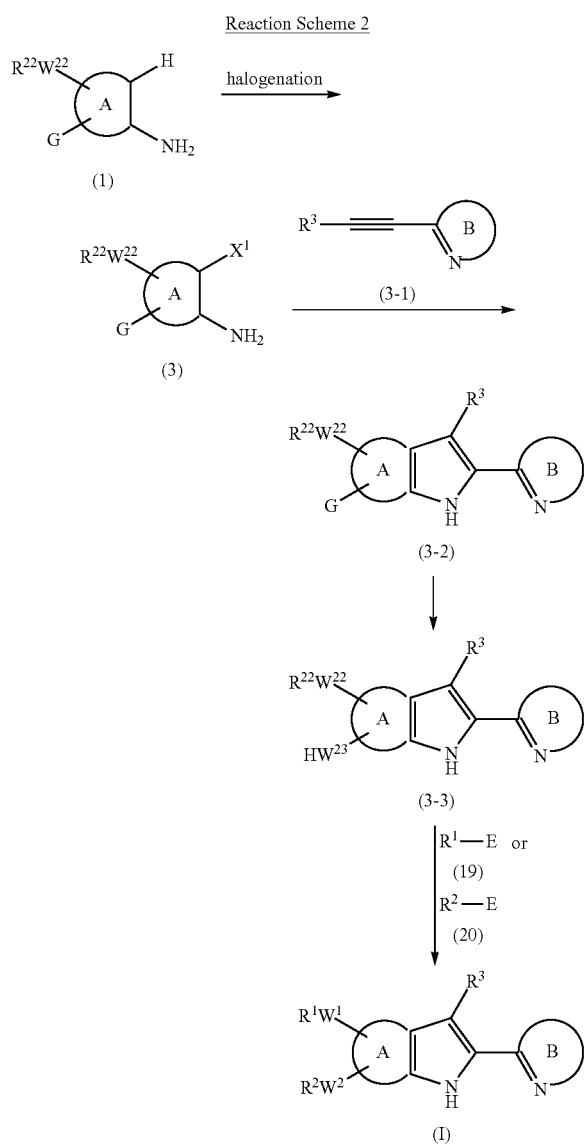

wherein G is a nitro group, an optionally protected amino group or an optionally protected hydroxy group; $X^1$ is a halogen atom; $R^{22}$ is any one of the aforementioned $R^1$ and $R^2$; $W^{22}$ is $W^1$ when $R^{22}$ is $R^1$, or $W^2$ when $R^{22}$ is $R^2$; $W^{23}$ is $W^2$ when $R^{22}$ is $R^1$, or $W^1$ when $R^{22}$ is $R^2$; E is a hydroxy group or a leaving group; and the other symbols are as defined above.

Examples of the "leaving group" for E include a halogen atom; an optionally halogenated $C_{1-6}$ alkylsulfonyloxy group (e.g., methanesulfonyloxy, ethanesulfonyloxy, trichloromethanesulfonyloxy, trifluoromethanesulfonyloxy); a $C_{6-10}$ arylsulfonyloxy group optionally having 1 to 3 substituents selected from a $C_{1-6}$ alkyl group, a $C_{1-6}$ alkoxy group and a nitro group (e.g., phenylsulfonyloxy, m-nitrophenylsulfonyloxy, p-toluenesulfonyloxy); a $C_{1-6}$ alkoxysulfonyloxy group; a $C_{6-10}$ aryloxysulfonyloxy group and the like.

Examples of the protecting group for an amino group of the "optionally protected amino group" for G include those mentioned below.

Examples of the protecting group for a hydroxyl group of the "optionally protected hydroxyl group" for G include those mentioned below.

Compound (3) can be produced by halogenating compound (1) with a halogenating agent, according to a method known per se (e.g., the method described in "Jikken Kagaku Koza (Experimental Chemistry Course)", 4th edition, vol. 19, pages 424 to 467) or a method analogous thereto.

Examples of the halogenating agent include N-chlorosuccinimide, N-bromosuccinimide, iodine, benzyltrimethylammonium dichloroiodate and the like.

This reaction is preferably carried out in a solvent inert to the reaction. The solvent is not particularly limited as long as the reaction proceeds, and examples thereof include alcohols such as methanol, ethanol, propanol, isopropanol, butanol, tert-butanol and the like; organic acids such as, acetic acid, formic acid and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate, tert-butyl acetate and the like; halogenated hydrocarbons such as dichloromethane, chloroform, 1,2-dichloroethane, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide; water and the like. These solvents may be used in a mixture at an, appropriate ratio.

The amount of the halogenating agent to be used is generally 1 to 10 mol, preferably 1 to 3 mol, per 1 mol of compound (1).

The reaction temperature is generally –30° C. to 120° C., preferably –10° C. to 100° C.

The reaction time is generally 0.5 to 24 hr, preferably 1 to 20 hr.

Compound (3-2) can be produced by reacting compound (3) with compound (3-1) in the presence of a metal reagent, according to a method known per se (e.g., the method described in Synthesis, 2005, page 1706; Organic Letters, 2003, page 3843 or the like) or a method analogous thereto.

Examples of the metal reagent used for this reaction include palladium reagents such as palladium(II) acetate, dichlorobis(triphenylphosphine)palladium(II), tetrakis(triphenylphosphine)palladium(0) and the like; copper reagents such as copper(I) iodide, (1,10-phenanthrolin)bis(triphenylphosphine)copper(I) nitrate and the like, and the like. These may be used in a mixture at an appropriate ratio.

The yield of this reaction may be improved when carried out in the co-presence of a base. Examples of the base include alkali metals hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogen carbonates such as sodium hydrogen carbonate, potassium hydrogen carbonate and the like; alkali metal phosphates such as potassium phosphate, sodium phosphate and the like; alkali metal $C_{1-6}$ alkoxides such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like, and the like.

This reaction is preferably carried out in a solvent inert to the reaction. Examples of the solvent include those exemplified in the aforementioned production Method of compound (3). In addition, the above-mentioned organic bases such as triethylamine, pyridine and the like may be used as a solvent.

The amount of compound (3-1) to be used is generally 1 to 5 mol, preferably 1 to 3 mol, per 1 mol of compound (3).

The amount of the metal reagent to be used is generally 0.05 to 3 mol, preferably 0.1 to 1 mol, per 1 mol of compound (3).

The amount of the base to be used is generally 1 to 10 mol, preferably 1 to 3 mol, per 1 mol of compound (3).

The reaction temperature is generally −30° C. to 140° C., preferably −10° C. to 100° C.

While the reaction time varies depending on the kind and amount of the metal reagent to be used, it is generally 0.5 to 24 hr, preferably 1 to 20 hr.

When G is a protected amino group or a protected hydroxy group, compound (3-3) can be produced by subjecting compound (3-2) to deprotection used generally in peptide chemistry and the like (e.g., an acid treatment, an alkali treatment, a catalytic reduction and the like), if desired.

When G is a nitro group, compound (3-3) can be produced by reducing compound (3-2) with a reducing agent.

Examples of the reducing agent include metals such as iron, zinc, tin and the like; sulfides such as sodium dithionite and the like; and the like.

The amount of the reducing agent to be used is appropriately determined depending on the kind of the reducing agent. For example, the amount of the metal to be used is generally 1 to 20 mol, preferably 1 to 5 mol, per 1 mol of compound (3-2), and the amount of the sulfide to be used is generally 1 to 20 mol, preferably 1 to 5 mol, per 1 mol of compound (3-2).

This reduction reaction can also be carried out by hydrogenation reaction. In this case, for example, a catalyst such as palladium carbon, palladium black, platinum dioxide, Raney-nickel, Raney-cobalt, iron trichloride and the like is used.

The amount of the catalyst to be used is generally 5 to 1000 wt %, preferably about 10 to 300 wt %, relative to compound (3-2).

The hydrogenation reaction can also be carried out using gas hydrogen or various hydrogen sources. Examples of the hydrogen source include formic acid, ammonium formate, triethylammonium formate, sodium phosphinate, hydrazine and the like.

The amount of the hydrogen source to be used is generally 1 to 100 mol, preferably 1 to 5 mol, per 1 mol of compound (3-2).

The reduction reaction is preferably carried out in a solvent inert to the reaction. The solvent is not particularly limited as long as the reaction proceeds, and examples thereof include alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like, and the like. These solvents may be used in a mixture at an appropriate ratio.

While the reaction time varies depending on the kind and amount of the reducing agent and catalyst to be used, it is generally 0.5 hr to 100 hr, preferably 1 hr to 50 hr.

The reaction temperature is generally −20 to 120° C., preferably 0 to 80° C.

Compound (I) can be produced by reacting compound (3-3) with compound (19) or compound (20).

When E is a hydroxy group, this reaction is carried out according to a method known per se, for example, the method described in Synthesis, 1981, page 1, or a method analogous thereto. Specifically, this reaction is generally carried out in the presence of an organic phosphorus compound and an electrophilic agent, in a solvent that does not adversely influence the reaction.

Examples of the organic phosphorus compound include triphenylphosphine, tributylphosphine and the like.

Examples of the electrophilic agent include diethyl azodicarboxylate, diisopropyl azodicarboxylate, azodicarbonyldipiperazine and the like.

The amount of the organic phosphorus compound and electrophilic agent to be used is preferably 1 to 5 mol, per 1 mol of compound (3-3), respectively.

The amount of compound (19) or compound (20) to be used is generally 1 to 10 mol, preferably 1 to 3 mol, per 1 mol of compound (3-3).

This reaction is preferably carried out in a solvent inert to the reaction. The solvent is not particularly limited as long as the reaction proceeds, and examples thereof include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethylsulfoxide and the like, and the like. These solvents may be used in a mixture at an appropriate ratio.

The reaction temperature is generally −50 to 150° C., preferably −10 to 100° C.

The reaction time is generally 0.5 to 20 hr, preferably 1 to 15 hr.

When E is a leaving group, this reaction is carried out in the presence of a base, according to a conventional method.

Examples of the base include inorganic bases such as potassium hydroxide, sodium hydroxide, sodium hydrogen carbonate, potassium carbonate, cesium carbonate and the like; amines such as pyridine, triethylamine, N,N-dimethylaniline, 1,8-diazabicyclo[5.4.0]undec-7-en and the like; metal hydrides such as potassium hydride, sodium hydride and the like; alkali metal alkoxides such as sodium methoxide, sodium ethoxide, potassium tert-butoxide and the like; alkyllithiums such as n-butyllithium, tert-butyllithium, methyllithium and the like, and the like.

The amount of the base to be used is preferably 1 to 5 mol, per 1 mol of compound (3-3).

The amount of compound (19) or compound (20) to be used is generally 1 to 10 mol, preferably 1 to 3 mol, per 1 mol of compound (3-3).

This reaction is preferably carried out in a solvent inert to the reaction. The solvent is not particularly limited as long as the reaction proceeds, and examples thereof include aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethylsulfoxide and the like, and the like. These solvents may be used in a mixture at an appropriate ratio.

The reaction temperature is generally −50 to 150° C., preferably −10 to 100° C.

The reaction time is generally 0.5 to 20 hr, preferably 1 to 15 hr.

Compound (I) can also be produced by reacting compound (3-3) with an alkylating agent.

Examples of the alkylating agent include diazomethane analogs such as diazomethane, trimethylsilyldiazomethane and the like; dialkyl sulfate such as dimethyl sulfate, diethyl sulfate and the like, and the like.

The amount of the alkylating agent to be used is preferably 1 to 5 mol, per 1 mol of compound (3-3).

This reaction is preferably carried out in a solvent inert to the reaction. The solvent is not particularly limited as long as the reaction proceeds, and examples thereof include aromatic hydrocarbons such as benzene, toluene, xylene and the like; ethers such as tetrahydrofuran, dioxane, diethyl ether and the like; ketones such as acetone, 2-butanone and the like; nitriles such as acetonitrile, propionitrile and the like; halogenated hydrocarbons such as chloroform, dichloromethane and the like; amides such as N,N-dimethylformamide and the like; sulfoxides such as dimethylsulfoxide and the like; water and the like. These solvents may be used in a mixture at an appropriate ratio.

When a dialkyl sulfate or the like is used, the reaction may be carried out in the presence of a base. Examples of the base include inorganic bases such as potassium hydroxide, sodium hydroxide, sodium hydrogen carbonate, potassium carbonate, cesium carbonate and the like; amines such as pyridine, triethylamine, N,N-dimethylaniline, 1,8-diazabicyclo[5.4.0]undec-7-en and the like; metal hydrides such as potassium hydride, sodium hydride and the like; alkali metal alkoxides such as sodium methoxide, sodium ethoxide, potassium tert-butoxide and the like; alkyllithiums such as n-butyllithium, tert-butyllithium, methyllithium and the like, and the like.

The amount of the base to be used is preferably 1 to 5 mol, per 1 mol of compound (3-3).

The reaction temperature is generally −50 to 150° C., preferably −10 to 120° C.

The reaction time is generally 0.5 to 100 hr, preferably 1 to 60 hr.

Compound (1) used as a starting material for this reaction can be produced according to the method shown in the below-mentioned Reaction Scheme 8, a method known per se or a method analogous thereto.

Compound (3-1), compound (19) and compound (20) used as starting materials for this reaction can be produced according to a method known per se or a method analogous thereto.

Reaction Scheme 3

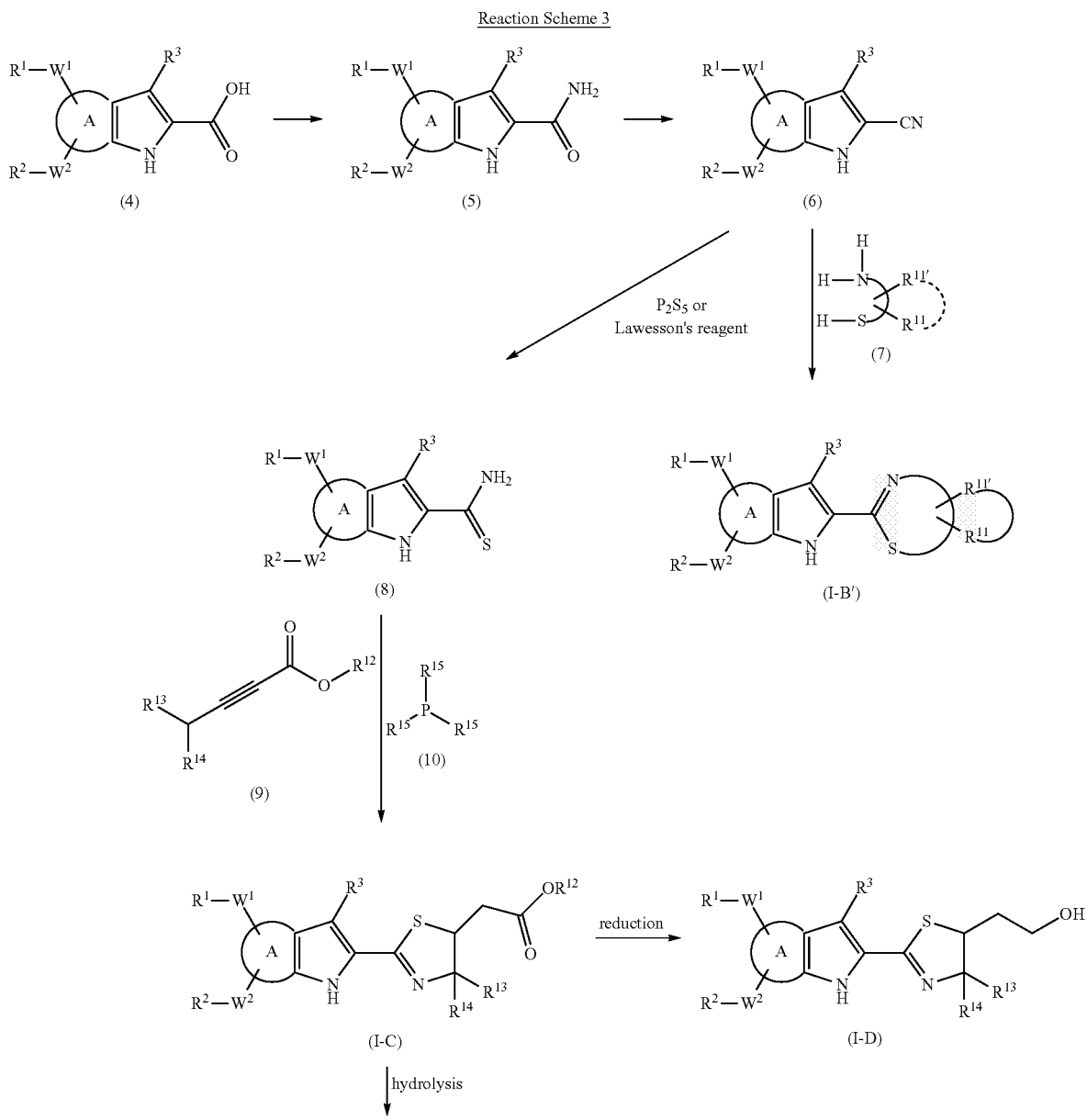

-continued

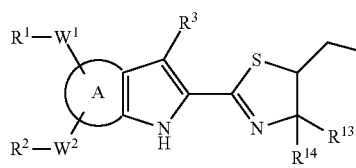 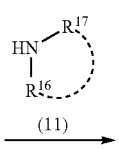 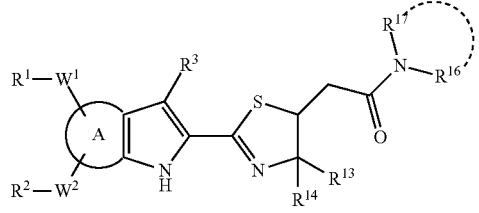

(I-E)     (11)     (I-F)

wherein $R^{11}$, $R^{11'}$, $R^{12}$ and $R^{14}$ are independently a hydrogen atom, or the aforementioned "substituent" for ring B; $R^{12}$ is an optionally substituted $C_{1-6}$ alkyl group or an optionally substituted $C_{3-10}$ cycloalkyl group; $R^{15}$ is an optionally substituted $C_{1-6}$ alkyl group or an optionally substituted aryl group; $R^{16}$ and $R^{17}$ are independently a hydrogen atom; a $C_{1-6}$ alkyl group optionally substituted by 1 to 3 substituents selected from a carboxy group, a hydroxy group, a $C_{1-6}$ alkoxy group, a $C_{1-6}$ alkoxy-carbonyl group, an amino group and a $C_{1-6}$ alkylsulfonyl group; a $C_{3-10}$ cycloalkyl group optionally substituted by 1 to 3 substituents selected from a $C_{1-6}$ alkyl group, a carboxy group, a hydroxy group, a $C_{1-6}$ alkoxy group, $C_{1-6}$ alkoxy-carbonyl group, an amino group and a $C_{1-6}$ alkylsulfonyl group; a $C_{1-6}$ alkylsulfonyl group optionally substituted by 1 to 3 substituents selected from a $C_{1-6}$ alkyl group, a carboxy group, a hydroxy group, a $C_{1-6}$ alkoxy-carbonyl group and an amino group; or an amino group optionally mono- or di-substituted by substituent(s) selected from a $C_{1-6}$ alkyl group, a carboxy group, a hydroxy group, a $C_{1-6}$ alkoxy-carbonyl group and a $C_{1-6}$ alkylsulfonyl group, or $R^{16}$ and $R^{17}$ in combination optionally form a nitrogen-containing heterocycle (e.g., morpholine) optionally substituted by 1 to 3 substituents selected from a $C_{1-6}$ alkyl group, a carboxy group, a hydroxy group, a $C_{1-6}$ alkoxy-carbonyl group, an amino group and a $C_{1-6}$ alkylsulfonyl group; and the other symbols are as defined above.

Examples of the "optionally substituted $C_{1-6}$ alkyl group" for $R^{12}$ or $R^{15}$ include those similar to the "optionally substituted $C_{1-6}$ alkyl group" for $R^2$.

Examples of the "optionally substituted $C_{3-10}$ cycloalkyl group" for $R^{12}$ include those similar to the "optionally substituted $C_{3-10}$ cycloalkyl group" for $R^1$.

Examples of the "optionally substituted $C_{6-14}$ aryl group" for $R^{15}$ include those similar to the "optionally substituted $C_{6-14}$ aryl group" for $R^1$.

Compound (I-B') can be produced using compound (4) in three steps.

In the first step, compound (5) can be produced by subjecting to compound (4) to an amidation reaction.

This reaction is carried out according to a method known per se, for example, (A) a method of subjecting compound (4) or a salt thereof and ammonia or a salt thereof to directly condensation with an condensing agent (e.g., dicyclohexylcarbodiimide), or (B) a method of appropriately reacting a reactive derivative of the carboxy group of compound (4) or a salt thereof with ammonia or a salt thereof, and the like.

Examples of the reactive derivative of the carboxy group of compound (4) include
1) an acid halide;
2) an acid azide;
3) a mixed acid anhydride with an acid (e.g., substituted phosphates such as dialkylphosphate, phenylphosphate, diphenylphosphate, dibenzylphosphate, halogenated phosphate and the like; dialkylphosphorous acid; sulfurous acid; thiosulfuric acid; sulfuric acid; sulfonic acids such as methanesulfonic acid and the like; aliphatic carboxylic acids such as formic acid, acetic acid, propionic acid, butyric acid, isobutyric acid, pivalic acid, pentanoic acid, isopentanoic acid, trichloroacetic acid and the like; aromatic carboxylic acids such as benzoic acid and the like);
4) a symmetric acid anhydride;
5) an activated amide with imidazole, 4-substituted imidazole, dimethylpyrazole, triazole or tetrazole;
6) an activated ester such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenylthioester, p-nitrophenyl ester, p-cresyl thioester, carboxymethyl thioester, pyranyl ester, pyridyl ester, piperidyl ester, 8-quinolylthio ester and the like;
7) a ester with a N-hydroxy compound (e.g., N,N-dimethylhydroxyamine, 1-hydroxy-2-(1H)-pyridone, N-hydroxysuccinimide, N-hydroxyphthalimide, 1-hydroxy-1H-benzotriazole);

and the like. These reactive derivatives are appropriately determined according to the kind of compound (4) to be used.

Preferable Examples of the salt of compound (4) or a reactive derivative of the carboxy group include salts with a base, such as alkali metal salts (e.g., sodium salt, potassium salt and the like), alkaline earth metal salts (e.g., calcium salt, magnesium salt and the like), ammonium salts, organic base salts (e.g., trimethylamine salt, triethylamine salt, pyridine salt, picoline salt, dicyclohexylamine salt, N,N-dibenzylethylenediamine salt and the like) and the like.

Examples of the ammonia or a salt thereof include aqueous ammonia, ammonium acetate, ammonium chloride, 1-hydroxybenztriazole ammonia complex and the like.

When an acid halide is used as a reactive derivative of the carboxy group, the reaction is carried out in the presence of a base, in a solvent that does not adversely influence the reaction.

Examples of the base include alkali metals such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; alkali metal $C_{1-6}$ alkoxides such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; lithium amides such as methyllithium, n-butyllithium, sec-butyllithium, tert-butyllithium and the like, and the like.

The amount of the base to be used is generally 1 to 10 mol, preferably 1 to 3 mol, per 1 mol of compound (4).

Examples of the solvent that does not adversely influence the reaction include halogenated hydrocarbons such as chloroform, dichloromethane and the like; aromatic hydrocarbons such as benzene, toluene and the like; ethers such as tetrahydrofuran, 1,4-dioxane, diethyl ether and the like; ethyl acetate, water and the like. These solvents may be used in a mixture at an appropriate ratio.

The amount of the ammonia or a salt thereof to be used is generally 1 to 10 mol, preferably 1 to 5 mol, per 1 mol of compound (4).

The reaction temperature is generally −30° C. to 100° C., preferably 0° C. to 50° C.

The reaction time is generally 0.5 to 20 hr, preferably 1 to 15 hr.

When a mixed acid anhydride is used as a reactive derivative of the carboxy group, the reaction is carried out by reacting compound (4) with a chlorocarbonate (e.g., methyl chlorocarbonate, ethyl chlorocarbonate, isobutyl chlorocarbonate etc.) in the presence of a base (e.g., triethylamine, N-methylmorpholine, N,N-dimethylaniline, sodium hydrogen carbonate, sodium carbonate, potassium carbonate etc.), in a solvent that does not adversely influence the reaction, and then by reacting the resulting compound with an ammonia or a salt thereof.

The amount of the chlorocarbonate to be used is generally 1 to 5 mol, preferably 1 to 3 mol, per 1 mol of compound (4).

The amount of the base to be used is generally 1 to 10 mol, preferably 1 to 3 mol, per 1 mol of compound (4).

The amount of the ammonia or a salt thereof to be used is generally 1 to 10 mol, preferably 1 to 5 mol, per 1 mol of compound (4).

Examples of the solvent that does not adversely influence the reaction include halogenated hydrocarbons such as chloroform, dichloromethane and the like; aromatic hydrocarbons such as benzene, toluene and the like; ethers such as tetrahydrofuran, 1,4-dioxane, diethyl ether and the like; ethyl acetate, water and the like. These solvents may be used in a mixture at an appropriate ratio.

The reaction temperature is generally −30° C. to 100° C.

The reaction time is generally 0.5 to 20 hr.

When compound (4) is used in the form of a free acid or a salt thereof, the reaction is carried out in a solvent inert to the reaction, in the presence of a conventional condensing agent such as a carbodiimide (e.g., N,N'-dicyclohexylcarbodiimide, N-cyclohexyl-N'morpholinoethylcarbodiimide, N-cyclohexyl-N'-(4-diethylaminocyclohexyl).carbodiimide, N,N'-diethylcarbodiimide, N,N'-diisopropylcarbodiimide, N-ethyl-N'-(3-dimethylaminopropyl)carbodiimide and the like), N,N'-carbonylbis(2-methylimidazole), a trialkyl phosphate, a polyphosphate (e.g., ethyl polyphosphate, isopropyl polyphosphate and the like), phosphorus oxychloride, diphenylphosphorylazide, thionyl chloride, oxalyl chloride, a lower alkyl haloformate (e.g., ethyl chloroformate, isopropyl chloroformate and the like), triphenylphosphine, N-hydroxybenzotriazole, 1-(p-chlorobenzenesulfonyloxy)-6-chloro-1H-benzotriazole, Vilsmeier-reagent (prepared by the reaction of N,N'-dimethylformamide and thionyl chloride, phosgene, trichloromethyl chloroformate, phosphorus oxychloride or the like), and the like.

The amount of the condensing agent to be used is generally 1 to 5 mol, preferably 1 to 3 mol, per 1 mol of compound (4).

The amount of the ammonia or a salt thereof to be used is generally 1 to 10 mol, preferably 1 to 5 mol, per 1 mol of compound (4).

This reaction may be carried out in the presence of a base, if desired. Examples of the base include triethylamine, N-methylmorpholine, N,N-dimethylaniline, sodium hydrogen carbonate, sodium carbonate, potassium carbonate and the like.

The amount of the base to be used is generally 1 to 10 mol, preferably 1 to 3 mol, per 1 mol of compound (4).

Examples of the solvent that does not adversely influence the reaction include halogenated hydrocarbons such as chloroform, dichloromethane and the like; aromatic hydrocarbons such as benzene, toluene and the like; ethers such as tetrahydrofuran, 1,4-dioxane, diethyl ether and the like; ethyl acetate, water and the like. These solvents may be used in a mixture at an appropriate ratio.

The reaction temperature is generally −30° C. to 100° C., preferably 0° C. to 60° C. The reaction time is generally 0.5 to 20 hr, preferably 1 to 15 hr.

When an acid azide, a symmetric acid anhydride, an activated amide, an activated ester, an ester with N-hydroxy compound, or the like is used as a reactive derivative of the carboxy group, the reaction can be carried out according to a method known per se.

Compound (4) used as a starting material for this reaction can be produced according to the method shown in the below-mentioned Reaction Scheme 6, or a method analogous thereto.

In the second step, compound (6) can be produced by reacting compound (5) with a dehydrating agent.

Examples of the dehydrating agent include acetic anhydride, trifluoroacetic anhydride, diphosphorus pentoxide, phosphorus pentachloride, phosphorus oxychloride, thionyl chloride, oxalyl chloride, 1,3-dicyclohexylcarbodiimide, cyanuric chloride and the like.

This reaction may be carried out in the presence of a base, if desired. Examples of the base include organic bases such as triethylamine, pyridine, 4-dimethylaminopyridine, diisopropylethylamine and the like; inorganic bases such as sodium carbonate, potassium carbonate and the like, and the like.

This reaction is carried out without solvent or in a solvent inert to the reaction. Examples of the solvent include halogenated hydrocarbons such as chloroform, dichloromethane and the like; aromatic hydrocarbons such as benzene, toluene and the like; ethers such as tetrahydrofuran, dioxane, diethyl ether and the like; esters such as methyl acetate, ethyl acetate, n-butyl acetate, tert-butyl acetate and the like; amides such as N,N-dimethylformamide, N,N-dimethylacetamide and the like; sulfoxides such as dimethylsulfoxide and the like, and the like. These solvents may be used in a mixture at an appropriate ratio.

The amount of the dehydrating agent and base to be used is generally 1 to 10 mol, preferably 1 to 3 mol, per 1 mol of compound (5), respectively.

The reaction temperature is generally −30° C. to 120° C., preferably −10° C. to 100° C. The reaction time is generally 0.5 to 20 hr, preferably 1 to 15 hr.

In the third step, compound (I-B') can be produced from compound (6).

This reaction is carried out by reacting compound (6) with compound (7), according to the method described in Eur. J. Med. Chem., 1993, vol. 28, page 29.

This reaction is carried out without a solvent or in a solvent inert to the reaction. The solvent is not particularly limited as long as the reaction proceeds, and examples thereof include alcohols such as methanol, ethanol, 1-propanol, 2-propanol, tert-butyl alcohol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like;

halogenated hydrocarbons such as dichloromethane, chloroform, carbon tetrachloride, trichloroethylene and the like; hydrocarbons such as n-hexane, benzene, toluene and the like; nitriles such as acetonitrile, propionitrile and the like, and the like. These solvents may be used in a mixture at an appropriate ratio.

This reaction may be carried out in the presence of an acid, if desired. Examples of the acid include mineral acids such as hydrochloric acid, sulfuric acid and the like; Lewis acids such as boron trihalide (e.g., boron trichloride, boron trifluoride), titanium tetrahalide (e.g., titanium tetrachloride, titanium tetrabromide), aluminum halide (e.g., aluminum chloride, aluminum bromide) and the like; organic acids such as acetic acid, formic acid, trifluoroacetic acid and the like, and the like.

The amount of compound (7) and the acid to be used is generally 0.1 to 10 mol, preferably 1 to 3 mol, per 1 mol of compound (6), respectively.

The reaction temperature is generally −30° C. to 120° C., preferably 0° C. to 100° C. The reaction time is generally 0.5 to 20 hr, preferably 1 to 15 hr.

Compound (7) used as a starting material for this reaction can be produced according to a method known per se or a method analogous thereto.

Compound (I-C) can be produced using compound (5) in two steps.

In the first step, compound (8) can be produced by reacting compound (5) with diphosphorus pentasulfide or Lawesson's reagent.

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; halogenated hydrocarbons such as dichloromethane, chloroform, carbon tetrachloride, trichloroethylene and the like; bases such as pyridine, N,N-dimethylaniline, and the like, and the like. These solvents may be used in a mixture at an appropriate ratio.

The amount of the diphosphorus pentasulfide or Lawesson's reagent to be used is generally 0.5 to 10 mol, preferably 0.5 to 3 mol, per 1 mol of compound (5).

The reaction temperature is generally −30° C. to 140° C., preferably −10° C. to 120° C. The reaction time is generally 0.5 to 20 hr, preferably 1 to 15 hr.

In the second step, compound (I-C) can be produced by reacting compound (8) with compound (9) in the presence of compound (10). This reaction is carried out according to the method described in J. Org. Chem., 2002, vol. 67, page 4595.

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; halogenated hydrocarbons such as dichloromethane, chloroform, carbon tetrachloride, trichloroethylene and the like, and the like. These solvents may be used in a mixture at an appropriate ratio.

The amount of compound (9) to be used is generally 1 to 10 mol, preferably 1 to 4 mol, per 1 mol of compound (8).

The amount of compound (10) to be used is generally 0.1 to 10 mol, preferably 0.1 to 4 mol, per 1 mol of compound (8).

The reaction temperature is generally −30° C. to 140° C., preferably −10° C. to 120° C. The reaction time is generally 0.5 to 20 hr, preferably 1 to 15 hr.

Compounds (9) and (10) used as starting materials for this reaction can be produced according to a method known per se or a method analogous thereto.

Compound (I-D) can be produced by subjecting compound (I-C) to a reduction reaction.

Examples of the reducing agent used for this reaction include metal hydrides such as aluminum hydride, diisobutylaluminum hydride, tributyltin hydride and the like; metal hydrogen complex compounds such as lithium aluminum hydride, sodium borohydride, lithium borohydride, calcium borohydride and the like; borane complexes such as borane-tetrahydrofuran complex, borane-dimethyl sulfide complex and the like; alkylboranes such as thexylborane, disiamylborane and the like; diborane and the like.

The amount of the reducing agent to be used is appropriately determined depending on the kind of the reducing agent. For example, the amount of the metal hydride or metal hydrogen complex compound to be used is 0.25 to 10 mol, preferably 0.5 to 5 mol, per 1 mol of compound (I-C), and the amount of the borane complex, alkylborane or diborane to be used is 1 to 10 mol, preferably 1 to 5 mol, per 1 mol of compound (I-C).

The reduction reaction is advantageously carried out in a solvent inert to the reaction. The solvent is not particularly limited as long as the reaction proceeds, and examples thereof include alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propionic acid, trifluoroacetic acid, methanesulfonic acid and the like, and the like. These solvents may be used in a mixture at an appropriate ratio.

While the reaction time varies depending on the kind and amount of the reducing agent to be used, it is generally 0.5 hr to 100 hr, preferably 1 hr to 50 hr. The reaction temperature is generally −20 to 120° C., preferably 0 to 80° C.

Compound (I-E) can be produced by subjecting compound (I-C) to a hydrolysis. The hydrolysis is carried out using an acid or a base according to a conventional method.

Examples of the acid include mineral acids such as hydrochloric acid, sulfuric acid and the like; Lewis acids such as boron trichloride, boron tribromide, aluminum trichloride, aluminum tribromide and the like; organic acids such as trifluoroacetic acid, p-toluenesulfonic acid and the like, and the like. The Lewis acid can be used in combination with a thiol (e.g., ethanethiol) or a sulfide (e.g., dimethylsulfide).

Examples of the base include alkali metal hydroxides such as lithium hydroxide, sodium hydroxide, potassium hydroxide, barium hydroxide and the like; alkali metal carbonates such as sodium carbonate, potassium carbonate and the like; alkali metal $C_{1-6}$ alkoxides such as sodium methoxide, sodium ethoxide, potassium tert-butoxide and the like; organic bases such as triethylamine, imidazole, formamidine and the like, and the like.

The amount of the acid or base to be used is generally about 0.5 to 10 mol, preferably about 0.5 to 6 mol, per 1 mol of compound (I-C).

The hydrolysis is carried out without a solvent or in a solvent inert to the reaction. The solvent is not particularly limited as long as the reaction proceeds, and examples thereof include alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methyl ethyl ketone and the like; sulfoxides such as dimethyl sulfoxide and the like; water and the like. These solvents may be used in a mixture at an appropriate ratio.

Examples of the reactive derivative of the carboxy group of compound (I-E) include those exemplified in the reaction for producing compound (5) from compound (4) in Reaction Scheme 3.

This reaction is carried out in the same manner as in the reaction for producing compound (5) from compound (4) in Reaction Scheme 3.

The amount of compound (11) to be used is generally 1 to 10 mol, preferably 1 to 5 mol, per 1 mol of compound (I-E)

The reaction temperature is generally −30° C. to 100° C., preferably 0° C. to 80° C. The reaction time is generally 0.5 to 20 hr, preferably 1 to 15 hr.

Compound (11) as a starting material for this reaction can be produced according to a method known per se or a method analogous thereto.

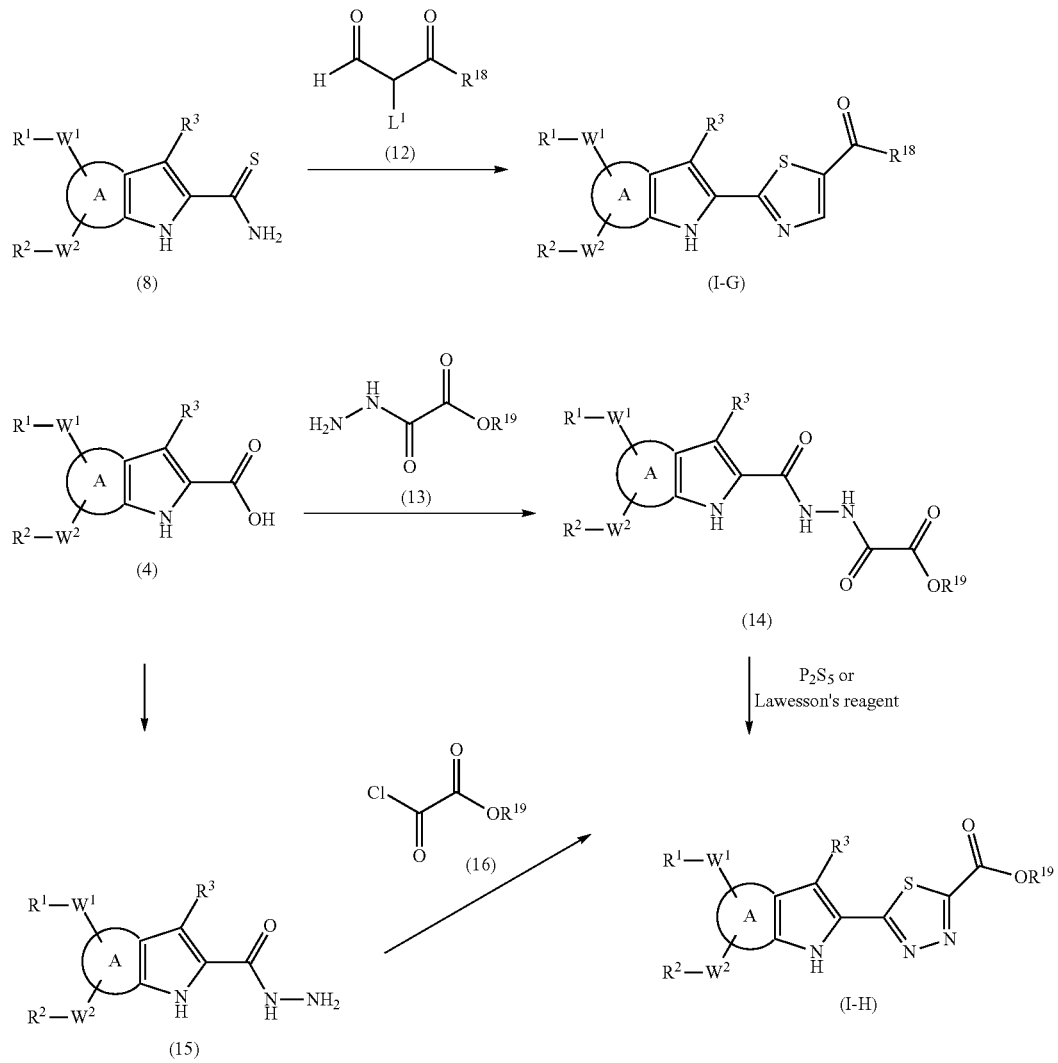

Reaction Scheme 4

The reaction time is generally 10 min to 60 hr, preferably 10 min to 12 hr. The reaction temperature is generally −10 to 200° C., preferably 0 to 120° C.

Compound (I-F) can be produced by reacting compound (I-E) or a reactive derivative of the carboxy group or a salt thereof with compound (11).

wherein $R^{18}$ is an optionally substituted $C_{1-6}$ alkyl group or an optionally substituted $C_{1-6}$ alkoxy group; $R^{19}$ is a $C_{1-6}$ alkyl group optionally substituted by 1 to 3 halogen atoms; $L^1$ is a leaving group; and the other symbols are as defined above.

n

Examples of the "leaving group" for $L^1$ include those exemplified as the aforementioned E.

Compound (I-G) can be produced by reacting compound (8) with compound (12).

This reaction may be carried out in the presence of an acid or a base, if desired.

Examples of the acid include mineral acids such as hydrochloric acid, sulfuric acid and the like; Lewis acids such as boron trihalide (e.g., boron trichloride, boron trifluoride), titanium tetrahalide (e.g., titanium tetrachloride, titanium tetrabromide), aluminum halide (e.g., aluminum chloride, aluminum bromide) and the like; organic acids such as acetic acid, formic acid, trifluoroacetic acid and the like, and the like.

Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate and the like, and the like.

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like. These solvents may be used in a mixture at an appropriate ratio.

When an acid is used, the amount of compound (12) and the acid to be used is generally 1 to 10 mol, preferably 1 to 3 mol, per 1 mol of compound (8), respectively.

While the reaction time varies depending on the kind and amount of compound (8), compound (12) and the acid, it is generally 0.5 hr to 100 hr, preferably 1 hr to 50 hr. The reaction temperature is generally −20 to 120° C., preferably 0 to 80° C.

When a base is used, the amount of compound (12) and the base to be used is generally 1 to 10 mol, preferably 1 to 3 mol, per 1 mol of compound (8), respectively.

While the reaction time varies depending on the kind and amount of compound (8), compound (12) and the base, it is generally 1 to 100 hr, preferably 1 to 50 hr. The reaction temperature is generally −20° C. to 120° C., preferably 0° C. to 80° C.

Compound (12) can be produced according to a method known per se or a method analogous thereto.

Compound (14) can be produced by reacting compound (4) or a reactive derivative of the carboxy group or a salt thereof with compound (13).

Examples of the reactive derivative of the carboxy group of compound (4) or a salt thereof include those exemplified in the reaction for producing compound (5) from compound (4) in Reaction Scheme 3.

This reaction is carried out in the same manner as in the reaction for producing compound (5) from compound (4) in Reaction Scheme 3.

Compound (14) can also be produced using compound (4) or a reactive derivative of the carboxy group or a salt thereof in two steps.

In the first step, compound (15) can be produced by reacting compound (4) or a reactive derivative of the carboxy group or a salt thereof with hydrazine or a salt thereof.

Examples of the reactive derivative of the carboxy group compound (4) or a salt thereof include those exemplified in the reaction for producing compound (5) from compound (4) in Reaction Scheme 3.

Examples of the hydrazine or a salt thereof include hydrazine hydrate, hydrazine hydrochloride, hydrazine sulfate and the like.

The amount of the hydrazine or a salt thereof to be used is generally 1 to 10 mol, preferably 1 to 5 mol, per 1 mol of compound (4).

This reaction is carried out in the same manner as in the reaction for producing compound (5) from compound (4) in Reaction Scheme 3.

In the second step, compound (14) can be produced by reacting compound (15) with compound (16).

This reaction is carried out in a solvent that does not adversely influence the reaction. Examples of the solvent that does not adversely influence the reaction include halogenated hydrocarbons such as chloroform, dichloromethane and the like; aromatic hydrocarbons such as benzene, toluene and the like; ethers such as tetrahydrofuran, dioxane, diethyl ether and the like, ethyl acetate, water and the like. These solvents may be used in a mixture at an appropriate ratio.

This reaction may be carried out in the presence of a base, if desired. Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate and the like, and the like.

The amount of compound (16) and the base to be used is generally 1 to 10 mol, preferably 1 to 3 mol, per 1 mol of compound (15), respectively.

The reaction temperature is generally −30° C. to 100° C., preferably −10° C. to 80° C. The reaction time is generally 0.5 to 20 hr, preferably 1 to 15 hr.

Compounds (13) and (16) can be produced according to a method known per se or a method analogous thereto.

Compound (I-H) can be produced by reacting compound (14) with diphosphorus pentasulfide or Lawesson's reagent.

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; halogenated hydrocarbons such as dichloromethane, chloroform, carbon tetrachloride, 1,2-dichloroethane and the like; bases such as pyridine, N,N-dimethylaniline, and the like, and the like. These solvents may be used in a mixture at an appropriate ratio.

The amount of the diphosphorus pentasulfide or Lawesson's reagent to be used is generally 0.5 to 10 mol, preferably 0.5 to 3 mol, per 1 mol of compound (14).

The reaction temperature is generally −30° C. to 100° C., preferably −10 to 80° C. The reaction time is generally 0.5 to 20 hr, preferably 1 to 15 hr.

Compound (2) can be produced, for example, according to the following method.

Reaction Scheme 5

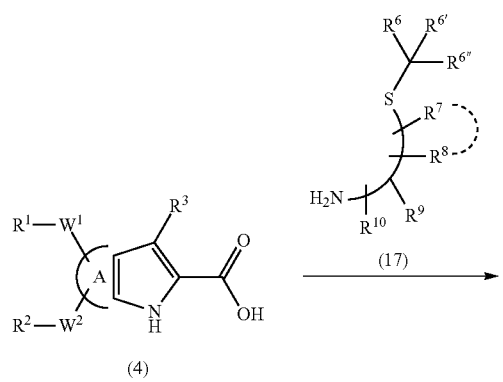

Reaction Scheme 6

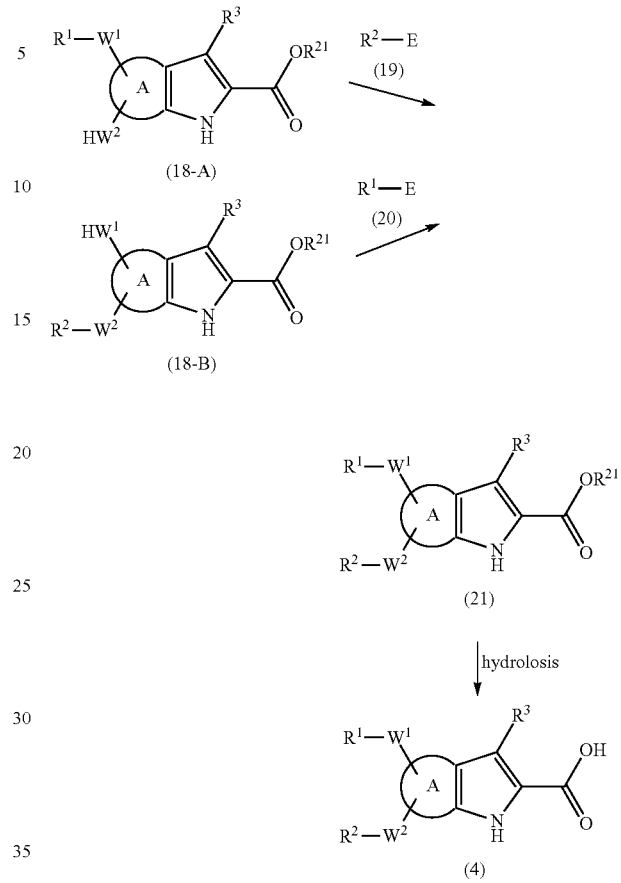

wherein each symbol is as defined above.

Compound (2) can be produced by reacting compound (4) or a reactive derivative of the carboxy group or a salt thereof with compound (17).

Examples of the reactive derivative of the carboxy group compound (4) or a salt thereof include those exemplified in the reaction for producing compound (5) from compound (4) in Reaction Scheme 3.

This reaction is carried out in the same manner as in the reaction for producing compound (5) from compound (4) in Reaction Scheme 3. This reaction may be carried out in the presence of a base, if desired.

The amount of compound (17) to be used is generally 1 to 10 mol, preferably 1 to 3 mol, per 1 mol of compound (4).

The amount of the base to be used is generally 1 to 10 mol, preferably 1 to 3 mol, per 1 mol of compound (4).

The reaction temperature is generally −30° C. to 100° C., preferably 0° C. to 80° C. The reaction time is generally 0.5 to 20 hr, preferably 1 to 15 hr.

Compound (17) as a starting material for this reaction can be produced according to a method known per se or a method analogous thereto.

Compound (4) can be produced, for example, according to the following method.

wherein $R^{21}$ is an optionally substituted $C_{1-6}$ alkyl group; and the other symbols are as defined above.

Examples of the "optionally substituted $C_{1-6}$ alkyl group" for $R^{21}$ include those similar to the "optionally substituted $C_{1-6}$ alkyl group" for $R^2$.

Compound (4) can be produced using compound (18-A) or compound (18-B) as a starting material in two steps.

In the first step, compound (21) can be produced by reacting compound (18-A) with compound (19). Alternatively, compound (21) can also be produced by reacting compound (18-B) with compound (20). Alternatively, compound (21) can also be produced by reacting compound (18-A) or compound (18-B) with an alkylating agent. This reaction is carried out in the same manner as in the reaction for producing compound (I) from compound (3-3) in Reaction Scheme 2.

In the second step, compound (4) can be produced by subjecting compound (21) to hydrolysis.

This reaction is carried out in the same manner as in the reaction for producing compound (I-E) from compound (I-C) in Reaction Scheme 3.

Compounds (19) and (20) as starting materials for this reaction can be produced according to a method known per se or a method analogous thereto.

Compound (18-A) or compound (18-B) as a starting material for this reaction can be produced, for example, according to the following method.

Reaction Scheme 7

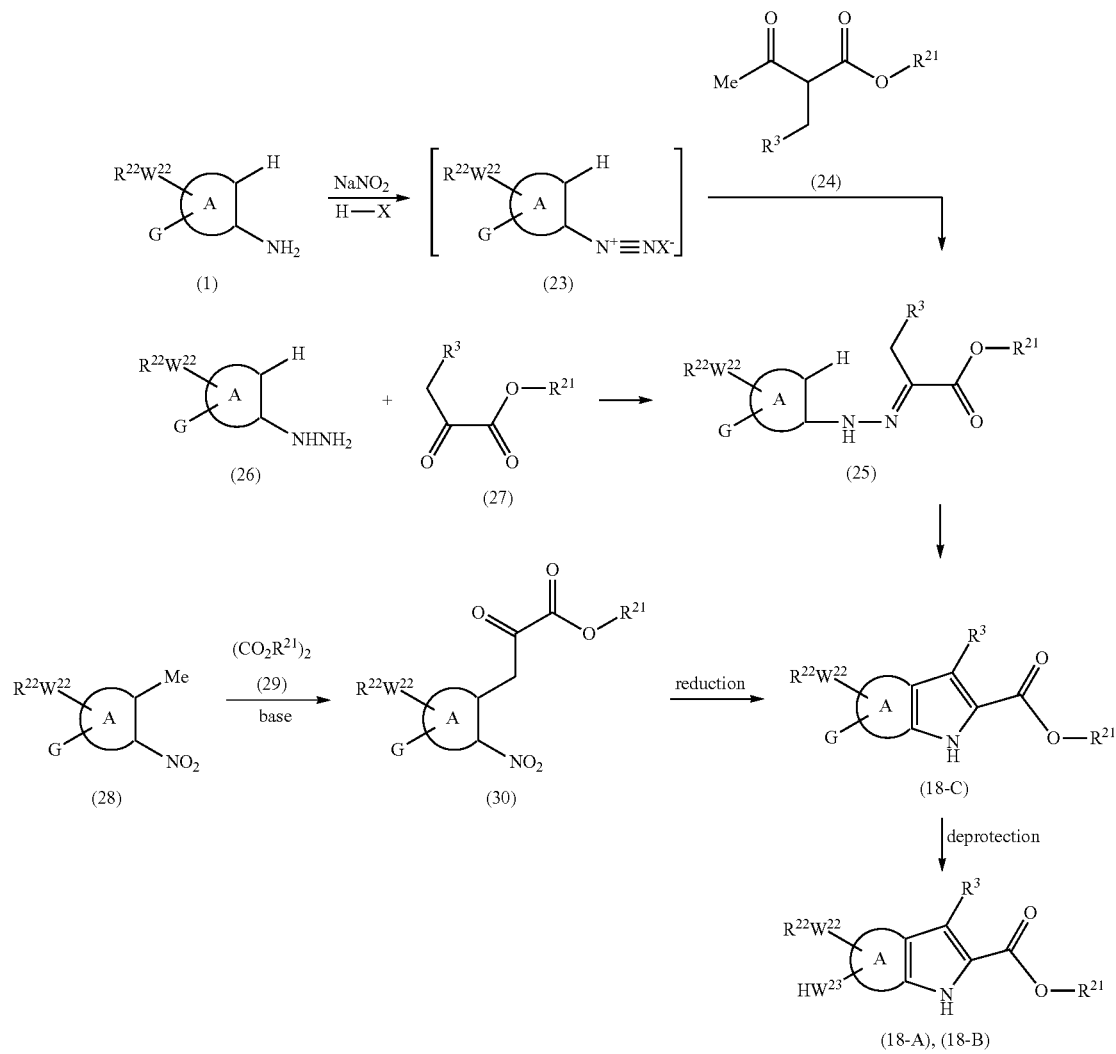

wherein H—X is a mineral acid such as hydrochloric acid, sulfuric acid and the like, or an organic acid such as acetic acid, formic acid, trifluoroacetic acid and the like, and each symbol is as defined above.

Compound (25) can be produced by reacting compound (26) with compound (27).

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like. These solvents may be used in a mixture at an appropriate ratio.

The reaction may be promoted by using an acid catalyst. Examples of the acid catalyst include mineral acids such as hydrochloric acid, sulfuric acid and the like; Lewis acids such as a boron trihalide (e.g., boron trichloride, boron trifluoride), a titanium tetrahalide (e.g., titanium tetrachloride, titanium tetrabromide), an aluminum halide (e.g., aluminum chloride, aluminum bromide) and the like; organic acids such as acetic acid, formic acid, trifluoroacetic acid and the like, and the like.

The amount of compound (27) and the acid catalyst to be used is generally 1 to 10 mol, preferably 1 to 3 mol, per 1 mol of compound (26), respectively.

While the reaction time varies depending on the kind and amount of compound (26), compound (27) and the acid catalyst to be used, it is generally 0.5 hr to 100 hr, preferably 1 hr to 50 hr. The reaction temperature is generally −20 to 120° C., preferably 0 to 80° C.

Compound (25) can also be produced by subjecting compound (1) to the Japp-Klingemann reaction [Org. Reactions, 1959, vol. 10, page 143; J. Chem. Soc., 1927, page 1].

This reaction is carried out by reacting compound (23) (which is produced by reacting compound (I) with an acid (H—X) and sodium nitrite according to a method known per se) with compound (24) in the presence of a base.

Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like, and the like.

This reaction is preferably carried out in a solvent inert to the reaction. The solvent is not particularly limited as long as the reaction proceeds, and examples thereof include alcohols such as methanol, ethanol, propanol, isopropanol, butanol, tert-butanol and the like; ethers such as 1,4-dioxane, tetrahydrofuran, diethyl ether, diphenyl ether, tert-butyl methyl ether, diisopropyl ether, 1,2-dimethoxyethane and the like; halogenated hydrocarbons such as dichloromethane, chloroform, carbon tetrachloride, trichloroethylene, chlorobenzene, 1,2-dichlorobenzene and the like; hydrocarbons such as n-hexane, benzene, toluene, xylene and the like; amides such as formamide, N,N-dimethylformamide, N,N-dimethylacetamide and the like; nitriles such as acetonitrile, propionitrile and the like; water and the like. These solvents may be used in a mixture at an appropriate ratio.

The amount of compound (24) to be used is generally 1 to 10 mol, preferably 1 to 3 mol, per 1 mol of compound (23).

The amount of the base to be used is generally 1 to 10 mol, preferably 1 to 3 mol, per 1 mol of compound (23).

The amount of the acid (H—X) to be used is generally 1 to 10 mol, preferably 1 to 5 mol, per 1 mol of compound (1).

The amount of the sodium nitrite to be used is generally 1 to 5 mol, preferably 1 to 3 mol, per 1 mol of compound (1).

The reaction time is generally 1 hr to about 100 hr, preferably 1 hr to 50 hr. The reaction temperature is generally $-20°$ C. to $120°$ C., preferably $0°$ C. to $80°$ C.

Compound (18-C) can be produced by subjecting compound (25) to the Fischer method [Berichte, 1883, vol. 16, page 2241].

This reaction is carried out by heating compound (25) with an acid.

Examples of the acid include zinc chloride, hydrogen chloride, sulfuric acid, acetic acid, boron fluoride, polyphosphoric acid, diphosphorus pentoxide, methanesulfonic acid, toluenesulfonic acid and the like. These may be used in a mixture at an appropriate ratio.

The amount of the acid to be used is generally 0.1 to 10 mol, preferably 0.5 to 3 mol, per 1 mol of compound (25).

This reaction is preferably carried out without solvent or in a solvent inert to the reaction. The solvent is not particularly limited as long as the reaction proceeds, and examples thereof include those exemplified in the production method of compound (25).

While the reaction time varies depending on the kind and amount of the acid to be used, it is generally 0.5 to 100 hr, preferably 1 to 50 hr. The reaction temperature is generally $0°$ C. to $200°$ C., preferably $50°$ C. to $190°$ C.

Compound (18-C) can also be produced by subjecting compound (28) to the Reissert method [Berichte, 1897, vol. 30, page 1030] in two steps.

In the first step, compound (30) is produced by reacting compound (28) with compound (29) in the presence of a base. In the second step, compound (18-C) is produced by subjecting compound (30) to a reduction reaction.

Examples of the base to be used in the first step include alkali metal $C_{1-6}$ alkoxides such as sodium methoxide, sodium ethoxide, potassium ethoxide, potassium tert-butoxide and the like, and the like.

This reaction is preferably carried out in a solvent inert to the reaction. The solvent is not particularly limited as long as the reaction proceeds, and examples thereof include those exemplified in the production method of compound (25).

The amount of compound (29) and the base to be used is generally 1 to 10 mol, preferably 1 to 3 mol, per 1 mol of compound (28), respectively.

The reaction temperature is generally $-30°$ C. to $140°$ C., preferably $-10°$ C. to $110°$ C. The reaction time is generally 0.5 to 20 hr, preferably 1 to 15 hr.

In the second step, the reduction reaction is carried out using a reducing agent.

Examples of the reducing agent include metals such as iron, zinc, tin and the like; sulfides such as sodium dithionite and the like; and the like.

The amount of the reducing agent to be used is appropriately determined depending to the kind of the reducing agent. For example, the amount of the metal to be used is generally 1 to 20 mol, preferably 1 to 5 mol, per 1 mol of compound (30), and the amount of the sulfide to be used is generally 1 to 20 mol, preferably 1 to 5 mol, per 1 mol of compound (30).

The reduction reaction can also be carried out by a hydrogenation reaction. In this case, for example, catalysts such as palladium carbon, palladium black, platinum dioxide, Raney-nickel, Raney-cobalt, iron trichloride and the like can be used.

The amount of the catalyst to be used is generally 5 to 1000 wt %, preferably about 10 to 300 wt %, relative to compound (30).

The hydrogenation reaction can also be carried out using hydrogen gas or various hydrogen sources. Examples of the hydrogen source include formic acid, ammonium formate, triethylammonium formate, sodium phosphinate, hydrazine and the like.

The amount of the hydrogen source to be used is generally about 1 to 100 mol, preferably about 1 to 5 mol, per 1 mol of compound (30).

The reduction reaction is preferably carried out in a solvent inert to the reaction. The solvent is not particularly limited as long as the reaction proceeds, and examples thereof include alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like, and the like. These solvents may be used in a mixture at an appropriate ratio.

While the reaction time varies depending on the kind and amount of the reducing agent and catalyst to be used, it is generally 0.5 to 100 hr, preferably 1 to 50 hr. The reaction temperature is generally $-20°$ C. to $120°$ C., preferably $0°$ C. to $80°$ C.

Compound (18-A) or compound (18-B) can be produced by subjecting compound (18-C) wherein G is a protected amino group, a protected sulfanyl group, or a protected hydroxy group to deprotection generally used in peptide chemistry and the like, such as an acid treatment, an alkali treatment, a catalytic reduction and the like, if desired.

Compounds (24), (26), (27), (28) and (29) can be produced according to a method known per se or a method analogous thereto.

Compound (1) can also be produced, for example, according to the method shown in the following Reaction Scheme.

Reaction Scheme 8

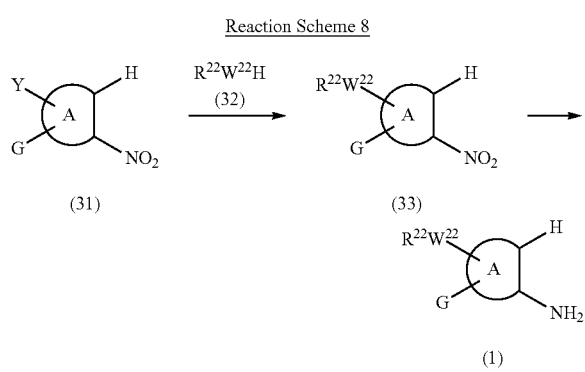

wherein Y is a halogen atom; and the other symbols are as defined above.

Compound (1) can be produced using compound (31) as a starting material in two steps.

In the first step, compound (33) can be produced by reacting compound (31) with compound (32).

This reaction may be carried out in the presence of a base, if desired.

Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate, sodium hydride and the like, and the like.

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like. These solvents may be used in a mixture at an appropriate ratio.

When a base is used, the amount of compound (32) and the base to be used is generally 1 to 10 mol, preferably 1 to 3 mol, per 1 mol of compound (31), respectively.

While the reaction time varies depending on the kind and amount of compound (31), compound (32) and the base, it is generally 0.5 to 100 hr, preferably 1 to 50 hr. The reaction temperature is generally −20° C. to 120° C., preferably 0° C. to 80° C.

In the second step, compound (1) can be produced by subjecting compound (33) to a reduction reaction.

The reduction reaction is carried out in the same manner as in the reaction for producing compound (18-C) from compound (30) in Reaction Scheme 7.

Compounds (31) and (32) as starting materials for this reaction can be produced according to a method known per se or a method analogous thereto.

Compound (17) can also be produced, for example, according to the following method.

Reaction Scheme 9

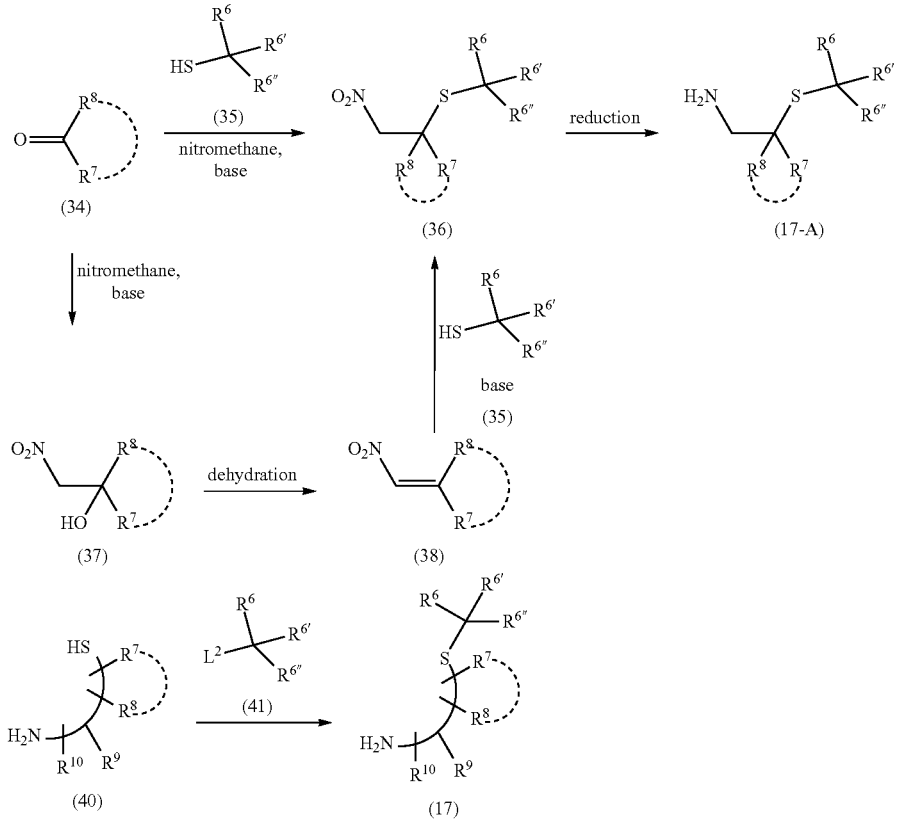

wherein L² is a leaving group, and the other symbols are as defined above.

Examples of the "leaving group" for L² include those exemplified as the aforementioned E.

Compound (36) can be produced from compound (34) according to a known method [J. Org. Chem. Soc., 1963, vol. 28, 1240 page; Tetrahedron, 2003, vol. 59, page 4979].

This reaction is carried out by reacting compound (34) with compound (35) and nitromethane in the presence of a base.

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; nitriles such as acetonitrile, propionitrile and the like; halogenated hydrocarbons such as dichloromethane, chloroform, 1,2-dichloroethane, carbon tetrachloride, trichloroethylene and the like. These solvents may be used in a mixture at an appropriate ratio.

Examples of the base include amines such as pyrrolidine, piperazine, morpholine, ethylenediamine and the like, and the to like.

The amount of the base to be used is generally 0.01 to 10 mol, preferably 0.05 to 2 mol, per 1 mol of compound (34).

The amount of compound (35) to be used is generally 1 to 10 mol, preferably 1 to 3 mol, per 1 mol of compound (34).

The amount of the nitromethane to be used is generally 1 to 50 mol, preferably 1 to 10 mol, per 1 mol of compound (34).

While the reaction time varies depending on the kind and amount of compound (34), compound (35), the nitromethane and the base to be used, it is generally about 0.5 hr to 100 hr, preferably 1 hr to 50 hr. The reaction temperature is generally 0° C. to 200° C., preferably 25° C. to 100° C.

Compound (36) can also be produced from compound (34) in three steps.

In the first step, compound (37) is produced by subjecting compound (34) to the Henry reaction [J. Org. Chem., 1963, vol. 28, page 1240; Synthesis, 1994, page 190; J. Am. Chem. Soc., 2003, vol. 125, page 3700] with nitromethane in the presence of a base.

This reaction is carried out without a solvent or in a solvent inert to the reaction. The solvent is not particularly limited as long as the reaction proceeds, and examples thereof include alcohols such as methanol, ethanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; nitriles such as acetonitrile, propionitrile and the like; halogenated hydrocarbons such as dichloromethane, chloroform, 1,2-dichloroethane, carbon tetrachloride, trichloroethylene and the like. These solvents may be used in a mixture at an appropriate ratio.

Examples of the base include alkali metal $C_{1-6}$ alkoxides such as sodium methoxide, sodium ethoxide, potassium ethoxide, potassium tert-butoxide and the like, and the like.

The amount of the base to be used is generally 0.01 to 10 mol, preferably 0.05 to 2 mol, per 1 mol of compound (34).

The amount of the nitromethane to be used is generally 1 to 50 mol, preferably 1 to 10 mol, per 1 mol of compound (34).

While the reaction time varies depending on the kind and amount of compound (34), the nitromethane and the base to be used, it is generally 0.5 hr to 100 hr, preferably 1 hr to 50 hr. The reaction temperature is generally 0° C. to 200° C., preferably 25° C. to 100° C.

In the second step, compound (38) is produced by subjecting compound (37) to a dehydration reaction.

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; nitriles such as acetonitrile, propionitrile and the like; halogenated hydrocarbons such as dichloromethane, chloroform, 1,2-dichloroethane, carbon tetrachloride, trichloroethylene and the like; pyridine and the like. These solvents may be used in a mixture at an appropriate ratio.

The dehydration reaction is generally carried out with a dehydrating agent. Examples of the dehydrating agent include chlorinating agents such as thionyl chloride, phosphoryl chloride and the like; sulfonylating agents such as methanesulfonyl chloride, methanesulfonic anhydride and the like; acylating agents such as acetyl chloride, acetic anhydride, trifluoroacetic anhydride and the like, and the like.

The amount of the dehydrating agent to be used is generally 1 to 10 mol, preferably 1 to 3 mol, per 1 mol of compound (37).

This reaction may be carried out in the presence of a base, if desired. Examples of the base include alkali metals such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; alkali metal $C_{1-6}$ alkoxides such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; lithium amides such as methyllithium, n-butyllithium, sec-butyllithium, tert-butyllithium and the like,
and the like.

The amount of the base to be used is generally 1 to 10 mol, preferably 1 to 3 mol, per 1 mol of compound (37).

The reaction temperature is generally −30° C. to 200° C., preferably −10° C. to 80° C. The reaction time is generally 0.5 to 20 hr, preferably 1 hr to 15 hr.

In the third step, compound (36) is produced by reacting compound (38) with compound (35) in the presence of a base.

This reaction is carried out without a solvent or in a solvent inert to the reaction. The solvent is not particularly limited as long as the reaction proceeds, and examples thereof include alcohols such as methanol, ethanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; nitriles such as acetonitrile, propionitrile and the like; halogenated hydrocarbons such as dichloromethane, chloroform, 1,2-dichloroethane, carbon tetrachloride, trichloroethylene and the like. These solvents may be used in a mixture at an appropriate ratio.

Examples of the base include those exemplified in the above-mentioned the second step.

The amount of compound (35) to be used is generally 1 to 10 mol, preferably 1 to 2 mol, per 1 mol of compound (38).

The amount of the base to be used is generally 0.05 to 10 mol, preferably 0.1 to 3 mol, per 1 mol of compound (38).

The reaction temperature is generally −30° C. to 100° C., preferably −10° C. to 80° C. The reaction time is generally 0.5 to 20 hr, preferably 1 hr to 15 hr.

Compound (17-A) can be produced by subjecting compound (36) to a reduction reaction.

The reduction reaction is carried out, for example, using a reducing agent. Examples of the reducing agent include metal hydrides such as aluminum hydride, diisobutylaluminum hydride, tributyltin hydride and the like; metal hydride complex compounds such as lithium aluminum hydride, sodium borohydride and the like; borane complexes such as borane-tetrahydrofuran complex, borane-dimethylsulfide complex and the like; alkylboranes such as thexylborane, disiamylborane and the like; diborane; metals such as zinc, aluminum, tin, iron and the like, and the like.

The amount of the reducing agent to be used is appropriately determined according to the kind of the reducing agent. For example, the amount of the metal hydride or metal hydride complex compound to be used is generally 0.25 to 10 mol, preferably 0.5 to 5 mol, per 1 mol of compound (36), the amount of the borane complex, alkylborane or diborane to be used is generally 1 to 10 mol, preferably 1 to 5 mol, per 1 mol of compound (36), and the amount of the metal to be used is generally 1 to 20 mol, preferably 1 to 5 mol, per 1 mol of compound (36).

The reduction reaction is preferably carried out in a solvent inert to the reaction. The solvent is not particularly limited as long as the reaction proceeds, and examples thereof include alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like, and the like. These solvents may be used in a mixture at an appropriate ratio.

While the reaction time varies depending on the kind and amount of the reducing agent to be used, it is generally 0.5 hr to 100 hr, preferably 1 hr to 50 hr. The reaction temperature is generally −20 to 120° C., preferably 0 to 80° C.

Compounds (34) and (35) as starting materials for this reaction can be produced according to a method known per se or a method analogous thereto.

Compound (17) can be produced by reacting compound (40) with compound (41) in the presence of an acid or a base, if desired.

Examples of the acid include mineral acids such as hydrochloric acid, sulfuric acid and the like; organic acids such as acetic acid, formic acid, trifluoroacetic acid and the like, and the like.

Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate and the like, and the like.

This reaction is carried out without a solvent or in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; esters such as ethyl formate, ethyl acetate, n-butyl acetate and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like. These solvents may be used in a mixture at an appropriate ratio.

When an acid is used, the amount of compound (41) and the acid to be used is generally 1 to 10 mol, preferably 1 to 3 mol, per 1 mol of compound (40), respectively.

While the reaction time varies depending on the kind and amount of compound (40), compound (41) and the acid, it is generally 0.5 to 100 hr, preferably 1 to 50 hr. The reaction temperature is generally −20° C. to 120° C., preferably 0° C. to 80° C.

When a base is used, the amount of compound (41) and the base to be used is generally 1 to 10 mol, preferably 1 to 3 mol, per 1 mol of compound (40), respectively.

While the reaction time varies depending on the kind and amount of compound (40), compound (41) and the base to be used, it is generally 1 hr to 100 hr, preferably 1 hr to 50 hr. The reaction temperature is generally −20 to 120° C., preferably 0 to 80° C.

Compound (41) as a starting material for this reaction can be produced according to a method known per se or a method analogous thereto.

Compound (33) can also be produced, for example, according to methods shown in the following Scheme 10.

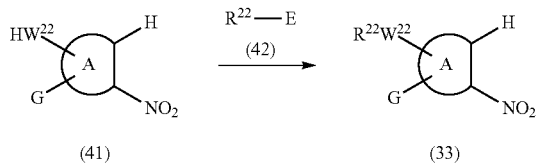

Reaction Scheme 10

(41) → (33)

wherein each symbol is as defined above.

Compound (33) can be produced from compound (41) in the same manner as in the reaction for producing compound (I) from compound (3-3) in Reaction Scheme 2, or a method analogous thereto.

Compound (41) used as a starting material for this reaction can be produced according to method known per se or a method analogous thereto.

Compound (I-I) can be produced, for example according to the method shown in Reaction Scheme 11.

Reaction Scheme 11

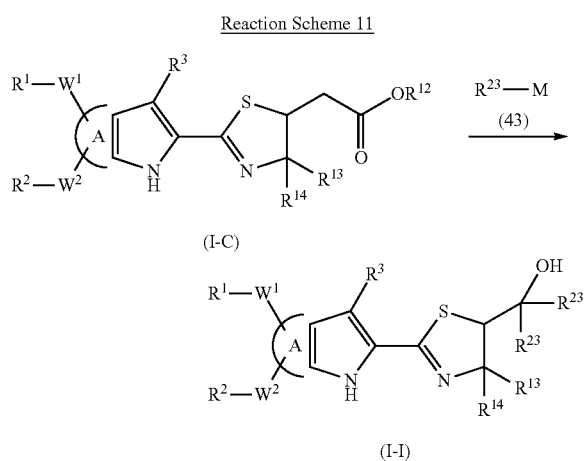

wherein M is a metal or a halogenated metal, each of $R^{23}$ is an optionally substituted $C_{1-6}$ alkyl group, an optionally substituted $C_{3-10}$ cycloalkyl group, an optionally substituted $C_{6-14}$ aryl group or an optionally substituted heterocyclic group, and the other symbols are as defined above.

Compound (I-I) can be produced by reacting compound (I-C) with compound (43). Preferable examples of compound (43) include organic lithiums such as methyllithium, n-butyllithium, phenyllithium and the like; Grignard reagents such as methylmagnesium bromide, methylmagnesium chloride, ethylmagnesium chloride, phenylmagnesium bromide and the like.

This reaction is advantageously carried out in a solvent inert to the reaction. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; saturated hydrocarbons such as cyclohexane, hexane and the like; aromatic hydrocarbons such as benzene, toluene and the like; halogenated hydrocarbons such as dichloromethane, chloroform, carbon tetrachloride, 1,2-dichloroethane and the like, and the like. These solvents may be used in a mixture at an appropriate ratio.

While the reaction time varies depending on the kind and amount of the reagent and solvent to be used, it is generally 10 min to 100 hr, preferably 30 min to 50 hr. The reaction temperature is generally –70 to 100° C., preferably 0 to 80° C.

The amount of compound (43) to be used is about 0.5 to about 20 mol, preferably about 1 to about 10 mol, per 1 mol of compound (I-C).

In the above-mentioned reaction resultant product and compound (I), the functional group in the molecule can be converted to a desired functional group by combination of chemical reactions known per se. Examples of the chemical reaction include oxidation reactions, reduction reactions, alkylation reactions, hydrolysis, amination reactions amidation reactions, esterification reactions, aryl coupling reactions, deprotection and the like.

In each of the aforementioned methods, when the starting material compound has an amino group, a carboxy group, a hydroxy group, a carbonyl group or a mercapto group as a substituent, a protecting group generally used in the peptide chemistry and the like may be introduced into these groups, and the object compound can be obtained by eliminating the protecting group as necessary after the reaction.

Examples of the amino-protecting group include a formyl group; a $C_{1-6}$ alkyl-carbonyl group (e.g., acetyl, propionyl), a $C_{1-6}$ alkoxy-carbonyl group (e.g., methoxycarbonyl, ethoxycarbonyl, tert-butoxycarbonyl), a benzoyl group, a $C_{7-13}$ aralkyl-carbonyl group (e.g., benzylcarbonyl), a $C_{7-13}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-20}$ aralkyl group (e.g., benzyl), a phenyl group, a trityl, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a trityl group, a $C_{7-13}$ aralkyl group (e.g., benzyl), a formyl group, a $C_{1-6}$ alkyl-carbonyl group, a benzoyl group, a $C_{7-13}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), a $C_{1-6}$ alkylsulfonyl group (e.g., methylsulfonyl, ethylsulfonyl), a $C_{6-10}$ arylsulfonyl group optionally substituted by 1 to 3 substituents selected from a $C_{1-6}$ alkyl group, a $C_{1-6}$ alkoxy group and a nitro group (e.g., phenylsulfonyl, m-nitrophenylsulfonyl, p-toluenesulfonyl), and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include a cyclic acetal (e.g., 1,3-dioxane), a non-cyclic acetal (e.g., a di-$C_{1-6}$ alkylacetal) and the like.

Examples of the mercapto-protecting group include a $C_{1-6}$ alkyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

Compound (I) obtained according to the above-mentioned production method can be isolated and purified by a known means, for example, concentration, concentration under reduced pressure, solvent extraction, crystallization, recrystallization, phase transfer, chromatography and the like. In addition, various starting compounds used in each of the above-mentioned production methods can be isolated and purified by a known means such as those mentioned above. Alternatively, the starting compounds may be directly used in the form of a reaction mixture without isolation as the starting materials of the next step.

For the production of Compound (I), when the starting compound can form a salt, the compound may also be used in the form of a salt. Examples of the salt include those similar to the salts of compound (I).

When Compound (I) contains an optical isomer, a stereoisomer, a regioisomer or a rotational isomer, these are encompassed in compound (I), and obtained as a single product according to a synthesis method and separation method known per se. For example, an optical isomer and an optical isomer resolved from this compound are also encompassed in compound (I).

Compound (I) may be in the form of a crystal.

The crystals of compound (I) (hereinafter sometimes to be abbreviated as the crystals of the present invention) can be produced by crystallization of compound (I) according to a crystallization method known per se.

In the present specification, the melting point refers to that measured using, for example, micromelting point measuring apparatus (Yanako, MP-500D or Buchi, B-545) or DSC (differential scanning calorimetry) device (SEIKO, EXSTAR6000) and the like.

In general, melting points vary depending on measurement apparatuses, measurement conditions and the like. The crystals in the present specification may show a different melting point described in the present specification, as long as it is within general error range.

The crystals of the present invention is superior in physicochemical properties (e.g., melting point, solubility, stability) and biological properties (e.g., pharmacokinetics (absorption, distribution, metabolism, excretion), efficacy expression), and is extremely useful as a pharmaceutical agent.

EXAMPLES

The present invention is explained in detail in the following by referring to the following Reference Examples, Examples, Experimental Examples and Formulation Examples, which are not to be construed as limitative. In addition, the present invention may be modified without departing from the scope of invention.

The term "room temperature" in the following Reference Examples and Examples indicates the range of generally from about 10° C. to about 35° C. As for "%", the yield is in mol/mol %, the solvent used for column chromatography is in % by volume and other "%" is in % by weight. OH proton, NH proton etc. on proton NMR spectrum that could not be confirmed due to broad peak are not included in the data.

The other symbols used herein mean the following:
s: singlet
d: doublet
t: triplet
q: quartet
spt: septet
m: multiplet
br: broad
brs: broad singlet
J: coupling constant
Hz: Hertz
CDCl$_3$: deuterated chloroform
DMSO-d$_6$: dimethyl sulfoxide-d$_6$
$^1$H-NMR: proton nuclear magnetic resonance
mp: melting point
TFA: trifluoroacetic acid
MgSO$_4$: magnesium sulfate
CO$_2$: carbon dioxide In the following Reference Examples and Examples, nuclear magnetic resonance spectrum (NMR) was measured under the following conditions.

NMR measurement tools: Varian Inc. Varian Gemini 200 (200 MHz), Varian Gemini 300 (300 MHz), Bruker BioSpin Corp. AVANCE 300.

In the following Examples, high performance liquid chromatography (HPLC)—mass spectrum (LC-MS) was measured under the following conditions.

measurement tools: Micromass Ltd., Quattro Micro and Agilent Technologies, Inc. HP1100, or Waters Corporation, MUX system (Micromass Ltd., ZQ)

Column: Shiseido Co., Ltd., Capcelpak C18 UG-120, 1.5×35 mm solvent: SOLUTION A; 5 mM ammonium acetate/2% acetonitrile/water, SOLUTION B; 5 mM ammonium acetate/95% acetonitrile/water gradient cycle: 0.00 min (SOLUTION A 100%), 2.00 min (SOLUTION B 100%), 3.00 min (SOLUTION B 100%), 3.01 min (SOLUTION A 100%), 3.80 min (SOLUTION A 100%)

flow rate: 0.5 ml/min, detection: UV 220 nm ionization method: Electron Spray Ionization: ESI In the following Reference Examples and Examples, purification by preparative high performance liquid chromatography (HPLC) was performed under the following conditions. In the case of a compound having a basic functional group, however, when trifluoroacetic acid is used in this operation, neutralization and the like may be necessary to obtain a free compound.

tools: Gilson, Inc., high through-put purification system

Column: Shiseido Co., Ltd., Capcelpak C18 UG-120, S-5 μM, 20×50 mm solvent: SOLUTION A; 0.1% trifluoroacetic acid-containing water, SOLUTION B; 0.1% trifluoroacetic acid-containing acetonitrile gradient cycle: 0.00 min (SOLUTION A/SOLUTION B=95/5), 1.10 min (SOLUTION A/SOLUTION B=95/5), 5.00 min (SOLUTION A/SOLUTION B=0/100), 6.40 min (SOLUTION A/SOLUTION B=0/100), 6.50 min (SOLUTION A/SOLUTION B=95/5).

flow rate: 20 ml/min, detection: UV 220 nm

Alternatively, tools: Waters mass preparative system (UV Purification System)

Column: Develosil ODS-UG-10 solvent: SOLUTION A; 0.1% trifluoroacetic acid-containing water, SOLUTION B; 0.1% trifluoroacetic acid-containing acetonitrile gradient cycle: 0.00 min (SOLUTION A/SOLUTION B=95/5), 1.00 min (SOLUTION A/SOLUTION B=95/5), 2.00 min (SOLUTION A/SOLUTION B=80/20), 5.00 min (SOLUTION A/SOLUTION B=5/95), 5:10 min (SOLUTION A/SOLUTION B=0/100), 7.00 min (SOLUTION A/SOLUTION=B 100/0)

flow rate: 150 ml/min, detection: UV 220 nm

In the following Reference Examples and Examples, preparative high performance liquid chromatography (HPLC) for chiral resolution was performed using K-Prep manufactured by YMC Co., Ltd. and preparative supercritical fluid chromatography (SFC) was performed using MultiGram II manufactured by METTLER-TOLEDO K.K.

Reference Example 1

2-(Benzyloxy)-4-fluoro-1-nitrobenzene

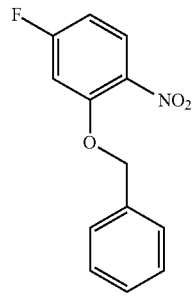 [SMILES: O=[N+]([O-])c1ccc(F)cc1OCc1ccccc1]

To a mixture of 5-fluoro-2-nitrophenol (50.0 g), potassium carbonate (44.0 g) and N,N-dimethylformamide (150 mL) was added benzyl bromide (59.9 g) under ice-cooling, and the mixture was stirred for 15 hr. The reaction mixture was concentrated under reduced pressure, water was added, and the mixture was subjected to extraction with ethyl acetate. The organic layer was washed with saturated brine, dried over magnesium sulfate, filtered, and concentrated under reduced pressure. The obtained solid was washed with hexane to give the title compound (77.1 g, yield 98%) as pale-yellow crystals.

$^1$H NMR (CDCl$_3$) δ 5.23 (2 H, s), 6.64-6.79 (1 H, m), 6.83 (1 H, dd, J=10.2, 2.5 Hz), 7.28-7.57 (5 H, m), 7.97 (1 H, dd, J=9.0, 6.0 Hz).

Reference Example 2

2-(Benzyloxy)-4-[4-(methylthio)phenoxy]-1-nitrobenzene

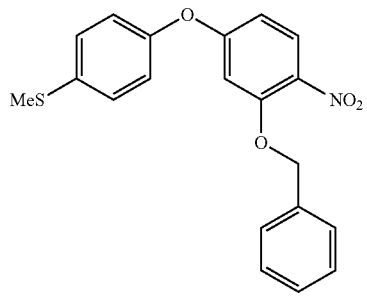 [SMILES: CSc1ccc(Oc2ccc([N+](=O)[O-])c(OCc3ccccc3)c2)cc1]

A mixture of 2-(benzyloxy)-4-fluoro-1-nitrobenzene (16.8 g), 4-methylthiophenol (10.0 g), potassium carbonate (14.1 g) and N,N-dimethylformamide (150 mL) was stirred at 80° C. for 2 hr. The reaction mixture was concentrated under reduced pressure, water was added, and the mixture was subjected to extraction with ethyl acetate. The organic layer was washed successively with water and saturated brine, dried over magnesium sulfate, filtered, and concentrated under reduced pressure. The obtained solid was washed with diethyl ether to give the title compound (23.2 g, yield 93%) as a pale-yellow solid. The pale-yellow solid was recrystallized from ethanol to give pale-yellow crystals melting point 81-82° C.

Reference Example 3

2-(Benzyloxy)-4-[4-(methylsulfonyl)phenoxy]-1-nitrobenzene

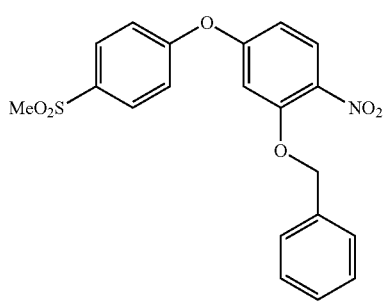 [SMILES: CS(=O)(=O)c1ccc(Oc2ccc([N+](=O)[O-])c(OCc3ccccc3)c2)cc1]

2-(Benzyloxy)-4-[4-(methylthio)phenoxy]-1-nitrobenzene (10.3 g) was dissolved in a mixed solvent of tetrahydrofuran (200 mL)-methanol (100 mL)-water (50 mL), OXONE (42.0 g) was added under ice-cooling, and the mixture was stirred at room temperature for 4 hr. The reaction mixture was filtered to remove a white solid, and the filtrate was concentrated. Water was added to the residue, and the mixture was subjected to extraction with ethyl acetate. The organic layer was washed successively with water and saturated brine, dried over magnesium sulfate, filtered, and concentrated under reduced pressure. The obtained solid was washed with a mixed solvent of diethyl ether-hexane to give the title compound (11.0 g, yield 98%) as pale-yellow crystals. melting point 142-143° C.

Reference Example 4

2-(Benzyloxy)-4-[4-(methylsulfonyl)phenoxy]aniline

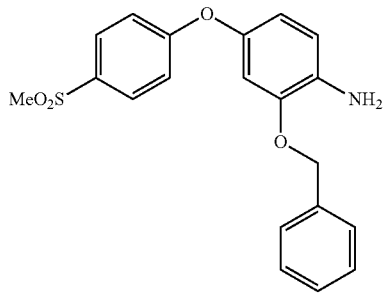 [SMILES: CS(=O)(=O)c1ccc(Oc2ccc(N)c(OCc3ccccc3)c2)cc1]

A mixture of 2-(benzyloxy)-4-[4-(methylsulfonyl)phenoxy]-1-nitrobenzene (11.0 g), iron powder (7.6 g), calcium chloride (0.3 g), water (30 mL) and ethanol (120 mL) was stirred at 80° C. for 2 hr. The reaction mixture was filtered through celite, and the filtrate was concentrated. Water was added to the residue, and the mixture was subjected to extraction with ethyl acetate. The organic layer was washed successively with water and saturated brine, dried over magnesium sulfate, filtered, and concentrated under reduced pressure. The obtained crude product was crystallized from toluene, and the obtained solid was washed with diethyl ether to give the title compound (9.3 g, yield 92%) as pale-brown crystals. MS 370 (MH+).

Reference Example 5

Ethyl 2-({2-(benzyloxy)-4-[4-(methylsulfonyl)phenoxy]phenyl}hydrazono)propanoate

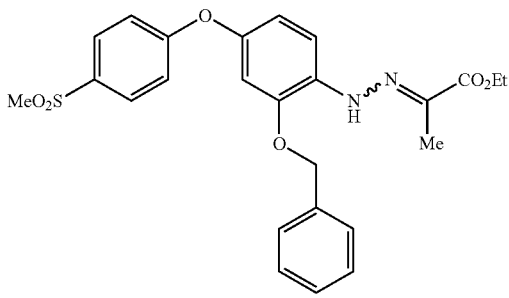 [SMILES: CCOC(=O)C(C)=NNc1ccc(Oc2ccc(S(C)(=O)=O)cc2)cc1OCc1ccccc1]

2-(Benzyloxy)-4-[4-(methylsulfonyl)phenoxy]aniline (43.8 g) was suspended in a mixed solvent of acetonitrile (50 mL)-ethanol (400 mL), and concentrated hydrochloric acid (25 mL) was added at 10° C. Then, ethanol (100 ml) was added. Sodium nitrite (9.8 g) dissolved in water (16 mL) was added dropwise at −5 to 0° C., and the mixture was stirred at −5° C. for 30 min. Water (100 mL) was added to reaction mixture, and the mixture was added dropwise to a mixture of ethyl 2-methyl-3-oxobutanoate (18.8 mL), potassium hydroxide (85%, 23 g), water (100 mL) and ethanol (100 mL) over 2 hr at −13° C. to −11° C. The reaction mixture was stirred at −11° C. for 40 min, and the precipitated orange solid was collected by filtration. The obtained solid was washed with ethanol and diethyl ether to give the title compound (52.3 g, yield 91%) as orange crystals.

$^1$H NMR (CDCl$_3$) δ 1.38 (3H, t, J=7.0 Hz), 2.06 (3H, s), 3.05 (3H, s), 4.32 (2H, q, J=6.9 Hz), 5.11 (2H, s), 6.67-6.77 (2H, m), 7.00 (2H, d, J=8.7 Hz), 7.33-7.42 (5H, m), 7.62 (1H, d, J=8.7 Hz), 7.84 (2H, d, J=8.7 Hz), 8.10 (1H, s).

Reference Example 6

Ethyl 7-(benzyloxy)-5-[4-(methylsulfonyl)phenoxy]-1H-indole-2-carboxylate

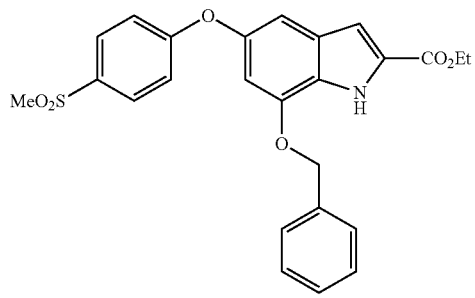

p-Toluenesulfonic acid monohydrate (16.1 g) was refluxed in toluene for 1.5 hr to remove water by azeotropic dehydration. This solution was cooled to 80° C., ethyl 2-({2-(benzyloxy)-4-[4-(methylsulfonyl)phenoxy]phenyl}hydrazono) propanoate (37.2 g) was added, and the mixture was stirred at 80° C. for 10 min. The reaction solution was washed successively with water, saturated aqueous sodium hydrogen carbonate solution and saturated brine, dried over magnesium sulfate, filtered, and concentrated under reduced pressure. The obtained crude product was subjected to silica gel column chromatography (ethyl acetate:hexane=5:95 to 50:50, volume ratio), the obtained solid was washed with diethyl ether to give the title compound (4.9 g, yield 14%) as a pale-yellow solid. The pale-yellow solid was recrystallized from ethyl acetate-hexane to give pale-yellow crystals. melting point 148-149° C.

Reference Example 7

7-(Benzyloxy)-5-[4-(methylsulfonyl)phenoxy]-1H-indole-2-carboxylic acid

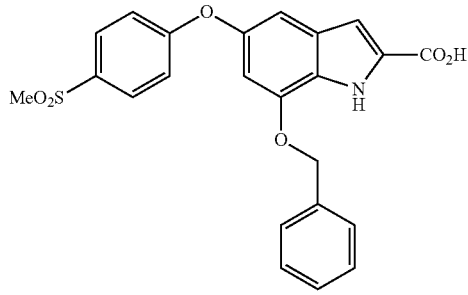 [SMILES: CCOC(=O)c1cc2cc(Oc3ccc(S(C)(=O)=O)cc3)cc(OCc3ccccc3)c2[nH]1]

Ethyl 7-(benzyloxy)-5-[4-(methylsulfonyl)phenoxy]-1H-indole-2-carboxylate (1.9 g) was dissolved in a mixed solvent of tetrahydrofuran (10 mL)-ethanol (10 mL), 1M aqueous sodium hydroxide solution (10 mL) was added, and the mixture was stirred at 50° C. for 45 min. The reaction solution was allowed to cool to room temperature, and concentrated under reduced pressure. Water was added to the residue, and the mixture was neutralized with 1M hydrochloric acid. The obtained crystals were collected by filtration, and washed successively with water and diethyl ether to give the title compound (1.6 g, yield 89%) as a pale-orange solid. The pale-orange solid was recrystallized from ethanol-hexane to give pale-orange crystals. melting point 232-233° C.

Reference Example 8

7-(Benzyloxy)-5-[4-(methylsulfonyl)phenoxy]-1H-indole-2-carboxamide

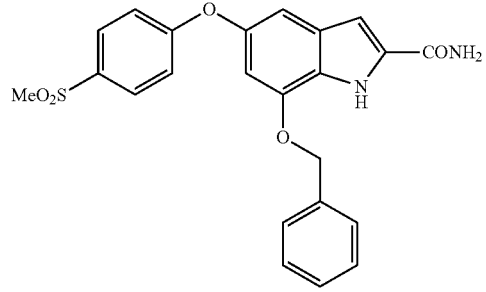 [SMILES: CS(=O)(=O)c1ccc(Oc2cc(OCc3ccccc3)c3[nH]c(C(N)=O)cc3c2)cc1]

A mixture of 7-(benzyloxy)-5-[4-(methylsulfonyl)phenoxy]-1H-indole-2-carboxylic acid (1.59 g), 1-[3-(dimethylamino)propyl-3-ethylcarbodiimide hydrochloride (1.4 g), 1-hydroxybenzotriazole ammonium salt (1.1 g) and N,N-dimethylformamide (40 mL) was stirred at room temperature for 16 hr. Water was added to the reaction solution, and the precipitated solid was collected by filtration, and washed successively with water, ethanol and diethyl ether to give the title compound (1.6 g, yield 100%) as a pale-yellow solid. The pale-yellow solid was recrystallized from N,N-dimethylformamide-water to give pale-yellow crystals. melting point 251-252° C.

Reference Example 9

Ethyl 7-hydroxy-5-[4-(methylsulfonyl)phenoxy]-1H-indole-2-carboxylate

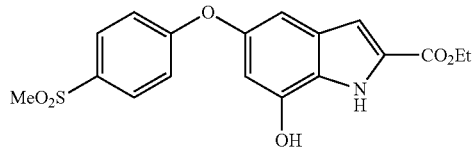 [SMILES: CCOC(=O)c1cc2cc(Oc3ccc(S(C)(=O)=O)cc3)cc(O)c2[nH]1]

Ethyl 7-(benzyloxy)-5-[4-(methylsulfonyl)phenoxy]-1H-indole-2-carboxylate (0.40 g) was dissolved in a mixed solvent of tetrahydrofuran (5 mL)-ethanol (5 mL), 10% palladium-carbon (50% containing water, 0.80 g) was added, and the mixture was stirred at room temperature for 4 hr under a hydrogen atmosphere. The reaction mixture was filtered, and the filtrate was concentrated under reduced pressure. The residue was crystallized from diethyl ether, and the obtained solid was washed with a mixed solvent of diethyl ether-hexane to give the title compound (0.31 g, yield 96%) as a pale-yellow solid. The pale-yellow solid was recrystallized from ethanol-hexane to give pale-yellow crystals. melting point 197-198° C.

Reference Example 10

7-(Benzyloxy)-5-[4-(methylsulfonyl)phenoxy]-1H-indole-2-carbonitrile

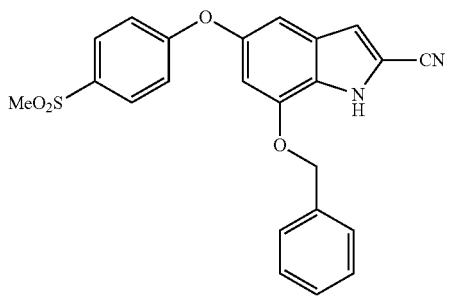 [SMILES: CS(=O)(=O)c1ccc(Oc2cc(OCc3ccccc3)c3[nH]c(C#N)cc3c2)cc1]

To a mixture of 7-(benzyloxy)-5-[4-(methylsulfonyl)phenoxy]-1H-indole-2-carboxamide (840 mg), pyridine (0.23 mL) and N,N-dimethylformamide (20 mL) was added dropwise oxalyl chloride (0.25 mL) under ice-cooling, and the mixture was stirred for 2 hr. Pyridine (0.23 mL) and oxalyl chloride (0.25 mL) were successively added, and the mixture was further stirred for 30 min. Water was added to the reaction solution, and the mixture was subjected to extraction with ethyl acetate. The organic layer was washed successively with 1M hydrochloric acid, saturated aqueous sodium hydrogen carbonate solution and saturated brine, dried over magnesium sulfate, filtered, and concentrated under reduced pressure. The obtained solid was washed with a mixed solvent of diethyl ether-hexane to give the title compound (660 mg, yield 92%) as yellow crystals. The obtained yellow crystals were recrystallized from ethanol-hexane to give yellow crystals. melting point 209-210° C.

Reference Example 11

Ethyl 7-[(6-chloropyridin-2-yl)methoxy]-5-[4-(methylsulfonyl)phenoxy]-1H-indole-2-carboxylate

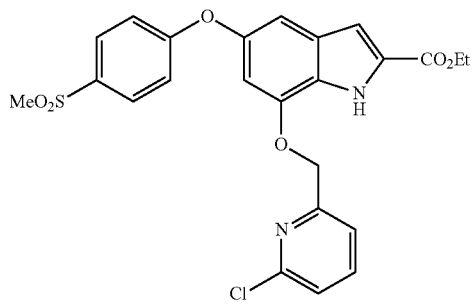 [SMILES: CCOC(=O)c1cc2cc(Oc3ccc(S(C)(=O)=O)cc3)cc(OCc3cccc(Cl)n3)c2[nH]1]

A mixture of ethyl 7-hydroxy-5-[4-(methylsulfonyl)phenoxy]-1H-indole-2-carboxylate (1.39 g), 2-(bromomethyl)-6-chloropyridine (840 mg), potassium carbonate (1.02 g) and N,N-dimethylformamide (20 mL) was stirred at room temperature for 2.5 hr. Water was added to the reaction mixture, and the mixture was subjected to extraction with ethyl acetate. The organic layer was washed successively with water and saturated brine, dried over magnesium sulfate, filtered, and concentrated under reduced pressure. The obtained crude product was subjected to basic silica gel column chromatography (ethyl acetate:hexane=10:90-65:35, volume ratio), and the obtained solid was washed with diethyl ether to give the title compound (1.0 g, yield 54%) as white crystals. MS 501 (MH$^+$).

Reference Example 12

7-[(6-Chloropyridin-2-yl)methoxy]-5-[4-(methylsulfonyl)phenoxy]-1H-indole-2-carboxylic acid

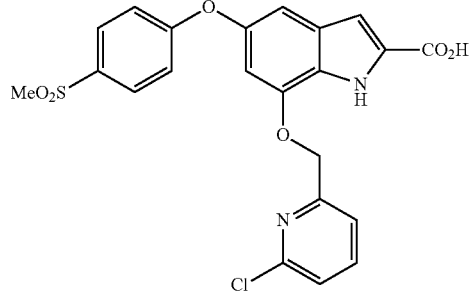 [SMILES: CS(=O)(=O)c1ccc(Oc2cc(OCc3cccc(Cl)n3)c3[nH]c(C(=O)O)cc3c2)cc1]

Ethyl 7-[(6-chloropyridin-2-yl)methoxy]-5-[4-(methylsulfonyl)phenoxy]-1H-indole-2-carboxylate (1.0 g) was dissolved in a mixed solvent of tetrahydrofuran (10 mL)-ethanol (10 mL), 1M aqueous sodium hydroxide solution (5 mL) was added, and the mixture was stirred at 50° C. for 50 min. The reaction solution was allowed to cool to room temperature, and concentrated under reduced pressure. Water was added to the residue, and the mixture was neutralized with 1M hydrochloric acid. The obtained crystals were collected by filtration, and washed successively with water and diethyl ether to give the title compound (840 mg, yield 90%) as a white solid. The obtained crystals were recrystallized from N,N-dimethylformamide-water to give colorless crystals. melting point 249-250° C. (decomposition).

Reference Example 13

7-[(6-Chloropyridin-2-yl)methoxy]-5-[4-(methylsulfonyl)phenoxy]-1H-indole-2-carboxamide

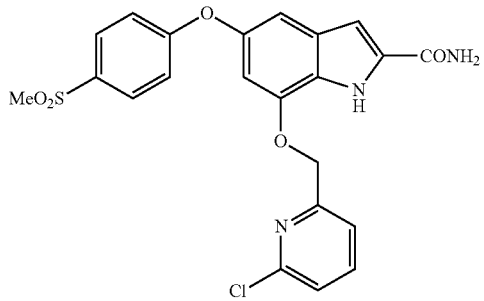 [SMILES: CS(=O)(=O)c1ccc(Oc2cc(OCc3cccc(Cl)n3)c3[nH]c(C(N)=O)cc3c2)cc1]

A mixture of 7-[(6-chloropyridin-2-yl)methoxy]-5-[4-(methylsulfonyl)phenoxy]-1H-indole-2-carboxylic acid (780 mg), 1-[3-(dimethylamino)propyl-3-ethylcarbodiimide hydrochloride (632 mg), 1-hydroxybenzotriazole ammonium salt (502 mg) and N,N-dimethylformamide (30 mL) was stirred at room temperature for 15 hr. Water was added to the reaction solution, and the precipitated solid was collected by filtration, and washed successively with water and diethyl ether to give the title compound (680 mg, yield 90%) as a white solid. The obtained crystals were recrystallized from N,N-dimethylformamide-water to give colorless crystals. melting point 259-260° C.

Reference Example 14

Ethyl 7-[(1-methyl-1H-imidazol-2-yl)methoxy]-5-[4-(methylsulfonyl)phenoxy]-1H-indole-2-carboxylate

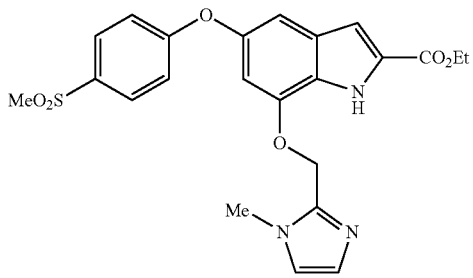 [SMILES: CCOC(=O)c1cc2cc(Oc3ccc(S(C)(=O)=O)cc3)cc(OCc3nccn3C)c2[nH]1]

A mixture of ethyl 7-hydroxy-5-[4-(methylsulfonyl)phenoxy]-1H-indole-2-carboxylate (100 mg), 2-(chloromethyl)-1-methyl-1H-imidazole hydrochloride (50 mg), potassium carbonate (83 mg) and N,N-dimethylformamide (20 mL) was stirred at 50° C. for 3 hr. Water was added to the reaction mixture, and the mixture was subjected to extraction with ethyl acetate. The organic layer was washed successively with water and saturated brine, dried over magnesium sulfate, filtered, and concentrated under reduced pressure. The obtained crude product was subjected to silica gel column to chromatography (ethyl acetate:hexane=60:40 to 100:0, volume ratio) to give the title compound (72 mg, yield 57%) as a white solid. The white solid was recrystallized from ethyl acetate-hexane to give colorless crystals. melting point 91-92° C.

Reference Example 15

7-[(1-Methyl-1H-imidazol-2-yl)methoxy]-5-[4-(methylsulfonyl)phenoxy]-1H-indole-2-carboxylic acid

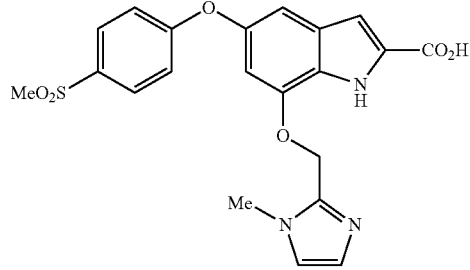 [SMILES: Cn1ccnc1COc1cc(Oc2ccc(S(C)(=O)=O)cc2)cc2cc(C(=O)O)[nH]c12]

Ethyl 7-[(1-methyl-1H-imidazol-2-yl)methoxy]-5-[4-(methylsulfonyl)phenoxy]-1H-indole-2-carboxylate (100 mg) was dissolved in a mixed solvent of tetrahydrofuran (2 mL)-ethanol (2 mL), 1M aqueous sodium hydroxide solution (2 mL) was added, and the mixture was stirred at 50° C. for 50 min. The reaction. solution was allowed to cool to room temperature, and concentrated under reduced pressure. Water was added to the residue, and the mixture was neutralized with 1M hydrochloric acid. The obtained crystals were collected by filtration, and washed successively with water and diethyl ether to give the title compound (80 mg, yield 86%) as a white solid. The white solid was recrystallized from N,N-dimethylformamide-water to give colorless crystals. melting point 209-210° C. (decomposition).

Reference Example 16

7-[(1-Methyl-1H-imidazol-2-yl)methoxy]-5-[4-(methylsulfonyl)phenoxy]-1H-indole-2-carboxamide

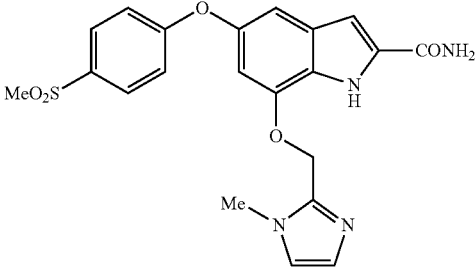 [SMILES: Cn1ccnc1COc1cc(Oc2ccc(S(C)(=O)=O)cc2)cc2cc(C(N)=O)[nH]c12]

A mixture of 7-[(1-methyl-1H-imidazol-2-yl)methoxy]-5-[4-(methylsulfonyl)phenoxy]-1H-indole-2-carboxylic acid (940 mg), 1-[3-(dimethylamino)propyl-3-ethylcarbodiimide hydrochloride (817 mg), 1-hydroxybenzotriazole ammonium salt (648 mg) and N,N-dimethylformamide (20 mL) was stirred at room temperature for 14 hr. Water was added to the reaction solution, and the mixture was subjected to extraction with ethyl acetate. The organic layer was washed with saturated brine, dried over magnesium sulfate, filtered, and concentrated under reduced pressure. The obtained solid was washed with a mixed solvent of ethyl acetate-diethyl ether to give the title compound (640 mg, yield 68%) as a pale-yellow solid. MS 441 (MH$^+$).

Reference Example 17

Ethyl 5-[4-(methylsulfonyl)phenoxy]-7-(tetrahydro-2H-pyran-4-ylmethoxy)-1H-indole-2-carboxylate

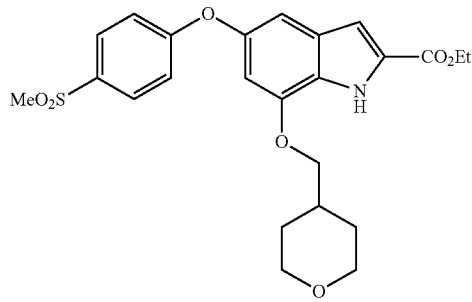

A mixture of ethyl 7-hydroxy-5-[4-(methylsulfonyl)phenoxy]-1H-indole-2-carboxylate (400 mg), tetrahydro-2H-pyran-4-ylmethanol (250 mg), 1,1'-(azodicarbonyl)dipiperidine (540 mg), tributylphosphine (0.5 mL) and tetrahydrofuran (10 mL) was stirred at 50° C. for 13 hr. The reaction solution was allowed to cool to room temperature, and the precipitated solid was filtered off. The filtrate was concentrated under reduced pressure, and the residue was subjected to basic silica gel column chromatography (ethyl acetate:hexane=3:97-45:55, volume ratio) to give the crude title compound (650 mg) as an orange oil. MS 474 (MH$^+$).

Reference Example 18

5-[4-(Methylsulfonyl)phenoxy]-7-(tetrahydro-2H-pyran-4-ylmethoxy)-1H-indole-2-carboxylic acid

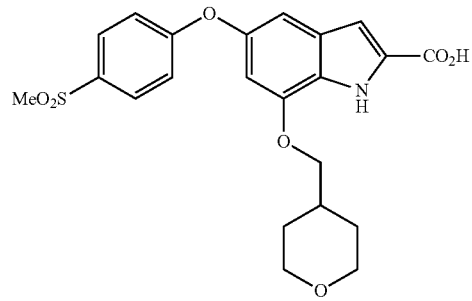 [SMILES: CCOC(=O)c1cc2cc(Oc3ccc(S(C)(=O)=O)cc3)cc(OCC3CCOCC3)c2[nH]1]

Ethyl 5-[4-(methylsulfonyl)phenoxy]-7-(tetrahydro-2H-pyran-4-ylmethoxy)-1H-indole-2-carboxylate (3.5 g) was dissolved in a mixed solvent of tetrahydrofuran (30 mL)-ethanol (30 mL), 1M aqueous sodium hydroxide solution (15 mL) was added, and the mixture was stirred at 50° C. for 1 hr. The reaction solution was allowed to cool to room temperature, and concentrated under reduced pressure. Water was added to the residue, and the mixture was neutralized with 1M hydrochloric acid, and subjected to extraction with ethyl acetate. The organic layer was washed with saturated brine, dried over magnesium sulfate, filtered, and concentrated under reduced pressure. The obtained crude product was crystallized from a mixed solvent of ethanol-hexane-diethyl ether. The obtained colorless crystals were recrystallized from acetone-hexane to give the title compound (1.1 g) as colorless crystals. melting point 256-258° C. (decomposition).

Reference Example 19

5-[4-(Methylsulfonyl)phenoxy]-7-(tetrahydro-2H-pyran-4-ylmethoxy)-1H-indole-2-carboxamide

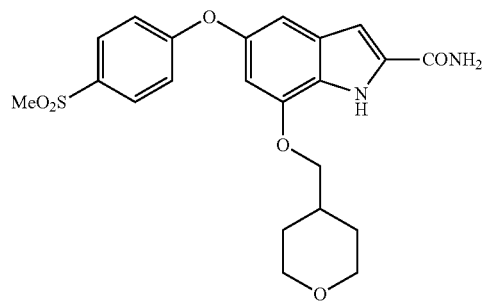 [SMILES: CS(=O)(=O)c1ccc(Oc2cc(OCC3CCOCC3)c3[nH]c(C(N)=O)cc3c2)cc1]

A mixture of 5-[4-(methylsulfonyl)phenoxy]-7-(tetrahydro-2H-pyran-4-ylmethoxy)-1H-indole-2-carboxylic acid (1.0 g), 1-[3-(dimethylamino)propyl-3-ethylcarbodiimide hydrochloride (0.9 g), 1-hydroxybenzotriazole (0.6 g) and N,N-dimethylformamide (15 mL) was stirred at room temperature for 15 min. 28% Aqueous ammonia solution (0.8 mL) was added to the reaction solution, and the mixture was stirred at room temperature for 2.5 hr. Water was added to the reaction solution, and the mixture was subjected to extraction with ethyl acetate. The organic layer was washed with saturated brine, dried over magnesium sulfate, filtrated, and concentrated under reduced pressure. The obtained crude product was crystallized from a mixed solvent of ethanol-diethyl ether, and the obtained crystals were washed with diethyl ether to give the title compound (0.8 g, yield 83%) as colorless crystals. MS 445 (MH⁺).

Reference Example 20

5-[4-(Methylsulfonyl)phenoxy]-7-(tetrahydro-2H-pyran-4-ylmethoxy)-1H-indole-2-carbonitrile

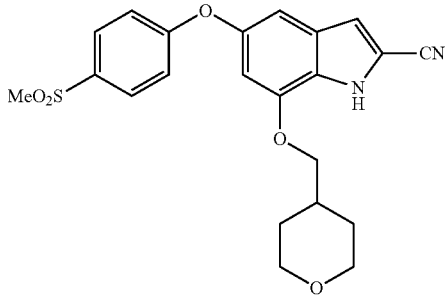 [SMILES: CS(=O)(=O)c1ccc(Oc2cc(OCC3CCOCC3)c3[nH]c(C#N)cc3c2)cc1]

5-[4-(Methylsulfonyl)phenoxy]-7-(tetrahydro-2H-pyran-4-ylmethoxy)-1H-indole-2-carboxamide (250 mg) was dissolved in N,N-dimethylformamide (5 mL), cyanuric chloride (311 mg) was added under ice-cooling, and the mixture was stirred for 1 hr. Water was added to the reaction solution, and the mixture was subjected to extraction with ethyl acetate. The organic layer was washed with saturated brine, dried over magnesium sulfate, filtered, and concentrated under reduced pressure. The obtained crude product was subjected to silica gel column chromatography (ethyl acetate:hexane=10:90-60:40, volume ratio) to give the title compound (240 mg, yield 100%) as a white solid. MS 445 (MH⁺).

Reference Example 21

Ethyl 7-(2-{[di-tert-butyl(phenyl)silyl]oxy}-1-methylethoxy)-5-[4-(methylsulfonyl)phenoxy]-1H-indole-2-carboxylate

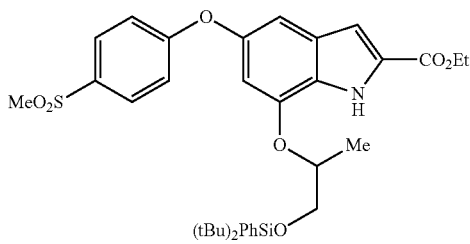

A mixture of ethyl 7-hydroxy-5-[4-(methylsulfonyl)phenoxy]-1H-indole-2-carboxylate (2.3 g), 1-{[di-tert-butyl(phenyl)silyl]oxy}propan-2-ol (3.9 g), 1,1'-(azodicarbonyl)dipiperidine (3.1 g), tributylphosphine (3.1 mL) and tetrahydrofuran (20 mL) was stirred at 50° C. for 18 hr. The reaction solution was allowed to cool to room temperature, and the precipitated white solid was filtered off. The filtrate was concentrated, and the residue was subjected to silica gel column chromatography (ethyl acetate:hexane=0:100 to 30:70, volume ratio) to give the title compound (2.4 g, yield 57%) as an orange oil. MS 672 (MH⁺).

Reference Example 22

7-(2-{[Di-tert-butyl(phenyl)silyl]oxy}-1-methylethoxy)-5-[4-(methylsulfonyl)phenoxy]-1H-indole-2-carboxylic acid

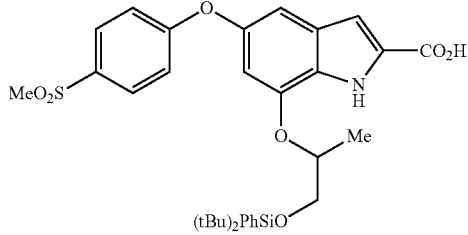

Ethyl 7-(2-{[di-tert-butyl(phenyl)silyl]oxy}-1-methylethoxy)-5-[4-(methylsulfonyl)phenoxy]-1H-indole-2-carboxylate (2.4 g) was dissolved in a mixed solvent of tetrahydrofuran (10 mL)-ethanol (10 mL), 1M aqueous sodium hydroxide solution (5 mL) was added, and the mixture was stirred at 50° C. for 1 hr. 1M Aqueous sodium hydroxide solution (1 mL) was added to the reaction solution, and the mixture was stirred at 50° C. for 40 min. 1M Aqueous sodium hydroxide solution (1 mL) was added again, and the mixture was further stirred at 50° C. for 30 min. The reaction solution was allowed to cool to room temperature, and concentrated under reduced pressure. Water was added to the residue, and the mixture was neutralized with 1M hydrochloric acid, and subjected to extraction with ethyl acetate. The organic layer was washed with saturated brine, dried over magnesium sulfate, filtrated, and concentrated under reduced pressure to give the title compound (1.9 g, yield 83%) as a pale-red amorphous solid. MS 644 (MH⁺).

Reference Example 23

7-(2-{[Di-tert-butyl(phenyl)silyl]oxy}-1-methylethoxy)-5-[4-(methylsulfonyl)phenoxy]-1H-indole-2-carboxamide

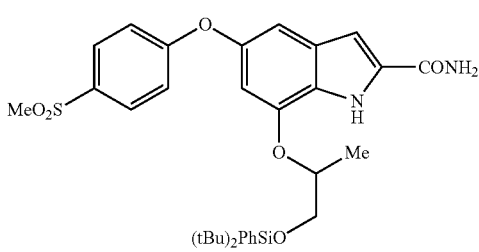

A mixture of 7-(2-{[di-tert-butyl(phenyl)silyl]oxy}-1-methylethoxy)-5-[4-(methylsulfonyl)phenoxy]-1H-indole-2-carboxylic acid (2.0 g), 1-[3-(dimethylamino)propyl-3-ethyl-carbodiimide hydrochloride (1.19 g), 1-hydroxybenzotriazole ammonium salt (943 mg) and N,N-dimethylformamide (20 mL) was stirred at room temperature for 9 hr. The reaction solution was allowed to cool to room temperature, and concentrated under reduced pressure. Water was added to the residue, and the mixture was subjected to extraction with ethyl acetate. The organic layer was washed successively with aqueous citric acid solution, water and saturated brine, dried over magnesium sulfate, filtered, and concentrated under reduced pressure. The obtained crude product was subjected to silica gel column chromatography (ethyl acetate:hexane=30:70-70:30, volume ratio) to give the title compound (1.37 g, yield 69%) as an orange oil. MS 643 (MH$^+$).

Reference Example 24

Ethyl [2-({7-(benzyloxy)-5-[4-(methylsulfonyl)phenoxy]-1H-indol-2-yl}carbonyl)hydrazino](oxo)acetate

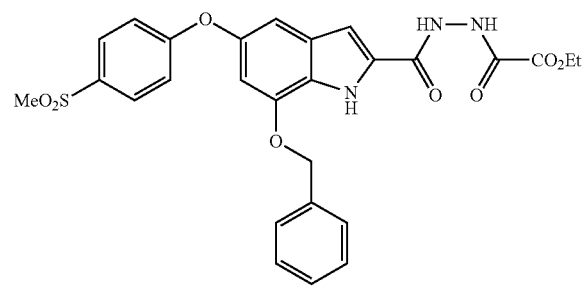 [SMILES: CCOC(=O)C(=O)NNC(=O)c1cc2cc(Oc3ccc(S(C)(=O)=O)cc3)cc(OCc3ccccc3)c2[nH]1]

A solution of hydrazine monohydrate (0.1 mL) in ethanol (2 mL) was added dropwise to a solution of diethyl oxalate (0.3 mL) in ethanol (2 mL) under ice-cooling. The reaction mixture was concentrated under reduced pressure to give a white solid. A mixture of 7-(benzyloxy)-5-[4-(methylsulfonyl)phenoxy]-1H-indole-2-carboxylic acid (450 mg), 1-[3-(dimethylamino)propyl-3-ethylcarbodiimide hydrochloride (403 mg), 1-hydroxybenzotriazole (284 mg) and N,N-dimethylformamide (20 mL) was stirred at room temperature for 30 min, the previous-obtained white solid was added, and the mixture was stirred at room temperature for 2 hr. Water was added to the reaction solution, and the mixture was subjected to extraction with ethyl acetate. The organic layer was washed with saturated brine, dried over magnesium sulfate, filtrated, and concentrated under reduced pressure. The obtained crude product was subjected to silica gel column chromatography (ethyl acetate:hexane=20:80-90:10, volume ratio) to give the title compound (420 mg, yield 83%) as an orange oil. MS 552 (MH$^+$).

Reference Example 25

Ethyl 7-(1-methylethoxy)-5-[4-(methylsulfonyl)phenoxy]-1H-indole-2-carboxylate

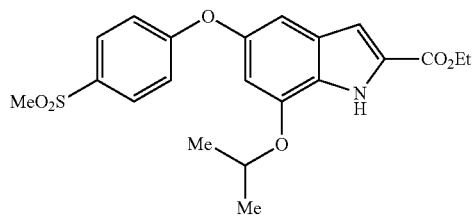 [SMILES: CCOC(=O)c1cc2cc(Oc3ccc(S(C)(=O)=O)cc3)cc(OC(C)C)c2[nH]1]

A mixture of ethyl 7-hydroxy-5-[4-(methylsulfonyl)phenoxy]-1H-indole-2-carboxylate (2.0 g), tributylphosphine (2.6 mL), 1,1'-(azodicarbonyl)dipiperidine (2.69 g), 2-propanol (0.81 mL) and tetrahydrofuran (50 mL) was stirred at 70° C. for 5.5 h. Furthermore, tributylphosphine (0.7 mL) and 1,1'-(azodicarbonyl)dipiperidine (0.7 g) were added to the mixture. After stirring at 70° C. for 2 h, the mixture was cooled to 0° C. and a precipitate was removed by filtration. The filtrate was concentrated and the residue was purified by basic silica gel column chromatography (ethyl acetate/hexane 1/99 to 40/60), followed by silica gel column chromatography (ethyl acetate/hexane=1/99 to 35/65, volume ratio) to give the title compound (1.87 g, 84%) as a white amorphous solid. MS 418 (MH$^+$).

Reference Example 26

7-(1-Methylethoxy)-5-[4-(methylsulfonyl)phenoxy]-1H-indole-2-carboxylic acid

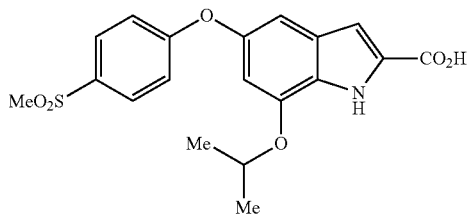 [SMILES: CC(C)Oc1cc(Oc2ccc(S(C)(=O)=O)cc2)cc2cc(C(=O)O)[nH]c12]

Ethyl 7-(1-methylethoxy)-5-[4-(methylsulfonyl)phenoxy]-1H-indole-2-carboxylate (1.87 g) was dissolved in a mixture of tetrahydrofuran (20 mL) and ethanol (20 mL), and 1M aqueous sodium hydroxide solution (9 mL) was added to the mixture. After stirring at 60° C. for 1 h, the mixture was concentrated under reduced pressure and the residue was dissolved in water. The mixture was cooled to 0° C. and 1M hydrochloric acid (10 mL) was added. The resulting white suspension was filtered to collect a white precipitate. The precipitate was dissolved in ethyl acetate and the solution was dried over magnesium sulfate, filtered, and concentrated to give the title compound (1.81 g, 100%) as a white amorphous solid. MS 390 (MH$^+$).

Reference Example 27

7-(1-Methylethoxy)-5-[4-(methylsulfonyl)phenoxy]-1H-indole-2-carboxamide

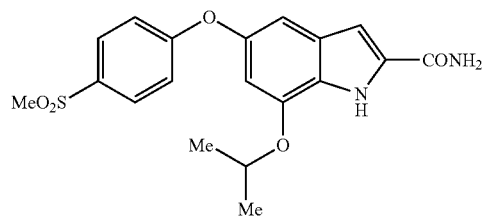 [SMILES: CC(C)Oc1cc(Oc2ccc(S(C)(=O)=O)cc2)cc2cc(C(N)=O)[nH]c12]

A mixture of 7-(1-methylethoxy)-5-[4-(methylsulfonyl)phenoxy]-1H-indole-2-carboxylic acid (1.8 g), N-ethyl-N'-(3-dimethylaminopropyl)carbodiimide hydrochloride (1.77 g), 1-hydroxybenzotriazole (1.24 g) and N,N-dimethylformamide (45 mL) was stirred at 50° C. for 25 min. The mixture was cooled to room temperature, and 28% aqueous ammonium hydroxide solution (1.3 mL) was added to the mixture at room temperature. After stirring at room temperature for 16 h, water was added to the mixture. The mixture was extracted with ethyl acetate. The organic layer was washed with saturated brine, dried over magnesium sulfate, filtered and concentrated. The residue was purified by silica gel column chromatography (ethyl acetate/hexane=20/80 to 100/0, volume ratio) to give the title compound (1.41 g, 79%) as a white solid. MS 389 (MH$^+$).

Reference Example 28

7-(1-Methylethoxy)-5-[4-(methylsulfonyl)phenoxy]-1H-indole-2-carbothioamide

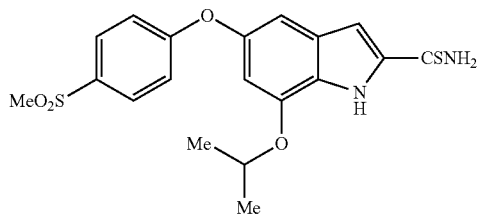

To a solution of 7-(1-methylethoxy)-5-[4-(methylsulfonyl)phenoxy]-1H-indole-2-carboxamide (700 mg) in tetrahydrofuran (40 mL) was added Lawesson's reagent (729 mg) and the mixture was stirred at 60° C. for 40 min. The mixture was concentrated under reduced pressure. The residue was purified by silica gel column chromatography (ethyl acetate/hexane=5/95 to 50/50, volume ratio) to give the title compound (857 mg, 100%) as a yellow amorphous solid. MS 405 (MH$^+$).

Reference Example 29

4-Fluoro-2-(1-methylethoxy)-1-nitrobenzene

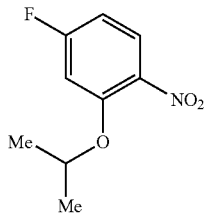 [SMILES: CC(C)Oc1cc(F)ccc1[N+](=O)[O-]]

A mixture of 5-fluoro-2-nitrophenol (91.0 g), 2-iodopropane (103.4 g), potassium carbonate (146 g) and N,N-dimethylformamide (600 mL) was stirred at 50° C. for 3.5 h. The mixture was concentrated under reduced pressure and water was added to the residue. The mixture was extracted with ethyl acetate. The organic layer was washed with saturated brine, dried over magnesium sulfate, filtered and concentrated. The residue was purified by basic silica gel column chromatography (ethyl acetate/hexane=0/100 to 30/70, volume ratio) to give the title compound (75.4 g, 65%) as a yellow oil.

$^1$H NMR (CDCl$_3$) δ 1.42 (6H, d, J=6.0 Hz), 4.63 (1H, spt, J=6.1 Hz), 6.64-6.73 (1H, m), 6.76 (1H, dd, J=10.6, 2.5 Hz), 7.88 (1H, dd, J=9.0, 6.0 Hz).

Reference Example 30

3-(1-Methylethoxy)-4-nitrophenol

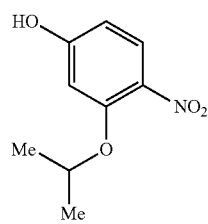 [SMILES: CC(C)Oc1cc(O)ccc1[N+](=O)[O-]]

To a solution of 4-fluoro-2-(1-methylethoxy)-1-nitrobenzene (20.34 g) in dimethylsulfoxide (150 mL) was added 20% aqueous sodium hydroxide solution (68 mL) at room temperature and the mixture was stirred at 60° C. for 3 h. The mixture was cooled to room temperature and 6M hydrochloric acid (50 mL) was added to the mixture. The mixture was extracted with ethyl acetate. The organic layer was washed with saturated brine, dried over magnesium sulfate, filtered and concentrated. The residual oil was solidified with hexane to give the title compound (14.94 g, 74%) as a yellow solid.

$^1$H NMR (CDCl$_3$) δ 1.41 (6H, d, J=6.1 Hz), 4.61 (1H, spt, J=6.1 Hz), 5.54 (1H, brs), 6.40 (1H, dd, J=8.9, 2.5 Hz), 6.51 (1H, d, J=2.7 Hz), 7.87 (1H, d, J=9.1 Hz).

Reference Example 31

2-[3-(1-Methylethoxy)-4-nitrophenoxy]-5-(methylsulfonyl)pyridine

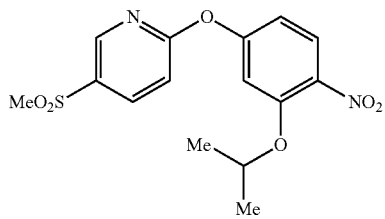 [SMILES: CC(C)Oc1cc(Oc2ccc(S(C)(=O)=O)cn2)ccc1[N+](=O)[O-]]

A mixture of 3-(1-methylethoxy)-4-nitrophenol (27.3 g), cesium carbonate (90.4 g), 2-bromo-5-(methylsulfonyl)pyridine (32.7 g) and N,N-dimethylformamide (250 mL) was stirred at 100° C. for 4 h. The mixture was concentrated under reduced pressure and water was added to the residue. The resulting brown suspension was filtered to collect a brown solid. The solid was washed with ethanol-hexane to give the title compound (38.82 g, 79%) as a brownish-yellow solid. MS 353 (MH+).

Reference Example 32

2-(1-Methylethoxy)-4-{[5-(methylsulfonyl)pyridin-2-yl]oxy}aniline

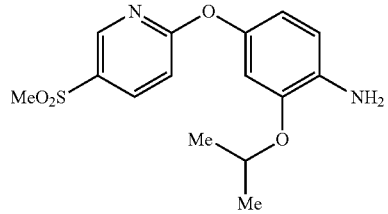

A mixture of 2-[3-(1-methylethoxy)-4-nitrophenoxy]-5-(methylsulfonyl)pyridine (39.89 g), iron powder (31 g), calcium chloride (1.3 g), ethanol (400 mL) and water (100 mL) was stirred at 80° C. for 3 h. The mixture was filtered through celite and the filtrate was concentrated under reduced pressure. Water and brine were added to the residue. The mixture was extracted with ethyl acetate. The organic layer was dried over magnesium sulfate, filtered and concentrated. The residual solid was washed with diethyl ether-hexane to give the title compound (32 g, 88%) as a brownish solid. MS 323 (MH+).

Reference Example 33

Ethyl 2-{[2-(1-methylethoxy)-4-{[5-(methylsulfonyl)pyridin-2-yl]oxy}phenyl]hydrazono}propanoate

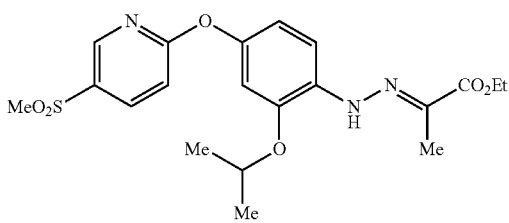 [SMILES: CCOC(=O)/C(C)=N/Nc1ccc(Oc2ccc(S(C)(=O)=O)cn2)cc1OC(C)C]

To a stirring suspension of 2-(1-methylethoxy)-4-{[5-(methylsulfonyl)pyridin-2-yl]oxy}aniline (32 g) in a mixture of acetonitrile (50 mL) and ethanol (100 mL) was added a concentrated hydrochloric acid (30 mL) at 0° C. After cooling to −5° C., a solution of sodium nitrite (8.2 g) in water (25 mL) was added dropwise to the mixture with keeping the temperature. below 0° C. The mixture was stirred at −10 to −5° C. for 30 min. The mixture was added to a mixture of ethyl 2-methyl-3-oxobutanoate (15.7 mL), potassium hydroxide (85%, 26 g), ethanol (140 mL) and water (140 mL) at −40 to −30° C. over 30 min. After stirring at −38° C. for 1 h, the resulting orange suspension was filtered to give the title compound as a wet orange solid. MS 434 (MH+).

Reference Example 34

Ethyl 7-(1-methylethoxy)-5-{[5-(methylsulfonyl)pyridin-2-yl]oxy}-1H-indole-2-carboxylate

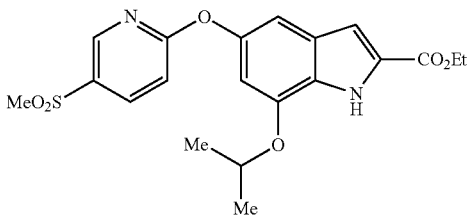 [SMILES: CCOC(=O)c1cc2cc(Oc3ccc(S(C)(=O)=O)cn3)cc(OC(C)C)c2[nH]1]

The orange solid obtained in Reference example 33 was dissolved in toluene (180 mL) and the solution was refluxed for 2 h with azeotropic removal of water. p-Toluenesulfonic acid monohydrate (37 g) was refluxed in toluene (200 mL) for 2 h with azeotropic removal of water, and the mixture was cooled to 90° C. The toluene solution prepared above was added to the mixture. The mixture was stirred. at 90° C. for 1 h. After cooling to room temperature, saturated aqueous sodium hydrogen carbonate solution was added to the mixture. The mixture was extracted with ethyl acetate. The organic layer was washed with saturated brine, dried over magnesium sulfate, filtered and concentrated: The residue was purified by basic silica gel column chromatography (ethyl acetate/hexane=30/70 to 60/40, volume ratio) to give the title compound (10.7 g, 26% from reference example 33) as a yellow amorphous solid. MS 419 (MH+).

Reference Example 35

5-[3-(Benzyloxy)-4-nitrophenoxy]-2-(methylsulfonyl)pyridine

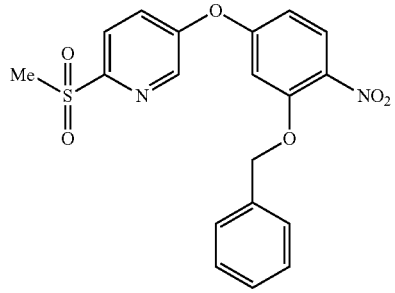 [SMILES: CS(=O)(=O)c1ccc(Oc2ccc([N+](=O)[O-])c(OCc3ccccc3)c2)cn1]

A mixture of 2-(benzyloxy)-4-fluoro-1-nitrobenzene (21.0 g), 6-(methylsulfonyl)pyridin-3-ol (14.7 g) and potassium carbonate (12.2 g) in N,N-dimethylformamide (130 mL) was stirred at 90° C. for 5 h and then at 60° C. for 15 h. The reaction mixture was concentrated and the residue was partitioned between ethyl acetate and aqueous citric acid. The organic layer was washed successively with water and brine, dried (MgSO4), filtered, and concentrated to give light yellow crystals, which were washed with ethyl acetate-hexane to give the title compound (28.0 g, 82%) as pale yellow crystals. MS 401 (MH⁺).

Reference Example 36

2-(Benzyloxy)-4-{[6-(methylsulfonyl)pyridin-3-yl]oxy}aniline

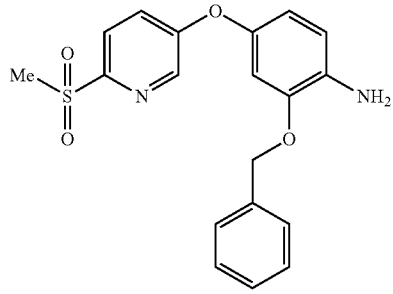

A mixture of 5-[3-(benzyloxy)-4-nitrophenoxy]-2-(methylsulfonyl)pyridine (28.0 g), calcium chloride (0.78 g), iron (powder, 19.0 g), ethanol (500 mL) and water (110 mL) was refluxed for 5 h. The mixture was cooled to 40° C. and filtered through a celite pad. The filtrate was concentrated in vacuo to remove ethanol. The residue was partitioned between ethyl acetate and brine. The organic layer was washed with brine, dried (MgSO$_4$), filtered, and concentrated in vacuo. The residue was purified by silica gel chromatography (ethyl acetate: hexane=2:1, volume ratio) to give the title compound (26.0 g, 100%) as light brown crystals. MS 371 (MH⁺).

Reference Example 37

2-Amino-5-{[6-(methylsulfonyl)pyridin-3-yl]oxy}phenol

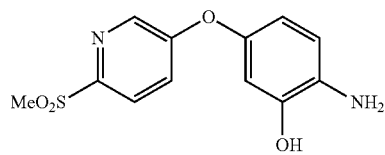 [SMILES: CS(=O)(=O)c1ccc(Oc2ccc(N)c(O)c2)cn1]

To a solution of 2-(benzyloxy)-4-{[6-(methylsulfonyl)pyridin-3-yl]oxy}aniline (26 g) in a mixture of tetrahydrofuran (200 mL) and methanol (50 mL) was added palladium on carbon (5 g, 10 wt %, wet), and the mixture was stirred at room temperature for 5 h under hydrogen atmosphere. The mixture was filtered to remove the catalyst and the filtrate was concentrated under reduced pressure. The residual oil was solidified with diethyl ether, and the solid was washed with ethyl acetate-diethyl ether to give the title compound (17.28 g, 88%) as a grayish solid. MS 281 (MH⁺).

Reference Example 38

Ethyl 2-[(2-hydroxy-4-{[6-(methylsulfonyl)pyridin-3-yl]oxy}phenyl)hydrazono]propanoate

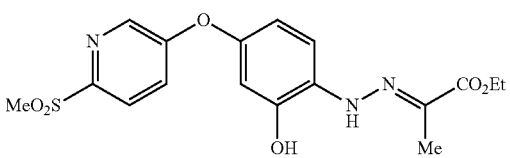 [SMILES: CCOC(=O)/C(C)=N/Nc1ccc(Oc2ccc(S(C)(=O)=O)nc2)cc1O]

To a stirring suspension of 2-amino-5-{[6-(methylsulfonyl)pyridin-3-yl]oxy}phenol (17.28 g) in ethanol (150 mL) was added concentrated hydrochloric acid (13.6 mL) at 0° C. After cooling to −5° C., a solution of sodium nitrite (5.1 g) in water (20 mL) was added dropwise to the mixture with keeping the temperature below −5° C. The mixture was stirred at −10° C. for 20 min. The mixture was added to a mixture of ethyl 2-methyl-3-oxobutanoate (9.8 mL), potassium hydroxide (85%, 14.2 g), ethanol (150 mL) and water (150 mL) at −30 to −25° C. After stirring at −30° C. for 30 min, 1M hydrochloric acid (110 mL) was added to the mixture. The mixture was extracted with ethyl acetate. The organic layer was washed with saturated brine, dried over magnesium sulfate, filtered and concentrated. The residual solid was washed with diethyl ether to give the title compound (21.1 g, 87%) as a brownish-yellow solid. MS 394 (MH⁺).

Reference Example 39

Ethyl 2-[(2-[(methylsulfonyl)oxy]-4-{[6-(methylsulfonyl)pyridin-3-yl]oxy}phenyl)hydrazono]propanoate

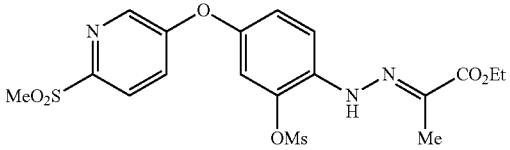 [SMILES: CCOC(=O)/C(C)=N/Nc1ccc(Oc2ccc(S(C)(=O)=O)nc2)cc1OS(C)(=O)=O]

To a solution of ethyl 2-[(2-hydroxy-4-{[6-(methylsulfonyl)pyridin-3-yl]oxy}phenyl)hydrazono]propanoate (21.1 g) in pyridine (220 mL) was added methanesulfonyl chloride (5.0 mL) at 0° C. The mixture was stirred at 0° C. for 2 h, and then at room temperature for 16 h. The mixture was cooled to 0° C., and methanesulfonyl chloride (5.0 mL) was added to the mixture again. After stirring at room temperature for 2 h, water was added to the mixture. The mixture was extracted with ethyl acetate. The organic layer was washed successively with 1M hydrochloric acid, water, saturated aqueous sodium hydrogen carbonate solution and saturated brine, dried over magnesium sulfate, filtered and concentrated. The residual oil was solidified with ethyl acetate-diethyl ether, and the resulting solid was washed with diethyl ether to give the title compound (20.0 g, 79%) as a pale yellow solid. MS 472 (MH⁺).

Reference Example 40

Ethyl 7-[(methylsulfonyl)oxy]-5-{[6-(methylsulfonyl)pyridin-3-yl]oxy}-1H-indole-2-carboxylate

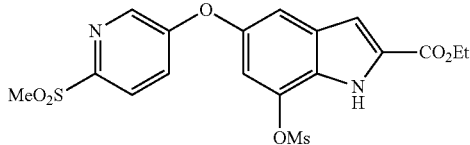 [SMILES: CCOC(=O)c1cc2cc(Oc3ccc(S(C)(=O)=O)nc3)cc(OS(C)(=O)=O)c2[nH]1]

Methanesulfonic acid (13 mL) was added to Eaton's reagent (19 g) at 80° C. After stirring at 80° C. for 20 min, toluene (200 mL) was added. Ethyl 2-[(2-[(methylsulfonyl)oxy]-4-{[6-(methylsulfonyl)pyridin-3-yl]oxy}phenyl)hydrazono]propanoate (19 g) was added to the mixture in 3 portions. The mixture was stirred at 80° C. for 40 min and cooled to room temperature. Water and sodium hydrogen carbonate were added, and the mixture was extracted with ethyl acetate. The organic layer was washed with saturated brine, dried over magnesium sulfate, filtered and concentrated. The residue was purified by silica gel column chromatography (ethyl acetate/hexane=5/95 to 50/50, volume ratio) to give the title compound (7.8 g, 43%) as a pale yellow amorphous solid. MS 455 (MH⁺).

Reference Example 41

7-Hydroxy-5-{[6-(methylsulfonyl)pyridin-3-yl]oxy}-1H-indole-2-carboxylic acid

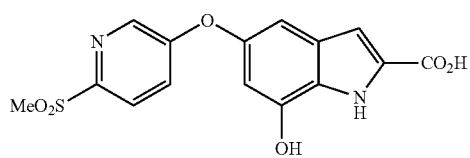

Ethyl 7-[(methylsulfonyl)oxy]-5-{[6-(methylsulfonyl)pyridin-3-yl]oxy}-1H-indole-2-carboxylate (1.56 g) was dissolved in a mixture of tetrahydrofuran (10 mL) and ethanol (15 mL). A solution of potassium hydroxide (85%, 0.8 g) in water (10 mL) was added to the mixture at 0° C. The mixture was allowed to warm to room temperature and stirred for 13 h. The mixture was concentrated under reduced pressure. The residue was dissolved in water and 1M hydrochloric acid (14 mL) was added to the mixture. The mixture was extracted with ethyl acetate. The organic layer was washed with saturated brine, dried over magnesium sulfate, filtered and concentrated. The residual solid was washed with diethyl ether to give the title compound (0.93 g, 81%) as a pale orange solid. MS 349 (MH⁺).

Reference Example 42

Methyl 7-hydroxy-5-{[6-(methylsulfonyl)pyridin-3-yl]oxy}-1H-indole-2-carboxylate

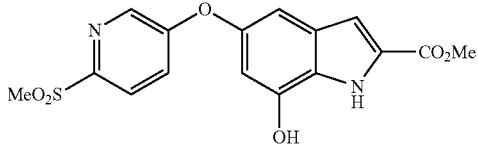 [SMILES: COC(=O)c1cc2cc(Oc3ccc(S(C)(=O)=O)nc3)cc(O)c2[nH]1]

To a solution of 7-hydroxy-5-{[6-(methylsulfonyl)pyridin-3-yl]oxy}-1H-indole-2-carboxylic acid (4.7 g) in a mixture of methanol (30 mL) and toluene (90 mL) was added dropwise 2M trimethylsilyldiazomethane diethyl ether solution (7.4 mL) at 0° C. The mixture was stirred at 0° C. for 30 min, and 2M trimethylsilyldiazomethane diethyl ether solution (3.7 mL) was added dropwise to the mixture. After stirring at 0° C. for 30 min, 1M hydrochloric acid (2 mL) was added to the mixture to quench the reaction. Water was added to the mixture and the mixture was extracted with ethyl acetate. The organic layer was washed with saturated brine, dried over magnesium sulfate, filtered and concentrated. The residual yellow oil was solidified with ethyl acetate-diethyl ether. The resulting solid was washed with diethyl ether to give the title compound (3.6 g, 74%) as a pale orange solid. MS 363 (MH⁺).

Reference Example 43

Methyl 7-methoxy-5-{[6-(methylsulfonyl)pyridin-3-yl]oxy}-1H-indole-2-carboxylate

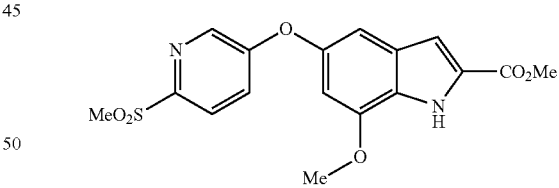

Methyl 7-hydroxy-5-{[6-(methylsulfonyl)pyridin-3-yl]oxy}-1H-indole-2-carboxylate (1.1 g) was dissolved in a mixture of ethyl acetate (20 mL) and methanol (5 mL). The mixture was cooled to 0° C., and 2M trimethylsilyldiazomethane diethyl ether solution (2 mL) was added dropwise to the mixture. The mixture was stirred at 0° C. for 30 min, and then 2M trimethylsilyldiazomethane diethyl ether solution (0.5 mL) was added dropwise to the mixture again. After stirring at 0° C. for 30 min, 1M hydrochloric acid (1 mL) was added to the mixture to quench the reaction. Water was added to the mixture and the mixture was extracted with ethyl acetate. The organic layer was washed successively with saturated aqueous sodium hydrogen carbonate solution and saturated brine, dried over magnesium sulfate, filtered and concentrated. The residual oil was solidified with diethyl ether to give the title compound (0.99 g, 88%) as a pale orange solid. MS 377 (MH⁺).

Reference Example 44

7-Methoxy-5-{[6-(methylsulfonyl)pyridin-3-yl]oxy}-1H-indole-2-carboxylic acid

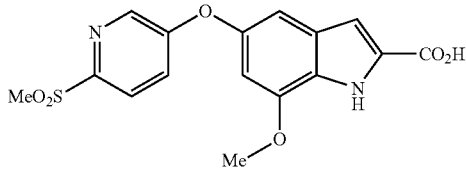 [SMILES: COc1cc(Oc2ccc(S(C)(=O)=O)nc2)cc2cc(C(=O)O)[nH]c12]

Methyl 7-methoxy-5-{[6-(methylsulfonyl)pyridin-3-yl]oxy}-1H-indole-2-carboxylate (0.99 g) was dissolved in a mixture of tetrahydrofuran (10 mL) and methanol (10 mL). 1M Aqueous sodium hydroxide solution (5 mL) was added and the mixture was stirred at 50° C. for 45 min. The mixture was concentrated under reduced pressure. The residue was dissolved in water, and 1M hydrochloric acid was added to the mixture. The mixture was extracted with ethyl acetate. The organic layer was washed with saturated brine, dried over magnesium sulfate, filtered and concentrated. The residual amorphous solid was solidified with diethyl ether to give the title compound (0.9 g, 95%) as a pale yellow solid. MS 363 (MH⁺).

Reference Example 45

7-Methoxy-5-{[6-(methylsulfonyl)pyridin-3-yl]oxy}-1H-indole-2-carboxamide

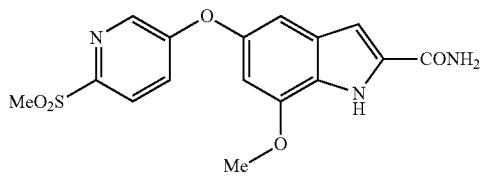 [SMILES: COc1cc(Oc2ccc(S(C)(=O)=O)nc2)cc2cc(C(N)=O)[nH]c12]

A mixture of 7-methoxy-5-{[6-(methylsulfonyl)pyridin-3-yl]oxy}-1H-indole-2-carboxylic acid (0.9 g), N-ethyl-N'-(3-dimethylaminopropyl)carbodiimide hydrochloride (0.95 g), 1-hydroxybenzotriazole (0.67 g) and N,N-dimethylformamide (15 mL) was stirred at 50° C. for 20 min. The mixture was cooled to room temperature, and 10% aqueous ammonium hydroxide solution (2 mL) was added to the mixture. After stirring at room temperature for 2 h, the mixture was concentrated under reduced pressure. Water was added to the residue and the resulting yellow suspension was filtered to give the title compound (0.66 g, 74%) as a yellow solid. MS 362 (MH⁺).

Reference Example 46

7-Methoxy-5-{[6-(methylsulfonyl)pyridin-3-yl]oxy}-1H-indole-2-carbothioamide

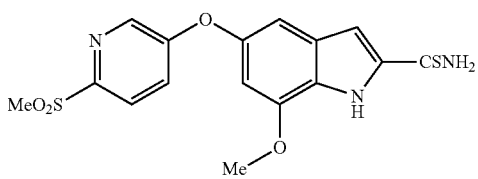

To a solution of 7-methoxy-5-{[6-(methylsulfonyl)pyridin-3-yl]oxy}-1H-indole-2-carboxamide (0.66 g) in tetrahydrofuran (150 mL) was added Lawesson's reagent (0.89 g), and the mixture was stirred at 50° C. for 1 h. Tetrahydrofuran (100 mL) and Lawesson's reagent (0.42 g) were added to the mixture. After stirring at 50° C. for 13 h, the mixture was concentrated under reduced pressure. The residue was purified by silica gel column chromatography (ethyl acetate/hexane=20/80 to 100/0, volume ratio) to give the title compound (0.68 g, 99%) as a yellow amorphous solid. MS 378 (MH⁺).

Reference Example 47

Methyl 7-[2-methoxy-1-(methoxymethyl)ethoxy]-5-{[6-(methylsulfonyl)pyridin-3-yl]oxy}-1H-indole-2-carboxylate

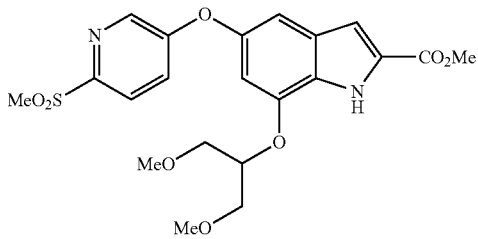

A mixture of methyl 7-hydroxy-5-{[6-(methylsulfonyl)pyridin-3-yl]oxy}-1H-indole-2-carboxylate (1.2 g), tributylphosphine (1.6 mL), 1,1'-(azodicarbonyl)dipiperidine (1.7 g), 1,3-dimethoxypropan-2-ol (0.8 g) and tetrahydrofuran (20 mL) was stirred at 50° C. for 13 h. Tributylphosphine (0.82 mL), 1,1'-(azodicarbonyl)dipiperidine (0.83 g) and 1,3-dimethoxypropan-2-ol (0.4 g) were added to the mixture again and the mixture was stirred at 70° C. for 5 h. Furthermore, tributylphosphine (1.64 mL), 1,1'-(azodicarbonyl)dipiperidine (1.66 g) and 1,3-dimethoxypropan-2-ol (0.8 g) were added to the mixture. After stirring at 70° C. for 3 h, the mixture was cooled to 0° C., and insoluble materials were removed by filtration. The filtrate was concentrated and the residue was purified basic silica gel column chromatography (ethyl acetate/hexane=20/80 to 85/15, volume ratio) to give the title compound (1.79 g, 84%) as an orange oil, MS 463 (MH⁻).

Reference Example 48

7-[2-Methoxy-1-(methoxymethyl)ethoxy]-5-{[6-(methylsulfonyl)pyridin-3-yl]oxy}-1H-indole-2-carboxylic acid

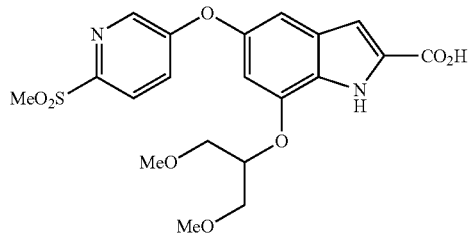 [SMILES: COCC(COC)Oc1cc(Oc2ccc(S(C)(=O)=O)nc2)cc2cc(C(=O)O)[nH]c12]

To a solution of methyl 7-[2-methoxy-1-(methoxymethyl)ethoxy]-5-{[6-(methylsulfonyl)pyridin-3-yl]oxy}-1H-indole-2-carboxylate (1.79 g) in a mixture of tetrahydrofuran (20 mL) and methanol (15 mL) was added 1M aqueous sodium hydroxide solution (15 mL), and the mixture was stirred at 50° C. for 30 min. The mixture was concentrated under reduced pressure and the residue was dissolved in water. The mixture was washed with diethyl ether three times. The diethyl ether layers were combined and extracted with water. The aqueous layers were combined and 1M hydrochloric acid (15 mL) was added to the mixture. The resulting white suspension was filtered to give the title compound (1.02 g, 69%) as a pale orange solid. MS 451 (MH⁺).

Reference Example 49

7-[2-Methoxy-1-(methoxymethyl)ethoxy]-5-{[6-(methylsulfonyl)pyridin-3-yl]oxy}-1H-indole-2-carboxamide

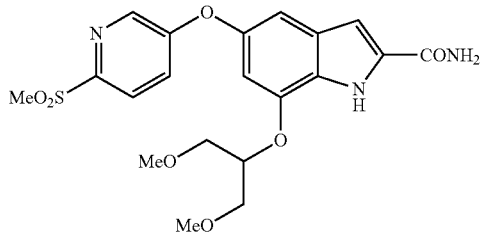 [SMILES: COCC(COC)Oc1cc(Oc2ccc(S(C)(=O)=O)nc2)cc2cc(C(N)=O)[nH]c12]

A mixture of 7-[2-methoxy-1-(methoxymethyl)ethoxy]-5-{[6-(methylsulfonyl)pyridin-3-yl]oxy}-1H-indole-2-carboxylic acid (1.02 g), N-ethyl-N'-(3-dimethylaminopropyl)carbodiimide hydrochloride (868 mg), 1-hydroxybenzotriazole (612 mg) and N,N-dimethylformamide (20 mL) was stirred at 50° C. for 25 min. The mixture was cooled to room temperature, and 10% ammonium hydroxide solution (3 mL) was added to the mixture. After stirring at room temperature for 2 days, the mixture was concentrated under reduced pressure. Water was added to the residue and the mixture was extracted with ethyl acetate. The organic layer was washed successively with water and saturated brine, dried over magnesium sulfate, filtered and concentrated to give the title compound (1.08 g, 100%) as an orange oil. MS 450 (MH⁺).

Reference Example 50

7-[2-Methoxy-1-(methoxymethyl)ethoxy]-5-{[6-(methylsulfonyl)pyridin-3-yl]oxy}-1H-indole-2-carbothioamide

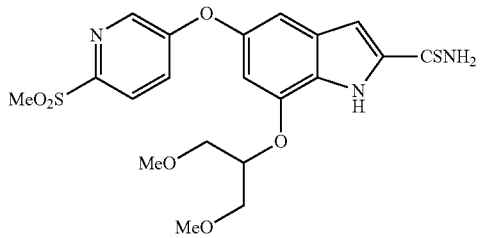

To a solution of 7-[2-methoxy-1-(methoxymethyl)ethoxy]-5-{[6-(methylsulfonyl)pyridin-3-yl]oxy}-1H-indole-2-carboxamide (1.0 g) in tetrahydrofuran (15 mL) was added Lawesson's reagent (1.0 g) and the mixture was stirred at 50° C. for 45 min. The mixture was concentrated under reduced pressure and the residue was purified by silica gel column chromatography (ethyl acetate/hexane=10/90 to 70/30, volume ratio) to give the title compound (0.94 g, 90%) as a yellow amorphous solid. MS 466 (MH⁺).

Reference Example 51

2-[3-(Benzyloxy)-4-nitrophenoxy]-5-(methylsulfonyl)pyridine

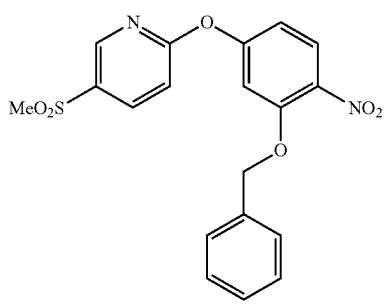

A mixture of 3-(benzyloxy)-4-nitrophenol (31.4 g), 2-bromo-5-(methylsulfonyl)pyridine (30.3 g), cesium carbonate (83.6 g) and N,N-dimethylformamide (300 mL) was stirred at 100° C. for 3 h. The mixture was concentrated under reduced pressure. Water was added to the residue and the resulting brown suspension was filtered to give the title compound (45.6 g, 89%) as a yellow solid.

$^1$H NMR (CDCl$_3$) δ 3.11 (3H, s), 5.22 (2H, s), 6.84 (1H, dd, J=8.9, 2.5 Hz), 6.96 (1H, d, J=2.3 Hz), 7.14 (1H, d, J=8.0 Hz), 7.33-7.48 (5H, m), 8.02 (1H, d, J=9.1 Hz), 8.24 (1H, dd, J=8.5, 2.5 Hz), 8.68 (1H, d, J=2.7 Hz).

Reference Example 52

2-(Benzyloxy)-4-{[5-(methylsulfonyl)pyridin-2-yl]oxy}aniline

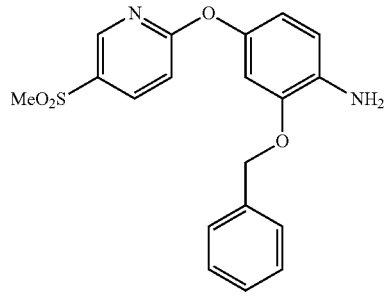 [SMILES: CS(=O)(=O)c1ccc(Oc2ccc([N+](=O)[O-])c(OCc3ccccc3)c2)nc1]

A mixture of 2-[3-(benzyloxy)-4-nitrophenoxy]-5-(methylsulfonyl)pyridine (45.56 g), iron powder (31.7 g), calcium chloride (1.26 g), ethanol (400 mL) and water (100 mL) was stirred at 80° C. for 3.5 h. The mixture was filtered through celite and the filtrate was concentrated. The residual solid was washed successively with water, ethanol, and diethyl ether to give the title compound (46.31 g, 100%) as a brownish-yellow solid. MS 371 (MH$^+$).

Reference Example 53

2-Amino-5-{[5-(methylsulfonyl)pyridin-2-yl]oxy}phenol

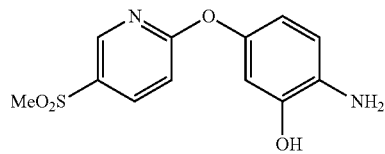

To a solution of 2-(benzyloxy)-4-{[5-(methylsulfonyl)pyridin-2-yl]oxy}aniline (46 g) in a mixture of tetrahydrofuran (400 mL) and methanol (150 mL) was added palladium on carbon (7 g, 10 weight %, wet), and the mixture was stirred at room temperature for 15 h under hydrogen atmosphere. The mixture was filtered to remove the catalyst and the filtrate was concentrated. The residual solid was washed with methanol-diethyl ether to give the title compound (26.91 g, 84%) as a greenish-gray solid. MS 281 (MH$^+$).

Reference Example 54

Ethyl 2-[(2-hydroxy-4-{[5-(methylsulfonyl)pyridin-2-yl]oxy}phenyl)hydrazono]propanoate

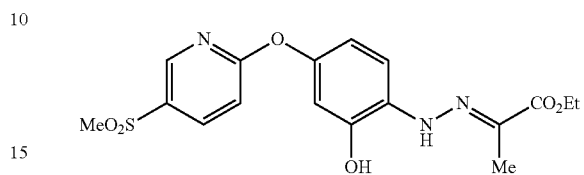

To a stirring suspension of 2-amino-5-{[5-(methylsulfonyl)pyridin-2-yl]oxy}phenol (27.68 g) in a mixture of ethanol (150 mL) and acetonitrile (20 mL) was added concentrated hydrochloric acid (21.8 mL) at 0° C. After cooling to −5° C., a solution of sodium nitrite (8.18 g) in water (20 mL) was added dropwise to the mixture with keeping the temperature below −5° C. The mixture was stirred at −10° C. for 30 min. The mixture was added to a mixture of ethyl 2-methyl-3-oxobutanoate (15.7 mL), potassium hydroxide (85%, 22.8 g), ethanol (50 mL) and water (150 mL) at −30 to −20° C. After stirring at −30° C. for 1 h, 1M hydrochloric acid (150 mL) was added to the mixture. Water and ethyl acetate were added. The resulting brown suspension was filtered to give the title compound (17.9 g) as a brown solid. Furthermore, the filtrate was extracted with ethyl acetate-tetrahydrofuran. The organic layer was washed with saturated brine, dried over magnesium sulfate, filtered and concentrated. The residual solid was washed with diethyl ether to give the title compound (15.3 g) as a brownish solid. Additionally, the filtrate was concentrated and the residual solid was washed with diethyl ether to give the title compound (4.5 g) as a brownish solid (total 37.7 g, 97%). MS 394 (MH$^+$).

Reference Example 55

Ethyl 2-[(2-[(methylsulfonyl)oxy]-4-{[5-(methylsulfonyl)pyridin-2-yl]oxy}phenyl)hydrazono]propanoate

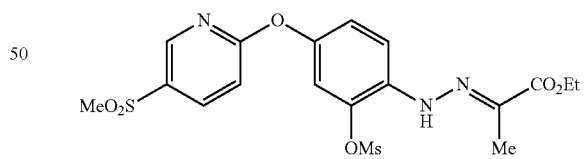

To a solution of ethyl 2-[(2-hydroxy-4-{[5-(methylsulfonyl)pyridin-2-yl]oxy}phenyl)-hydrazono]propanoate (37.7 g) in pyridine (450 mL) was added methanesulfonyl chloride (8.9 mL) at 0° C., and the mixture was stirred at room temperature for 1 h. Methanesulfonyl chloride (8.9 mL) was added to the mixture at 0° C. again, and the mixture was stirred at room temperature for 1 h. Furthermore, methanesulfonyl chloride (8.9 mL) was added to the mixture at 0° C., and the mixture was stirred at room temperature for 15 h. The mixture was concentrated under reduced pressure. Water was added to the residue and the mixture was extracted with ethyl acetate-tetrahydrofuran. The organic layer was washed successively with 1M hydrochloric acid, water, saturated aqueous sodium hydrogen carbonate solution and saturated brine, dried over magnesium sulfate, filtered and concentrated. The residual solid was washed with diethyl ether to give the title compound (37.05 g, 83%) as an off-white solid. MS 472 (MH$^+$).

Reference Example 56

Ethyl 7-[(methylsulfonyl)oxy]-5-{[5-(methylsulfonyl)pyridin-2-yl]oxy}-1H-indole-2-carboxylate

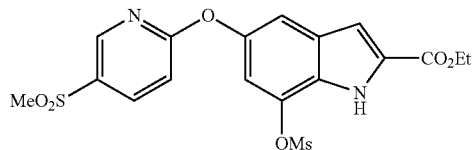 [SMILES: CCOC(=O)c1cc2cc(Oc3ccc(S(C)(=O)=O)cn3)cc(OS(C)(=O)=O)c2[nH]1]

Methanesulfonic acid (24 mL) was added to Eaton's reagent (36 g) at 90° C. After stirring at 90° C. for 1 h, toluene (200 mL) was added to the mixture. Ethyl 2-[(2-[(methylsulfonyl)oxy]-4-{[5-(methylsulfonyl)pyridin-2-yl]oxy}phenyl)hydrazono]propanoate (36.1 g) was added to the mixture in 3 portions. The mixture was stirred at 90° C. for 50 min and then cooled to room temperature. Water and sodium hydrogen carbonate were added, and the mixture was extracted with ethyl acetate-tetrahydrofuran. The organic layer was washed with saturated brine, dried over magnesium sulfate, filtered and concentrated. The residue was purified twice by silica gel column chromatography (ethyl acetate/hexane=20/80 to 75/25, volume ratio) to give a yellow solid. The solid was washed with diethyl ether to give the title compound (8.57 g, 25%) as a pale yellow solid. MS 455 (MH$^+$).

Reference Example 57

7-Hydroxy-5-{[5-(methylsulfonyl)pyridin-2-yl]oxy}-1H-indole-2-carboxylic acid

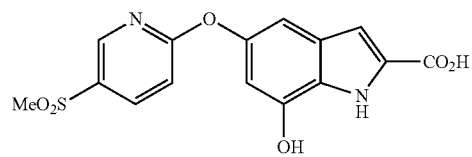 [SMILES: CS(=O)(=O)c1ccc(Oc2cc(O)c3[nH]c(C(=O)O)cc3c2)nc1]

Ethyl 7-[(methylsulfonyl)oxy]-5-{[5-(methylsulfonyl)pyridin-2-yl]oxy}-1H-indole-2-carboxylate (11.74 g) was suspended in a mixture of tetrahydrofuran (300 mL) and ethanol (150 mL). A solution of potassium hydroxide (85%, 6.8 g) in water (100 mL) was added to the mixture at 0° C. The mixture was allowed to warm to room temperature and stirred for 12 h. The mixture was concentrated and 1M hydrochloric acid (130 mL) was added to the residue. The mixture was extracted with ethyl acetate. The organic layer was washed with saturated brine, dried over magnesium sulfate, filtered and concentrated. The residual solid was washed with diethyl ether to give the title compound (8.39 g, 93%) as a brown solid. MS 349 (MH$^+$).

Reference Example 58

Methyl 7-hydroxy-5-{[5-(methylsulfonyl)pyridin-2-yl]oxy}-1H-indole-2-carboxylate

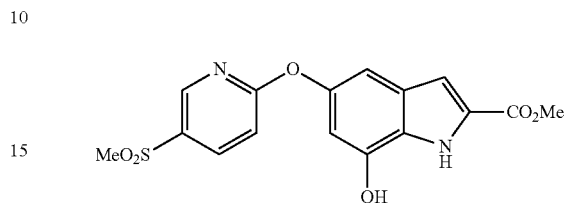

To a suspension of 7-hydroxy-5-{[5-(methylsulfonyl)pyridin-2-yl]oxy}-1H-indole-2-carboxylic acid (8.71 g) in a mixture of methanol (300 mL) and toluene (300 mL) was added dropwise 2M trimethylsilyldiazomethane diethyl ether solution (12.5 mL) at 0° C., and the mixture was stirred at 0° C. for 1.5 h. Furthermore 2M trimethylsilyldiazomethane diethyl ether solution (10 mL) was added to the mixture and the mixture was stirred at 0° C. for 1 h, which was repeated three times. And then 2M trimethylsilyldiazomethane diethyl ether solution (5 mL) was added and the mixture was stirred at 0° C. for 30 min, which was repeated two times. To quench the reaction, 1M hydrochloric acid (80 mL) was added to the mixture. Water was added to the mixture and the mixture was extracted with ethyl acetate. The organic layer was washed with saturated brine, dried over magnesium sulfate, filtered and concentrated. The residual solid was washed with diethyl ether to give the title compound (8.25 g, 92%) as a purple solid. MS 363 (MH$^+$).

Reference Example 59

Methyl 7-methoxy-5-{[5-(methylsulfonyl)pyridin-2-yl]oxy}-1H-indole-2-carboxylate

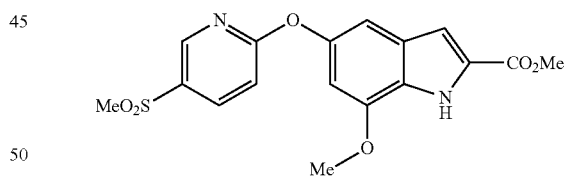

To a solution of methyl 7-hydroxy-5-{[5-(methylsulfonyl)pyridin-2-yl]oxy}-1H-indole-2-carboxylate (3.12 g) in a mixture of tetrahydrofuran (30 mL) and methanol (5 mL) was added dropwise 2M trimethylsilyldiazomethane diethyl ether solution (4.3 mL) at 0° C. The mixture was stirred at 0° C. for 1 h, 2M trimethylsilyldiazomethane diethyl ether solution (8.0 mL) was added dropwise to the mixture again, and the mixture was stirred at 0° C. for 2.5 h. Furthermore, 2M trimethylsilyldiazomethane diethyl ether solution (4.0 mL) was added dropwise to the mixture, and the mixture was stirred at room temperature for 1 h. To quench the reaction, 6M hydrochloric acid (9 mL) was added to the mixture. Water was added and the mixture was extracted with ethyl acetate. The organic layer was washed successively with saturated aqueous sodium carbonate solution and saturated brine, dried over magnesium sulfate, filtered and concentrated. The residual solid was washed with diethyl ether to give the title compound (2.78 g, 86%) as a brown solid. MS 377 (MH⁺).

Reference Example 60

7-Methoxy-5-{[5-(methylsulfonyl)pyridin-2-yl]oxy}-1H-indole-2-carboxylic acid

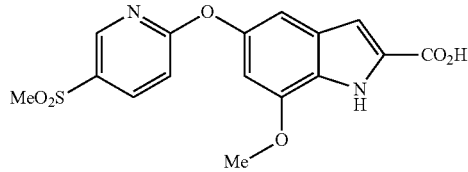

To a solution of methyl 7-methoxy-5-{[5-(methylsulfonyl)pyridin-2-yl]oxy}-1H-indole-2-carboxylate (2.78 g) in a mixture of tetrahydrofuran (25 mL) and ethanol (20 mL) was added 1M aqueous sodium hydroxide solution (11 mL), and the mixture was stirred at 50° C. for 40 min. The mixture was concentrated under reduced pressure. The residue was dissolved in water, and 1M hydrochloric acid (11 mL) was added to the mixture. The mixture was extracted with ethyl acetate. The organic layer was washed with saturated brine, dried over magnesium sulfate, filtered and concentrated. The residual oil was solidified with diethyl ether to give the title compound (2.18 g, 81%) as a pale orange solid. MS 363 (MH⁺).

Reference Example 61

7-Methoxy-5-{[5-(methylsulfonyl)pyridin-2-yl]oxy}-1H-indole-2-carboxamide

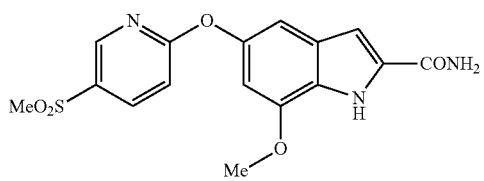

A mixture of 7-methoxy-5-{[5-(methylsulfonyl)pyridin-2-yl]oxy}-1H-indole-2-carboxylic acid (2.18 g), N-ethyl-N'-(3-dimethylaminopropyl)carbodiimide hydrochloride (2.3 g), 1-hydroxybenzotriazole (1.6 g) and N,N-dimethylformamide (20 ml) was stirred at 50° C. for 25 min. The mixture was cooled to room temperature, and 10% aqueous ammonium hydroxide solution (3 mL) was added to the mixture. After stirring at room temperature for 2 days, the mixture was concentrated under reduced pressure. Water was added to the residue and the mixture was extracted with ethyl acetate. The organic layer was washed successively with water and saturated brine, dried over magnesium sulfate, filtered and concentrated to give the title compound (2.09 g, 96%) as an orange oil. MS 362 (MH⁺).

Reference Example 62

7-Methoxy-5-{[5-(methylsulfonyl)pyridin-2-yl]oxy}-1H-indole-2-carbothioamide

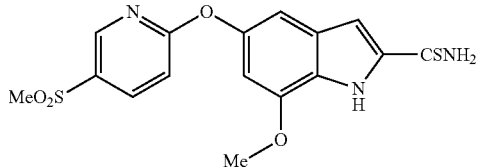

To a solution of 7-methoxy-5-{[5-(methylsulfonyl)pyridin-2-yl]oxy}-1H-indole-2-carboxamide (2.1 g) in tetrahydrofuran (400 mL) was added Lawesson's reagent (2.3 g) and the mixture was stirred at 60° C. for 50 min. The mixture was concentrated under reduced pressure and the residue was dissolved in ethyl acetate. The mixture was washed with saturated brine, dried over magnesium sulfate, filtered and concentrated. The residue was solidified with ethyl acetate and the resulting solid was washed with diethyl ether to give the title compound (2.06 g, 94%) as a pale yellow solid. MS 378 (MH⁺).

Reference Example 63

Methyl 7-[2-methoxy-1-(methoxymethyl)ethoxy]-5-{[5-(methylsulfonyl)pyridin-2-yl]oxy}-1H-indole-2-carboxylate

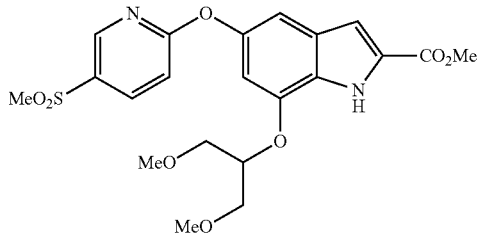

A mixture of methyl 7-hydroxy-5-{[5-(methylsulfonyl)pyridin-2-yl]oxy}-1H-indole-2-carboxylate (2.75 g), tributylphosphine (3.7 mL), 1,1'-(azodicarbonyl)dipiperidine (3.8 g), 1,3-dimethoxypropan-2-ol (1.8 g) and tetrahydrofuran (50 mL) was stirred at 50° C. for 8 h. Tributylphosphine (1.9 mL), 1,1'-(azodicarbonyl)dipiperidine (1.9 g) and 1,3-dimethoxypropan-2-ol (0.9 g) were added to the mixture again, and the mixture was stirred at 50° C. for 8 h. Furthermore, tributylphosphine (3.7 mL), 1,1'-(azodicarbonyl)dipiperidine (3.8 g) and 1,3-dimethoxypropan-2-ol (1.8 g) were added to the mixture. After stirring at 50° C. for 24 h, the mixture was cooled to 0° C. and a precipitate was removed by filtration. The filtrate was concentrated and the residue was purified by silica gel column chromatography (ethyl acetate/hexane=10/90 to 80/20, volume ratio) twice, followed by basic silica gel column chromatography (ethyl acetate/hexane 20/80 to 85/15) to give the crude title compound (3.42 g) as a yellow oil. MS 465 (MH+).

Reference Example 64

7-[2-Methoxy-1-(methoxymethyl)ethoxy]-5-{[5-(methylsulfonyl)pyridin-2-yl]oxy}-1H-indole-2-carboxylic acid

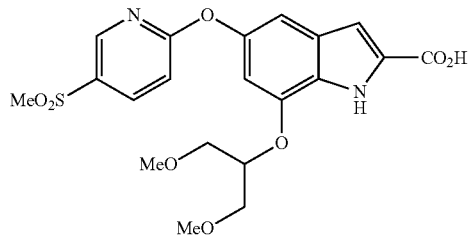 [SMILES: COCC(COC)Oc1cc(Oc2ccc(S(C)(=O)=O)cn2)cc2cc(C(=O)O)[nH]c12]

To a solution of methyl 7-[2-methoxy-1-(methoxymethyl)ethoxy]-5-{[5-(methylsulfonyl)pyridin-2-yl]oxy}-1H-indole-2-carboxylate (3.42 g) in a mixture of tetrahydrofuran (20 mL) and ethanol (15 mL) was added 1M aqueous sodium hydroxide solution (18 mL), and the mixture was stirred at 50° C. for 50 min. The mixture was concentrated under reduced pressure and the residue was dissolved in water. The mixture was washed with diethyl ether. To the aqueous layer was added 1M hydrochloric acid (18.5 mL) and the mixture was extracted with ethyl acetate. The organic layer was washed with saturated brine, dried over magnesium sulfate, filtered and concentrated. The residual amorphous solid was solidified with diethyl ether to give the title compound (1.66 g) as a pale yellow solid. MS 553 (MH+).

Reference Example 65

7-[2-Methoxy-1-(methoxymethyl)ethoxy]-5-{[5-(methylsulfonyl)pyridin-2-yl]oxy}-1H-indole-2-carboxamide

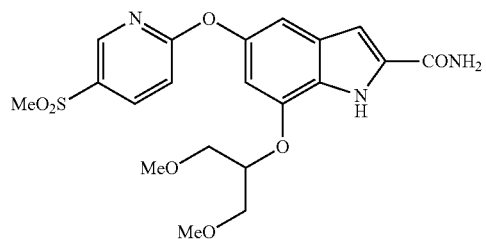 [SMILES: COCC(COC)Oc1cc(Oc2ccc(S(C)(=O)=O)cn2)cc2cc(C(N)=O)[nH]c12]

A mixture of 7-[2-methoxy-1-(methoxymethyl)ethoxy]-5-{[5-(methylsulfonyl)pyridin-2-yl]oxy}-1H-indole-2-carboxylic acid (1.66 g), N-ethyl-N'-(3-dimethylaminopropyl)carbodiimide hydrochloride (1.4 g), 1-hydroxybenzotriazole (1.0 g) and N,N-dimethylformamide (15 mL) was stirred at 50° C. for 30 min. The mixture was cooled to room temperature, and 25% ammonium hydroxide solution (1.5 mL) was added to the mixture. After stirring at room temperature for 14 h, the mixture was concentrated under reduced pressure. Water was added to the residue and the mixture was extracted with ethyl acetate. The organic layer was washed with satu-rated brine, dried over magnesium sulfate, filtered and concentrated. The residue was purified by basic silica gel column chromatography (methanol/ethyl acetate/hexane=0/60/40 to 10/90/0, volume ratio) to give the title compound (1.66 g, 100%) as a colorless amorphous solid. MS 450 (MH+).

Reference Example 66

7-[2-Methoxy-1-(methoxymethyl)ethoxy]-5-{[5-(methylsulfonyl)pyridin-2-yl]oxy}-1H-indole-2-carbothioamide

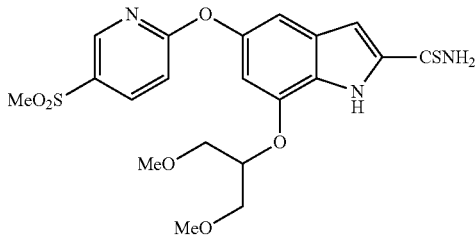

To a solution of 7-[2-methoxy-1-(methoxymethyl)ethoxy]-5-{[5-(methylsulfonyl)pyridin-2-yl]oxy}-1H-indole-2-carboxamide (1.66 g) in tetrahydrofuran (40 mL) was added Lawesson's reagent (1.5 g), and the mixture was stirred at 50° C. for 2 h. Lawesson's reagent (0.5 g) was added to the mixture again. After stirring at 50° C. for 1 h, the mixture was concentrated under reduced pressure. The residue was dissolved in ethyl acetate and the mixture was washed with saturated brine, dried over magnesium sulfate, filtered and concentrated. The residue was purified by basic silica gel column chromatography (methanol/ethyl acetate/hexane=0/10/90 to 10/90/0, volume ratio) to give the title compound (1.69 g, 98%) as a yellow amorphous solid. MS 466 (MH+).

Reference Example 67

Ethyl 7-methoxy-5-{[6-(methoxymethyl)pyridin-3-yl]oxy}-1H-indole-2-carboxylate

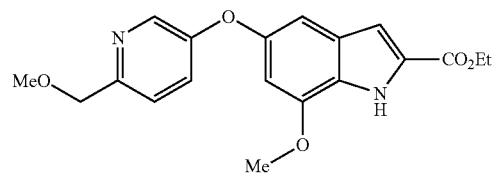 [SMILES: CCOC(=O)c1cc2cc(Oc3ccc(COC)nc3)cc(OC)c2[nH]1]

p-Toluenesulfonic acid monohydrate (11.8 g) was refluxed in toluene (200 mL) for 2 h with azeotropic removal of water. The mixture was cooled to 110° C. and a solution of ethyl 2-[(2-methoxy-4-{[6-(methoxymethyl)pyridin-3-yl]oxy}phenyl)hydrazono]propanoate (11.58 g) in toluene (50 mL) was added. The mixture was stirred at 110° C. for 5.5 h. After cooling to room temperature, saturated aqueous sodium hydrogen carbonate solution was added to the mixture. The mixture was extracted with ethyl acetate. The organic layer was washed with saturated brine, dried over magnesium sulfate, filtered and concentrated. The residue was purified by silica gel column chromatography (ethyl acetate/hexane=10/90 to 75/25), followed by basic silica gel column chromatography (ethyl acetate/hexane=10/90 to 50/50, volume ratio) to afford a yellow solid. The solid was washed with diethyl ether to give the title compound (2.32 g, 21%) as a yellow solid. MS 357 (MH+).

Reference Example 68

7-Methoxy-5-{[6-(methoxymethyl)pyridin-3-yl]oxy}-1H-indole-2-carboxylic acid

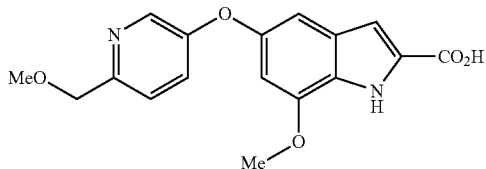 [SMILES: COCc1ccc(Oc2cc(OC)c3[nH]c(C(=O)O)cc3c2)cn1]

To a solution of ethyl 7-methoxy-5-{[6-(methoxymethyl)pyridin-3-yl]oxy}-1H-indole-2-carboxylate (2.39 g) in a mixture of tetrahydrofuran (15 mL) and ethanol (10 mL) was added 1M aqueous sodium hydroxide solution (10 mL), and the mixture was stirred at 50° C. for 1 h. The mixture was concentrated under reduced pressure. The residue was dissolved in water, and 1M hydrochloric acid (10 mL) was added to the mixture. The mixture was extracted with ethyl acetate. The organic layer was washed with saturated brine, dried over magnesium sulfate, filtered and concentrated to give the title compound (2.28 g, 100%) as a pale yellow amorphous solid. MS 329 (MH+).

Reference Example 69

7-Methoxy-5-{[6-(methoxymethyl)pyridin-3-yl]oxy}-1H-indole-2-carboxamide

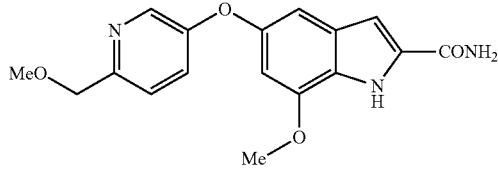 [SMILES: COCc1ccc(Oc2cc(OC)c3[nH]c(C(N)=O)cc3c2)cn1]

A mixture of 7-methoxy-5-{[6-(methoxymethyl)pyridin-3-yl]oxy}-1H-indole-2-carboxylic acid (2.28 g), N-ethyl-N'-(3-dimethylaminopropyl)carbodiimide hydrochloride (2.66 g), 1-hydroxybenzotriazole (2.13 g) and N,N-dimethylformamide (30 mL) was stirred at room temperature for 20 min. A solution of 25% ammonium hydroxide (3 mL) was added to the mixture. After stirring at room temperature for 15.5 h, the mixture was concentrated under reduced pressure. Water was added to the residue and the mixture was extracted with ethyl acetate. The organic layer was washed with saturated brine, dried over magnesium sulfate, filtered and concentrated. The residual oil was solidified with ethyl acetate-diethyl ether and the resulting solid was washed with diethyl ether to give the title compound (1.65 g, 73%) as a pale orange solid. MS 328 (MH+).

Reference Example 70

7-Methoxy-5-{[6-(methoxymethyl)pyridin-3-yl]oxy}-1H-indole-2-carbothioamide

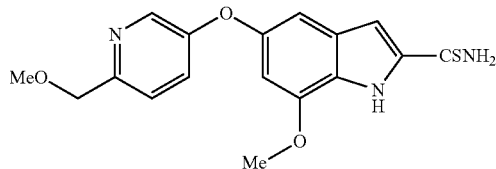

To a solution of 7-methoxy-5-{[6-(methoxymethyl)pyridin-3-yl]oxy}-1H-indole-2-carboxamide (1.86 g) in tetrahydrofuran (40 mL) was added Lawesson's reagent (2.3 g), and the mixture was stirred at 50° C. for 2 h. The mixture was concentrated under reduced pressure. The residue was dissolved in ethyl acetate and the mixture was washed with saturated brine, dried over magnesium sulfate, filtered and concentrated. The residue was purified by basic silica gel column chromatography (ethyl acetate/hexane=30/70 to 90/10, volume ratio) to give the title compound (2.04 g, 100%) as a yellow amorphous solid. MS 344 (MH+).

Reference Example 71

Ethyl 7-(2-methoxy-1-methylethoxy)-5-[4-(methylsulfonyl)phenoxy]-1H-indole-2-carboxylate

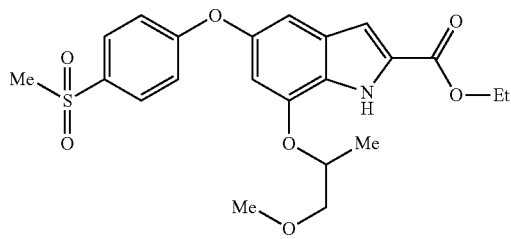 [SMILES: CCOC(=O)c1cc2cc(Oc3ccc(S(C)(=O)=O)cc3)cc(OC(C)COC)c2[nH]1]

To a solution of ethyl 7-hydroxy-5-[4-(methylsulfonyl)phenoxy]-1H-indole-2-carboxylate (2.0 g) in tetrahydrofuran (80 mL) were added 1-methoxypropan-2-ol (1.04 mL), tributylphosphine (2.46 mL) and 1,1'-(azodicarbonyl)dipiperidine (2.69 g) at room temperature. The mixture was stirred at 50° C. for 1 h. Then 1-methoxypropan-2-ol (0.5 mL), tributylphosphine (1.2 mL) and 1,1'-(azodicarbonyl)dipiperidine (1.34 g) were added to the mixture and the mixture was stirred at 50° C. overnight. The mixture was concentrated in vacuo. Ethyl acetate was added to the residue and insoluble materials were filtered off. The filtrate was concentrated in vacuo. The residue was purified by silica gel chromatography (ethyl acetate:hexane=1:9 to 6:4, volume ratio) to give the title compound (2.08 g, 87%) as a brown oil. MS 448 (MH⁺).

Reference Example 72

7-(2-Methoxy-1-methylethoxy)-5-[4-(methylsulfonyl)phenoxy]-1H-indole-2-carboxylic acid

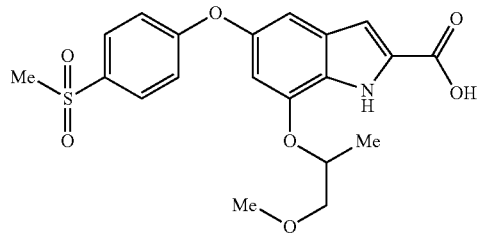 [SMILES: COCC(C)Oc1cc(Oc2ccc(S(C)(=O)=O)cc2)cc2cc(C(=O)O)[nH]c12]

To a mixture of ethyl 7-(2-methoxy-1-methylethoxy)-5-[4-(methylsulfonyl)phenoxy]-1H-indole-2-carboxylate (2.36 g), tetrahydrofuran (20 mL) and ethanol (20 mL) was added 1M aqueous sodium hydroxide solution (7.9 mL). The mixture was stirred at 50° C. for 2 h and at room temperature over night. To the mixture was added 1M aqueous sodium hydroxide solution (10.5 mL). The whole was stirred at 50° C. for further 1 h. The reaction mixture was concentrated in vacuo. The residue was acidified with 1M hydrochloric acid. Ethyl acetate and water were added to the mixture and the organic layer was separated. The organic layer was washed with water, dried (MgSO₄), filtered, and concentrated in vacuo. The residue was triturated and washed with hexane to give the title compound (1.288 g, 58%) as a pink solid. The solid was recrystallized from ethyl acetate-hexane to give white crystals. mp 135.9-137.4° C.

Reference Example 73

7-(2-Methoxy-1-methylethoxy)-5-[4-(methylsulfonyl)phenoxy]-1H-indole-2-carboxamide

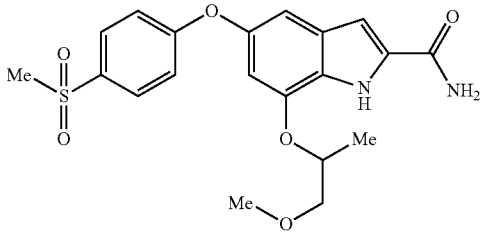 [SMILES: COCC(C)Oc1cc(Oc2ccc(S(C)(=O)=O)cc2)cc2cc(C(N)=O)[nH]c12]

To a solution of 7-(2-methoxy-1-methylethoxy)-5-[4-(methylsulfonyl)phenoxy]-1H-indole-2-carboxylic acid (1.072 g) in N,N-dimethylformamide (15 mL) were added 1-ethyl-3-(3-dimethylaminopropyl)carbodiimide hydrochloride (0.98 g) and 1-hydroxybenzotriazole ammonium salt (0.788 g) at room temperature. The mixture was stirred at room temperature for 1 h. The mixture was concentrated in vacuo. Water and ethyl acetate were added to the residue and the resultant was extracted with ethyl acetate. The organic layer was washed successively with brine and water, dried (MgSO₄), filtered, and concentrated in vacuo. The residue was purified by silica gel chromatography (ethyl acetate:

methanol=100:0 to 95:5, volume ratio) to give the title compound. (910 mg, 85%) as a white amorphous solid. MS 419 (MH⁺).

Reference Example 74

7-(1-Methylethoxy)-5-{[5-(methylsulfonyl)pyridin-2-yl]oxy}-1H-indole-2-carboxylic acid

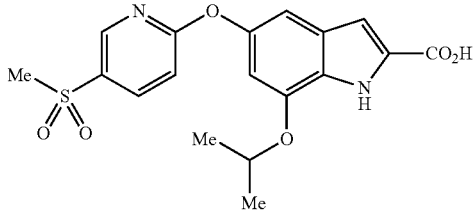 [SMILES: CC(C)Oc1cc(Oc2ccc(S(C)(=O)=O)cn2)cc2cc(C(=O)O)[nH]c12]

A mixture of ethyl 7-(1-methylethoxy)-5-{[5-(methylsulfonyl)pyridin-2-yl]oxy}-1H-indole-2-carboxylate (10.7 g), 1M aqueous sodium hydroxide solution (50 mL), ethanol (50 mL) and tetrahydrofuran (50 mL) was stirred at 50° C. for 2 h. 1M Hydrochloric acid (50 mL) was added to the mixture and the mixture was adjusted to pH=6 by 1M aqueous sodium hydroxide solution and water. The whole was extracted with ethyl acetate. The organic layer was washed with brine, dried (MgSO₄), filtered, and concentrated in vacuo to give the title compound (6.35 g, 64%) as a brown amorphous solid. MS 391 (MH⁺).

Reference Example 75

7-(1-Methylethoxy)-5-{[5-(methylsulfonyl)pyridin-2-yl]oxy}-1H-indole-2-carboxamide

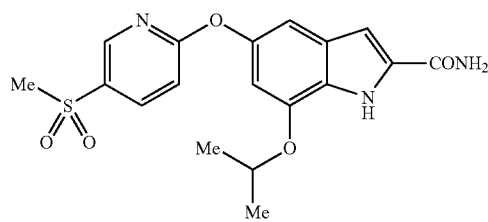 [SMILES: CC(C)Oc1cc(Oc2ccc(S(C)(=O)=O)cn2)cc2cc(C(N)=O)[nH]c12]

A mixture of 7-(1-methylethoxy)-5-{[5-(methylsulfonyl)pyridin-2-yl]oxy}-1H-indole-2-carboxylic acid (4.0 g), 1-hydroxybenzotriazole (2.07 g), 1-ethyl-3-(3-dimethylaminopropyl)carbodiimide hydrochloride (2.93 g) and N,N-dimethylformamide (50 mL) was stirred at 50° C. for 30 min, and then cooled to room temperature. An aqueous solution of ammonium hydroxide (10%, 10 mL) was added to the mixture. The whole was stirred at room temperature for 12 h. Water was added to the mixture and the mixture was extracted with ethyl acetate. The organic layer was washed successively with water, saturated aqueous solution of sodium hydrogen carbonate, and brine, dried (MgSO₄), filtered, and concentrated in vacuo. The residue was crystallized from diisopropyl ether-ethyl acetate to give the title compound (2.26 g, 57%) as brown crystals. MS 390 (MH+).

Reference Example 76

2-(Methoxymethyl)-5-[3-(1-methylethoxy)-4-nitrophenoxy]pyridine

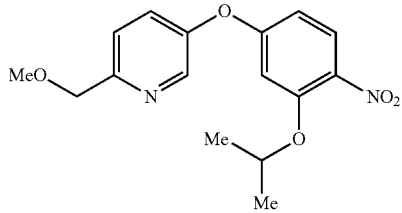

A mixture of 6-(bromomethyl)pyridin-3-yl benzenesulfonate (60.0 g), sodium methoxide (49.4 g) and methanol (800 mL) was refluxed for 20 h, and then cooled to 0° C. To the mixture was added hydrogen chloride in methanol (10%, 400 mL) at 0° C. After stirring at 0° C. for 15 min, the mixture was concentrated in vacuo. Toluene was added to the residue and the mixture was concentrated in vacuo to remove methanol. A mixture of the residue, 4-fluoro-2-(1-methylethoxy)-1-nitrobenzene (36.4 g), potassium carbonate (75.9 g) and N,N-dimethylformamide (300 mL) was stirred at 60° C. for 15 h, and then concentrated in vacuo. Water was added to the residue and the mixture was extracted with ethyl acetate. The organic layer was washed with brine, dried (MgSO$_4$), filtered, and concentrated in vacuo. The residue was purified by silica gel chromatography (ethyl acetate:hexane=1:4 to 1:1, volume ratio) to give the title compound (20.5 g, 35%) as a yellow oil. MS 319 (MH+).

Reference Example 77

4-{[6-(Methoxymethyl)pyridin-3-yl]oxy}-2-(1-methylethoxy)aniline

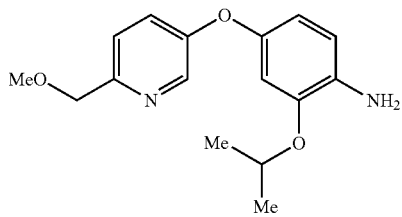 [SMILES: COCc1ccc(Oc2ccc([N+](=O)[O-])c(OC(C)C)c2)cn1]

A mixture of 2-(methoxymethyl)-5-[3-(1-methylethoxy)-4-nitrophenoxy]pyridine (20.5 g), iron (powder, 17.9 g), calcium chloride (710 mg), ethanol (400 mL) and water (100 mL) was refluxed for 5 h. The mixture was filtered with celite. The filtrate was concentrated in vacuo to remove ethanol. Water was added to the residue and the mixture was extracted with ethyl acetate. The organic layer was washed with brine, dried (MgSO$_4$), filtered, and concentrated in vacuo. The residue was purified by basic silica gel chromatography (ethyl acetate:hexane=5:95 to 1:3, volume ratio) to give the title compound (13.77 g, 74%) as a brown oil. MS 289 (MH+).

Reference Example 78

Ethyl 5-{[6-(methoxymethyl)pyridin-3-yl]oxy}-7-(1-methylethoxy)-1H-indole-2-carboxylate

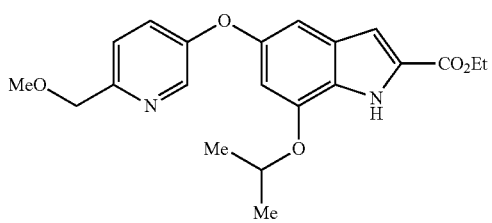 [SMILES: CCOC(=O)c1cc2cc(Oc3ccc(COC)nc3)cc(OC(C)C)c2[nH]1]

To a mixture of 4-{[6-(methoxymethyl)pyridin-3-yl]oxy}-2-(1-methylethoxy)aniline (13.7 g), ethanol (200 mL) and acetonitrile (20 mL) was added concentrated hydrochloric acid (8.7 mL) at 0° C. A solution of sodium nitrite (3.93 g) in water (10 mL) was added dropwise to the mixture at 0-5° C. The whole was stirred at 5° C. for 30 min to give a diazonium mixture. To a cooled (−20° C.) solution of potassium hydroxide (85%, 9.4 g) in ethanol (40 mL) and water (40 mL) was added ethyl 2-methyl-3-oxobutanoate (7.53 g). The diazonium mixture prepared above was added to the solution at −30 to −20° C. over a period of 15 min. The whole was stirred at −20° C. for 30 min. Water was added to the mixture and the mixture was extracted with ethyl acetate. The organic layer was washed successively with water and brine, dried (MgSO$_4$), filtered, and concentrated in vacuo. The residue was purified by silica gel chromatography (ethyl acetate:hexane=1:2 to 2:1, volume ratio) to give a yellow oil (9.45 g).

A mixture of p-toluenesulfonic acid monohydrate (8.9 g) and toluene (50 mL) was refluxed for 2 h with azeotropic removal of water, and then cooled to 90° C. A solution of the yellow oil described above (9.45 g) in toluene (50 mL) was added to the mixture at 90° C. The whole was stirred at 90° C. for 1 h, and then cooled to room temperature. An aqueous solution of sodium hydrogen carbonate was added to the mixture and the mixture was extracted with ethyl acetate. The organic layer was washed with brine, dried (MgSO$_4$), filtered, and concentrated in vacuo. The residue was purified by silica gel chromatography (ethyl acetate:hexane=1:4 to 1:1, volume ratio) to give a yellow oil (4.10 g).

A mixture of p-toluenesulfonic acid monohydrate (3.80 g) and toluene (50 mL) was refluxed for 2 h with azeotropic removal of water, and then cooled to 90° C. A solution of the yellow oil described above (4.0 g) in toluene (15 mL) was added to the mixture at 90° C. The whole was refluxed for 24 h, and then cooled to room temperature. An aqueous solution of sodium hydrogen carbonate was added to the mixture and the mixture was extracted with ethyl acetate-tetrahydrofuran. The organic layer was washed with brine, dried (MgSO$_4$), filtered, and concentrated in vacuo. The residue was purified by silica gel chromatography (ethyl acetate:hexane=1:4 to 2:1, volume ratio) to give title compound (1.32 g, 15%) as an orange oil. MS 385 (MH$^+$).

Reference Example 79

5-{[6-(Methoxymethyl)pyridin-3-yl]oxy}-7-(1-methylethoxy)-1H-indole-2-carboxylic acid

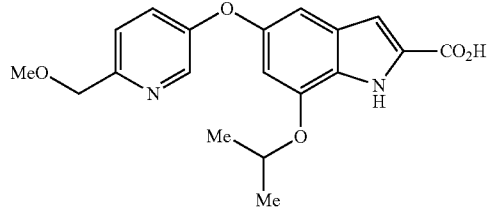 [SMILES: COCc1ccc(Oc2cc(OC(C)C)c3[nH]c(C(=O)O)cc3c2)cn1]

A mixture of ethyl 5-{[6-(methoxymethyl)pyridin-3-yl]oxy}-7-(1-methylethoxy)-1H-indole-2-carboxylate (1.65 g), 1M aqueous sodium hydroxide solution (10 mL), tetrahydrofuran (10 mL) and ethanol (10 mL) was stirred at room temperature for 15 h. Water and 1M hydrochloric acid (10 mL) were added to the mixture and the mixture was extracted with ethyl acetate. The organic layer was washed with brine, dried (MgSO$_4$), filtered, and concentrated in vacuo to give the title compound (1.43 g, 93%) as a brown amorphous solid. MS 357 (MH$^+$).

Reference Example 80

5-{[6-(Methoxymethyl)pyridin-3-yl]oxy}-7-(1-methylethoxy)-1H-indole-2-carboxamide

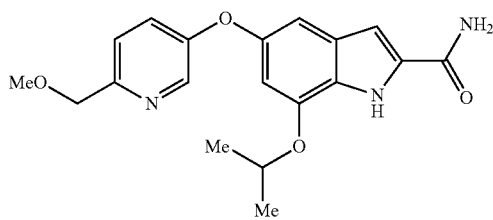 [SMILES: COCc1ccc(Oc2cc(OC(C)C)c3[nH]c(C(N)=O)cc3c2)cn1]

A mixture of 5-{[6-(methoxymethyl)pyridin-3-yl]oxy}-7-(1-methylethoxy)-1H-indole-2-carboxylic acid (1.43 g), 1-hydroxybenzotriazole (810 mg), 1-ethyl-3-(3-dimethylaminopropyl)carbodiimide hydrochloride (1.15 g) and N,N-dimethylformamide (50 mL) was stirred at room temperature for 30 min. An aqueous solution of ammonium hydroxide (25%, 5 mL) was added to the mixture. The whole was stirred at room temperature for 4.5 days. Water was added to the mixture and the mixture was extracted with ethyl acetate. The organic layer was washed successively with water, saturated aqueous solution of sodium hydrogen carbonate and brine, dried (MgSO$_4$) filtered, and concentrated in vacuo. The residue was washed with diisopropyl ether to give the title compound (1.05 g, 74%) as pale brown crystals. MS 356 (MH$^+$).

Reference Example 81

2-(Methoxymethyl)-5-(3-methoxy-4-nitrophenoxy)pyridine

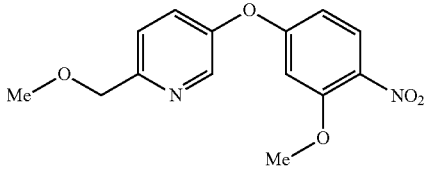

A mixture of 6-(bromomethyl)pyridin-3-yl benzenesulfonate (40.7 g), sodium methoxide (33.5 g) and methanol (600 mL) was refluxed for 15 h, and then cooled to 0° C. To the mixture was added hydrogen chloride in methanol (2M, 500 mL) at 0° C. After stirring at room temperature for 30 min, the mixture was concentrated in vacuo. Toluene was added to the residue and the mixture was concentrated in vacuo to remove methanol. A mixture of the residue, 4-fluoro-2-methoxy-1-nitrobenzene (21.2 g), potassium carbonate (120 g) and N,N-dimethylformamide (800 mL) was stirred at 90° C. for 20 h, and then concentrated in vacuo. Water was added to the residue and the mixture was extracted with ethyl acetate. The organic layer was washed with brine, dried (MgSO$_4$), filtered, and concentrated in vacuo. The residue was crystallized from ethyl acetate-hexane and the resultant was collected by filtration to give 25.45 g of the title compound as pale brown crystals. The mother liquid was concentrated in vacuo and the residue was purified by silica gel chromatography (ethyl acetate:hexane=1:9 to 1:1, volume ratio) to give 1.70 g of the title compound as yellow crystals. Total yield 27.15 g (75%). The crystals were recrystallized from ethyl acetate-hexane to give yellow prisms. MS 291 (MH$^+$).

Reference Example 82

2-Methoxy-4-{[6-(methoxymethyl)pyridin-3-yl]oxy}aniline

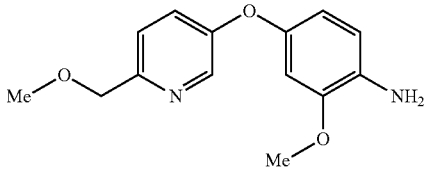 [SMILES: COCc1ccc(Oc2ccc([N+](=O)[O-])c(OC)c2)cn1]

A mixture of 2-(methoxymethyl)-5-(3-methoxy-4-nitrophenoxy)pyridine (27.0 g), iron (powder, 25.9 g), calcium chloride (1.03 g), ethanol (400 mL) and water (100 mL) was refluxed for 6 h. Then iron (powder, 12.9 g) and calcium chloride (1.03 g) were added to the mixture, and the whole was refluxed for further 2 h. The mixture was cooled to room temperature and filtered with celite. The filtrate was concentrated in vacuo to remove ethanol. Water was added to the residue and the mixture was extracted with ethyl acetate. The organic layer was washed with brine, dried (MgSO$_4$), filtered, and concentrated in vacuo. The residue was purified by silica gel chromatography (ethyl acetate:hexane=1:3 to 3:1, volume ratio) to give the title compound (20.1 g, 83%) as a brown oil. MS 261 (MH+).

Reference Example 83

Ethyl 2-[(2-methoxy-4-{[6-(methoxymethyl)pyridin-3-yl]oxy}phenyl)hydrazono]propanoate

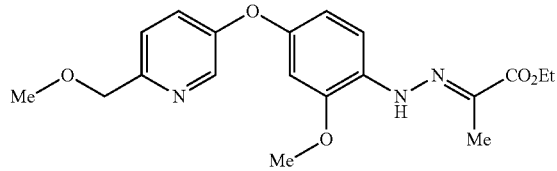 [SMILES: CCOC(=O)/C(C)=N/Nc1ccc(Oc2ccc(COC)nc2)cc1OC]

To a mixture of 2-methoxy-4-{[6-(methoxymethyl)pyridin-3-yl]oxy}aniline (20.1 g), ethanol (300 mL) and acetonitrile (30 mL) was added concentrated hydrochloric acid (14.2 mL) at 5° C. A solution of sodium nitrite (6.39 g) in water (20 mL) was added dropwise to the mixture at 5° C. The whole was stirred at room temperature for 30 min. The mixture was added to the mixture of potassium hydroxide (85%, 15.2 g), ethyl 2-methyl-3-oxobutanoate (12.2 g), ethanol (60 mL) and water (60 mL) at −20 to −10° C. over a period of 15 min. The whole was stirred at −20° C. for 30 min. Water was added to the mixture and the mixture was extracted with ethyl acetate. The organic layer was washed with brine, dried (MgSO4), filtered, and concentrated in vacuo. The residue was purified by silica gel chromatography (ethyl acetate:hexane=2:3 to 2:1, volume ratio) to give the title compound (12.58 g, 44%) as a brown oil. MS 374 (MH+).

Reference Example 84

Ethyl 7-methoxy-5-{[6-(methoxymethyl)pyridin-3-yl]oxy}-1H-indole-2-carboxylate

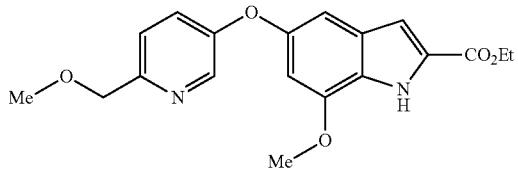 [SMILES: CCOC(=O)c1cc2cc(Oc3ccc(COC)nc3)cc(OC)c2[nH]1]

A mixture of p-toluenesulfonic acid hydrate (1.03 g) and toluene (15 mL) was refluxed for 2 h with azeotropic removal of water, and then cooled to 90° C. A solution of ethyl 2-[(2-methoxy-4-{[6-(methoxymethyl)pyridin-3-yl]oxy}phenyl)hydrazono]propanoate (1.0 g) in toluene (10 mL) was added to the mixture at 90° C. The whole was stirred at 90° C. for 1 h, and then refluxed for 2 h. An aqueous solution of sodium hydrogen carbonate was added to the mixture and the mixture was extracted with ethyl acetate. The organic layer was washed with brine, dried (MgSO4), filtered, and concentrated in vacuo. The residue was purified by basic silica gel chromatography (ethyl acetate:hexane=1:4 to 2:1, volume ratio) and then by silica gel chromatography (ethyl acetate:hexane=1:9 to 2:1, volume ratio) to give the title compound (140 mg, 15%) as pale yellow crystals. MS 357 (MH+).

Reference Example 85

7-(2-Methoxy-1-methylethoxy)-5-{[6-(methylsulfonyl)pyridin-3-yl]oxy}-1H-indole-2-carboxylic acid

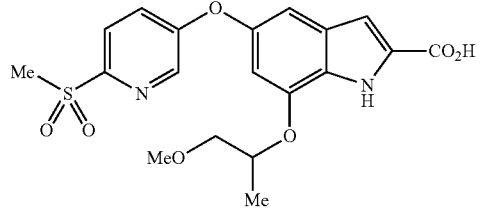 [SMILES: COCC(C)Oc1cc(Oc2ccc(S(C)(=O)=O)nc2)cc2cc(C(=O)O)[nH]c12]

To a solution of methyl 7-hydroxy-5-{[6-(methylsulfonyl)pyridin-3-yl]oxy}-1H-indole-2-carboxylate (2.5 g), tributylphosphine (2.79 g) and 1-methoxypropan-2-ol (1.24 g) in tetrahydrofuran (50 mL) was added 1,1'-(azodicarbonyl)dipiperidine (3.48 g) at 60° C. The whole was stirred at 60° C. for 1.5 h and then concentrated in vacuo. Diisopropyl ether was added to the residue and insoluble materials were removed by filtration. The filtrate was concentrated in vacuo. The residue was purified by silica gel chromatography (ethyl acetate:hexane=1:2 to 2:1, volume ratio) and then by basic silica gel chromatography (ethyl acetate:hexane=1:2 to 2:1, volume ratio) to give a colorless oil. A mixture of the oil, 1M aqueous sodium hydroxide solution (15 mL), tetrahydrofuran (15 mL) and methanol (15 mL) was stirred at room temperature for 20 h. The mixture was washed with diethyl ether. The organic layer was extracted with 1M aqueous sodium hydroxide solution. The water layers were combined, acidified by 1M hydrochloric acid, and extracted with ethyl acetate. The organic layer was washed with brine, dried (MgSO4), filtered, and concentrated in vacuo. The residue was washed with hexane to give the title compound (1.50 g, 52%) as colorless crystals. MS 421 (MH+).

Reference Example 86

7-(2-Methoxy-1-methylethoxy)-5-{[6-(methylsulfonyl)pyridin-3-yl]oxy}-1H-indole-2-carboxamide

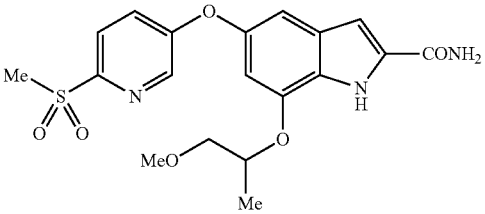 [SMILES: COCC(C)Oc1cc(Oc2ccc(S(C)(=O)=O)nc2)cc2cc(C(N)=O)[nH]c12]

A mixture of 7-(2-methoxy-1-methylethoxy)-5-{[6-(methylsulfonyl)pyridin-3-yl]oxy}-1H-indole-2-carboxylic acid (1.40 g), 1-hydroxybenzotriazole (670 mg), 1-ethyl-3-(3-dimethylaminopropyl)carbodiimide hydrochloride (0.95 g) and N,N-dimethylformamide (50 mL) was stirred at room temperature for 30 min. An aqueous solution of ammonium hydroxide (25%, 5 mL) was added to the mixture. The whole was stirred at room temperature for 15 h. Water was added to the mixture and the mixture was extracted with ethyl acetate. The organic layer was washed successively with water, saturated aqueous solution of sodium hydrogen carbonate and brine, dried (MgSO₄), filtered, and concentrated in vacuo. The residue was washed with ethyl acetate-hexane to give the title compound (1.35 g, 98%) as colorless crystals. MS 420 (MH⁺).

Reference Example 87

Ethyl 2-({2-hydroxy-4-[4-(methylsulfonyl)phenoxy]phenyl}hydrazono)propanoate

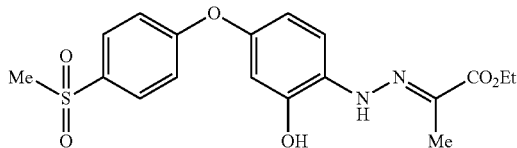 [SMILES: CCOC(=O)/C(C)=N/Nc1ccc(Oc2ccc(S(C)(=O)=O)cc2)cc1O]

To an ice-cooled and stirred mixture of 2-amino-5-[4-(methylsulfonyl)phenoxy]phenol (4.3 g) and concentrated hydrochloric acid (2.8 mL) in ethanol (40 mL) and acetonitrile (10 ml) was added a solution of sodium nitrite (1.27 g) in water (5 mL) at −5 to −10° C., and the mixture was diluted with water (20 mL). After stirred at −5 to −10° C. for 30 min, the resulting clear brown solution was added dropwise to a cooled solution of potassium hydroxide (85%, 3.05 g) and ethyl 2-methyl-3-oxobutanoate (2.44 mL) in ethanol (30 mL) and water (30 ml) at −10 to −20° C. After stirred at −10 to −20° C. for 20 min, the mixture was partitioned between ethyl acetate and aqueous citric acid solution. The organic layer was washed with brine, dried (MgSO₄), filtered, and concentrated in vacuo. The residual light brown solid was washed with ethyl acetate-hexane to give the title compound (5.81 g, 96%) as a light orange solid. MS 391 (MH⁺).

Reference Example 88

Ethyl 2-({2-[(methylsulfonyl)oxy]-4-[4-(methylsulfonyl)phenoxy]phenyl}hydrazono)propanoate

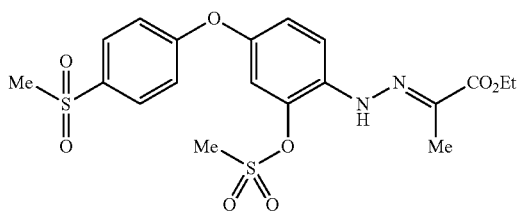 [SMILES: CCOC(=O)/C(C)=N/Nc1ccc(Oc2ccc(S(C)(=O)=O)cc2)cc1OS(C)(=O)=O]

To an ice-cooled and stirred solution of ethyl 2-({2-hydroxy-4-[4-(methylsulfonyl)phenoxy]phenyl}hydrazono)propanoate (5.8 g) in pyridine (60 mL) was added methanesulfonyl chloride (1.4 mL), and the mixture was stirred at 4° C. for 1 h and then at room temperature for 3 h. The reaction mixture was concentrated in vacuo and the residue was partitioned between ethyl acetate and aqueous citric acid solution. The organic layer was washed successively with aqueous citric acid solution and brine, dried (MgSO₄), filtered, and concentrated in vacuo. The residue was purified by short silica gel chromatography (ethyl acetate) to give light orange crystals, which were washed with ethyl acetate-hexane to give the title compound (6.49 g, 93%) as light orange crystals. MS 471 (MH⁺).

Reference Example 89

Ethyl 7-[(methylsulfonyl)oxy]-5-[4-(methylsulfonyl)phenoxy]-1H-indole-2-carboxylate

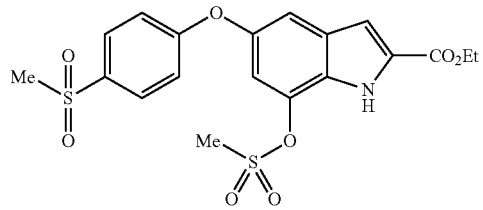 [SMILES: CCOC(=O)c1cc2cc(Oc3ccc(S(C)(=O)=O)cc3)cc(OS(C)(=O)=O)c2[nH]1]

A mixture of p-toluenesulfonic acid hydrate (0.63 g) and toluene (40 mL) was refluxed for 2 h with azeotropic removal of water, and then cooled to 50° C. Ethyl 2-({2-[(methylsulfonyl)oxy]-4-[4-(methylsulfonyl)phenoxy]phenyl}hydrazono)propanoate (0.52 g) was added to the mixture at 50° C. After stirring at 50° C. for 30 min, the reaction mixture was partitioned between ethyl acetate and aqueous sodium hydrogen carbonate. The organic layer was washed successively with aqueous sodium hydrogen carbonate and brine, dried (MgSO₄), filtered, and concentrated in vacuo. The residue was purified by silica gel chromatography (ethyl acetate:hexane=35:65 to 45:55, volume ratio) to give the title compound (235 mg, 46%) as pale yellow crystals. MS 452 (MH⁺).

Reference Example 90

7-Hydroxy-5-[4-(methylsulfonyl)phenoxy]-1H-indole-2-carboxylic acid

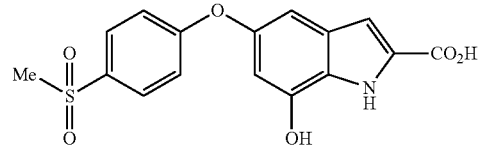 [SMILES: CS(=O)(=O)c1ccc(Oc2cc(O)c3[nH]c(C(=O)O)cc3c2)cc1]

To a mixture of ethyl 7-[(methylsulfonyl)oxy]-5-[4-(methylsulfonyl)phenoxy]-1H-indole-2-carboxylate (2.81 g), tetrahydrofuran (30 mL) and methanol (20 mL) was added a solution of potassium hydroxide (85%, 1.8 g) in water (20 mL). The mixture was stirred at room temperature for 15 h and then partitioned between ethyl acetate and aqueous citric acid solution. The organic layer was washed with brine, dried (MgSO₄), filtered, and concentrated to give a light brown solid, which was washed with ethyl acetate-hexane to give the title compound (2.12 g, 98%) as a light orange solid.

¹H NMR (DMSO-d₆) δ 3.17 (3H, s), 6.40 (1H, d, J=1.8 Hz), 6.87 (1H, d, J=1.8 Hz), 7.04 (1H, d, J=2.4 Hz), 7.10 (2H, dd, J=1.8, 6.9 Hz), 7.86 (2H, dd, J=1.8, 6.9 Hz), 9.91 (1H, s).

Reference Example 91

N-[2-(Benzylsulfanyl)-3,3-dimethoxypropyl]-7-hydroxy-5-[4-(methylsulfonyl)phenoxy]-1H-indole-2-carboxamide

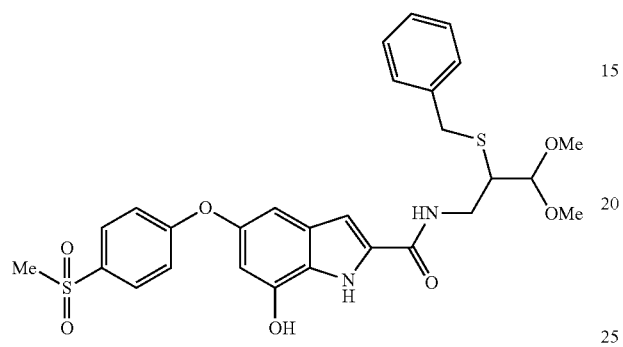

To an ice-cooled and stirred mixture of 7-hydroxy-5-[4-(methylsulfonyl)phenoxy]-1H-indole-2-carboxylic acid (2.1 g) and 2-(benzylsulfanyl)-3,3-dimethoxypropan-1-amine (2.9 g) in N,N-dimethylformamide (50 mL) were added 1-hydroxybenzotriazole (1.1 g), and 1-ethyl-3-(3-dimethylaminopropyl)carbodiimide hydrochloride (1.6 g). After stirred at 4° C. to room temperature for 15 h, the reaction mixture was concentrated in vacuo and the residue was purified by silica gel chromatography (ethyl acetate:hexane=35:65 to 60:40, volume ratio) to give light yellow crystals, which were washed with ethyl acetate-hexane to give the title compound (1.73 g, 50%) as pale yellow needles. MS 569 (MH⁺).

Reference Example 92

N-[2-(Benzylsulfanyl)-3,3-dimethoxypropyl]-7-(2-methoxy-1-methylethoxy)-5-[4-(methylsulfonyl)phenoxy]-1H-indole-2-carboxamide

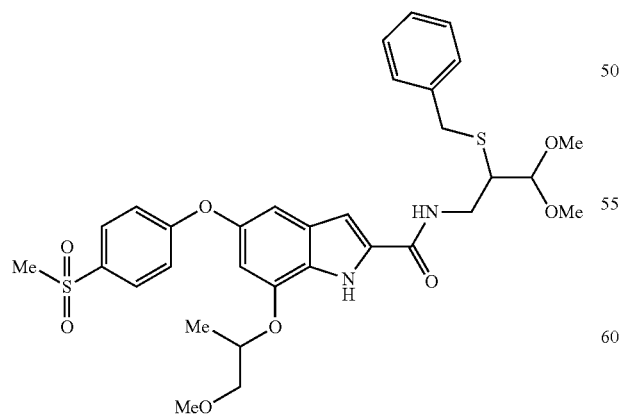

To a stirred solution of N-[2-(benzylsulfanyl)-3,3-dimethoxypropyl]-7-hydroxy-5-[4-(methylsulfonyl)phenoxy]-1H-indole-2-carboxamide (1.73 g), tributylphosphine (1.4 mL) and 1-methoxypropan-2-ol (0.59 mL) in tetrahydrofuran (50 mL) was added 1,1'-(azodicarbonyl)dipiperidine (1.53 g) at room temperature under argon atmosphere. The whole mixture was stirred at 50° C. for 4 h, and tributylphosphine (1.4 mL), and 1-methoxypropan-2-ol (0.59 mL) and 1,1'-(azodicarbonyl)dipiperidine (1.53 g) were added thereto. After stirred at 50° C. for 3 h, the reaction mixture was concentrated in vacuo. The residue was diluted with diethyl ether and the insoluble materials were removed by filtration and washed with diethyl ether. The combined filtrate and washings were concentrated in vacuo and the residue was purified by silica gel chromatography (ethyl acetate:hexane=35:65 to 60:40) to give a light yellow oil. The oil was partitioned between ethyl acetate and water. The organic layer was washed with successively water and brine, dried (MgSO₄), filtered, and concentrated to give a yellow oil, which was purified by silica gel chromatography (ethyl acetate:hexane=35:65 to 70:30, volume ratio) to give the title compound (1.6 g, 82%) as a pale yellow oil. MS 641 (MH⁺).

Reference Example 93

2-(Benzyloxy)-3,4-difluoro-1-nitrobenzene

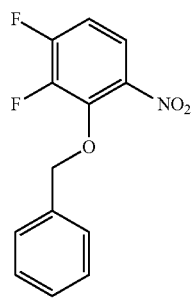 [SMILES: O=[N+]([O-])c1ccc(F)c(F)c1OCc1ccccc1]

A mixture of 2,3-difluoro-6-nitrophenol (15.1 g), benzyl bromide (10.8 mL) and potassium carbonate (11.9 g) in N,N-dimethylformamide (60 mL) was stirred at room temperature for 15 h. The reaction mixture was concentrated in vacuo and the residue was partitioned between ethyl acetate and water. The organic layer was washed with successively water and brine, dried (MgSO₄), filtered, and concentrated to give the title compound (22.1 g, 97%) as a light yellow solid. MS 264 (MH⁺).

Reference Example 94

5-[3-(Benzyloxy)-2-fluoro-4-nitrophenoxy]-2-(methylsulfonyl)pyridine

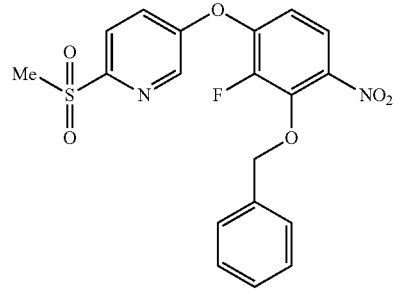

A mixture of 2-(benzyloxy)-3,4-difluoro-1-nitrobenzene (7.65 g), 6-(methylsulfonyl)pyridin-3-ol (5.0 g) and potassium carbonate (4.4 g) in N,N-dimethylformamide (40 mL) was stirred at 90° C. for 5 h. The reaction mixture was concentrated in vacuo and the residue was partitioned between ethyl acetate and water. The organic layer was washed with successively water and brine, dried (MgSO₄), filtered, and concentrated in vacuo. The residue was purified by silica gel chromatography (ethyl acetate:hexane=25:75 to 40:60, volume ratio) to give light yellow crystals, which were washed with ethyl acetate-hexane to give the title compound (8.4 g, 69%) as pale yellow crystals.

$^1$H NMR (CDCl$_3$) δ 3.25 (3H, s), 5.31 (2H, s), 6.94 (1H, dd, J=5.1, 9.6 Hz), 7.32-7.48 (6H, m), 7.72 (1H, dd, J=2.1, 9.6 Hz), 8.09 (1H, d, J=9.6 Hz), 8.46 (1H, d, J=2.7 Hz).

Reference Example 95

2-(Benzyloxy)-3-fluoro-4-{[6-(methylsulfonyl)pyridin-3-yl]oxy}aniline

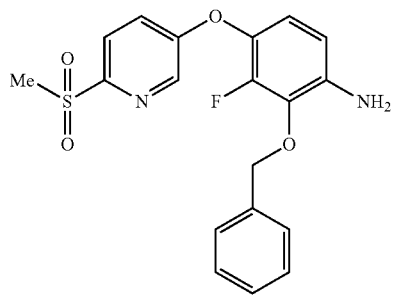 [SMILES: CS(=O)(=O)c1ccc(Oc2ccc([N+](=O)[O-])c(OCc3ccccc3)c2F)cn1]

A mixture of 5-[3-(benzyloxy)-2-fluoro-4-nitrophenoxy]-2-(methylsulfonyl)pyridine (8.4 g), iron (powder, 5.5 g), calcium chloride (0.24 g), ethanol (200 mL) and water (40 mL) was refluxed for 4 h. The mixture was cooled to room temperature and filtered through a celite pad. The filtrate was concentrated in vacuo to remove ethanol. The residue was partitioned between ethyl acetate and brine. The organic layer was washed with brine, dried (MgSO₄), filtered, and concentrated in vacuo. The residue was purified by silica gel chromatography (ethyl acetate:hexane=20:80 to 40:60, volume ratio) to give the title compound (5.5 g, 70%) as a dark green oil. MS 389 (MH⁺).

Reference Example 96

6-Amino-2-fluoro-3-{[6-(methylsulfonyl)pyridin-3-yl]oxy}phenol

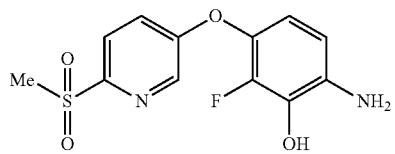 [SMILES: CS(=O)(=O)c1ccc(Oc2ccc(N)c(O)c2F)cn1]

A mixture of 2-(benzyloxy)-3-fluoro-4-{[6-(methylsulfonyl)pyridin-3-yl]oxy}aniline (5.5 g), 10% palladium on carbon (containing 50% water, 1.6 g), tetrahydrofuran (100 mL) and methanol (80 mL) was hydrogenated at room temperature for 20 h under balloon pressure. The catalyst was removed by filtration and washed with tetrahydrofuran-methanol. The combined filtrate and washings were concentrated in vacuo and the residue was dissolved in ethyl acetate. The solution was concentrated in vacuo to give the title compound (4.2 g, 100%) as a light brown amorphous solid. MS 299 (MH⁺).

Reference Example 97

Ethyl 2-[(3-fluoro-2-hydroxy-4-{[6-(methylsulfonyl)pyridin-3-yl]oxy}phenyl)hydrazono]propanoate

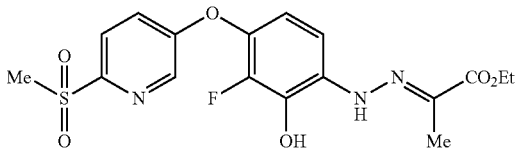 [SMILES: CCOC(=O)/C(C)=N/Nc1ccc(Oc2ccc(S(C)(=O)=O)nc2)c(F)c1O]

To an ice-cooled and stirred mixture of 6-amino-2-fluoro-3-{[6-(methylsulfonyl)pyridin-3-yl]oxy}phenol (4.2 g) and concentrated hydrochloric acid (2.6 mL) in ethanol (40 mL) and water (10 mL) was added portionwise a solution of sodium nitrite (1.16 g) in water (20 mL) at −10° C. After stirred at −10° C. for 10 min, the solution was added dropwise to a cooled solution of potassium hydroxide (85%, 2.8 g) and ethyl 2-methyl-3-oxobutanoate (2.2 mL) in ethanol (25 mL) and water (25 mL) below −5° C. After stirred at −5 to −10° C. for 30 min, the mixture was partitioned between ethyl acetate and aqueous citric acid solution. The organic layer was washed with brine, dried (MgSO₄), filtered, and concentrated in vacuo. The residual brown oil was purified by silica gel chromatography (ethyl acetate:hexane=2:1 to 4:1, volume ratio) to give the title compound (4.94 g, 85%) as light brown prisms. MS 412 (MH⁺).

Reference Example 98

Ethyl 2-[(3-fluoro-2-[(methylsulfonyl)oxy]-4-{[6-(methylsulfonyl)pyridin-3-yl]oxy}phenyl)hydrazono]propanoate

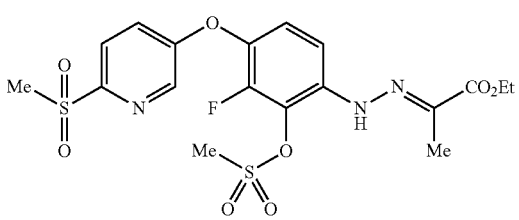 [SMILES: CCOC(=O)/C(C)=N/Nc1ccc(Oc2ccc(S(C)(=O)=O)nc2)c(F)c1OS(C)(=O)=O]

To an ice-cooled and stirred solution of ethyl 2-[(3-fluoro-2-hydroxy-4-{[6-(methylsulfonyl)pyridin-3-yl]oxy}phenyl)hydrazono]propanoate (4.95 g) in pyridine (50 mL) was added methanesulfonyl chloride (1.1 mL), and the mixture was stirred at 4° C. to room temperature for 15 h. The reaction mixture was concentrated in vacuo and the residue was partitioned between ethyl acetate and aqueous citric acid solution. The organic layer was washed successively with aqueous citric acid solution and brine, dried (MgSO₄), filtered, and concentrated in vacuo. The residual light brown solid was washed with ethyl acetate-hexane to give the title compound (5.4 g, 92%) as a pale brown solid. MS 490 (MH+).

Reference Example 99

Ethyl 6-fluoro-7-[(methylsulfonyl)oxy]-5-{[6-(methylsulfonyl)pyridin-3-yl]oxy}-1H-indole-2-carboxylate

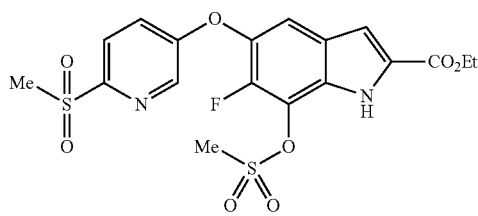 [SMILES: CCOC(=O)c1cc2cc(Oc3ccc(S(C)(=O)=O)nc3)c(F)c(OS(C)(=O)=O)c2[nH]1]

A mixture of p-toluenesulfonic acid monohydrate (6.2 g) and toluene (180 mL) was refluxed for 1 h with azeotropic removal of water, and then cooled to 60° C. Ethyl 2-[(3-fluoro-2-[(methylsulfonyl)oxy]-4-{[6-(methylsulfonyl)pyridin-3-yl]oxy}phenyl)hydrazono]propanoate (5.4 g) was added to the mixture at 60° C. After stirring at 60° C. for 1 h, the reaction mixture was partitioned between ethyl acetate and aqueous sodium hydrogen carbonate. The organic layer was washed successively with aqueous sodium hydrogen carbonate and brine, dried (MgSO4), filtered, and concentrated in vacuo to give a pale yellow solid.

Methanesulfonic acid (3.6 mL) was added to Eaton's reagent (5.3 g) at 90° C., and the mixture was stirred at 90° C. for 30 min, followed by an addition of toluene (30 mL). After the mixture was stirred at 90° C. for 10 min, a suspension of the pale yellow solid described above in toluene (50 mL) was added portionwise to the mixture. The mixture was stirred at 90° C. for 2 h and then cooled to room temperature. The mixture was partitioned between ethyl acetate and aqueous sodium hydrogen carbonate. The organic layer was washed with brine, dried (MgSO4), filtered, and concentrated in vacuo. The residual brown oil was purified by silica gel chromatography (ethyl acetate:hexane=35:65 to 50:50, volume ratio) to give a pale yellow solid, which was washed with ethyl acetate-hexane to give the title compound (3.1 g, 62%) as colorless crystals. MS 473 (MH+).

Reference Example 100

6-Fluoro-7-hydroxy-5-{[6-(methylsulfonyl)pyridin-3-yl]oxy}-1H-indole-2-carboxylic acid

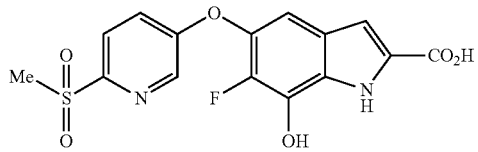 [SMILES: CS(=O)(=O)c1ccc(Oc2cc3cc(C(=O)O)[nH]c3c(O)c2F)cn1]

To a mixture of ethyl 6-fluoro-7-[(methylsulfonyl)oxy]-5-{[6-(methylsulfonyl)pyridin-3-yl]oxy}-1H-indole-2-carboxylate (3.1 g), tetrahydrofuran (25 mL) and methanol (25 mL) was added a solution of potassium hydroxide (85%, 1.9 g) in water (15 mL). The mixture was stirred at room temperature for 15 h and then concentrated in vacuo. The residue was partitioned between ethyl acetate and aqueous citric acid solution. The organic layer was washed with brine, dried (MgSO4), filtered, and concentrated to give a light pink solid, which was washed with ethyl acetate-hexane to give the title compound (2.52 g, 100%) as a light pink solid. MS 365 (MH+).

Reference Example 101

6-Fluoro-7-hydroxy-5-{[6-(methylsulfonyl)pyridin-3-yl]oxy}-1H-indole-2-carboxamide

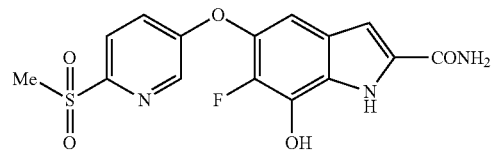 [SMILES: CS(=O)(=O)c1ccc(Oc2cc3cc(C(N)=O)[nH]c3c(O)c2F)cn1]

To an ice-cooled and stirred mixture of 6-fluoro-7-hydroxy-5-{[6-(methylsulfonyl)pyridin-3-yl]oxy}-1H-indole-2-carboxylic acid (2.5 g) in N,N-dimethylformamide (30 mL) were added 1-hydroxybenzotriazole ammonium salt (1.25 g) and 1-ethyl-3-(3-dimethylaminopropyl)carbodiimide hydrochloride (1.57 g). After stirred at 4° C. to room temperature for 15 h, the reaction mixture was partitioned between ethyl acetate and aqueous citric acid solution. The organic layer was washed successively with aqueous sodium hydrogen carbonate and brine, dried (MgSO4), filtered, and concentrated to give a light brown solid, which was washed with tetrahydrofuran-ethyl acetate to give the title compound (0.55 g, 22%) as a light pink solid. MS 366 (MH+).

Reference Example 102

6-Fluoro-7-(2-methoxyethoxy)-5-{[6-(methylsulfonyl)pyridin-3-yl]oxy}-1H-indole-2-carboxamide

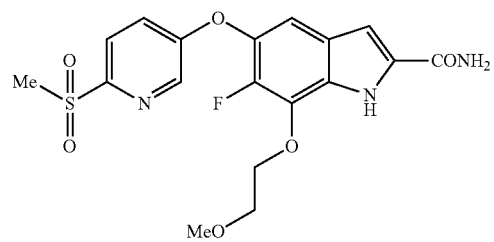 [SMILES: COCCOc1c(F)c(Oc2ccc(S(C)(=O)=O)nc2)cc2cc(C(N)=O)[nH]c12]

A mixture of 6-fluoro-7-hydroxy-5-{[6-(methylsulfonyl)pyridin-3-yl]oxy}-1H-indole-2-carboxamide (0.98 g), 2-methoxyethanol (0.43 mL), tributylphosphine (1.24 mL) and 1,1'-(azodicarbonyl)dipiperidine (1.35 g) in tetrahydrofuran (130 ml) was stirred at 50° C. for 6 h under argon atmosphere. To the mixture were added 2-methoxyethanol (0.43 mL), tributylphosphine (1.24 mL) and 1,1'-(azodicarbonyl)dipiperidine (1.35 g) and the mixture was stirred at 50° C. for 15 h under argon atmosphere. Furthermore, 2-methoxyethanol (0.43 mL), tributylphosphine (1.24 mL) and 1,1'-(azodicarbonyl)dipiperidine (1.35 g) were added to the mixture. After stirred at 50° C. for 18 h under argon atmosphere, the mixture was concentrated in vacuo. The resulting insoluble materials were filtered off and the filtrate was concentrated in vacuo. The residue was purified by basic silica gel chromatography (ethyl acetate:hexane=30:70 to 100:0, volume ratio) to give the title compound (0.61 g, 54%) as a pale pink amorphous solid. MS 424 (MH⁺).

Reference Example 103

6-Fluoro-7-(2-methoxyethoxy)-5-{[6-(methylsulfonyl)pyridin-3-yl]oxy}-1H-indole-2-carbothioamide

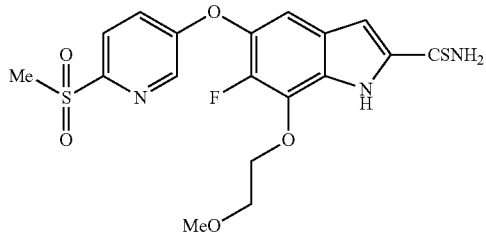

A mixture of 6-fluoro-7-(2-methoxyethoxy)-5-{[6-(methylsulfonyl)pyridin-3-yl]oxy}-1H-indole-2-carboxamide (0.61 g) and Lawesson's reagent (0.61 g) in tetrahydrofuran (25 mL) was stirred at 55° C. for 2 h. The reaction mixture was concentrated in vacuo. The residue was purified by silica gel chromatography (ethyl acetate:hexane=40:60 to 70:30, volume ratio) to give light yellow crystals, which were washed with ethyl acetate-hexane to give the title compound (585 mg, 92%) as light yellow crystals. MS 440 (MH⁺).

Reference Example 104

Methyl 7-ethoxy-5-{[6-(methylsulfonyl)pyridin-3-yl]oxy}-1H-indole-2-carboxylate

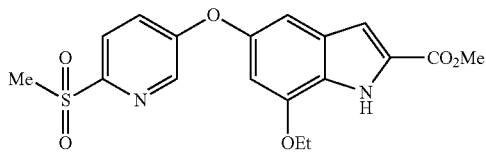 [SMILES: CCOc1cc(Oc2ccc(S(C)(=O)=O)nc2)cc2cc(C(=O)OC)[nH]c12]

To an ice-cooled and stirred solution of methyl 7-hydroxy-5-{[6-(methylsulfonyl)pyridin-3-yl]oxy}-1H-indole-2-carboxylate (1.2 g) and potassium carbonate (0.50 g) in N,N-dimethylformamide (10 mL)-tetrahydrofuran (30 mL) was added ethyl iodide (0.28 mL), and the mixture was stirred at room temperature for 18 h and then at 55° C. for 15 h. The reaction mixture was concentrated in vacuo. The residue was partitioned between ethyl acetate and aqueous citric acid solution. The organic layer was washed successively with water and brine, dried (MgSO₄), filtered, and concentrated in vacuo. The residue was purified by silica gel chromatography (ethyl acetate:hexane=25:75 to 40:60, volume ratio) to give the title compound (0.65 g, 50%) as light yellow crystals. MS 391 (MH⁺).

Reference Example 105

7-Ethoxy-5-{[6-(methylsulfonyl)pyridin-3-yl]oxy}-1H-indole-2-carboxylic acid

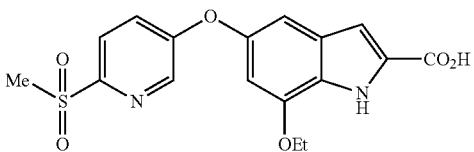 [SMILES: CCOc1cc(Oc2ccc(S(C)(=O)=O)nc2)cc2cc(C(=O)O)[nH]c12]

To a mixture of methyl 7-ethoxy-5-{[6-(methylsulfonyl)pyridin-3-yl]oxy}-1H-indole-2-carboxylate (0.65 g), tetrahydrofuran (10 mL) and methanol (10 mL) was added a solution of potassium hydroxide (85%, 0.33 g) in water (5 mL). The mixture was stirred at room temperature for 15 h and then partitioned between ethyl acetate and aqueous citric acid solution. The organic layer was washed with brine, dried (MgSO₄), filtered, and concentrated to give a light yellow oil, which was crystallized from ethyl acetate-hexane to give the title compound (548 mg, 88%) as pale yellow crystals. MS 377 (MH⁺).

Reference Example 106

7-Ethoxy-5-{[6-(methylsulfonyl)pyridin-3-yl]oxy}-1H-indole-2-carboxamide

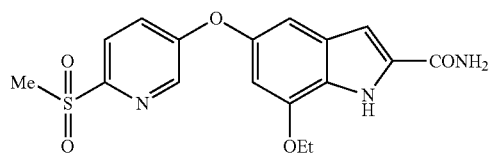 [SMILES: CCOc1cc(Oc2ccc(S(C)(=O)=O)nc2)cc2cc(C(N)=O)[nH]c12]

To an ice-cooled and stirred mixture of 7-ethoxy-5-{[6-(methylsulfonyl)pyridin-3-yl]oxy}-1H-indole-2-carboxylic acid (0.54 g) in N,N-dimethylformamide (20 mL) were added 1-hydroxybenzotriazole ammonium salt (0.33 g) and 1-ethyl-3-(3-dimethylaminopropyl)carbodiimide hydrochloride (0.42 g). After stirred at 4° C. to room temperature for 15 h, the reaction mixture was partitioned between ethyl acetate and water. The organic layer was washed successively with aqueous sodium hydrogen carbonate and brine, dried (MgSO₄), filtered, and concentrated to give a light yellow oil,

Reference Example 107

7-Ethoxy-5-{[6-(methylsulfonyl)pyridin-3-yl]oxy}-1H-indole-2-carbothioamide

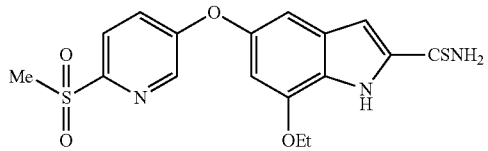

A mixture of 7-ethoxy-5-{[6-(methylsulfonyl)pyridin-3-yl]oxy}-1H-indole-2-carboxamide (0.43 g) and Lawesson's reagent (0.28 g) in tetrahydrofuran (30 mL) was stirred at 55° C. for 2 h. The reaction mixture was concentrated to give a light yellow oil, which was crystallized from ethyl acetate-hexane to give the title compound (414 mg, 92%) as light yellow crystals. MS 392 (MH+).

Reference Example 108

Ethyl 7-methoxy-5-[4-(methylsulfonyl)phenoxy]-1H-indole-2-carboxylate

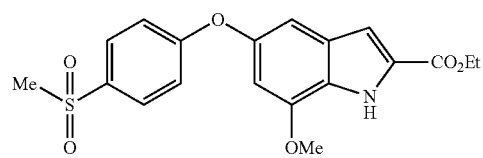 [SMILES: CCOC(=O)c1cc2cc(Oc3ccc(S(C)(=O)=O)cc3)cc(OC)c2[nH]1]

To an ice-cooled and stirred solution of ethyl 7-hydroxy-5-[4-(methylsulfonyl)phenoxy]-1H-indole-2-carboxylate (1.08 g) in ethyl acetate (30 mL)-methanol (8 mL) was added 2M trimethylsilyldiazomethane (diethyl ether solution, 2.8 mL), and the mixture was stirred at 4° C. for 2 h, followed by an addition of 2M trimethylsilyldiazomethane (diethyl ether solution, 2.8 mL). After stirred at 4° C. for 1 h, the reaction mixture was quenched with 1M hydrochloric acid and extracted with ethyl acetate. The organic layer was washed successively with aqueous sodium hydrogen carbonate and brine, dried (MgSO4), filtered, and concentrated to give a light yellow oil, which was crystallized from ethyl acetate-hexane to give the title compound (933 mg, 83%) as pale yellow crystals. mp 161-162° C.

Reference Example 109

7-Methoxy-5-[4-(methylsulfonyl)phenoxy]-1H-indole-2-carboxylic acid

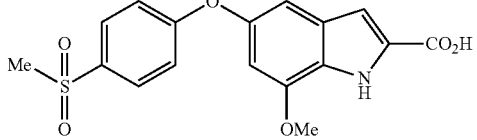

To a stirred solution of ethyl 7-methoxy-5-[4-(methylsulfonyl)phenoxy]-1H-indole-2-carboxylate (0.93 g) in tetrahydrofuran (15 mL) and methanol (15 mL) was added a solution of potassium hydroxide (85%, 0.50 g) in water (10 mL). The mixture was stirred at room temperature for 15 h and then concentrated in vacuo. The residue was partitioned between ethyl acetate and aqueous citric acid solution. The organic layer was washed with brine, dried (MgSO4), filtered, and concentrated to give a light yellow amorphous solid, which was crystallized from ethyl acetate-hexane to give the title compound (783 mg, 91%) as pale yellow crystals. MS 362 (MH+).

Reference Example 110

7-Methoxy-5-[4-(methylsulfonyl)phenoxy]-1H-indole-2-carboxamide

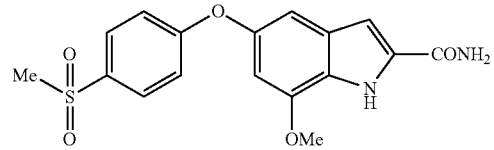

To an ice-cooled and stirred mixture of 7-methoxy-5-[4-(methylsulfonyl)phenoxy]-1H-indole-2-carboxylic acid (0.78 g) in N,N-dimethylformamide (20 mL) were added 1-hydroxybenzotriazole ammonium salt (0.66 g) and 1-ethyl-3-(3-dimethylaminopropyl)carbodiimide hydrochloride (0.83 g). After stirred at room temperature for 7 h, the reaction mixture was partitioned between ethyl acetate and water. The organic layer was washed successively with aqueous sodium hydrogen carbonate and brine, dried (MgSO4), filtered, and concentrated to give a light yellow amorphous solid, which was crystallized from ethyl acetate-hexane to give the title compound (733 mg, 94%) as pale yellow crystals. MS 361 (MH+).

Reference Example 111

7-Methoxy-5-[4-(methylsulfonyl)phenoxy]-1H-indole-2-carbothioamide

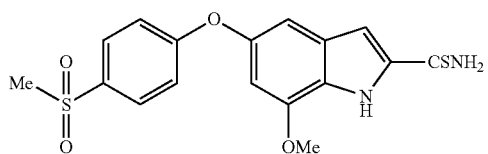

A mixture of 7-methoxy-5-[4-(methylsulfonyl)phenoxy]-1H-indole-2-carboxamide (0.73 g) and Lawesson's reagent (0.49 g) in tetrahydrofuran (30 mL) was stirred at 55° C. for 3 h. The reaction mixture was concentrated to give a light yellow oil, which was crystallized from ethyl acetate-hexane to give the title compound (691 mg, 91%) as light yellow prisms. MS 375 (MH+).

Example 1

Ethyl (2-{7-(benzyloxy)-5-[4-(methylsulfonyl)phenoxy]-1H-indol-2-yl}-4,5-dihydro-1,3-thiazol-5-yl)acetate

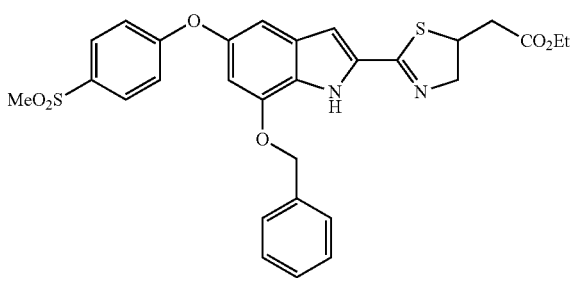 [SMILES: CCOC(=O)CC1CN=C(c2cc3cc(Oc4ccc(S(C)(=O)=O)cc4)cc(OCc4ccccc4)c3[nH]2)S1]

7-(Benzyloxy)-5-[4-(methylsulfonyl)phenoxy]-1H-indole-2-carboxamide (640 mg) was dissolved in tetrahydrofuran (20 mL), Lawesson's reagent (593 mg) was added, and the mixture was stirred at 50° C. for 50 min. The reaction solution was concentrated under reduced pressure, and the residue was crystallized from a mixed solvent of tetrahydrofuran-hexane. The obtained yellow crystals were washed with diisopropyl ether, and dried. The obtained yellow crystals were dissolved in a mixed solvent of tetrahydrofuran (12 mL)-toluene (20 mL), ethyl 2-butynoate (0.49 mL) and tributylphosphine (0.42 mL) were added, and the mixture was stirred at 50° C. for 1.5 hr. The reaction solution was concentrated under reduced pressure, and the residue was subjected to silica gel column chromatography (ethyl acetate:hexane=5:95 to 55:45, volume ratio) to give the title compound (529 mg, yield 64%) as a yellow amorphous solid. MS 565 (MH+).

Example 2

2-(2-{7-(Benzyloxy)-5-[4-(methylsulfonyl)phenoxy]-1H-indol-2-yl}-4,5-dihydro-1,3-thiazol-5-yl)ethanol

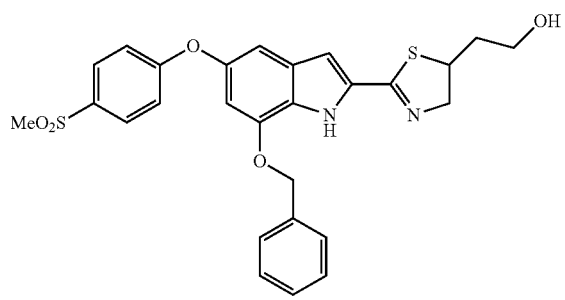 [SMILES: CS(=O)(=O)c1ccc(Oc2cc(OCc3ccccc3)c3[nH]c(C4=NCC(CCO)S4)cc3c2)cc1]

Ethyl (2-{7-(benzyloxy)-5-[4-(methylsulfonyl)phenoxy]-1H-indol-2-yl}-4,5-dihydro-1,3-thiazol-5-yl)acetate (470 mg) was dissolved in tetrahydrofuran (8 mL), lithium borohydride (100 mg) was added, and the mixture was stirred at room temperature for 13 hr. 1M Hydrochloric acid was added to the reaction mixture, and the mixture was subjected to extraction with ethyl acetate. The organic layer was washed successively with saturated aqueous sodium hydrogen carbonate solution and saturated brine, dried over magnesium sulfate, filtrated, and concentrated under reduced pressure. The obtained crude product was subjected to silica gel column chromatography (ethyl acetate:hexane=30:70 to 100:0, volume ratio), and the obtained yellow oil was crystallized from ethanol. The obtained crystals were recrystallized from ethanol to give the title compound (52 mg, yield 12%) as colorless crystals. melting point 97-98° C. MS 523 (MH+).

Example 3

(2-{7-(Benzyloxy)-5-[4-(methylsulfonyl)phenoxy]-1H-indol-2-yl}-4,5-dihydro-1,3-thiazol-5-yl)acetic acid

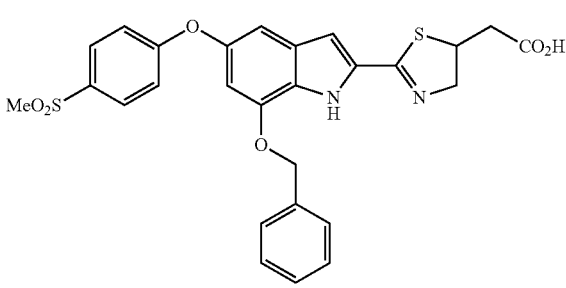 [SMILES: CS(=O)(=O)c1ccc(Oc2cc(OCc3ccccc3)c3[nH]c(C4=NCC(CC(=O)O)S4)cc3c2)cc1]

Ethyl (2-{7-(benzyloxy)-5-[4-(methylsulfonyl)phenoxy]-1H-indol-2-yl}-4,5-dihydro-1,3-thiazol-5-yl)acetate (1.0 g) was dissolved in a mixed solvent of tetrahydrofuran (6 mL)-ethanol (6 mL), 1M aqueous sodium hydroxide solution (6 mL) was added, and the mixture was stirred at room temperature for 10 min. The reaction solution was concentrated under reduced pressure. Water was added to the residue, and the mixture was neutralized with 1M hydrochloric acid, and filtered. The obtained solid was washed successively with water, ethanol and diethyl ether to give the title compound (640 mg, yield 67%) as a pale-orange solid. The obtained solid was recrystallized from ethanol-hexane to give colorless crystals. melting point 218-219° C. MS 537 (MH+).

Example 4

2-(2-{7-(Benzyloxy)-5-[4-(methylsulfonyl)phenoxy]-1H-indol-2-yl}-4,5-dihydro-1,3-thiazol-5-yl)acetamide

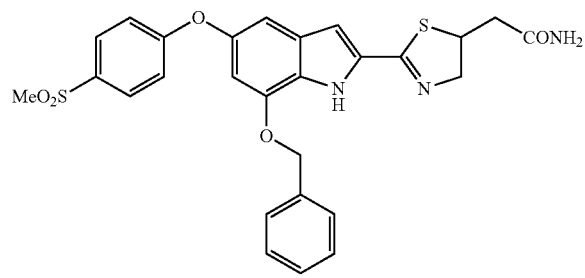 [SMILES: CS(=O)(=O)c1ccc(Oc2cc(OCc3ccccc3)c3[nH]c(C4=NCC(CC(N)=O)S4)cc3c2)cc1]

A mixture of (2-{7-(benzyloxy)-5-[4-(methylsulfonyl)phenoxy]-1H-indol-2-yl}-4,5-dihydro-1,3-thiazol-5-yl)acetic acid (500 mg), 1-[3-(dimethylamino)propyl-3-ethylcarbodiimide hydrochloride (356 mg), 1-hydroxybenzotriazole ammonium salt (283 mg) and N,N-dimethylformamide (20 mL) was stirred at room temperature for 14 hr. Water was added to the reaction solution, and the precipitated solid was collected by filtration, and washed successively with water, ethanol and diethyl ether. The obtained brown solid was recrystallized from ethanol to give the title compound (300 mg, yield 60%) as colorless crystals. melting point 134-135° C. MS 536 (MH+).

Example 5

Ethyl (2-{7-[(6-chloropyridin-2-yl)methoxy]-5-[4-(methylsulfonyl)phenoxy]-1H-indol-2-yl}-4,5-dihydro-1,3-thiazol-5-yl)acetate

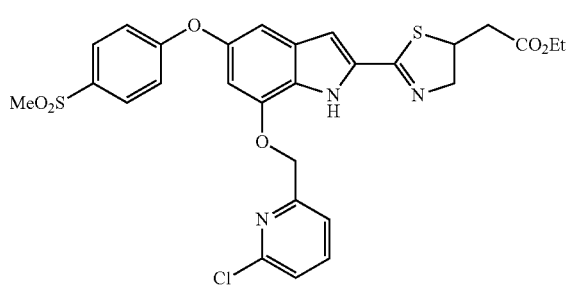 [SMILES: CCOC(=O)CC1CN=C(c2cc3cc(Oc4ccc(S(C)(=O)=O)cc4)cc(OCc4cccc(Cl)n4)c3[nH]2)S1]

7-[(6-Chloropyridin-2-yl)methoxy]-5-[4-(methylsulfonyl)phenoxy]-1H-indole-2-carboxamide (630 mg) was dissolved in tetrahydrofuran (30 mL), Lawesson's reagent (537 mg) was added, and the mixture was stirred at 50° C. for 50 min. The reaction solution was concentrated under reduced pressure, and the residue was subjected to silica gel column chromatography (ethyl acetate:hexane=10:90-50:50, volume ratio), The obtained yellow solid (680 mg) was dissolved in a mixed solvent of tetrahydrofuran (10 mL)-toluene (20 mL), ethyl 2-butynoate (0.34 mL) and tributylphosphine (0.49 mL) were added, and the mixture was stirred at 50° C. for 1 hr. The reaction solution was concentrated under reduced pressure, and the residue was subjected to silica gel column chromatography (ethyl acetate:hexane=10:90 to 50:50, volume ratio) to give the title compound (640 mg, yield 81%) as a yellow oil. MS 600 (MH+).

Example 6

2-(2-{7-[(6-Chloropyridin-2-yl)methoxy]-5-[4-(methylsulfonyl)phenoxy]-1H-indol-2-yl}-4,5-dihydro-1,3-thiazol-5-yl)ethanol

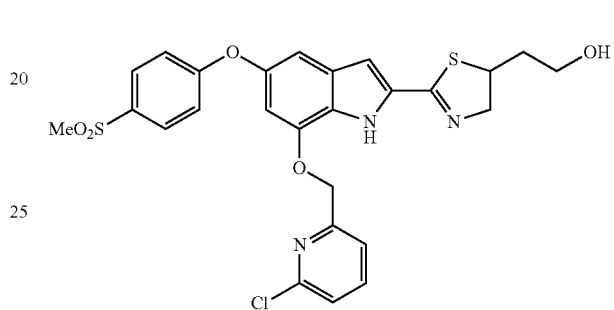

Ethyl (2-{7-[(6-chloropyridin-2-yl)methoxy]-5-[4-(methylsulfonyl)phenoxy]-1H-indol-2-yl}-4,5-dihydro-1,3-thiazol-5-yl)acetate (400 mg) was dissolved in tetrahydrofuran (8 mL), lithium borohydride (43 mg) was added under ice-cooling, and the mixture was stirred at room temperature for 17 hr. 1M Hydrochloric acid was added to the reaction mixture, and the mixture was subjected to extraction with ethyl acetate. The organic layer was washed successively with saturated aqueous sodium hydrogen carbonate solution and saturated brine, dried over magnesium sulfate, filtered, and concentrated under reduced pressure. The obtained crude product was subjected to silica gel column chromatography (ethyl acetate:hexane=40:60 to 100:0, volume ratio) to give the title compound (75 mg, yield 20%) as an amorphous solid. The amorphous solid was crystallized from diethyl ether to give pale-yellow crystals. melting point 93-94° C. MS 558 (MH+).

Example 7

(2-{7-[(6-Chloropyridin-2-yl)methoxy]-5-[4-(methylsulfonyl)phenoxy]-1H-indol-2-yl}-4,5-dihydro-1,3-thiazol-5-yl)acetic acid

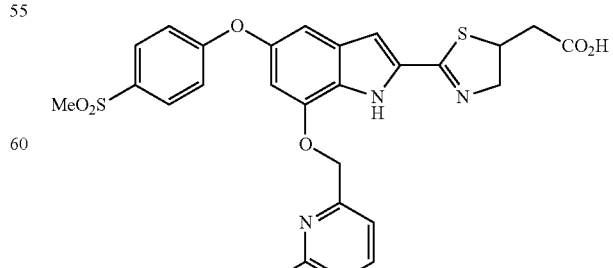

123

Ethyl (2-{7-[(6-chloropyridin-2-yl)methoxy]-5-[(methylsulfonyl)phenoxy]-1H-indol-2-yl}-4,5-dihydro-1,3-thiazol-5-yl)acetate (250 mg) was dissolved in a mixed solvent of tetrahydrofuran (6 mL)-ethanol (8 mL), 1M aqueous sodium hydroxide solution (2 mL) was added under ice-cooling, and the mixture was stirred for 30 min, and then at room temperature for 30 min. The reaction solution was concentrated under reduced pressure. Water was added to the residue, and the mixture was neutralized with 1M hydrochloric acid. The reaction mixture was filtered, and the obtained solid was washed successively with water and diethyl ether to give the title compound (240 mg, yield 100%) as a yellow solid. The obtained yellow solid was recrystallized from ethanol to give pale-yellow crystals. melting point 175-176° C. MS 572 (MH$^+$).

Example 8

2-(2-{7-[(6-Chloropyridin-2-yl)methoxy]-5-[4-(methylsulfonyl)phenoxy]-1H-indol-2-yl}-4,5-dihydro-1,3-thiazol-5-yl)acetamide

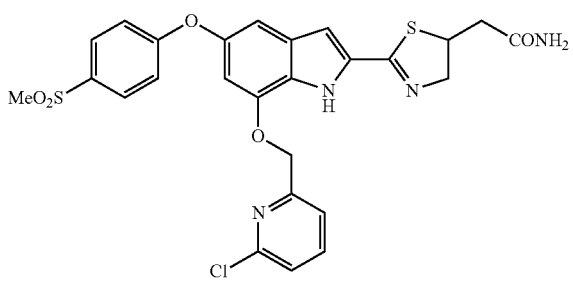 [SMILES: CS(=O)(=O)c1ccc(Oc2cc(OCc3cccc(Cl)n3)c3[nH]c(C4=NCC(CC(N)=O)S4)cc3c2)cc1]

A mixture of (2-{7-[(6-chloropyridin-2-yl)methoxy]-5-[4-(methylsulfonyl)phenoxy]-1H-indol-2-yl}-4,5-dihydro-1,3-thiazol-5-yl)acetic acid (180 mg), 1-[3-(dimethylamino)propyl-3-ethylcarbodiimide hydrochloride (161 mg), 1-hydroxybenzotriazole ammonium salt (128 mg) and N,N-dimethylformamide (10 mL) was stirred at room temperature for 15.5 hr. Water was added to the reaction solution, and the precipitated solid was collected by filtration, and washed successively with water, ethanol and diethyl ether. The obtained brown solid was recrystallized from ethanol to give the title compound (115 mg, yield 64%) as colorless crystals. melting point 147-148° C. MS 571 (MH$^+$).

124

Example 9

Ethyl (2-{7-[(1-methyl-1H-imidazol-2-yl)methoxy]-5-[4-(methylsulfonyl)phenoxy]-1H-indol-2-yl}-4,5-dihydro-1,3-thiazol-5-yl)acetate

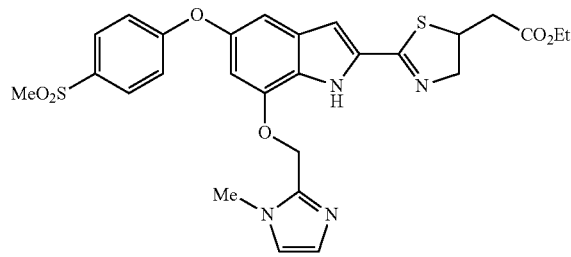

7-[(1-Methyl-1H-imidazol-2-yl)methoxy]-5-[4-(methylsulfonyl)phenoxy]-1H-indole-2-carboxamide (940 mg) was dissolved in tetrahydrofuran (30 mL), Lawesson's reagent (1.36 g) was added, and the mixture was stirred at 50° C. for 13 hr. The white solid in mixture was collected by filtration, and suspended in tetrahydrofuran (30 mL). Ethyl 2-butynoate (0.5 mL) and tributylphosphine (0.7 mL) were added, and the mixture was stirred at 60° C. for 1 hr. The reaction solution was concentrated under reduced pressure, and the residue was subjected to basic silica gel column chromatography (methanol:ethyl acetate:hexane=0:50:50 to 20:80:0, volume ratio) to give the title compound (53 mg) as an orange oil crude product. On the other hand, the previous-obtained filtrate was concentrated under reduced pressure, and the residue was suspended in a mixed solvent of tetrahydrofuran (20 mL)-toluene (15 mL). Ethyl 2-butynoate (0.5 mL) and tributylphosphine (0.7 mL) were added, and the mixture was stirred at 60° C. for 30 min. Ethyl 2-butynoate (1.4 mL) and tributylphosphine (2.0 mL) were added again to the reaction solution, and the mixture was further stirred at 60° C. for 1 hr. Ethyl 2-butynoate (1.0 mL) and tributylphosphine (1.5 mL) was added again, and the mixture was further stirred at 60° C. for 1 hr. The reaction solution was concentrated under reduced pressure, and the residue was subjected to basic silica gel column chromatography (methanol:ethyl acetate:hexane=0:50:50 to 20:80:0, volume ratio) to give the title compound (1 g) as an orange oil crude product. MS 569 (MH$^+$). The obtained crude product was used for the next reaction without an additional purification.

Example 10

(2-{7-[(1-Methyl-1H-imidazol-2-yl)methoxy]-5-[4-(methylsulfonyl)phenoxy]-1H-indol-2-yl}-4,5-dihydro-1,3-thiazol-5-yl)acetic acid

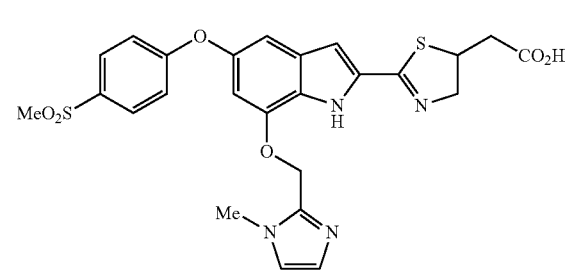 [SMILES: CCOC(=O)CC1CN=C(c2cc3cc(Oc4ccc(S(C)(=O)=O)cc4)cc(OCc4nccn4C)c3[nH]2)S1]

Ethyl (2-{7-[(1-methyl-1H-imidazol-2-yl)methoxy]-5-[4-(methylsulfonyl)phenoxy]-1H-indol-2-yl}-4,5-dihydro-1,3-thiazol-5-yl)acetate (1 g) was dissolved in a mixed solvent of tetrahydrofuran (10 mL)-ethanol (10 mL), 1M aqueous sodium hydroxide solution (5 mL) was added, and the mixture was stirred at room temperature for 1 hr. The reaction solution was concentrated under reduced pressure. Water was added to the residue, and the mixture was neutralized with 1M hydrochloric acid. The mixture was washed with ethyl acetate, and the aqueous layer was concentrated under reduced pressure. Ethanol was added to the residue, and the insoluble substance was filtered off. The filtrate was concentrated, and the obtained yellow solid was recrystallized from ethanol to give the title compound (170 mg) as yellow crystals. MS 541 (MH$^+$).

Example 11

2-(2-{7-[(1-Methyl-1H-imidazol-2-yl)methoxy]-5-[4-(methylsulfonyl)phenoxy]-1H-indol-2-yl}-4,5-dihydro-1,3-thiazol-5-yl)acetamide

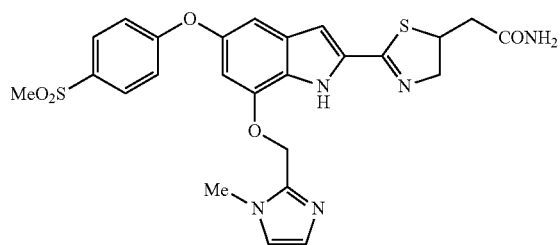 [SMILES: Cn1ccnc1COc1cc(Oc2ccc(S(C)(=O)=O)cc2)cc2cc(C3=NCC(CC(N)=O)S3)[nH]c12]

A mixture of (2-{7-[(1-methyl-1H-imidazol-2-yl)methoxy]-5-[4-(methylsulfonyl)phenoxy]-1H-indol-2-yl}-4,5-dihydro-1,3-thiazol-5-yl)acetic acid (210 mg), 1-[3-(dimethylamino)propyl-3-ethylcarbodiimide hydrochloride (150 mg), 1-hydroxybenzotriazole ammonium salt (118 mg) and N,N-dimethylformamide was stirred at room temperature for 5 hr. The reaction solution was concentrated under reduced pressure, water was added to the residue, and the mixture was washed with diisopropyl ether. Sodium chloride was added to the aqueous layer to give a saturated solution, and the mixture was subjected to extraction with ethyl acetate. The organic layer was dried over magnesium sulfate, filtrated, and concentrated under reduced pressure. The obtained crude product was subjected to silica gel column chromatography (methanol:ethyl acetate=0:100 to 25:75, volume ratio), and the obtained amorphous solid was crystallized from diethyl ether to give the title compound (50 mg, yield 24%) as colorless crystals. melting point 130-131° C. MS 540 (MH$^+$).

Example 12

Ethyl (2-{7-(2-{[di-tert-butyl(phenyl)silyl]oxy}-1-methylethoxy)-5-[4-(methylsulfonyl)phenoxy]-1H-indol-2-yl}-4,5-dihydro-1,3-thiazol-5-yl)acetate

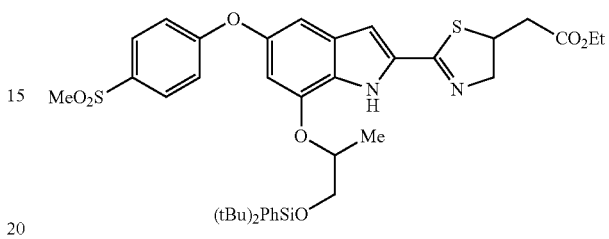

7-(2-{[Di-tert-butyl(phenyl)silyl]oxy}-1-methylethoxy)-5-[4-(methylsulfonyl)phenoxy]-1H-indole-2-carboxamide (1.37 g) was dissolved in tetrahydrofuran (40 mL), Lawesson's reagent (1.05 g) was added, and the mixture was stirred at 50° C. for 50 min. The reaction solution was concentrated under reduced pressure, and the residue was subjected to silica gel column chromatography (ethyl acetate:hexane=1:99-40:60, volume ratio) to give a yellow oil (1.3 g). The yellow oil was dissolved in a mixed solvent of tetrahydrofuran (20 mL)-toluene (20 mL), ethyl 2-butynoate (0.6 mL) and tributylphosphine (0.7 mL) were added, and the mixture was stirred at 50° C. for 50 min. The reaction solution was concentrated under reduced pressure, and the residue was subjected to silica gel column chromatography (ethyl acetate:hexane=5:95 to 40:60, volume ratio) to give the title compound (1.0 g, yield 62%) as a yellow oil. MS 771 (MH$^+$).

Example 13

2-(2-{7-(2-{[Di-tert-butyl(phenyl)silyl]oxy}-1-methylethoxy)-5-[4-(methylsulfonyl)phenoxy]-1H-indol-2-yl}-4,5-dihydro-1,3-thiazol-5-yl)ethanol

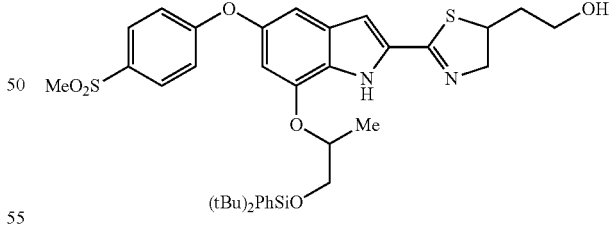

Ethyl (2-{7-(2-{[di-tert-butyl(phenyl)silyl]oxy}-1-methylethoxy)-5-[4-(methylsulfonyl)phenoxy]-1H-indol-2-yl}-4,5-dihydro-1,3-thiazol-5-yl)acetate (500 mg) was dissolved in tetrahydrofuran (20 mL), lithium borohydride (21 mg) was added under ice-cooling, and the mixture was stirred for 1 hr. Lithium borohydride (28 mg) was added again to the reaction solution, and the mixture was further stirred at room temperature for 1 hr, and then at 50° C. for 7 hr. 1M Hydrochloric acid was added to the reaction mixture, and the mixture was subjected to extraction with ethyl acetate. The organic layer was washed successively with saturated aqueous sodium hydrogen carbonate solution and saturated brine, dried over magnesium sulfate, filtrated, and concentrated under reduced pressure. The obtained crude product was subjected to silica gel column chromatography (ethyl acetate:hexane=20:80 to 70:30, volume ratio) to give the title compound (123 mg, yield 55%) as a yellow oil. MS 729 (MH⁺).

Example 14

(2-{7-(2-{[Di-tert-butyl(phenyl)silyl]oxy}-1-methylethoxy)-5-[4-(methylsulfonyl)phenoxy]-1H-indol-2-yl}-4,5-dihydro-1,3-thiazol-5-yl)acetic acid

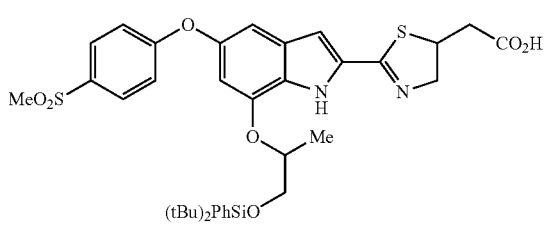

Ethyl (2-{7-(2-{[di-tert-butyl(phenyl)silyl]oxy}-1-methylethoxy)-5-[4-(methylsulfonyl)phenoxy]-1H-indol-2-yl]-4,5-dihydro-1,3-thiazol-5-yl)acetate (480 mg) was dissolved in a mixed solvent of tetrahydrofuran (10 mL)-ethanol (10 mL), 1M aqueous sodium hydroxide solution (7 mL) was added, and the mixture was stirred at room temperature for 1 hr. The reaction solution was concentrated under reduced pressure. Water was added to the residue, and the mixture was neutralized with 1M hydrochloric acid. The precipitated solid was collected by filtration to give the title compound (320 mg, yield 70%) as a yellow solid. MS 743 (MH⁺).

Example 15

2-(2-{7-(2-{[Di-tert-butyl(phenyl)silyl]oxy}-1-methylethoxy)-5-[4-(methylsulfonyl)phenoxy]-1H-indol-2-yl}-4,5-dihydro-1,3-thiazol-5-yl)acetamide

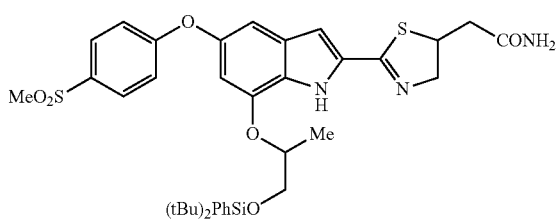

A mixture of (2-{7-(2-{[di-tert-butyl(phenyl)silyl]oxy}-1-methylethoxy)-5-[4-(methylsulfonyl)phenoxy]-1H-indol-2-yl]-4,5-dihydro-1,3-thiazol-5-yl)acetic acid (320 mg), 1-[3-(dimethylamino)propyl-3-ethylcarbodiimide hydrochloride (165 mg), 1-hydroxybenzotriazole ammonium salt (131 mg) and N,N-dimethylformamide (8 mL) was stirred at room temperature for 18 hr. Water was added to the reaction solution, and the mixture was subjected to extraction with ethyl acetate. The organic layer was washed with saturated brine, dried over magnesium sulfate, filtrated, and concentrated under reduced pressure. The obtained crude product was subjected to basic silica gel column chromatography (ethyl acetate:hexane=30:70 to 100:0, volume ratio) to give the title compound (262 mg, yield 55%) as an orange oil. MS 742 (MH⁺).

Example 16

2-({2-[5-(2-Hydroxyethyl)-4,5-dihydro-1,3-thiazol-2-yl]-5-[4-(methylsulfonyl)phenoxy]-1H-indole-7-yl}oxy)propan-1-ol

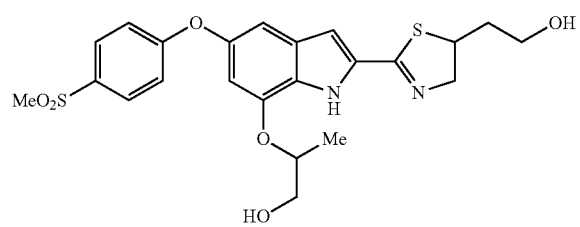 [SMILES: CC(CO)Oc1cc(Oc2ccc(S(C)(=O)=O)cc2)cc2cc(C3=NCC(CCO)S3)[nH]c12]

2-(2-{7-(2-{[Di-tert-butyl(phenyl)silyl]oxy}-1-methylethoxy)-5-[4-(methylsulfonyl)phenoxy]-1H-indol-2-yl]-4,5-dihydro-1,3-thiazol-5-yl)ethanol (270 mg) was dissolved in tetrahydrofuran (2 mL), tetrabutylammonium fluoride (0.6 mL) was added, and the mixture was stirred at room temperature for 18 hr. Saturated aqueous ammonium chloride solution was added to the reaction solution, and the mixture was subjected to extraction with ethyl acetate. The organic layer was washed successively with saturated aqueous sodium hydrogen carbonate solution and saturated brine, dried over magnesium sulfate, filtrated, and concentrated under reduced pressure. The obtained crude product was subjected to silica gel column chromatography (methanol:ethyl acetate:hexane=0:20:80 to 5:95:0, volume ratio) to give the title compound (117 mg, yield 65%) as a white solid. The obtained white solid was recrystallized from ethyl acetate-diethyl ether to give colorless crystals. melting point 165-169° C. MS 491 (MH⁺).

Example 17

2-(2-{7-(2-Hydroxy-1-methylethoxy)-5-[4-(methylsulfonyl)phenoxy]-1H-indol-2-yl}-4,5-dihydro-1,3-thiazol-5-yl)acetamide

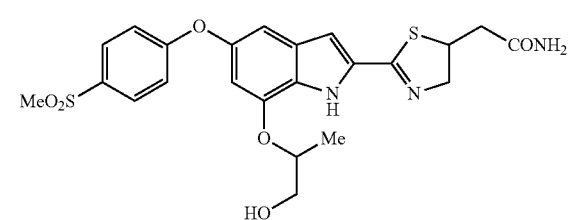 [SMILES: CC(CO)Oc1cc(Oc2ccc(S(C)(=O)=O)cc2)cc2cc(C3=NCC(CC(N)=O)S3)[nH]c12]

2-(2-{7-(2-{[Di-tert-butyl(phenyl)silyl]oxy}-1-methylethoxy)-5-[4-(methylsulfonyl)phenoxy]-1H-indol-2-yl]-4,5-dihydro-1,3-thiazol-5-yl)acetamide (262 mg) was dissolved in tetrahydrofuran (2 mL), tetrabutylammonium fluoride (0.5 mL) was added, and the mixture was stirred at room temperature for 15 hr. Saturated aqueous ammonium chloride solution was added to the reaction solution, and the mixture was subjected to extraction with ethyl acetate. The organic layer was washed successively with saturated aqueous sodium hydrogen carbonate solution and saturated brine, dried over magnesium sulfate, filtrated, and concentrated under reduced pressure. The obtained crude product was subjected to silica gel column chromatography (methanol:ethyl acetate=0:100 to 10:90, volume ratio) to give the title compound (144 mg, yield 81%) as a white solid. The obtained white solid was recrystallized from ethyl acetate-hexane to give colorless crystals. melting point 137-142° C. MS 504 (MH⁺).

Example 18

Ethyl (2-{5-[4-(methylsulfonyl)phenoxy]-7-(tetrahydro-2H-pyran-4-ylmethoxy)-1H-indol-2-yl}-4,5-dihydro-1,3-thiazol-5-yl)acetate

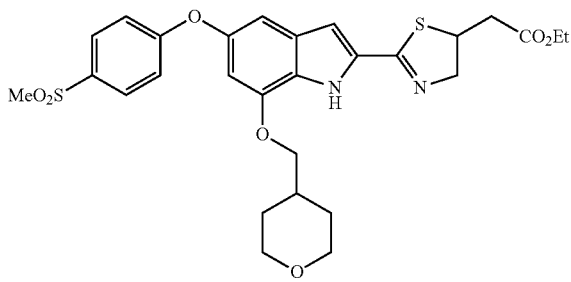 [SMILES: CCOC(=O)CC1CN=C(c2cc3cc(Oc4ccc(S(C)(=O)=O)cc4)cc(OCC4CCOCC4)c3[nH]2)S1]

5-[4-(Methylsulfonyl)phenoxy]-7-(tetrahydro-2H-pyran-4-ylmethoxy)-1H-indole-2-carboxamide (500 mg) was dissolved in tetrahydrofuran (20 mL), Lawesson's reagent (455 mg) was added, and the mixture was stirred at 50° C. for 1 hr. The reaction solution was concentrated under reduced pressure, and the residue was subjected to silica gel column chromatography (ethyl acetate:hexane=20:80 to 70:30, volume ratio) to give a yellow oil. The obtained yellow oil was dissolved in a mixed solvent of tetrahydrofuran (10 mL)-toluene (15 mL), ethyl 2-butynoate (0.26 mL) and tributylphosphine (0.30 mL) were added, and the mixture was stirred at 50° C. for 2.5 hr. The reaction solution was concentrated under reduced pressure, and the obtained residue was subjected to silica gel column chromatography (ethyl acetate:hexane=10:90 to 100:0, volume ratio) to give the title compound (310 mg, yield 48%) as an orange oil. MS 573 (MH⁺).

Example 19

2-(2-{5-[4-(Methylsulfonyl)phenoxy]-7-(tetrahydro-2H-pyran-4-ylmethoxy)-1H-indol-2-yl}-4,5-dihydro-1,3-thiazol-5-yl)ethanol

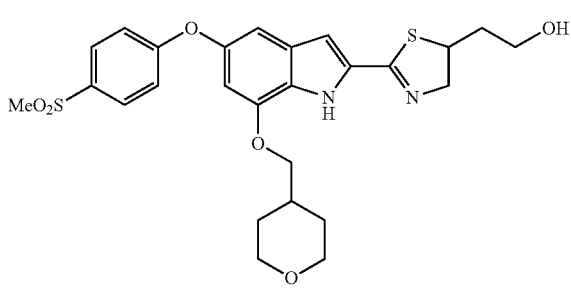 [SMILES: CS(=O)(=O)c1ccc(Oc2cc(OCC3CCOCC3)c3[nH]c(C4=NCC(CCO)S4)cc3c2)cc1]

Ethyl (2-{5-[4-(methylsulfonyl)phenoxy]-7-(tetrahydro-2H-pyran-4-ylmethoxy)-1H-indol-2-yl}-4,5-dihydro-1,3-thiazol-5-yl)acetate (310 mg) was dissolved in tetrahydrofuran (15 mL), lithium borohydride (24 mg) was added under ice-cooling, and the mixture was stirred at room temperature for 2.5 hr, and then at 50° C. for 2.5 hr. Lithium borohydride (24 mg) was added to the reaction mixture, and the mixture was stirred at 50° C. for 30 hr. Water was added to the reaction mixture, and the mixture was subjected to extraction with ethyl acetate. The organic layer was washed with saturated brine, dried over magnesium sulfate, filtrated, and concentrated under reduced pressure. The crude product was subjected to silica gel column chromatography (ethyl acetate:hexane=20:80 to 100:0, volume ratio), and the obtained amorphous solid was washed with diethyl ether to give the title compound (123 mg, yield 55%) as a pale-yellow solid. melting point 104-105° C. MS 531 (MH⁺).

Example 20

Ethyl 5-{7-(benzyloxy)-5-[4-(methylsulfonyl)phenoxy]-1H-indol-2-yl}-1,3,4-thiadiazole-2-carboxylate

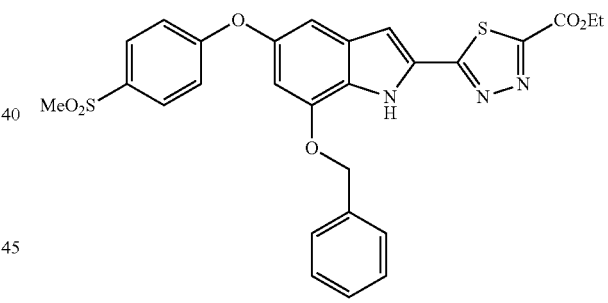

Ethyl [2-({7-(benzyloxy)-5-[4-(methylsulfonyl)phenoxy]-1H-indol-2-yl}carbonyl)hydrazino](oxo)acetate (420 mg) was dissolved in tetrahydrofuran (15 mL), Lawesson's reagent (308 mg) was added, and the mixture was stirred at 50° C. for 5 hr. Lawesson's reagent (300 mg) was added again to the reaction solution, and the mixture was further stirred at 50° C. for 1 hr. The reaction solution was concentrated under reduced pressure. The residue was subjected to silica gel column chromatography (ethyl acetate:hexane=10:90-40:60, volume ratio), and the obtained yellow oil was crystallized from methanol to give the title compound (310 mg, yield 74%) as pale-yellow crystals. The obtained crystals was recrystallized from ethyl acetate-diethyl ether to give pale-yellow crystals. melting point 194-195° C. MS 550 (MH+).

Example 21

(5-{7-(Benzyloxy)-5-[4-(methylsulfonyl)phenoxy]-1H-indol-2-yl}-1,3,4-thiadiazol-2-yl)methanol

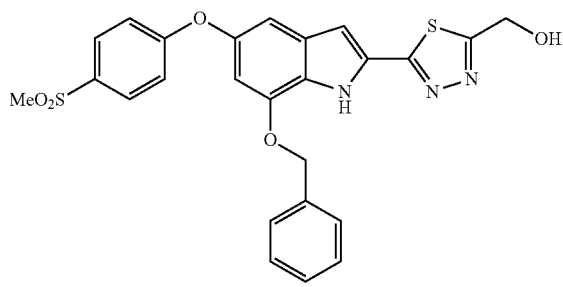 [SMILES: CS(=O)(=O)c1ccc(Oc2cc(OCc3ccccc3)c3[nH]c(-c4nnc(CO)s4)cc3c2)cc1]

Ethyl 5-{7-(benzyloxy)-5-[4-(methylsulfonyl)phenoxy]-1H-indol-2-yl}-1,3,4-thiadiazole-2-carboxylate (230 mg) was dissolved in a mixed solvent of tetrahydrofuran (8 mL)-methanol (2 mL), sodium borohydride (32 mg) was added under ice-cooling, and the mixture was stirred for 40 min. Water and 1M hydrochloric acid were added to the reaction mixture, and the mixture was subjected to extraction with ethyl acetate. The organic layer was washed successively with saturated aqueous sodium hydrogen carbonate solution and saturated brine, dried over magnesium sulfate, filtrated, and concentrated under reduced pressure. The obtained crude product was subjected to silica gel column chromatography (ethyl acetate:hexane=10:90 to 90:10, volume ratio) to give the title compound (220 mg, yield 100%) as a pale-yellow solid. The obtained pale-yellow solid was recrystallized from ethyl acetate-diethyl ether to give pale-yellow crystals. melting point 159-160° C. MS 508 (MH+).

Example 22

Ethyl 2-{7-(benzyloxy)-5-[4-(methylsulfonyl)phenoxy]-1H-indol-2-yl}-1,3-thiazole-5-carboxylate

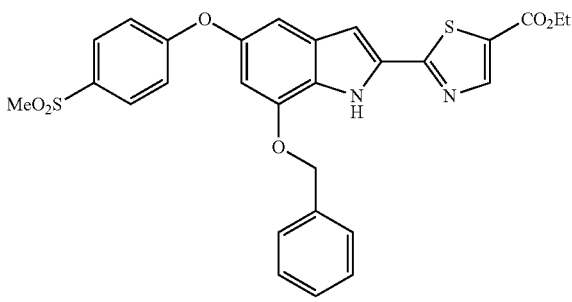 [SMILES: CCOC(=O)c1cnc(-c2cc3cc(Oc4ccc(S(C)(=O)=O)cc4)cc(OCc4ccccc4)c3[nH]2)s1]

A mixture of 7-(benzyloxy)-5-[4-(methylsulfonyl)phenoxy]-1H-indole-2-carbothioamide (280 mg), ethyl 2-chloro-3-oxopropanoate potassium salt (234 mg), acetic acid (0.5 mL) and N,N-dimethylacetamide (5 mL) was stirred at 100° C. for 4 h. Ethyl 2-chloro-3-oxopropanoate potassium salt (234 mg) and acetic acid (0.5 mL) were added again, and the mixture was stirred at 100° C. for 3 h. Furthermore, ethyl 2-chloro-3-oxopropanoate potassium salt (234 mg) and acetic acid (0.5 mL) were added and the mixture was stirred at 100° C. for 7 h. Water was added to the mixture and the mixture was extracted with ethyl acetate. The organic layer was washed successively with saturated aqueous sodium hydrogen carbonate solution and saturated brine, dried over magnesium sulfate, filtered and concentrated. The residue was purified by silica gel column chromatography (ethyl acetate/hexane=5/95 to 50/50, volume ratio) to give the title compound (242 mg, crude yield 71%) as a yellow solid. MS 549 (MH+).

Example 23

(2-{7-(Benzyloxy)-5-[4-(methylsulfonyl)phenoxy]-1H-indol-2-yl}-1,3-thiazol-5-yl)methanol

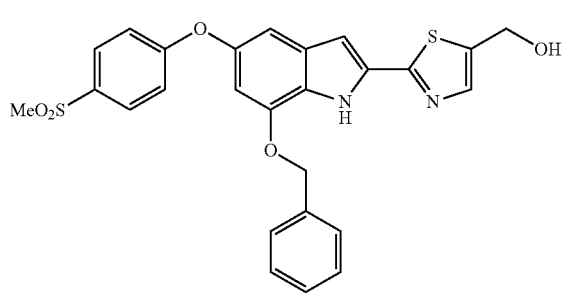 [SMILES: CS(=O)(=O)c1ccc(Oc2cc(OCc3ccccc3)c3[nH]c(-c4ncc(CO)s4)cc3c2)cc1]

To a solution of ethyl 2-{7-(benzyloxy)-5-[4-(methylsulfonyl)phenoxy]-1H-indol-2-yl}-1,3-thiazole-5-carboxylate (242 mg) in tetrahydrofuran (25 mL) was added lithium aluminum hydride (50 mg) at 0° C. After the mixture was stirred at 0° C. for 30 min, ethanol was added dropwise until hydrogen did not generate. A saturated aqueous ammonium chloride solution was added to the mixture and the resulting yellow suspension was filtered through celite. The filtrate was concentrated and the residue was purified by silica gel column chromatography (ethyl acetate/hexane=20/80 to 100/0, volume ratio) to give yellow crystals. The crystals were recrystallized from ethanol-ethyl acetate to give yellow crystals. The crystals were purified by silica gel column chromatography (ethyl acetate/hexane=20/80 to 90/10, volume ratio) to give yellow crystals. The crystals were recrystallized from ethanol-hexane to give the title compound (52 mg, 23%) as yellow crystals. MS 507 (MH+). mp 125-126° C.

Example 24

Ethyl (2-{7-(1-methylethoxy)-5-[4-(methylsulfonyl)phenoxy]-1H-indol-2-yl}-4,5-dihydro-1,3-thiazol-5-yl)acetate

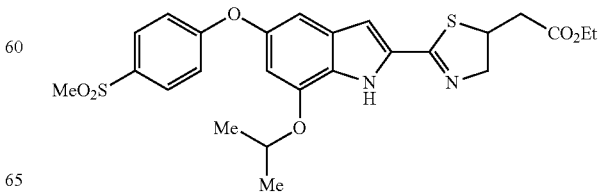

A mixture of 7-(1-methylethoxy)-5-[4-(methylsulfonyl)phenoxy]-1H-indole-2-carbothioamide (857 mg), ethyl 2-butynoate (0.6 mL), tributylphosphine (0.6 mL), tetrahydrofuran (10 mL) and toluene (15 mL) was stirred at 60° C. for 1.5 h. The mixture was cooled to room temperature and concentrated under reduced pressure. The residue was purified by silica gel column chromatography (ethyl acetate/hexane=1/99 to 40/60, volume ratio) to give the title compound (381 mg, 41%) as a yellow amorphous solid. MS 517 (MH$^+$).

$^1$H NMR (CDCl$_3$) δ1.28 (3H, t, J=7.2 Hz), 1.38 (6H, d, J=6.0 Hz), 2.69-2.76 (2H, m), 3.04 (3H, s), 4.19 (2H, q, J=7.1 Hz), 4.24-4.49 (3H, m), 4.63 (1H, spt, J=6.0 Hz), 6.44 (1H, d, J=1.9 Hz), 6.84 (1H, d, J=2.3 Hz), 6.91 (1H, d, J=1.5 Hz), 7.01-7.11 (2H, m), 7.81-7.90 (2H, m), 9.22 (1H, brs).

Example 25

2-(2-{7-(1-Methylethoxy)-5-[4-(methylsulfonyl)phenoxy]-1H-indol-2-yl}-4,5-dihydro-1,3-thiazol-5-yl)ethanol

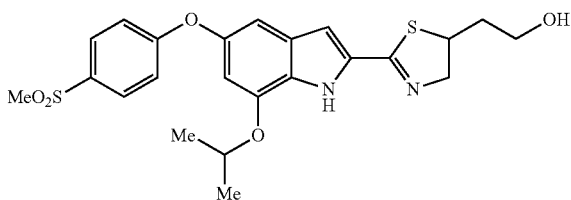 [SMILES: CC(C)Oc1cc(Oc2ccc(S(C)(=O)=O)cc2)cc2cc(C3=NCC(CCO)S3)[nH]c12]

Ethyl (2-{7-(1-methylethoxy)-5-[4-(methylsulfonyl)phenoxy]-1H-indol-2-yl}-4,5-dihydro-1,3-thiazol-5-yl)acetate (330 mg) was dissolved in a mixture of tetrahydrofuran (15 mL) and methanol (3 mL). Lithium borohydride (30 mg) was added to the mixture at room temperature and the mixture was stirred at room temperature for 30 min. Water was added to the mixture and the mixture was extracted with ethyl acetate. The organic layer was washed successively with saturated aqueous sodium hydrogen carbonate solution and saturated brine, dried over magnesium sulfate, filtered and concentrated. The residue was purified by silica gel column chromatography (ethyl acetate/hexane=10/90 to 80/20, volume ratio) to give the title compound (112 mg, 37%) as a pale yellow amorphous solid. MS 475 (MH$^+$).

$^1$H NMR (CDCl$_3$) δ 1.37-1.41 (7H, m), 1.82-2.10 (2H, m), 3.04 (3H, s), 3.74-3.86 (2H, m), 4.13-4.34 (2H, m), 4.36-4.49 (1H, m), 4.59-4.67 (1H, m), 6.44 (1H, d, J=1.9 Hz), 6.85 (1H, d, J=1.9 Hz), 6.91 (1H, d, J=1.5 Hz), 7.02-7.11 (2H, m), 7.81-7.90 (2H, m), 9.23 (1H, brs).

Example 26

2-Methyl-1-(2-{7-(1-methylethoxy)-5-[4-(methylsulfonyl)phenoxy]-1H-indol-2-yl}-4,5-dihydro-1,3-thiazol-5-yl)propan-2-ol

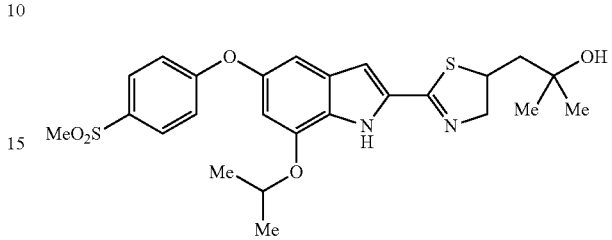

To a solution of ethyl (2-{7-(1-methylethoxy)-5-[4-(methylsulfonyl)phenoxy]-1H-indol-2-yl}-4,5-dihydro-1,3-thiazol-5-yl)acetate (490 mg) in tetrahydrofuran (10 mL) was added 1M methylmagnesium bromide tetrahydrofuran solution (7.6 mL) at 0° C. After the mixture was stirred at room temperature for 1.5 h, 1M methylmagnesium bromide tetrahydrofuran solution (3.4 mL) was added to the mixture again at room temperature. The mixture was stirred at room temperature for 2 h. Furthermore, 1M methylmagnesium bromide tetrahydrofuran solution (3.4 mL) was added to the mixture at room temperature and the mixture was stirred at room temperature for 30 min. The mixture was acidified with 1M hydrochloric acid, and the mixture was extracted with ethyl acetate. The organic layer was washed with saturated brine, dried over magnesium sulfate, filtered and concentrated. The residue was purified by silica gel column chromatography (ethyl acetate/hexane=3/97 to 60/40, volume ratio) to give a yellow oil. The oil was crystallized from ethyl acetate-diethyl ether-hexane to give pale yellow crystals. The crystals were recrystallized from ethyl acetate-diisopropyl ether to give the title compound (50 mg, 10%) as pale yellow crystals. MS 503 (MH$^+$).

$^1$H NMR (CDCl$_3$) δ 1.30 (3H, s), 1.32 (3H, s), 1.38 (6H, d, J=6.1 Hz), 1.93-2.11 (2H, m), 3.04 (3H, s), 4.03-4.14 (1H, m), 4.14-4.28 (1H, m), 4.47-4.71 (2H, m), 6.44 (1H, dd, J=1.9 Hz), 6.84 (1H, d, J=1.9 Hz), 6.91 (1H, d, J=1.9 Hz) 7.06% (2H, d, J=9.1 Hz), 7.85 (2H, d, J=9.1 Hz), 9.23 (1H, brs).

Example 27

Ethyl [2-(7-methoxy-5-{[6-(methylsulfonyl)pyridin-3-yl]oxy}-1H-indol-2-yl)-4,5-dihydro-1,3-thiazol-5-yl]acetate

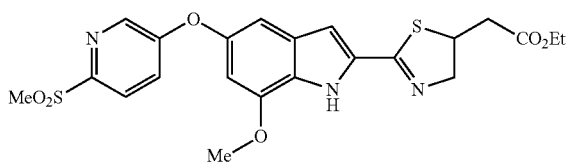 [SMILES: CCOC(=O)CC1CN=C(c2cc3cc(Oc4ccc(S(C)(=O)=O)nc4)cc(OC)c3[nH]2)S1]

A mixture of 7-methoxy-5-{[6-(methylsulfonyl)pyridin-3-yl]oxy}-1H-indole-2-carbothioamide (10.7 g), ethyl 2-butynoate (8.2 mL), tributylphosphine (7.0 mL) and tetrahydrofuran (400 mL) was stirred at 60° C. for 1 h. The mixture was concentrated under reduced pressure. The residue was purified by silica gel column chromatography (ethyl acetate/hexane=5/95 to 100/0, volume ratio) to give the title compound (11.06 g, 80%) as an orange amorphous solid. MS 490 (MH$^+$).

$^1$H NMR (CDCl$_3$) δ 1.28 (3H, t, J=7.2 Hz), 2.73 (2H, d, J=6.1 Hz), 3.21 (3H, s), 3.93 (3H, s), 4.19 (2H, q, J=7.2 Hz), 4.27-4.48 (3H, m), 6.45 (1H, d, J=1.9 Hz), 6.85 (1H, d, J=2.3 Hz), 6.96 (1H, d, J=1.9 Hz), 7.34 (1H, dd, J=8.7, 3.0 Hz), 8.00 (1H, d, J=8.7 Hz), 8.45 (1H, d, J=2.7 Hz), 9.27 (1H, brs).

Example 28

[2-(7-Methoxy-5-{[6-(methylsulfonyl)pyridin-3-yl]oxy}-1H-indol-2-yl)-4,5-dihydro-1,3-thiazol-5-yl] acetic acid

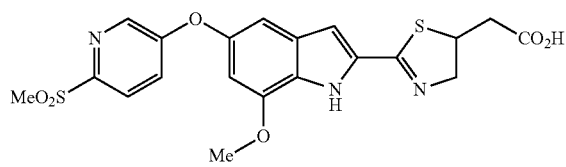 [SMILES: COc1cc(Oc2ccc(S(C)(=O)=O)nc2)cc2cc(C3=NCC(CC(=O)O)S3)[nH]c12]

Ethyl [2-(7-methoxy-5-{[6-(methylsulfonyl)pyridin-3-yl]oxy}-1H-indol-2-yl)-4,5-dihydro-1,3-thiazol-5-yl]acetate (11.06 g) was dissolved in a mixture of tetrahydrofuran (100 mL) and ethanol (100 mL). To the mixture was added 1M aqueous sodium hydroxide solution (37 mL) and the mixture was stirred at room temperature for 1 h. The mixture was concentrated under reduced pressure. The residue was dissolved in water and 1M hydrochloric acid (37 mL) was added to the mixture. The resulting yellow suspension was filtered to collect a yellow solid. The solid was dissolved in ethyl acetate-tetrahydrofuran. The solution was dried over magnesium sulfate, filtered and concentrated. The residual solid was washed with diethyl ether to give the title compound (9.65 g, 93%) as a yellow solid. MS 462 (MH$^+$).

$^1$H NMR (DMSO-d$_6$) δ 2.54-2.64 (1H, m), 2.71-2.85 (1H, m), 3.24 (3H, s), 3.88 (3H, s), 4.17-4.30 (2H, m), 4.32-4.48 (1H, m), 6.69 (1H, d, J=1.9 Hz), 6.86 (1H, d, J=2.3 Hz), 7.02 (1H, d, J=1.9 Hz), 7.48 (1H, dd, J=8.7, 3.0 Hz), 8.00 (1H, d, J=9.0 Hz), 8.54 (1H, d, J=2.6 Hz), 11.88 (1H, s), 12.48 (1H, brs).

Example 29

2-[2-(7-Methoxy-5-{[6-(methylsulfonyl)pyridin-3-yl]oxy}-1H-indol-2-yl)-4,5-dihydro-1,3-thiazol-5-yl]acetamide

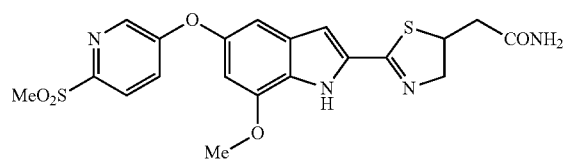 [SMILES: COc1cc(Oc2ccc(S(C)(=O)=O)nc2)cc2cc(C3=NCC(CC(N)=O)S3)[nH]c12]

A mixture of [2-(7-methoxy-5-{[6-(methylsulfonyl)pyridin-3-yl]oxy}-1H-indol-2-yl)-4,5-dihydro-1,3-thiazol-5-yl] acetic acid (90 mg), N-ethyl-N'-(3-dimethylaminopropyl)carbodiimide hydrochloride (75 mg), 1-hydroxybenzotriazole ammonium salt (59 mg) and N,N-dimethylformamide (4 mL) was stirred at room temperature for 12 h. The mixture was concentrated under reduced pressure. The residue was dissolved in water and the mixture was extracted with ethyl acetate-tetrahydrofuran. The organic layer was washed with saturated brine, dried over magnesium sulfate, filtered and concentrated. The residual oil was crystallized from acetonitrile and the crystals were washed with acetonitrile-diethyl ether. The crystals were recrystallized from ethanol to give the title compound (58 mg, 64%) as off-white crystals. MS 461 (MH$^+$). mp 225-227° C.

Example 30

2-[2-(7-Methoxy-5-{[6-(methylsulfonyl)pyridin-3-yl]oxy}-1H-indol-2-yl)-4,5-dihydro-1,3-thiazol-5-yl]-N-Methylacetamide

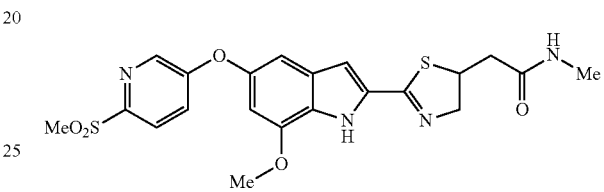

A mixture of [2-(7-methoxy-5-{[6-(methylsulfonyl)pyridin-3-yl]oxy}-1H-indol-2-yl)-4,5-dihydro-1,3-thiazol-5-yl] acetic acid (800 mg), 1-ethyl-3-(3-dimethylaminopropyl)carbodiimide hydrochloride (500 mg), 1-hydroxybenzotriazole (350 mg) and N,N-dimethylformamide (15 mL) was stirred at room temperature for 30 min. Then triethylamine (440 mg) and methylamine hydrochloride (230 mg) were added to the mixture. The whole was stirred at room temperature for 20-h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 95:5, volume ratio) to give pale yellow crystals. The crystals were washed with ethyl acetate-hexane to give the title compound (540 mg, 67%) as pale yellow crystals. The crystals were recrystallized from acetone-hexane to give colorless prisms. MS 475 (MH$^+$). mp 201-202° C.

Example 31

2-[2-(7-Methoxy-5-{[6-(methylsulfonyl)pyridin-3-yl]oxy}-1H-indol-2-yl)-4,5-dihydro-1,3-thiazol-5-yl]-N-methylacetamide

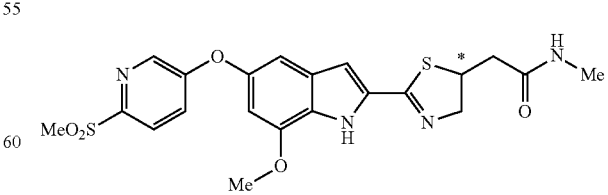

A solution of 2-[2-(7-methoxy-5-{[6-(methylsulfonyl)pyridin-3-yl]oxy}-1H-indol-2-yl)-4,5-dihydro-1,3-thiazol-5-yl]-N-methylacetamide (425 mg) in methanol (425 mL) was resolved by preparative supercritical fluid chromatography (SFC), using CHIRALPAK AS (2 cm i.d.×25 cm, Daicel Chemical Industries, Ltd.) and supercritical carbon dioxide/methanol (60/40) as the mobile phase with the flow rate of 50 mL/min at 10 MPa and 35° C. The fractions containing a single enantiomer, eluted at a retention time of 4.8 min, were collected and concentrated to give the title compound (198 mg) as white crystals. Recrystallization from acetone-hexane gave colorless crystals (181 mg). MS 475 (MH+). mp 196-197° C.

Example 32

2-[2-(7-Methoxy-5-{[6-(methylsulfonyl)pyridin-3-yl]oxy}-1H-indol-2-yl)-4,5-dihydro-1,3-thiazol-5-yl]-N-methylacetamide

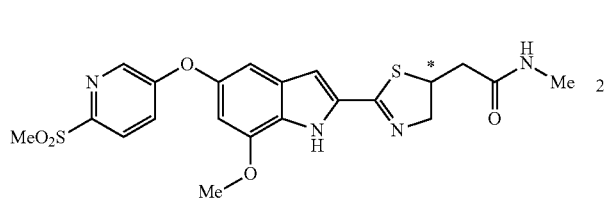

A solution of 2-[2-(7-methoxy-5-{[6-(methylsulfonyl)pyridin-3-yl]oxy}-1H-indol-2-yl)-4,5-dihydro-1,3-thiazol-5-yl]-N-methylacetamide (425 mg) in methanol (425 mL) was resolved by preparative supercritical fluid chromatography (SFC), using CHIRALPAK AS (2 cm i.d.×25 cm, Daicel Chemical Industries, Ltd.) and supercritical carbon dioxide/methanol (60/40) as the mobile phase with the flow rate of 50 mL/min at 10 MPa and 35° C. The fractions containing a single enantiomer, eluted at a retention time of 6.0 min, were collected and concentrated to give the title compound (196 mg) as white crystals. Recrystallization from acetone-hexane gave colorless crystals (173 mg). MS 475 (MH+). mp 195-197° C.

Example 33

Ethyl [2-(7-[2-methoxy-1-(methoxymethyl)ethoxy]-5-{[6-(methylsulfonyl)pyridin-3-yl]oxy}-1H-indol-2-yl)-4,5-dihydro-1,3-thiazol-5-yl]acetate

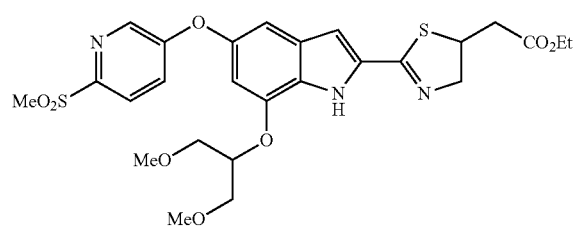 [SMILES: CCOC(=O)CC1CN=C(c2cc3cc(Oc4ccc(S(C)(=O)=O)nc4)cc(OC(COC)COC)c3[nH]2)S1]

A mixture of 7-[2-methoxy-1-(methoxymethyl)ethoxy]-5-{[6-(methylsulfonyl)pyridin-3-yl]oxy}-1H-indole-2-carbothioamide (940 mg), ethyl 2-butynoate (0.6 mL), tributylphosphine (0.5 mL), tetrahydrofuran (15 mL) and toluene (20 mL) was stirred at 60° C. for 50 min. The mixture was concentrated under reduced pressure and the residue was purified by silica gel column chromatography (methanol/ethyl acetate/hexane=0/5/95 to 5/95/0, volume ratio) to give the title compound (610 mg, 52%) as a yellow amorphous solid. MS 578 (MH+).

$^1$H NMR (CDCl$_3$) δ 1.28 (3H, t, J=7.2 Hz), 2.69-2.76 (2H, m), 3.21 (3H, s), 3.45 (3H, s), 3.46 (3H, s), 3.61-3.74 (4H, m), 4.19 (2H, q, J=7.2 Hz), 4.25-4.53 (4H, m), 6.68 (1H, d, J=1.9 Hz), 6.85 (1H, d, J=1.9 Hz), 7.06 (1H, d, J=1.9 Hz), 7.33 (1H, dd, J=8.7, 2.7 Hz), 7.99 (1H, d, J=8.7 Hz), 8.45 (1H, d, J=2.7 Hz), 10.53 (1H, s).

Example 34

[2-(7-[2-Methoxy-1-(methoxymethyl)ethoxy]-5-{[6-(methylsulfonyl)pyridin-3-yl]oxy}-1H-indol-2-yl)-4,5-dihydro-1,3-thiazol-5-yl]acetic acid

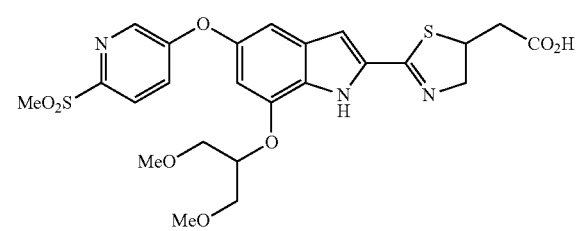

Ethyl [2-(7-[2-methoxy-1-(methoxymethyl)ethoxy]-5-{[6-(methylsulfonyl)pyridin-3-yl]oxy}-1H-indol-2-yl)-4,5-dihydro-1,3-thiazol-5-yl]acetate (390 mg) was dissolved in a mixture of tetrahydrofuran (5 mL) and methanol (5 mL). To the mixture was added 1M aqueous sodium hydroxide solution (2 mL) and the mixture was stirred at room temperature for 1 h. The mixture was concentrated under reduced pressure. The residue was dissolved in water and 1M hydrochloric acid (2 mL) was added to the mixture. The mixture was extracted with ethyl acetate. The organic layer was washed with saturated brine, dried over magnesium sulfate, filtered and concentrated to give the title compound (370 mg, 100%) as a pale orange amorphous solid. MS 550 (MH+).

$^1$H NMR (CDCl$_3$) δ 2.80 (2H, d, J=7.2 Hz), 3.21 (3H, s), 3.45 (3H, s), 3.46 (3H, s), 3.60-3.78 (4H, m), 4.25-4.56 (4H, m), 6.67 (1H, d, J=1.9 Hz), 6.85 (1H, d, J=1.9 Hz), 7.05 (1H, d, J=1.9 Hz), 7.33 (1H, dd, J=8.7, 2.7 Hz), 7.99 (1H, d, J=8.7 Hz), 8.45 (1H, dd, J=2.7 Hz), 10 54 (1H, s).

Example 35

2-[2-(7-[2-Methoxy-1-(methoxymethyl)ethoxy]-5-{[6-(methylsulfonyl)pyridin-3-yl]oxy}-1H-indol-2-yl)-4,5-dihydro-1,3-thiazol-5-yl]acetamide

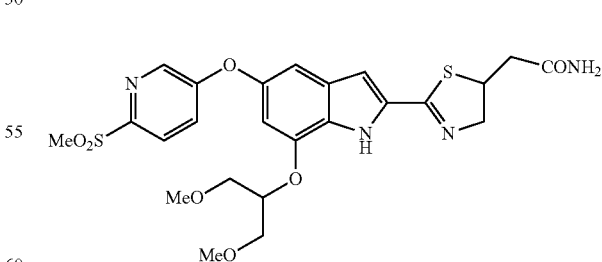

A mixture of [2-(7-[2-methoxy-1-(methoxymethyl)ethoxy]-5-{[6-(methylsulfonyl)pyridin-3-yl]oxy}-1H-indol-2-yl)-4,5-dihydro-1,3-thiazol-5-yl]acetic acid (190 mg), N-ethyl-N'-(3-dimethylaminopropyl)carbodiimide hydrochloride (133 mg), 1-hydroxybenzotriazole (93 mg) and N,N-dimethylformamide (5 mL) was stirred at 50° C. for 20 min.

After cooling to room temperature, 10% aqueous ammonium hydroxide solution (0.5 mL) was added to the mixture and the mixture was stirred at room temperature for 14 h. The mixture was concentrated under reduced pressure. The residue was dissolved in water and the mixture was extracted with ethyl acetate. The organic layer was washed with saturated brine, dried over magnesium sulfate, filtered and concentrated. The residual oil was crystallized from ethyl acetate. The resulting crystals were washed with diethyl. ether. The crystals were recrystallized from acetonitrile to give the title compound (139 mg, 74%) as colorless crystals. MS 549 (MH⁺). mp 172-173° C.

Example 36

2-[2-(7-[2-Methoxy-1-(methoxymethyl)ethoxy]-5-{[6-(methylsulfonyl)pyridin-3-yl]oxy}-1H-indol-2-yl)-4,5-dihydro-1,3-thiazol-5-yl]-N-methylacetamide

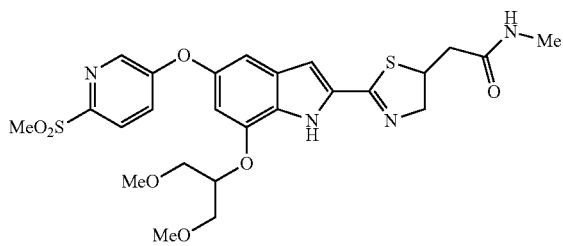 [SMILES: CNC(=O)CC1CN=C(c2cc3cc(Oc4ccc(S(C)(=O)=O)nc4)cc(OC(COC)COC)c3[nH]2)S1]

A mixture of [2-(7-[2-methoxy-1-(methoxymethyl) ethoxy]-5-{[6-(methylsulfonyl)pyridin-3-yl]oxy}-1H-indol-2-yl)-4,5-dihydro-1,3-thiazol-5-yl]acetic acid (180 mg), N-ethyl-N'-(3-dimethylaminopropyl)carbodiimide hydrochloride (126 mg), 1-hydroxybenzotriazole (88 mg), methylammonium chloride (44 mg), triethylamine (0.09 mL) and N,N-dimethylformamide (5 mL) was stirred at room temperature for 14 h. The mixture was concentrated under reduced pressure. The residue was dissolved in water and the mixture was extracted with ethyl acetate. The organic layer was washed with saturated brine, dried over magnesium sulfate, filtered and concentrated. The residue was purified by basic silica gel column chromatography (methanol/ethyl acetate/hexane=0/50/50 to 5/95/0, volume ratio) to give a white solid. The solid was recrystallized from acetonitrile-diethyl ether to give the title compound (140 mg, 75%) as colorless crystals. MS 563 (MH⁺). mp 149-151° C.

Example 37

2-[2-(7-[2-Methoxy-1-(methoxymethyl)ethoxy]-5-{[6-(methylsulfonyl)pyridin-3-yl]oxy}-1H-indol-2-yl)-4,5-dihydro-1,3-thiazol-5-yl]ethanol

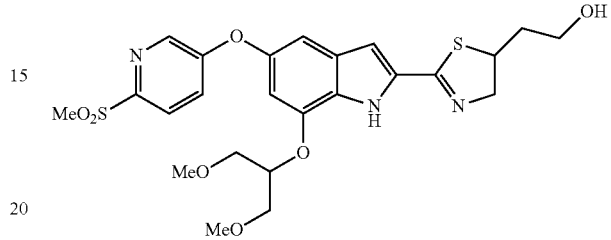

Ethyl [2-(7-[2-methoxy-1-(methoxymethyl)ethoxy]-5-{[6-(methylsulfonyl)pyridin-3-yl]oxy}-1H-indol-2-yl)-4,5-dihydro-1,3-thiazol-5-yl]acetate (220 mg) was dissolved in a mixture of tetrahydrofuran (2 mL) and methanol (1 mL). Lithium borohydride (41 mg) was added to the mixture at 0° C. and the mixture was stirred at room temperature for 6.5 h. Water was added to the mixture and the mixture was extracted with ethyl acetate. The organic layer was washed with saturated brine, dried over magnesium sulfate, filtered and concentrated. The residue was purified by silica gel column chromatography (methanol/ethyl acetate/hexane=0/40/60 to 15/85/0, volume ratio) to give an orange oil. The oil was crystallized from acetonitrile. The crystals were recrystallized from acetonitrile-diethyl ether to give the title compound (105 mg, 75%) as colorless crystals. MS 536 (MH⁺). mp 69-71° C.

Example 38

Ethyl [2-(7-methoxy-5-{[5-(methylsulfonyl)pyridin-2-yl]oxy}-1H-indol-2-yl)-4,5-dihydro-1,3-thiazol-5-yl]acetate

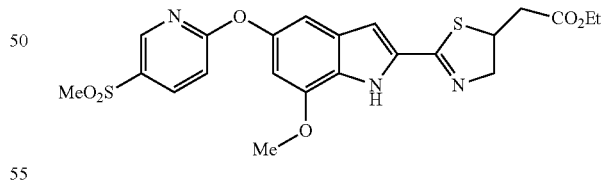

A mixture of 7-methoxy-5-{[5-(methylsulfonyl)pyridin-2-yl]oxy}-1H-indole-2-carbothioamide (2.06 g), ethyl 2-butynoate (0.95 mL), tributylphosphine (1.35 mL), tetrahydrofuran (50 mL) and toluene (100 mL) was stirred at 50° C. for 2 h. The mixture was concentrated under reduced pressure. The residue was purified by silica gel column chromatography (ethyl acetate/hexane=10/90 to 85/15, volume ratio) to give the title compound (1.36 g, 51%) as a pale yellow amorphous solid. MS 490 (MH⁺).

¹H NMR (CDCl₃) δ 1.28 (3H, t, J=7.2 Hz), 2.69-2.76 (2H, m), 3.09 (3H, s), 3.93 (3H, s), 4.19 (2H, q, J=7.2 Hz), 4.24-

4.47 (3H, m), 6.50 (1H, d, J=1.9 Hz), 6.86 (1H, d, J=2.3 Hz), 6.99-7.06 (2H, m), 8.15 (1H, dd, J=8.7, 2.6 Hz), 8.74 (1H, d, J=1.9 Hz), 9.24 (1H, s).

Example 39

1-[2-(7-Methoxy-5-{[5-(methylsulfonyl)pyridin-2-yl]oxy}-1H-indol-2-yl)-4,5-dihydro-1,3-thiazol-5-yl]-2-methylpropan-2-ol

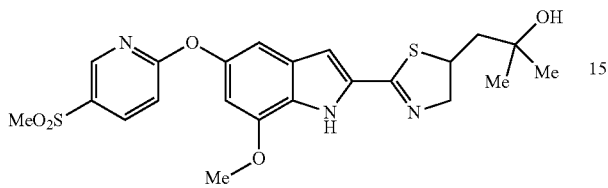

To a solution of ethyl [2-(7-methoxy-5-{[5-(methylsulfonyl)pyridin-2-yl]oxy}-1H-indol-2-yl)-4,5-dihydro-1,3-thiazol-5-yl]acetate (600 mg) in tetrahydrofuran (20 mL) was added 1M methylmagnesium bromide tetrahydrofuran solution (5 mL) at 0° C., and the mixture was stirred at room temperature for 30 min. Furthermore, 1M methylmagnesium bromide tetrahydrofuran solution (5 mL) was added to the mixture at room temperature, and the mixture was stirred at room temperature for 30 min. The mixture was acidified with 1M hydrochloric acid, and the mixture was extracted with ethyl acetate. The organic layer was washed with saturated brine, dried over magnesium sulfate, filtered and concentrated. The residue was purified by silica gel column chromatography (ethyl acetate/hexane=50/50 to 85/15, volume ratio), followed by basic silica gel column chromatography (ethyl acetate/hexane=50/50 to 100/0, volume ratio) to give the title compound (1.36 g, 51%) as a pale yellow amorphous solid. The amorphous solid was crystallized from ethyl acetate-diethyl ether. The crystals were recrystallized from ethyl acetate-diethyl ether. MS 490 (MH$^+$). mp 171-173° C.

Example 40

2-[2-(7-Methoxy-5-{[5-(methylsulfonyl)pyridin-2-yl]oxy}-1H-indol-2-yl)-4,5-dihydro-1,3-thiazol-5-yl]ethanol

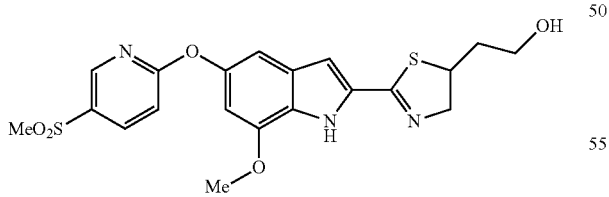

Ethyl [2-(7-methoxy-5-{[5-(methylsulfonyl)pyridin-2-yl]oxy}-1H-indol-2-yl)-4,5-dihydro-1,3-thiazol-5-yl]acetate (270 mg) was dissolved in a mixture of tetrahydrofuran (3 mL) and methanol (1.5 mL). Lithium borohydride (62 mg) was added to the mixture at 0° C. and the mixture was stirred at room temperature for 4 h. Water was added to the mixture and the mixture was extracted with ethyl acetate. The organic layer was washed with saturated brine, dried over magnesium sulfate, filtered and concentrated. The residue was purified by silica gel column chromatography (ethyl acetate/hexane=20/80 to 100/0, volume ratio), followed by basic silica gel column chromatography (methanol/ethyl acetate/hexane=0/20/80 to 10/90/0) to give the title compound (110 mg, 43%) as a white amorphous solid. MS 448 (MH$^+$).

$^1$H NMR (CDCl$_3$) δ 1.40 (1H, t, J=4.9 Hz), 1.82-2.03 (2H, m), 3.09 (3H, s), 3.73-3.85 (2H, m), 3.93 (3H, s), 4.09-4.32 (2H, m), 4.36-4.49 (1H, m), 6.50 (1H, d, J=1.9 Hz), 6.87 (1H, d, J=2.3 Hz), 6.98-7.05 (2H, m), 8.15 (1H, dd, J=8.9, 2.5 Hz), 8.74 (1H, d, J=2.7 Hz), 9.24 (1H, brs).

Example 41

[2-(7-Methoxy-5-{[5-(methylsulfonyl)pyridin-2-yl]oxy}-1H-indol-2-yl)-4,5-dihydro-1,3-th-iazol-5-yl]acetic acid

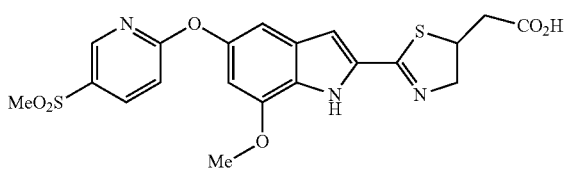 [SMILES: COc1cc(Oc2ccc(S(C)(=O)=O)cn2)cc2cc(C3=NCC(CC(=O)O)S3)[nH]c12]

Ethyl [2-(7-methoxy-5-{[5-(methylsulfonyl)pyridin-2-yl]oxy}-1H-indol-2-yl)-4,5-dihydro-1,3-thiazol-5-yl]acetate (500 mg) was dissolved in a mixture of tetrahydrofuran (5 mL) and ethanol (5 mL). To the mixture was added 1M aqueous sodium hydroxide solution (3 mL) and the mixture was stirred at room temperature for 50 min. The mixture was cooled to room temperature and concentrated under reduced pressure. The residue was dissolved in water and the mixture was washed with diethyl ether. The aqueous layer was acidified with 1M hydrochloric acid (3 mL). The mixture was extracted with ethyl acetate. The organic layer was washed with saturated brine, dried over magnesium sulfate, filtered and concentrated. The residual solid was washed with diethyl ether to give the title compound (450 mg, 96%) as a pale yellow solid. MS 462 (MH$^+$).

$^1$H NMR (DMSO-d$_6$) δ 2.55-2.88 (2H, m), 3.27 (3H, s), 3.87 (3H, s), 4.14-4.32 (2H, m), 4.40 (1H, d, J=7.9 Hz), 6.65 (1H, dd, J=1.9 Hz), 6.84 (1H, d, J=1.9 Hz), 7.00 (1H, d, J=1.9 Hz), 7.15 (1H, d, J=8.7 Hz), 8.28 (1H, dd, J=8.7, 2.6 Hz), 8.64 (1H, d, J=2.6 Hz), 11.77 (1H, s).

Example 42

2-[2-(7-Methoxy-5-{[5-(methylsulfonyl)pyridin-2-yl]oxy}-1H-indol-2-yl)-4,5-dihydro-1,3-thiazol-5-yl]-N-methylacetamide

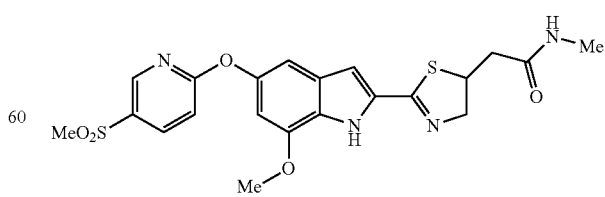

A mixture of [2-(7-methoxy-5-{[5-(methylsulfonyl)pyridin-2-yl]oxy}-1H-indol-2-yl)-4,5-dihydro-1,3-thiazol-5-yl]acetic acid (280 mg), N-ethyl-N'-(37-dimethylaminopropyl)

carbodiimide hydrochloride (233 mg), 1-hydroxybenzotriazole (164 mg), methylammonium chloride (82 mg), triethylamine (0.2 mL) and N,N-dimethylformamide (12 mL) was stirred at room temperature for 5 h. The mixture was concentrated under reduced pressure. The residue was dissolved in water and the mixture was extracted with ethyl acetate-tetrahydrofuran. The organic layer was washed successively with 1M hydrochloric acid, water, saturated aqueous sodium hydrogen carbonate solution and saturated brine, dried over magnesium sulfate, filtered and concentrated. The residue was purified by basic silica gel column chromatography (methanol/ethyl acetate/hexane=0/75/25 to 10/90/0, volume ratio) to give a pale yellow amorphous solid. The amorphous solid was crystallized from ethyl acetate-diethyl ether to give white crystals. The crystals were washed with methanol-acetone to give the title compound (178 mg, 62%) as colorless crystals. MS 475 (MH$^+$). mp 207-209° C.

Example 43

Ethyl [2-(7-[2-methoxy-1-(methoxymethyl)ethoxy]-5-{[5-(methylsulfonyl)pyridin-2-yl]oxy}-1H-indol-2-yl)-4,5-dihydro-1,3-thiazol-5-yl]acetate

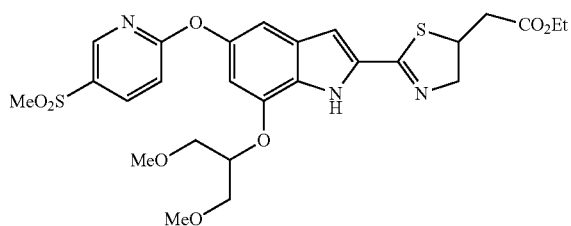 [SMILES: CCOC(=O)CC1CN=C(c2cc3cc(Oc4ccc(S(C)(=O)=O)cn4)cc(OC(COC)COC)c3[nH]2)S1]

A mixture of 7-[2-methoxy-1-(methoxymethyl)ethoxy]-5-{[5-(methylsulfonyl)pyridin-2-yl]oxy}-1H-indole-2-carbothioamide (1.69 g), ethyl 2-butynoate (0.84 mL), tributylphosphine (0.9 mL), tetrahydrofuran (20 mL) and toluene (30 mL) was stirred at 50° C. for 13 h. The mixture was concentrated under reduced pressure and the residue was purified by silica gel column chromatography (methanol/ethyl acetate/hexane=0/20/80 to 5/95/0, volume ratio), followed by basic silica gel column chromatography (ethyl acetate/hexane=20/80 to 90/10, volume ratio) to give the title compound (1.14 g, 55%) as a brownish amorphous solid. MS 578 (MH$^+$).

$^1$H NMR (CDCl$_3$) δ 1.28 (3H, t, J=7.2 Hz), 2.69-2.76 (2H, m), 3.09 (3H, s), 3.45 (3H, s), 3.46 (3H, s), 3.64-3.74 (4H, m), 4.19 (2H, q, J=7.2 Hz), 4.25-4.54 (4H, m), 6.71 (1H, d, J=1.9 Hz), 6.86 (1H, d, J=2.3 Hz), 7.01 (1H, d, J=8.7 Hz), 7.12 (1H, d, J=1.9 Hz), 8.14 (1H, dd, J=8.9, 2.5 Hz), 8.73 (1H, d, J=2.6 Hz), 10 47 (1H, s).

Example 44

1-[2-(7-[2-Methoxy-1-(methoxymethyl)ethoxy]-5-{[5-(methylsulfonyl)pyridin-2-yl]oxy}-1H-indol-2-yl)-4,5-dihydro-1,3-thiazol-5-yl]-2-methylpropan-2-ol

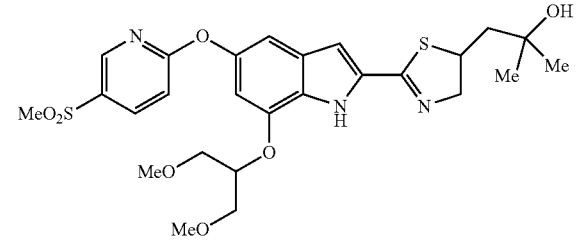 [SMILES: COCC(COC)Oc1cc(Oc2ccc(S(C)(=O)=O)cn2)cc2cc(C3=NCC(CC(C)(C)O)S3)[nH]c12]

To a solution of ethyl [2-(7-[2-methoxy-1-(methoxymethyl)ethoxy]-5-{[5-(methylsulfonyl)pyridin-2-yl]oxy}-1H-indol-2-yl)-4,5-dihydro-1,3-thiazol-5-yl]acetate (600 mg) in tetrahydrofuran (15 mL) was added 1M methylmagnesium bromide tetrahydrofuran solution (4 mL) at 0° C., and the mixture was stirred at room temperature for 30 min. Furthermore, 1M methylmagnesium bromide tetrahydrofuran solution (4 mL) was added to the mixture at room temperature and the mixture was stirred for 1 h. The mixture was acidified with 1M hydrochloric acid, and the mixture was extracted with ethyl acetate. The organic layer was washed with saturated brine, dried over magnesium sulfate, filtered and concentrated. The residue was purified by silica gel column chromatography (methanol/ethyl acetate/hexane=0/50/50 to 15/85/0, volume ratio), followed by basic silica gel column chromatography (ethyl acetate/hexane=40/60 to 0/100, volume ratio) to give the title compound (200 mg, 34%) as a white amorphous solid. MS 564 (MH$^+$).

$^1$H NMR (CDCl$_3$) δ 1.30 (3H, s), 1.32 (3H, s), 1.94-2.10 (2H, m), 3.09 (3H, s), 3.45 (6H, s), 3.64-3.74 (4H, m), 4.02-4.27 (2H, m), 4.43-4.61 (2H, m), 6.70 (1H, d, J=1.9 Hz), 6.86 (1H, d, J=2.3 Hz), 7.00 (1H, d, J=8.7 Hz), 7.11 (1H, d, J=1.9 Hz), 8.14 (1H, dd, J=8.7, 2.3 Hz), 8.73 (1H, d, J=2.3 Hz), 10.04 (1H, brs).

Example 45

[2-(7-[2-Methoxy-1-(methoxymethyl)ethoxy]-5-{[5-(methylsulfonyl)pyridin-2-yl]oxy}-1H-indol-2-yl)-4,5-dihydro-1,3-thiazol-5-yl]acetic acid

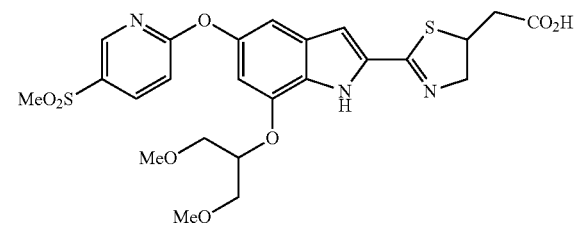

Ethyl [2-(7-[2-methoxy-1-(methoxymethyl)ethoxy]-5-{5-(methylsulfonyl)pyridin-2-yl]oxy}-1H-indol-2-yl)-4,5-dihydro-1,3-thiazol-5-yl]acetate (540 mg) was dissolved in a mixture of tetrahydrofuran (10 mL) and ethanol (10 mL). To the mixture was added 1M aqueous sodium hydroxide solution (3 mL) and the mixture was stirred at room temperature for 50 min. The mixture was concentrated under reduced pressure. The residue was dissolved in water and the mixture was acidified with 1M hydrochloric acid. The mixture was extracted with ethyl acetate. The organic layer was washed with saturated brine, dried over magnesium sulfate, filtered and concentrated to give the title compound (500 mg, 98%) as a brownish amorphous solid. MS 550 (MH$^+$).

$^1$H NMR (CDCl$_3$) δ 2.78 (2H, d, J=7.2 Hz), 3.09 (3H, s), 3.45 (3H, s), 3.46 (3H, s), 3.63-3.78 (4H, m), 4.22-4.59 (4H, m), 6.70 (1H, d, J=2.3 Hz), 6.86 (1H, d, J=2.3 Hz), 7.02 (1H, d, J=9.5 Hz), 7.11 (1H, d, J=1.9 Hz), 8.14 (1H, dd, J=8.9, 2.5 Hz), 8.73 (1H, d, J=1.9 Hz), 10.47 (1H, s).

Example 46

2-[2-(7-[2-Methoxy-1-(methoxymethyl)ethoxy]-5-{[5-(methylsulfonyl)pyridin-2-yl]oxy}-1H-indol-2-yl)-4,5-dihydro-1,3-thiazol-5-yl]-N-methylacetamide

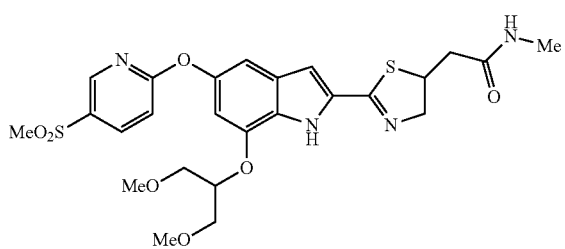 [SMILES: CNC(=O)CC1CN=C(c2cc3cc(Oc4ccc(S(C)(=O)=O)cn4)cc(OC(COC)COC)c3[nH]2)S1]

A mixture of [2-(7-[2-methoxy-1-(methoxymethyl)ethoxy]-5-{[5-(methylsulfonyl)pyridin-2-yl]oxy}-1H-indol-2-yl)-4,5-dihydro-1,3-thiazol-5-yl]acetic acid (280 mg), N-ethyl-N'-(3-dimethylaminopropyl)carbodiimide hydrochloride (195 mg), 1-hydroxybenzotriazole (138 mg), methylammonium chloride (69 mg), triethylamine (0.14 mL) and N,N-dimethylformamide (15 mL) was stirred at room temperature for 2.5 h. The mixture was concentrated under reduced pressure. The residue was dissolved in water and the mixture was extracted with ethyl acetate-tetrahydrofuran. The organic layer was washed with saturated brine, dried over magnesium sulfate, filtered and concentrated. The residue was purified by basic silica gel column chromatography (methanol/ethyl acetate=0/100 to 5/95, volume ratio) to give a pale yellow amorphous solid. The amorphous solid was crystallized from acetonitrile-diethyl ether to give white crystals. The crystals were recrystallized from ethyl acetate-diethyl ether to give the title compound (174 mg, 61%) as colorless crystals. MS 563 (MH$^+$). mp 123-125° C.

Example 47

Ethyl [2-(7-methoxy-5-{[6-(methoxymethyl)pyridin-3-yl]oxy}-1H-indol-2-yl)-4,5-dihydro-1,3-thiazol-5-yl]acetate

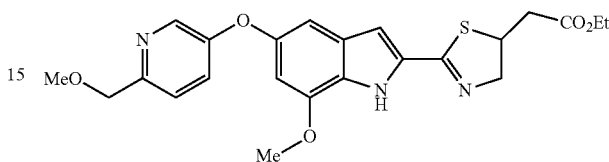

A mixture of 7-methoxy-5-{[6-(methoxymethyl)pyridin-3-yl]oxy}-1H-indole-2-carbothioamide (2.04 g), ethyl 2-butynoate (1.8 mL), tributylphosphine (1.5 mL), tetrahydrofuran (25 mL) and toluene (30 mL) was stirred at 50° C. for 1 h. The mixture was concentrated under reduced pressure. The residue was purified by silica gel column chromatography (ethyl acetate/hexane=10/90 to 70/30, volume ratio) to give the title compound (1.36 g, 52%) as a yellow amorphous solid. MS 578 (MH$^+$).

$^1$H NMR (CDCl$_3$) δ 1.28 (3H, t, J=7.2 Hz), 2.72 (2H, d, J=6.4 Hz), 3.47 (3H, s), 3.91 (3H, s), 4.19 (2H, q, J=7.2 Hz), 4.23-4.46 (3H, m), 4.55 (2H, s), 6.48 (1H, d, J=1.9 Hz), 6.80 (1H, d, J=2.3 Hz), 6.85 (1H, d, J=1.9 Hz), 7.22-7.29 (1H, m), 7.31-7.37 (1H, m), 8.36 (1H, d, J=2.3 Hz), 9.20 (1H, brs).

Example 48

[2-(7-Methoxy-5-{[6-(methoxymethyl)pyridin-3-yl]oxy}-1H-indol-2-yl)-4,5-dihydro-1,3-thiazol-5-yl]acetic acid

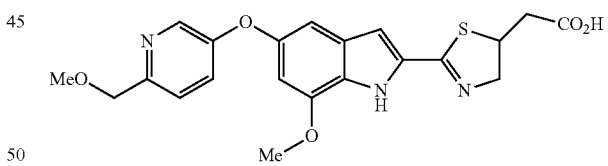

Ethyl [2-(7-methoxy-5-{[6-(methoxymethyl)pyridin-3-yl]oxy}-1H-indol-2-yl)-4,5-dihydro-1,3-thiazol-5-yl]acetate (1.36 g) was dissolved in a mixture of tetrahydrofuran (15 mL) and ethanol (15 mL). To the mixture was added 1M aqueous sodium hydroxide solution (5 mL) and the mixture was stirred at room temperature for 30 min. The mixture was concentrated under reduced pressure. The residue was dissolved in water and the mixture was neutralized with 1M hydrochloric acid. The mixture was extracted with ethyl acetate. The organic layer was washed with saturated brine, dried over magnesium sulfate, filtered and concentrated to give the title compound (1.30 g, 100%) as a yellow amorphous solid. MS 428 (MH$^+$).

$^1$H NMR (CDCl$_3$) δ 2.78 (2H, d, J=7.2 Hz), 3.48 (3H, s), 3.92 (3H, s), 4.25-4.47 (3H, m), 4.56 (2H, m), 6.48 (1H, d,

J=1.9 Hz), 6.83 (1H, d, J=1.9 Hz), 6.85 (1H, d, J=1.9 Hz), 7.24-7.39 (2H, m), 8.33 (1H, d, J=2.6 Hz), 9.51 (1H, s).

Example 49

2-[2-(7-Methoxy-5-{[6-(methoxymethyl)pyridin-3-yl]oxy}-1H-indol-2-yl)-4,5-dihydro-1,3-thiazol-5-yl]acetamide

A mixture of [2-(7-methoxy-5-{[6-(methoxymethyl)pyridin-3-yl]oxy}-1H-indol-2-yl)-4,5-dihydro-1,3-thiazol-5-yl] acetic acid (160 mg), N-ethyl-N'-(3-dimethylaminopropyl)carbodiimide hydrochloride (144 mg), 1-hydroxybenzotriazole monohydrate (115 mg), 25% aqueous ammonium hydroxide solution (1 mL) and N,N-dimethylformamide (8 mL) was stirred at room temperature for 3.5 h. The mixture was concentrated under reduced pressure. The residue was dissolved in water and the mixture was extracted with ethyl acetate. The organic layer was washed with saturated brine, dried over magnesium sulfate, filtered and concentrated. The residue was purified by basic silica gel column chromatography (methanol/ethyl acetate=0/100 to 8/92, volume ratio) to give a white amorphous solid. The amorphous solid was crystallized from ethyl acetate-diethyl ether to give white crystals. The crystals were recrystallized from ethyl acetate-hexane to give the title compound (68 mg, 43%) as colorless crystals. MS 427 (MH$^+$). mp 135-136° C.

Example 50

2-[2-(7-Methoxy-5-{[6-(methoxymethyl)pyridin-3-yl]oxy}-1H-indol-2-yl)-4,5-dihydro-1,3-thiazol-5-yl]-N-methylacetamide

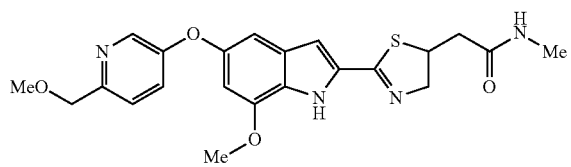 [SMILES: CNC(=O)CC1CN=C(c2cc3cc(Oc4ccc(COC)nc4)cc(OC)c3[nH]2)S1]

A mixture of [2-(7-methoxy-5-{[6-(methoxymethyl)pyridin-3-yl]oxy}-1H-indol-2-yl)-4,5-dihydro-1,3-thiazol-5-yl] acetic acid (300 mg), N-ethyl-N'-(3-dimethylaminopropyl)carbodiimide hydrochloride (270 mg), 1-hydroxybenzotriazole monohydrate (216 mg), methylammonium chloride (95 mg), triethylamine (0.2 mL) and N,N-dimethylformamide (13 mL) was stirred at room temperature for 2 h. The mixture was concentrated under reduced pressure. The residue was dissolved in water and the mixture was extracted with ethyl acetate. The organic layer was washed with saturated brine, dried over magnesium sulfate, filtered and concentrated. The residue was purified by basic silica gel column chromatography (methanol/ethyl acetate=0/100 to 5/95, volume ratio), followed by silica gel column chromatography (methanol/ethyl acetate=0/100 to 8/92, volume ratio) to give a yellow oil. The oil was crystallized from acetonitrile-diethyl ether to give white crystals. The crystals were recrystallized from acetonitrile-diethyl ether to give the title compound (204 mg, 66%) as colorless crystals. MS 441 (MH$^+$). mp 102-104° C.

Example 51

N-Ethyl-2-[2-(7-methoxy-5-{[6-(methoxymethyl)pyridin-3-yl]oxy}-1H-indol-2-yl)-4,5-dihydro-1,3-thiazol-5-yl]acetamide

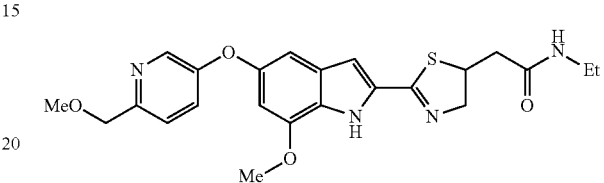

A mixture of [2-(7-methoxy-5-{[6-(methoxymethyl)pyridin-3-yl]oxy}-1H-indol-2-yl)-4,5-dihydro-1,3-thiazol-5-yl] acetic acid (300 mg), N-ethyl-N'-(3-dimethylaminopropyl)carbodiimide hydrochloride (268 mg), 1-hydroxybenzotriazole monohydrate (214 mg), 2M ethylamine tetrahydrofuran solution (0.7 mL) and N,N-dimethylformamide (10 mL) was stirred at room temperature for 16 h. The mixture was concentrated under reduced pressure. The residue was dissolved in water and the mixture was extracted with ethyl acetate. The organic layer was washed with saturated brine, dried over magnesium sulfate, filtered and concentrated. The residue was purified by basic silica gel column chromatography (methanol/ethyl acetate/hexane=0/70/30 to 8/92/0, volume ratio) to give a pale yellow amorphous solid. The amorphous solid was crystallized from acetonitrile to give white crystals. The crystals were recrystallized from acetonitrile to give the title compound (222 mg, 70%) as colorless crystals. MS 455 (MH$^+$). mp 130-132° C.

Example 52

Ethyl (2-{7-(2-methoxy-1-methylethoxy)-5-[4-(methylsulfonyl)phenoxy]-1H-indol-2-yl}-4,5-dihydro-1,3-thiazol-5-yl)acetate

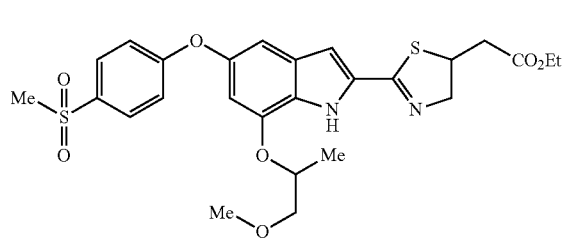 [SMILES: CCOC(=O)CC1CN=C(c2cc3cc(Oc4ccc(S(C)(=O)=O)cc4)cc(OC(C)COC)c3[nH]2)S1]

To a solution of 7-(2-methoxy-1-methylethoxy)-5-[4-(methylsulfonyl)phenoxy]-1H-indole-2-carboxamide (874 mg) in tetrahydrofuran (20 mL) was added Lawesson's reagent (845 mg) at room temperature. The mixture was stirred at 50° C. for 45 min, and then cooled to room temperature. The mixture was concentrated in vacuo. The residue was purified by silica gel chromatography (ethyl acetate:hexane=50:50 to 100:0, volume ratio) to give a yellow amorphous solid. To a solution of the solid in tetrahydrofuran (20 mL) were added ethyl 2-butynoate (0.507 mL) and tributylphosphine (0.652 mL). The whole was stirred at 50° C. for 45 min. The mixture was cooled to room temperature and concentrated in vacuo. The residue was purified by silica gel chromatography (ethyl acetate:hexane=50:50 to 100:0) to give the title compound (531 mg, 46%) as a brown amorphous solid. MS 547 (MH$^+$).

$^1$H NMR (DMSO-d$_6$) δ 1.13-1.23 (6H, m), 2.59-2.75 (1H, m), 2.81-2.93 (1H, m), 3.17 (3H, s), 3.30 (3H, s), 3.45-3.53 (1H, m), 3.55-3.65 (1H, m), 4.04-4.16 (2H, m), 4.20-4.47 (3H, m), 4.58-4.74 (1H, m), 6.69 (1H, d, J=1.89 Hz), 6.84 (1H, d, J=1.89 Hz), 6.96 (1H, d, J=1.89 Hz), 7.06-7.14 (2H, m), 7.79-7.92 (2H, m), 11.66 (1H, s).

Example 53

(2-{7-(2-Methoxy-1-methylethoxy)-5-[4-(methylsulfonyl)phenoxy]-1H-indol-2-yl}-4,5-dihydro-1,3-thiazol-5-yl)acetic acid

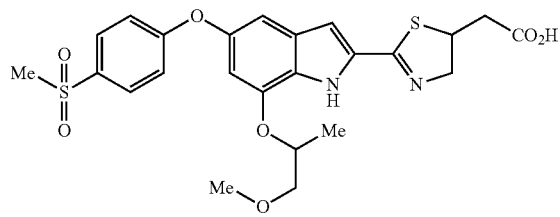 [SMILES: COCC(C)Oc1cc(Oc2ccc(S(C)(=O)=O)cc2)cc2cc(C3=NCC(CC(=O)O)S3)[nH]c12]

To a mixture of ethyl (2-{7-(2-methoxy-1-methylethoxy)-5-[4-(methylsulfonyl)phenoxy]-1H-indol-2-yl}-4,5-dihydro-1,3-thiazol-5-yl)acetate (134 mg), tetrahydrofuran (1 mL) and ethanol (1 mL) was added 1M aqueous sodium hydroxide solution (0.51 mL). The whole was stirred at room temperature for 2 h, and then concentrated in vacuo. The residue was acidified by 1M hydrochloric acid, and then extracted with ethyl acetate-tetrahydrofuran. The organic layer was washed successively with water and brine, dried (MgSO$_4$), filtered, and concentrated in vacuo to give the title compound (57 mg, 43%) as a yellow amorphous solid. MS 519 (MH$^+$).

$^1$H NMR (DMSO-d$_6$) δ 1.25 (3H, d, J=6.06 Hz), 2.52-2.63 (1H, m), 2.66-2.83 (1H, m), 3.17 (3H, s), 3.31 (3H, s), 3.44-3.54 (1H, m), 3.57-3.66 (1H, m), 4.14-4.34 (2H, m), 4.34-4.50 (1H, m), 4.62-4.74 (1H, m), 6.68 (1H, d, J=1.89 Hz), 6.83 (1H, d, J=1.89 Hz), 6.96 (1H, d, J=1.89 Hz), 7.04-7.18 (2H, m), 7.78-7.94 (2H, m), 11.63 (1H, s).

Example 54

2-(2-{7-(2-Methoxy-1-methylethoxy)-5-[4-(methylsulfonyl)phenoxy]-1H-indol-2-yl}-4,5-dihydro-1,3-thiazol-5-yl)acetamide

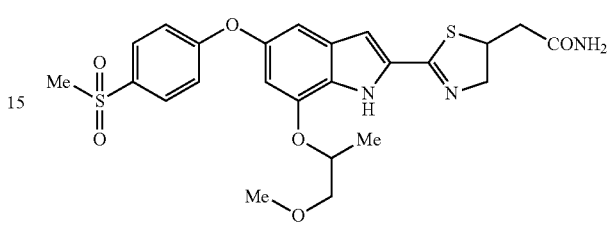

To a solution of (2-{7-(2-methoxy-1-methylethoxy)-5-[4-(methylsulfonyl)phenoxy]-1H-indol-2-yl}-4,5-dihydro-1,3-thiazol-5-yl)acetic acid (48 mg) in N,N-dimethylformamide (2 mL) were added 1-ethyl-3-(3-dimethylaminopropyl)carbodiimide hydrochloride (35 mg) and 1-hydroxybenzotriazole ammonium salt (28 mg) at room temperature. The mixture was stirred at room temperature over night. The mixture was concentrated in vacuo. Ethyl acetate was added to the residue and the resultant was washed with water, dried (MgSO$_4$), filtered, and concentrated in vacuo. The residue was purified by silica gel chromatography (ethyl acetate:methanol=100:0 to 90:10, volume ratio) to give the title compound. The compound was triturated and washed with diethyl ether-ethyl acetate-hexane to give the title compound (11 mg, 23%) as a white powder. mp 107-112° C.

$^1$H NMR (CDCl$_3$) δ 1.20-1.42 (3H, m), 2.49-2.74 (2H, m), 3.04 (3H, s), 3.37-3.58 (4H, m), 3.57-3.77 (1H, m), 4.22-4.46 (3H, m), 4.44-4.64 (1H, m), 5.24-5.56 (2H, m), 6.58 (1H, s), 6.85 (1H, s), 6.96-7.12 (3H, m), 7.85 (2H, d, J=8.71 Hz), 9.96 (1H, brs).

Example 55

2-(2-{7-(2-Methoxy-1-methylethoxy)-5-[4-(methylsulfonyl)phenoxy]-1H-indol-2-yl}-4,5-dihydro-1,3-thiazol-5-yl)ethanol

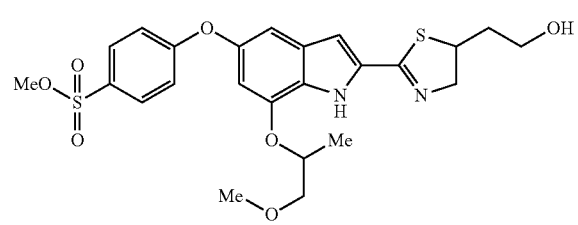 [SMILES: COCC(C)Oc1cc(Oc2ccc(S(=O)(=O)OC)cc2)cc2cc(C3=NCC(CCO)S3)[nH]c12]

To a solution of ethyl (2-{7-(2-methoxy-1-methylethoxy)-5-[4-(methylsulfonyl)phenoxy]-1H-indol-2-yl}-4,5-dihydro-1,3-thiazol-5-yl)acetate (277 mg) in tetrahydrofuran (5 mL) was added lithium borohydride (55 mg) at 0° C. After stirring at 0° C. for 1.5 h, lithium borohydride (22 mg) was added to the mixture. The whole was stirred at 0° C. for 2 h, at room temperature for 2.5 h, and then at 50° C. overnight. Water was added to the mixture and the mixture was extracted with ethyl acetate. The organic layer was washed with water, dried (MgSO$_4$), filtered, and concentrated in vacuo. The residue was purified by silica gel chromatography (ethyl acetate:methanol=100:0 to 95:5, volume ratio) to give the title compound (37% mg, 15%) as a white amorphous solid. MS 505 (MH$^+$).

$^1$H NMR (DMSO-d$_6$) δ 1.25 (3H, d, J=6.40 Hz), 1.60-1.78 (1H, m), 1.79-1.94 (1H, m), 3.17 (3H, s), 3.30 (3H, s), 3.43-3.54 (3H, m), 3.55-3.66 (1H, m), 4.07-4.27 (2H, m), 4.35-4.47 (1H, m), 4.60-4.74 (2H, m), 6.68 (1H, d, J=2.07 Hz), 6.84 (1H, d, J=2.0 Hz), 6.97 (1H, d, J=1.88 Hz), 7.07-7.14 (2H, m), 7.82-7.91 (2H, m), 11.63 (1H, s).

Example 56

2-(2-{7-(2-Methoxy-1-methylethoxy)-5-[4-(methylsulfonyl)phenoxy]-1H-indol-2-yl}-4,5-dihydro-1,3-thiazol-5-yl)ethanol

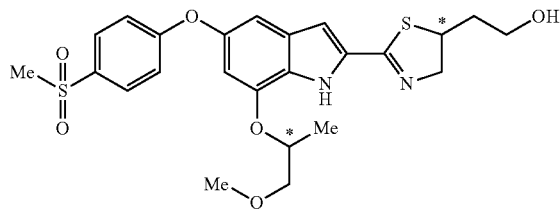 [SMILES: COCC(C)Oc1cc(Oc2ccc(S(C)(=O)=O)cc2)cc2cc(C3=NCC(CCO)S3)[nH]c12]

A solution of 2-(2-{7-(2-methoxy-1-methylethoxy)-5-[4-(methylsulfonyl)phenoxy]-1H-indol-2-yl}-4,5-dihydro-1,3-thiazol-5-yl)ethanol (40 mg) in ethanol (10 mL) was resolved by preparative high performance liquid chromatography (HPLC), using CHIRALPAK AD (50 mm i.d.×50 mm L, Daicel Chemical Industries, Ltd.) and ethanol (100%) as the mobile phase with the flow rate of 60 mL/min at 30° C. The fractions containing a single enantiomer, eluted at a retention time of 29 min, were collected and concentrated to give the title compound (10 mg) as a white powder. The compound was dissolved in methanol and the solution was filtered. The filtrate was concentrated to give the title compound (10.7 mg) as a colorless amorphous solid. MS 505 (MH$^+$).

Example 57

2-(2-{7-(2-Methoxy-1-methylethoxy)-5-[4-(methylsulfonyl)phenoxy]-1H-indol-2-yl}-4,5-dihydro-1,3-thiazol-5-yl)ethanol

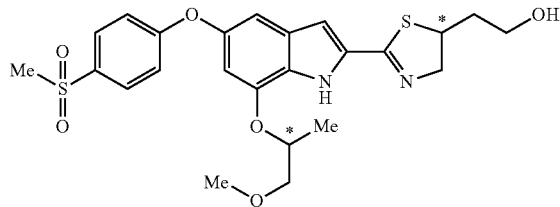 [SMILES: COCC(C)Oc1cc(Oc2ccc(S(C)(=O)=O)cc2)cc2cc(C3=NCC(CCO)S3)[nH]c12]

A solution of 2-(2-{7-(2-methoxy-1-methylethoxy)-5-[4-(methylsulfonyl)phenoxy]-1H-indol-2-yl}-4,5-dihydro-1,3-thiazol-5-yl)ethanol (40 mg) in ethanol (10 mL) was resolved by preparative high performance liquid chromatography (HPLC), using CHIRALPAK AD (50 mm i.d.×50 mm L, Daicel Chemical Industries, Ltd.) and ethanol (100%) as the mobile phase with the flow rate of 60 mL/min at 30° C. The fractions containing a single enantiomer, eluted at a retention time of 35 min, were collected and concentrated to give the title compound (11 mg) as a white powder. The compound was dissolved in methanol and the solution was filtered. The filtrate was concentrated to give the title compound (10.7 mg) as a colorless amorphous solid. MS 505 (MH$^+$).

Example 58

2-(2-{7-(2-Methoxy-1-methylethoxy)-5-[4-(methylsulfonyl)phenoxy]-1H-indol-2-yl}-4,5-dihydro-1,3-thiazol-5-yl)ethanol

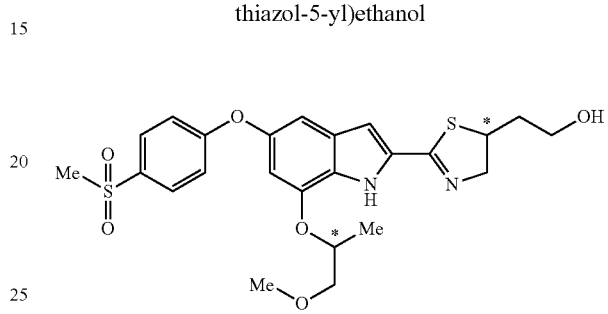

A solution of 2-(2-{7-(2-methoxy-1-methylethoxy)-5-[4-(methylsulfonyl)phenoxy]-1H-indol-2-yl}-4,5-dihydro-1,3-thiazol-5-yl)ethanol (40 mg) in ethanol (10 mL) was resolved by preparative high performance liquid chromatography (HPLC), using CHIRALPAK AD (50 mm i.d.×50 mm L, Daicel Chemical Industries, Ltd.) and ethanol (100%) as the mobile phase with the flow rate of 60 mL/min at 30° C. The fractions containing a single enantiomer, eluted at a retention time of 41 min, were collected and concentrated to give the title compound (10 mg) as a white powder. The compound was dissolved in methanol and the solution was filtered. The filtrate was concentrated to give the title compound (10.6 mg) as a colorless amorphous solid. MS 505 (MH$^+$).

Example 59

2-(2-{7-(2-Methoxy-1-methylethoxy)-5-[4-(methylsulfonyl)phenoxy]-1H-indol-2-yl}-4,5-dihydro-1,3-thiazol-5-yl)ethanol

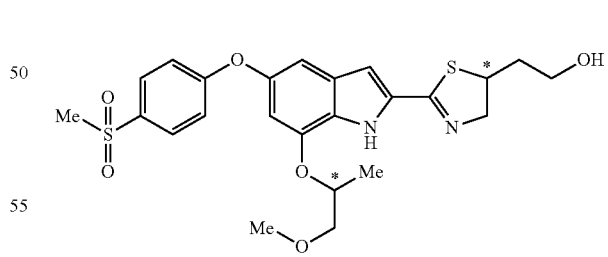

A solution of 2-(2-{7-(2-methoxy-1-methylethoxy)-5-[4-(methylsulfonyl)phenoxy]-1H-indol-2-yl}-4,5-dihydro-1,3-thiazol-5-yl)ethanol (40 mg) in ethanol (10 mL) was resolved by preparative high performance liquid chromatography (HPLC), using CHIRALPAK AD (50 mm i.d.×50 mm L, Daicel Chemical Industries, Ltd.) and ethanol (100%) as the mobile phase with the flow rate of 60 mL/min at 30° C. The fractions containing a practically pure single enantiomer, eluted at a retention time of 52 min, were collected and concentrated to give the title compound (12 mg) as a white powder. The compound was dissolved in methanol and the mixture was filtered. The filtrate was concentrated to give the title compound (11.5 mg) as a colorless amorphous solid. MS 505 (MH$^+$).

Example 60

1-(2-{7-(2-Methoxy-1-methylethoxy)-5-[4-(methyl-sulfonyl)phenoxy]-1H-indol-2-yl}-4,5-dihydro-1,3-thiazol-5-yl)-2-methylpropan-2-ol

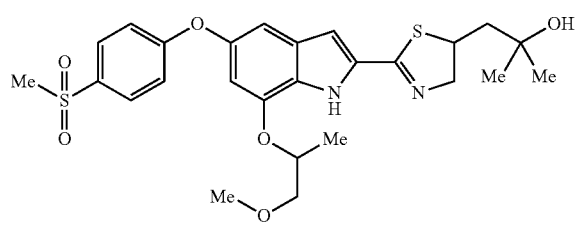 [SMILES: COCC(C)Oc1cc(Oc2ccc(S(C)(=O)=O)cc2)cc2cc(C3=NCC(CC(C)(C)O)S3)[nH]c12]

To a solution of ethyl (2-{7-(2-methoxy-1-methylethoxy)-5-[4-(methylsulfonyl)phenoxy]-1H-indol-2-yl}-4,5-dihydro-1,3-thiazol-5-yl)acetate (490 mg) in tetrahydrofuran (20 mL) was added methylmagnesium bromide (1M in tetrahydrofuran, 5.4 mL) at 0° C. After stirring at room temperature for 1 h, methylmagnesium bromide (1M in tetrahydrofuran, 5.4 mL) was added to the mixture. Then the whole was stirred at room temperature for 1 h. Methylmagnesium bromide (1M in tetrahydrofuran, 5.4 mL) was added to the mixture again and the whole was stirred at room temperature for further 1 h. Water and 1M hydrochloric acid were added to the mixture, and the mixture was extracted with ethyl acetate. The organic layer was washed with brine, dried (MgSO$_4$), filtered, and concentrated in vacuo. The residue was purified by silica gel chromatography (hexane:ethyl acetate=1:1 to 1:9, volume ratio) to give a pale yellow oil. The oil was crystallized from ethyl acetate-diethyl ether to give the title compound (40 mg, 8%) as colorless crystals. The crystals were recrystallized from ethyl acetate-diethyl ether to give colorless prisms. MS 533 (MH$^+$). mp 112-113° C.

Example 61

Ethyl {2-[7-(1-methylethoxy)-5-{[5-(methylsulfonyl)pyridin-2-yl]oxy}-1H-indol-2-yl]-4,5-dihydro-1,3-thiazol-5-yl}acetate

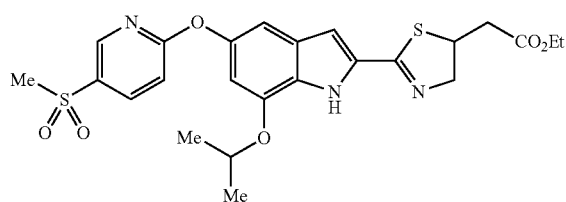 [SMILES: CCOC(=O)CC1CN=C(c2cc3cc(Oc4ccc(S(C)(=O)=O)cn4)cc(OC(C)C)c3[nH]2)S1]

A mixture of 7-(1-methylethoxy)-5-{[5-(methylsulfonyl)pyridin-2-yl]oxy}-1H-indole-2-carboxamide (2.0 g), Lawesson's reagent (2.27 g) and tetrahydrofuran (70 mL) was stirred at 65° C. for 1 h. The mixture was concentrated in vacuo. Toluene and diisopropyl ether were added to the residue to give crystals. The crystals were collected by filtration and washed with toluene-diisopropyl ether to give yellow crystals. A mixture of the crystals, ethyl 2-butynoate (1.44 g), tributylphosphine (1.03 g) and tetrahydrofuran (100 mL) was stirred at 70° C. for 2 h, and then concentrated in vacuo. The residue was purified by silica gel chromatography (ethyl acetate:hexane=1:4 to 2:1, volume ratio) to give the title compound (1.18 g, 45%) as a yellow amorphous solid. MS 518 (MH$^+$).

$^1$H NMR (CDCl$_3$) δ 1.28 (3H, t, J=7.19 Hz), 1.39 (6H, J=6.06 Hz), 2.73 (2H, d, J=6.44 Hz), 3.09 (3H, s), 4.05-4.48 (5H, m), 4.55-4.73 (1H, m), 6.49 (1H, d, J=1.89 Hz), 6.85 (1H, d, J=2.27 Hz), 6.97 (1H, d, J=1.51 Hz), 7.01 (1H, d, J=9.47 Hz), 8.14 (1H, dd, J=8.71, 2.65 Hz), 8.73 (1H, d, J=1.89 Hz), 9.25 (1H, brs).

Example 62

2-{2-[(7-(1-Methylethoxy)-5-{[5-(methylsulfonyl)pyridin-2-yl]oxy}-1H-indol-2-yl]-4,5-dihydro-1,3-thiazol-5-yl}ethanol

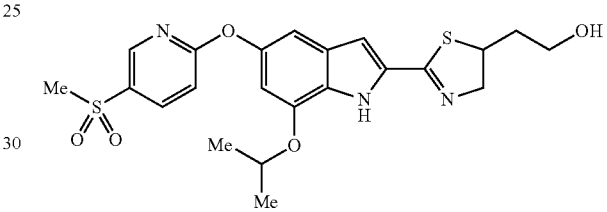

To a mixture of ethyl {2-[7-(1-methylethoxy)-5-{[5-(methylsulfonyl)pyridin-2-yl]oxy}-1H-indol-2-yl]-4,5-dihydro-1,3-thiazol-5-yl}acetate (500 mg), tetrahydrofuran (20 mL) and methanol (5 mL) was added lithium borohydride (110 mg) at 0° C. The whole was stirred at room temperature for 2 h. Water was added to the mixture and the mixture was extracted with ethyl acetate. The organic layer was washed with brine, dried (MgSO$_4$), filtered, and concentrated in vacuo. The residue was purified by silica gel chromatography (ethyl acetate:hexane=1:2 to 9:1, volume ratio) to give a pale yellow amorphous solid. The solid was crystallized from ethyl acetate-diethyl ether to give the title compound (210 mg, 46%) as pale yellow crystals. The crystals were recrystallized from ethyl acetate-diethyl ether to give pale yellow prisms. MS 476 (MH$^+$). mp 172-173° C.

Example 63

2-Methyl-1-{2-[7-(1-methylethoxy)-5-{[5-(methylsulfonyl)pyridin-2-yl]oxy}-1H-indol-2-yl]-4,5-dihydro-1,3-thiazol-5-yl}propan-2-ol

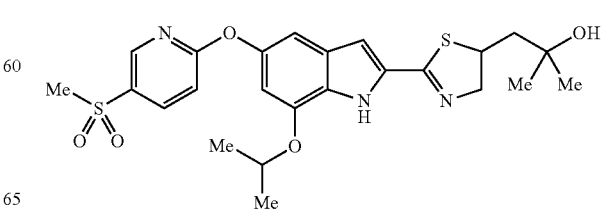

To a solution of ethyl {2-[7-(1-methylethoxy)-5-{[5-(methylsulfonyl)pyridin-2-yl]oxy}-1H-indol-2-yl]-4,5-dihydro-1,3-thiazol-5-yl}acetate (680 mg) in tetrahydrofuran (30 mL) was added methylmagnesium bromide (1M in tetrahydrofuran, 5.2 mL) at room temperature. After stirring at room temperature for 2 h, saturated aqueous solution of ammonium chloride was added to the mixture, and the mixture was extracted with ethyl acetate. The organic layer was washed with brine, dried (MgSO$_4$), filtered, and concentrated in vacuo. The residue was purified by silica gel chromatography (hexane:ethyl acetate=2:1 to 1:9, volume ratio) to give a yellow amorphous solid. The solid was crystallized from ethyl acetate-diethyl ether to give the title compound (95 mg, 15%) as pale yellow crystals. The crystals were recrystallized from ethyl acetate-diethyl ether to give pale yellow prisms. MS 504 (MH$^+$). mp 151-153° C.

Example 64

2-Methyl-1-{2-[7-(1-methylethoxy)-5-{[5-(methylsulfonyl)pyridin-2-yl]oxy}-1H-indol-2-yl]-4,5-dihydro-1,3-thiazol-5-yl}propan-2-ol

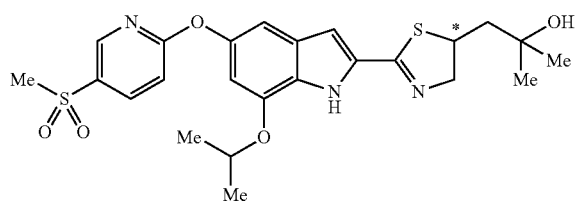 [SMILES: CC(C)Oc1cc(Oc2ccc(S(C)(=O)=O)cn2)cc2cc(C3=NCC(CC(C)(C)O)S3)[nH]c12]

A solution of 2-methyl-1-{2-[7-(1-methylethoxy)-5-{[5-(methylsulfonyl)pyridin-2-yl]oxy}-1H-indol-2-yl]-4,5-dihydro-1,3-thiazol-5-yl}propan-2-ol (150 mg) in methanol (7.5 mL) was resolved by preparative supercritical fluid chromatography (SFC), using CHIRALPAK IA (2 cm i.d.×25 cm, Daicel Chemical Industries, Ltd.) and supercritical carbon dioxide/ethanol/acetonitrile (620/304/76) as the mobile phase with the flow rate of 50 mL/min at 10 MPa and 35° C. The fractions containing a single enantiomer, eluted at a retention time of 5.0 min, were collected and concentrated to give the title compound (54 mg) as white crystals. Recrystallization from acetonitrile gave colorless crystals (45 mg). MS 504 (MH$^+$). mp 145-146° C.

Example 65

2-Methyl-1-{2-[7-(1-methylethoxy)-5-{[5-(methylsulfonyl)pyridin-2-yl]oxy}-1H-indol-2-yl]-4,5-dihydro-1,3-thiazol-5-yl}propan-2-ol

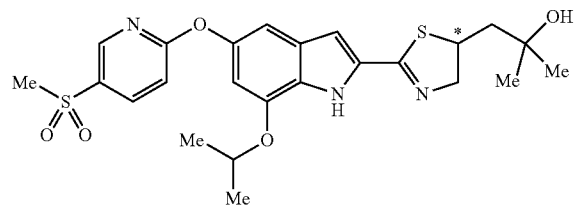 [SMILES: CC(C)Oc1cc(Oc2ccc(S(C)(=O)=O)cn2)cc2cc(C3=NCC(CC(C)(C)O)S3)[nH]c12]

A solution of 2-methyl-1-{2-[7-(1-methylethoxy)-5-{[5-(methylsulfonyl)pyridin-2-yl]oxy}-1H-indol-2-yl]-4,5-dihydro-1,3-thiazol-5-yl}propan-2-ol (150 mg) in methanol (7.5 mL) was resolved by preparative supercritical fluid chromatography (SFC), using CHIRALPAK IA (2 cm i.d.×25 cm, Daicel Chemical Industries, Ltd.) and supercritical carbon dioxide/ethanol/acetonitrile (620/304/76) as the mobile phase with the flow rate of 50 mL/min at 10 MPa and 35° C. The fractions containing a single enantiomer, eluted at a retention time of 5.8 min, were collected and concentrated to give the title compound (60 mg) as white crystals. Recrystallization from acetonitrile gave colorless crystals (50 mg). MS 504 (MH$^+$). mp 145-146° C.

Example 66

{2-[7-(1-Methylethoxy)-5-{[5-(methylsulfonyl)pyridin-2-yl]oxy}-1H-indol-2-yl]-4,5-dihydro-1,3-thiazol-5-yl}acetic acid

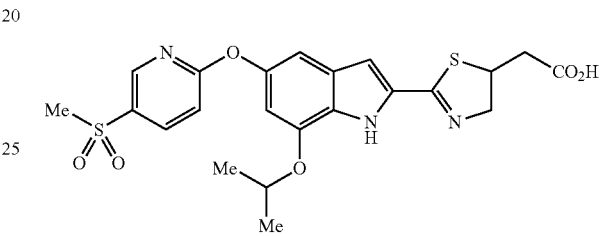

A mixture of ethyl {2-[7-(1-methylethoxy)-5-{[5-(methylsulfonyl)pyridin-2-yl]oxy}-1H-indol-2-yl]-4,5-dihydro-1,3-thiazol-5-yl}acetate (980 mg), tetrahydrofuran (10 mL), ethanol (10 mL) and 1M aqueous sodium hydroxide solution (10 mL) was stirred at 50° C. for 3 h. Water and 1M hydrochloric acid (10 mL) were added to the mixture and the mixture was extracted with ethyl acetate. The organic layer was washed with brine, dried (MgSO$_4$), filtered, and concentrated in vacuo. The residual crystals were washed with ethyl acetate and hexane to give the title compound (830 mg, 89%) as brown crystals. MS 490 (MH$^+$).

$^1$H NMR (DMSO-d$_6$) δ 1.32 (6H, d, J=6.06 Hz), 2.53-2.66 (1 H, m), 2.75-2.86 (1H, m), 3.27 (3H, s), 4.19-4.33 (2H, m), 4.34-4.50 (1H, m), 4.68 (1H, dt, J=11.83, 6.01 Hz), 6.65 (1H, d, J=1.89 Hz), 6.83 (1H, d, J=1.89 Hz), 6.97 (1H, d, J=1.89 Hz), 7.14 (1H, d, J=8.71 Hz), 8.27 (1H, dd, J=8.71, 2.65 Hz), 8.64 (1H, d, J=2.27 Hz), 11.63 (1H, d, J=1.51 Hz), 12.49 (1H, brs).

Example 67

2-{2-[7-(1-Methylethoxy)-5-{[5-(methylsulfonyl)pyridin-2-yl]oxy}-1H-indol-2-yl]-4,5-dihydro-1,3-thiazol-5-yl}acetamide

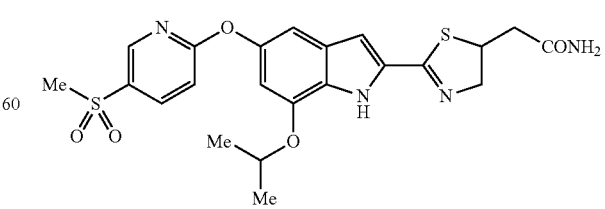

A mixture of {2-[7-(1-methylethoxy)-5-{[5-(methylsulfonyl)pyridin-2-yl]oxy}-1H-indol-2-yl]-4,5-dihydro-1,3-thiazol-5-yl}acetic acid (230 mg), 1-ethyl-3-(3-dimethylaminopropyl)carbodiimide hydrochloride (140 mg), 1-hydroxybenzotriazole (100 mg) and N,N-dimethylformamide (5 mL) was stirred at 50° C. for 30 min, and then cooled to 0° C. To the mixture was added aqueous ammonium hydroxide solution (10%, 1 mL). The whole was stirred at room temperature for 15 h. Water was added to the residue and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 90:10, volume ratio) to give pale yellow crystals. The crystals were recrystallized from acetone-hexane to give the title compound (90 mg, 39%) as pale yellow prisms. MS 489 (MH$^+$). mp 212-213° C.

Example 68

N-Methyl-2-{2-[7-(1-methylethoxy)-5-{[5-(methylsulfonyl)pyridin-2-yl]oxy}-1H-indol-2-yl]-4,5-dihydro-1,3-thiazol-5-yl}acetamide

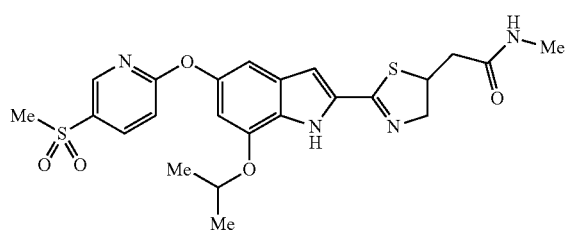 [SMILES: CNC(=O)CC1CN=C(c2cc3cc(Oc4ccc(S(C)(=O)=O)cn4)cc(OC(C)C)c3[nH]2)S1]

A mixture of {2-[7-(1-methylethoxy)-5-{[5-(methylsulfonyl)pyridin-2-yl]oxy}-1H-indol-2-yl]-4,5-dihydro-1,3-thiazol-5-yl}acetic acid (200 mg), 1-ethyl-3-(3-dimethylaminopropyl)carbodiimide hydrochloride (120 mg), 1-hydroxybenzotriazole (80 mg), methylamine hydrochloride (60 mg), triethylamine (70 mg) and N,N-dimethylformamide (3 mL) was stirred at room temperature for 15 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 95:5, volume ratio) to give colorless crystals. The crystals were recrystallized from ethyl acetate-hexane to give the title compound (120 mg, 57%) as colorless prisms. MS 503 (MH$^+$). mp 190-192° C.

Example 69

Ethyl {2-[5-{[6-(methoxymethyl)pyridin-3-yl]oxy}-7-(1-methylethoxy)-1H-indol-2-yl]-4,5-dihydro-1,3-thiazol-5-yl}acetate

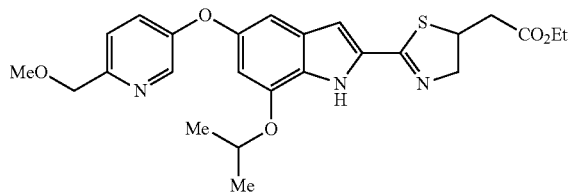 [SMILES: CCOC(=O)CC1CN=C(c2cc3cc(Oc4ccc(COC)nc4)cc(OC(C)C)c3[nH]2)S1]

A mixture of 5-{[6-(methoxymethyl)pyridin-3-yl]oxy}-7-(1-methylethoxy)-1H-indol-2-carboxamide (1.0 g), Lawesson's reagent (1.25 g) and tetrahydrofuran (100 mL) was stirred at 70° C. for 2 h. The mixture was concentrated in vacuo. The residue was purified by silica gel chromatography (ethyl acetate:hexane=1:9 to 1:1) to give a yellow amorphous solid. A mixture of the solid, ethyl 2-butynoate (0.78 g), tributylphosphine (565 mg) and tetrahydrofuran (50 mL) was refluxed for 15 h, and then ethyl 2-butynoate (0.78 g) and tributylphosphine (565 mg) were added to the mixture. The whole was refluxed for further 30 min, and then concentrated in vacuo. The residue was purified by basic silica gel chromatography (ethyl acetate:hexane=1:9 to 1:1, volume ratio) and then by silica gel chromatography (ethyl acetate:hexane=1:9 to 2:1) to give the title compound (0.68 g, 50%) as a yellow oil. MS 484 (MH$^+$).

$^1$H NMR (CDCl$_3$) δ 1.25-1.32 (3H, m), 1.37 (6H, d, J=6.06 Hz), 2.72 (2H, d, J=6.44 Hz), 3.47 (3H, s), 4.04-4.48 (5H, m), 4.55 (2H, s), 4.56-4.69 (1H, m), 6.47 (1H, d, J=1.89 Hz), 6.81 (2H, dd, J=7.00, 2.08 Hz), 7.16-7.28 (1H, m), 7.29-7.37 (1H, m), 8.36 (1H, d, J=2.65 Hz), 9.20 (1H, brs).

Example 70

{2-[5-{[6-(Methoxymethyl)pyridin-3-yl]oxy}-7-(1-methylethoxy)-1H-indol-2-yl]-4,5-dihydro-1,3-thiazol-5-yl}acetic acid

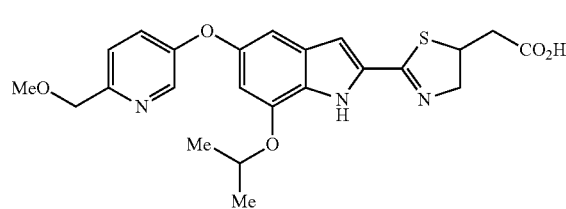 [SMILES: COCc1ccc(Oc2cc(OC(C)C)c3[nH]c(C4=NCC(CC(=O)O)S4)cc3c2)cn1]

A mixture of ethyl {2-[5-{[6-(methoxymethyl)pyridin-3-yl]oxy}-7-(1-methylethoxy)-1H-indol-2-yl]-4,5-dihydro-1,3-thiazol-5-yl}acetate (680 mg), tetrahydrofuran (5 mL), ethanol (5 mL) and 1M aqueous sodium hydroxide solution (5 mL) was stirred at 50° C. for 30 min, and then cooled to room temperature. Water and 1M hydrochloric acid (5 mL) were added to the mixture and the mixture was extracted with ethyl acetate. The organic layer was washed with brine, dried (MgSO$_4$), filtered, and concentrated in vacuo to give the title compound (600 mg, 94%) as a yellow amorphous solid. MS 456 (MH$^+$).

$^1$H NMR (CDCl$_3$) δ 1.39 (6H, d, J=5.68 Hz), 2.70-2.84 (2H, m), 3.47 (3H, s), 4.25-4.47 (3H, m), 4.57 (2H, s), 4.58-4.68 (1H, m), 6.48 (1H, d, J=1.89 Hz), 6.80-6.88 (2H, m), 7.27-7.40 (2H, m), 8.33 (1H, d, J=2.27 Hz), 9.70 (1H, brs).

Example 71

2-{2-[5-{[6-(Methoxymethyl)pyridin-3-yl]oxy}-7-(1-methylethoxy)-1H-indol-2-yl]-4,5-dihydro-1,3-thiazol-5-yl}-N-methylacetamide

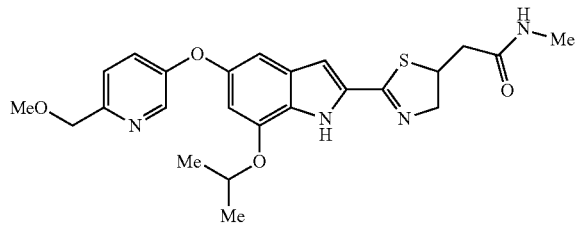 [SMILES: CNC(=O)CC1CN=C(c2cc3cc(Oc4ccc(COC)nc4)cc(OC(C)C)c3[nH]2)S1]

A mixture of {2-[5-{[6-(methoxymethyl)pyridin-3-yl]oxy}-7-(1-methylethoxy)-1H-indol-2-yl]-4,5-dihydro-1,3-thiazol-5-yl}acetic acid (300 mg), 1-ethyl-3-(3-dimethylaminopropyl)carbodiimide hydrochloride (190 mg), 1-hydroxybenzotriazole (130 mg), methylamine hydrochloride (90 mg), triethylamine (150 mg) and N,N-dimethylformamide (5 mL) was stirred at room temperature for 13 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 95:5, volume ratio) to give the title compound (210 mg, 68%) as a yellow amorphous solid. MS 469 (MH$^+$).

$^1$H NMR (CDCl$_3$) δ 1.37 (6H, d, J=6.06 Hz), 2.39-2.68 (2H, m), 2.84 (3H, d, J=4.92 Hz), 3.47 (3H, s), 4.23-4.47 (3H, m), 4.55 (2H, s), 4.57-4.71 (1H, m), 5.39-5.58 (1H, m), 6.47 (1H, d, J=1.89 Hz), 6.81 (2H, dd, J=6.63, 2.08 Hz), 7.22-7.29 (1H, m), 7.29-7.37 (1H, m), 8.35 (1H, d, J=2.65 Hz), 9.16 (1H, brs).

Example 72

N-Cyclopropyl-2-{2-[5-{[6-(methoxymethyl)pyridin-3-yl]oxy}-7-(1-methylethoxy)-1H-indol-2-yl]-4,5-dihydro-1,3-thiazol-5-yl}acetamide

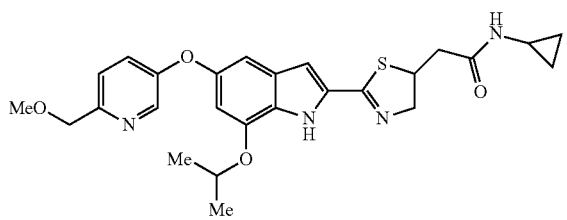 [SMILES: COCc1ccc(Oc2cc(OC(C)C)c3[nH]c(C4=NCC(CC(=O)NC5CC5)S4)cc3c2)cn1]

A mixture of {2-[5-{[6-(methoxymethyl)pyridin-3-yl]oxy}-7-(1-methylethoxy)-1H-indol-2-yl]-4,5-dihydro-1,3-thiazol-5-yl}acetic acid (300 mg), 1-ethyl-3-(3-dimethylaminopropyl)carbodiimide hydrochloride (190 mg), 1-hydroxybenzotriazole (130 mg), cyclopropylamine (75 mg) and N,N-dimethylformamide (3 mL) was stirred at room temperature for 15 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 95:5, volume ratio) to give yellow crystals. The crystals were recrystallized from ethyl acetate-hexane to give the title compound (170 mg, 52%) as pale yellow prisms. MS 495 (MH$^+$). mp 100-101° C.

Example 73

N-(2-Hydroxy-2-methylpropyl)-2-[2-(7-methoxy-5-{[6-(methylsulfonyl)pyridin-3-yl]oxy}-1H-indol-2-yl)-4,5-dihydro-1,3-thiazol-5-yl]acetamide

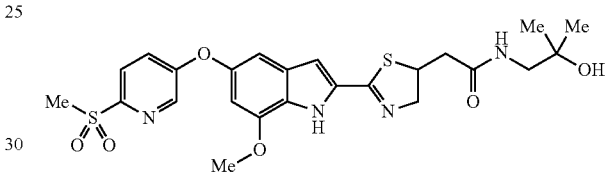

A mixture of [2-(7-methoxy-5-{[6-(methylsulfonyl)pyridin-3-yl]oxy}-1H-indol-2-yl)-4,5-dihydro-1,3-thiazol-5-yl]acetic acid (200 mg), 1-ethyl-3-(3-dimethylaminopropyl)carbodiimide hydrochloride (120 mg), 1-hydroxybenzotriazole (90 mg) and N,N-dimethylformamide (3 mL) was stirred at room temperature for 30 min. A solution of 1-amino-2-methylpropan-2-ol (77 mg) in N,N-dimethylformamide (1 mL) was added to the mixture. The whole was stirred at room temperature for 15 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 95:5, volume ratio) to give colorless crystals. The crystals were recrystallized from acetone-hexane to give the title compound (150 mg, 65%) as colorless prisms. MS 533 (Me). mp 200-201° C.

Example 74

N-(2-Hydroxy-2-methylpropyl)-2-[(2-(7-methoxy-5-{[6-(methylsulfonyl)pyridin-3-yl]oxy}-1H-indol-2-yl)-4,5-dihydro-1,3-thiazol-5-yl]acetamide

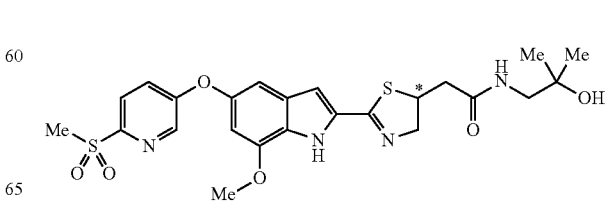

A solution of N-(2-hydroxy-2-methylpropyl)-2-[2-(7-methoxy-5-{[6-(methylsulfonyl)pyridin-3-yl]oxy}-1H-indol-2-yl)-4,5-dihydro-1,3-thiazol-5-yl]acetamide (420 mg) in methanol (182 mL) was resolved by preparative supercritical fluid chromatography (SFC), using CHIRALCEL OJ-H (2 cm i.d.×25 cm, Daicel Chemical Industries, Ltd.) and supercritical $CO_2$/methanol (65/35) as the mobile phase with the flow rate of 50 mL/min at 10 MPa and 35° C. The fractions containing a single enantiomer, eluted at a retention time of 8.8 min, were collected and concentrated to give the title compound (210 mg) as white crystals. The crystals were recrystallized from acetone-hexane to give the title compound (165 mg) as colorless prisms. MS 533 (MH$^+$). mp 173-174° C.

Example 75

N-(2-Hydroxy-2-methylpropyl)-2-[2-(7-methoxy-5-{[6-(methylsulfonyl)pyridin-3-yl]oxy}-1H-indol-2-yl)-4,5-dihydro-1,3-thiazol-5-yl]acetamide

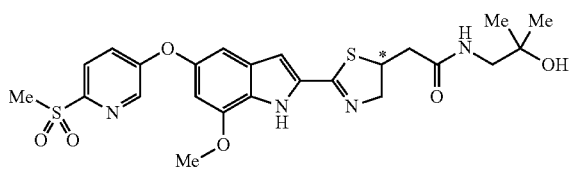 [SMILES: COc1cc(Oc2ccc(S(C)(=O)=O)nc2)cc2cc(C3=NCC(CC(=O)NCC(C)(C)O)S3)[nH]c12]

A solution of N-(2-hydroxy-2-methylpropyl)-2-[2-(7-methoxy-5-{[6-(methylsulfonyl)pyridin-3-yl]oxy}-1H-indol-2-yl)-4,5-dihydro-1,3-thiazol-5-yl]acetamide (420 mg) in methanol (182 mL) was resolved by preparative supercritical fluid chromatography (SFC), using CHIRALCEL OJ-H (LA001) (2 cm i.d.×25 cm, Daicel Chemical Industries, Ltd.) and supercritical $CO_2$/methanol (65/35) as the mobile phase with the flow rate of 50 mL/min at 10 MPa and 35° C. The fractions containing a single enantiomer, eluted at a retention time of 10.4 min, were collected and concentrated to give the title compound (203 mg) as white crystals. The crystals were recrystallized from acetone-hexane to give the title compound (157 mg) as colorless prisms. MS 533 (MH$^+$). mp 173-174° C.

Example 76

N-Cyclopropyl-2-[2-(7-methoxy-5-{[6-(methylsulfonyl)pyridin-3-yl]oxy}-1H-indol-2-yl)-4,5-dihydro-1,3-thiazol-5-yl]acetamide

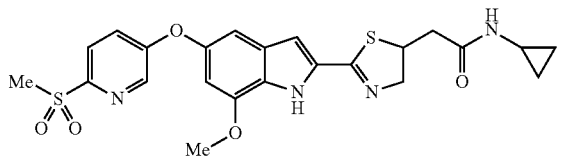 [SMILES: COc1cc(Oc2ccc(S(C)(=O)=O)nc2)cc2cc(C3=NCC(CC(=O)NC4CC4)S3)[nH]c12]

A mixture of [2-(7-methoxy-5-{[6-(methylsulfonyl)pyridin-3-yl]oxy}-1H-indol-2-yl)-4,5-dihydro-1,3-thiazol-5-yl]acetic acid (200 mg), 1-ethyl-3-(3-dimethylaminopropyl)carbodiimide hydrochloride (120 mg), 1-hydroxybenzotriazole (90 mg) and N,N-dimethylformamide (3 mL) was stirred at room temperature for 30 min, and then cyclopropylamine (50 mg) was added to the mixture. The whole was stirred at room temperature for 15 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residual crystals were washed with ethyl acetate-hexane and collected by filtration to give pale yellow crystals. The crystals were recrystallized from acetone-methanol to give the title compound (150 mg, 68%) as colorless prisms. MS 501 (MH$^+$). mp 248-249° C.

Example 77

N-Ethyl-2-[2-(7-methoxy-5-{[6-(methylsulfonyl)pyridin-3-yl]oxy}-1H-indol-2-yl)-4,5-dihydro-1,3-thiazol-5-yl]acetamide

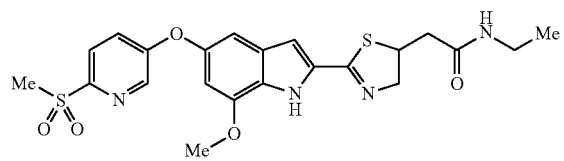 [SMILES: CCNC(=O)CC1CN=C(c2cc3cc(Oc4ccc(S(C)(=O)=O)nc4)cc(OC)c3[nH]2)S1]

A mixture of [2-(7-methoxy-5-{[6-(methylsulfonyl)pyridin-3-yl]oxy}-1H-indol-2-yl)-4,5-dihydro-1,3-thiazol-5-yl]acetic acid (200 mg), 1-ethyl-3-(3-dimethylaminopropyl)carbodiimide hydrochloride (120 mg), 1-hydroxybenzotriazole (90 mg) and N,N-dimethylformamide (3 mL) was stirred at room temperature for 30 min, and then ethylamine (2M solution in tetrahydrofuran, 0.43 mL) was added to the mixture. The whole was stirred at room temperature for 15 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residual crystals were washed with ethyl acetate-hexane and collected by filtration to give pale yellow crystals. The crystals were recrystallized from acetone-methanol to give the title compound (130 mg, 62%) as colorless prisms. MS 489 (MH$^+$). mp 236-237° C.

Example 78

N-(2-Methoxyethyl)-2-[2-(7-methoxy-5-{[6-(methylsulfonyl)pyridin-3-yl]oxy}-1H-indol-2-yl)-4,5-dihydro-1,3-thiazol-5-yl]acetamide

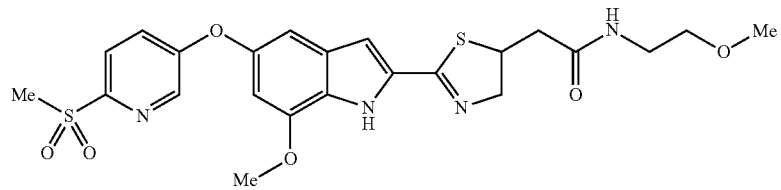 [SMILES: COCCNC(=O)CC1CN=C(c2cc3cc(Oc4ccc(S(C)(=O)=O)nc4)cc(OC)c3[nH]2)S1]

A mixture of [2-(7-methoxy-5-{[6-(methylsulfonyl)pyridin-3-yl]oxy}-1H-indol-2-yl)-4,5-dihydro-1,3-thiazol-5-yl]acetic acid (300 mg), 1-ethyl-3-(3-dimethylaminopropyl)carbodiimide hydrochloride (190 mg), 1-hydroxybenzotriazole (130 mg), 2-methoxyethylamine (100 mg) and N,N-dimethylformamide (5 mL) was stirred at room temperature for 20 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 95:5, volume ratio) to give pale yellow crystals. The crystals were recrystallized from acetone-methanol to give the title compound (200 mg, 59%) as pale yellow prisms. MS 519 (MH$^+$). mp 175-176° C.

Example 79

2-[2-(7-Methoxy-5-{[6-(methylsulfonyl)pyridin-3-yl]oxy}-1H-indol-2-yl)-4,5-dihydro-1,3-thiazol-5-yl]-N,N-dimethylacetamide

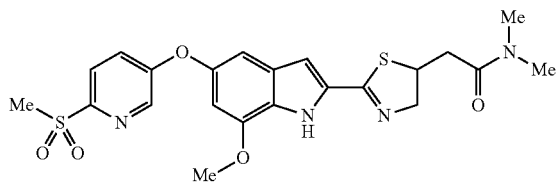 [SMILES: COc1cc(Oc2ccc(S(C)(=O)=O)nc2)cc2cc(C3=NCC(CC(=O)N(C)C)S3)[nH]c12]

A mixture of [2-(7-methoxy-5-{[6-(methylsulfonyl)pyridin-3-yl]oxy}-1H-indol-2-yl)-4,5-dihydro-1,3-thiazol-5-yl]acetic acid (500 mg), 1-ethyl-3-(3-dimethylaminopropyl)carbodiimide hydrochloride (330 mg), 1-hydroxybenzotriazole (230 mg), dimethylamine (2M solution in tetrahydrofuran, 1.1 mL) and N,N-dimethylformamide (10 mL) was stirred at room temperature for 15 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 95:5, volume ratio) to give pale yellow crystals. The crystals were recrystallized from acetone-methanol to give the title compound (370 mg, 69%) as pale yellow prisms. MS 489 (MH$^+$). mp 206-207° C.

Example 80

N-[(2S)-2-Hydroxypropyl]-2-[2-(7-methoxy-5-{[6-(methylsulfonyl)pyridin-3-yl]oxy}-1H-indol-2-yl)-4,5-dihydro-1,3-thiazol-5-yl]acetamide

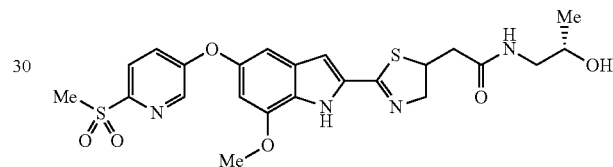

A mixture of [2-(7-methoxy-5-{[6-(methylsulfonyl)pyridin-3-yl]oxy}-1H-indol-2-yl)-4,5-dihydro-1,3-thiazol-5-yl]acetic acid (300 mg), 1-ethyl-3-(3-dimethylaminopropyl)carbodiimide hydrochloride (190 mg), 1-hydroxybenzotriazole (130 mg), (2S)-1-aminopropan-2-ol (100 mg) and N,N-dimethylformamide (5 mL) was stirred at room temperature for 40 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was washed with ethyl acetate-diethyl ether to give pale yellow crystals. The crystals were recrystallized from acetone-methanol to give the title compound (230 mg, 68%) as colorless prisms. MS 519 (MH$^+$). mp 185-186° C.

Example 81

N-[(2R)-2-Hydroxypropyl]-2-[2-(7-methoxy-5-{[6-(methylsulfonyl)pyridin-3-yl]oxy}-1H-indol-2-yl)-4,5-dihydro-1,3-thiazol-5-yl]acetamide

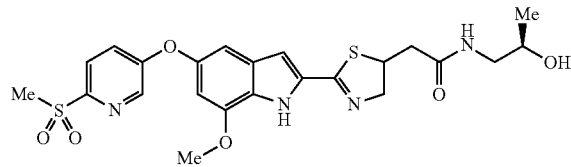 [SMILES: COc1cc(Oc2ccc(S(C)(=O)=O)nc2)cc2cc(C3=NCC(CC(=O)NC[C@@H](C)O)S3)[nH]c12]

A mixture of [2-(7-methoxy-5-{[6-(methylsulfonyl)pyridin-3-yl]oxy}-1H-indol-2-yl)-4,5-dihydro-1,3-thiazol-5-yl]acetic acid (300 mg), 1-ethyl-3-(3-dimethylaminopropyl)carbodiimide hydrochloride (190 mg), 1-hydroxybenzotriazole (130 mg), (2R)-1-aminopropan-2-ol (100 mg) and N,N-dimethylformamide (5 mL) was stirred at room temperature for 15 h. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was washed with ethyl acetate-diethyl ether to give pale yellow crystals. The crystals were recrystallized from acetone-methanol to give the title compound (220 mg, 65%) as colorless prisms. MS 519 (MH$^+$). mp 185-186° C.

Example 82

7-Methoxy-5-{[6-(methylsulfonyl)pyridin-3-yl]oxy}-2-{5-[2-(morpholin-4-yl)-2-oxoethyl]-4,5-dihydro-1,3-thiazol-2-yl}-1H-indole

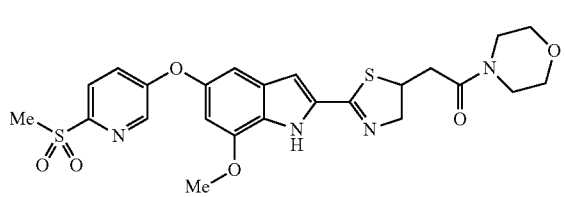 [SMILES: COc1cc(Oc2ccc(S(C)(=O)=O)nc2)cc2cc(C3=NCC(CC(=O)N4CCOCC4)S3)[nH]c12]

A mixture of [2-(7-methoxy-5-{[6-(methylsulfonyl)pyridin-3-yl]oxy}-1H-indol-2-yl)-4,5-dihydro-1,3-thiazol-5-yl]acetic acid (500 mg), 1-ethyl-3-(3-dimethylaminopropyl)carbodiimide hydrochloride (330 mg), 1-hydroxybenzotriazole (230 mg), morpholine (190 mg) and N,N-dimethylformamide (10 mL) was stirred at room temperature for 3 days. Water was added to the mixture and the resultant was extracted with ethyl acetate. The organic layer was washed successively with saturated aqueous sodium hydrogen carbonate solution and brine, dried (MgSO$_4$), filtered, and concentrated in vacuo. The residue was purified by silica gel chromatography (ethyl acetate:methanol=100:0 to 95:5, volume ratio) to give pale yellow crystals. The crystals were recrystallized from acetone-hexane and then recrystallized from acetone-methanol to give the title compound (250 mg, 43%) as colorless prisms. MS 531 (MH$^+$). mp 148-149° C.

Example 83

Ethyl {2-[7-(2-methoxy-1-methylethoxy)-5-{[6-(methylsulfonyl)pyridin-3-yl]oxy}-1H-indol-2-yl]-4,5-dihydro-1,3-thiazol-5-yl}acetate

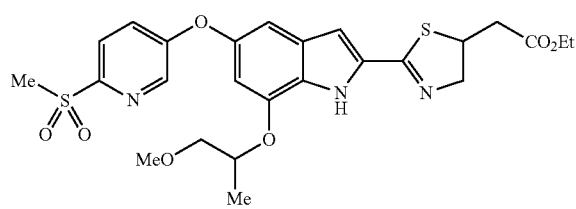 [SMILES: CCOC(=O)CC1CN=C(c2cc3cc(Oc4ccc(S(C)(=O)=O)nc4)cc(OC(C)COC)c3[nH]2)S1]

A mixture of 7-(2-methoxy-1-methylethoxy)-5-{[6-(methylsulfonyl)pyridin-3-yl]oxy}-1H-indole-2-carboxamide (1.28 g), Lawesson's reagent (1.38 g) and tetrahydrofuran (100 mL) was stirred at 70° C. for 2 h. The mixture was concentrated in vacuo. The residue was dissolved in ethyl acetate and the solution was passed through a basic silica gel short column (ethyl acetate). The ethyl acetate solution was concentrated in vacuo. A mixture of the residue, ethyl 2-butynoate (0.87 g), tributylphosphine (0.63 g) and tetrahydrofuran (50 mL) was stirred at 70° C. for 30 min under argon atmosphere, and then concentrated in vacuo. The residue was purified by silica gel chromatography (ethyl acetate:hexane=1:2 to 3:1, volume ratio) to give the title compound (1.26 g, 74%) as a brown amorphous solid. MS 548 (MH$^+$).

$^1$H NMR (DMSO-d$_6$) δ 1.20 (3H, d, J=7.20 Hz), 1.25 (3H, d, J=6.44 Hz), 2.59-2.73 (1H, m), 2.80-2.97 (1H, m), 3.24 (3H, s), 3.32 (3H, s), 3.43-3.68 (2H, m), 4.10 (2H, q, J=6.94 Hz), 4.19-4.48 (3H, m), 4.62-4.78 (1H, m), 6.77 (1H, d, J=1.89 Hz), 6.85 (1H, d, J=1.89 Hz), 7.02 (1H, d, J=1.51 Hz), 7.47 (1H, dd, J=8.90, 2.84 Hz), 8.00 (1H, d, J=8.71 Hz), 8.53 (1H, d, J=2.65 Hz), 11.71 (1H, s).

Example 84

2-{2-[7-(2-Methoxy-1-methylethoxy)-5-{[6-(methylsulfonyl)pyridin-3-yl]oxy}-1H-indol-2-yl]-4,5-dihydro-1,3-thiazol-5-yl}ethanol

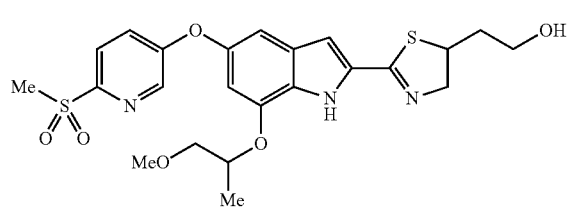 [SMILES: COCC(C)Oc1cc(Oc2ccc(S(C)(=O)=O)nc2)cc2cc(C3=NCC(CCO)S3)[nH]c12]

To a mixture of ethyl {2-[7-(2-methoxy-1-methylethoxy)-5-{[6-(methylsulfonyl)pyridin-3-yl]oxy}-1H-indol-2-yl]-4,5-dihydro-1,3-thiazol-5-yl}acetate (660 mg), tetrahydrofuran (30 mL) and methanol (5 mL) was added lithium borohydride (130 mg) at 0° C. The whole was stirred at room temperature for 5 h. Water was added to the mixture and the mixture was extracted with ethyl acetate. The organic layer was washed with brine, dried (MgSO$_4$), filtered, and concentrated in vacuo. The residue was purified by silica gel chromatography (ethyl acetate:hexane=1:1 to 1:0, volume ratio) to give pale yellow crystals. The crystals were recrystallized from ethyl acetate-hexane to give the title compound (380 mg, 62%) as pale yellow prisms. MS 506 (MH+). mp 138-139° C.

Example 85

{2-[7-(2-Methoxy-1-methylethoxy)-5-{[6-(methylsulfonyl)pyridin-3-yl]oxy}-1H-indol-2-yl]-4,5-dihydro-1,3-thiazol-5-yl}acetic acid

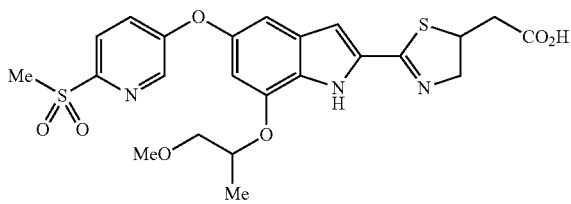

A mixture of ethyl {2-[7-(2-methoxy-1-methylethoxy)-5-{[6-(methylsulfonyl)pyridin-3-yl]oxy}-1H-indol-2-yl]-4,5-dihydro-1,3-thiazol-5-yl}acetate (580 mg), tetrahydrofuran (3 mL), ethanol (3 mL) and 1M aqueous sodium hydroxide solution (3 mL) was stirred at room temperature for 4 h. Water and 1M hydrochloric acid (3 mL) were added to the mixture and the mixture was extracted with ethyl acetate. The organic layer was washed with brine, dried (MgSO₄), filtered, and concentrated in vacuo to give the title compound (510 mg, 93%) as a brown amorphous solid. MS 520 (MH+).
$^1$H NMR (DMSO-$d_6$) δ 1.25 (3H, d, J=6.44 Hz), 2.53-2.88 (2H, m), 3.24 (3H, s), 3.30 (3H, s), 3.45-3.68 (2H, m), 4.17-4.50 (3H, m), 4.62-4.78 (1H, m), 6.77 (1H, d, J=1.89 Hz), 6.85 (1H, d, J=2.27 Hz), 7.02 (1H, d, J=1.89 Hz), 7.47 (1H, dd, J=8.71, 2.65 Hz), 8.00 (1H, d, J=8.71 Hz), 8.53 (1H, d, J=2.65 Hz), 11.72 (1H, d, J=1.51 Hz), 12.42 (1H, brs).

Example 86

2-{2-[7-(2-Methoxy-1-methylethoxy)-5-{[6-(methylsulfonyl)pyridin-3-yl]oxy}-1H-indol-2-yl]-4,5-dihydro-1,3-thiazol-5-yl}acetamide

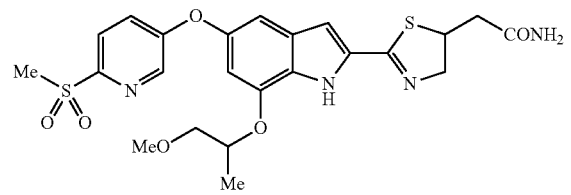 [SMILES: COCC(C)Oc1cc(Oc2ccc(S(C)(=O)=O)nc2)cc2cc(C3=NCC(CC(N)=O)S3)[nH]c12]

A mixture of {2-[7-(2-methoxy-1-methylethoxy)-5-{[6-(methylsulfonyl)pyridin-3-yl]oxy}-1H-indol-2-yl]-4,5-dihydro-1,3-thiazol-5-yl}acetic acid (250 mg), 1-ethyl-3-(3-dimethylaminopropyl)carbodiimide hydrochloride (140 mg), 1-hydroxybenzotriazole (100 mg) and N,N-dimethylformamide (3 mL) was stirred at room temperature for 30 min. To the mixture was added aqueous ammonium hydroxide solution (25%, 1 mL). The whole was stirred at room temperature for 15 h. Water was added to the mixture and the resultant was extracted with ethyl acetate. The organic layer was washed successively with saturated aqueous sodium hydrogen carbonate solution and brine, dried (MgSO₄), filtered, and concentrated in vacuo. The residue was purified by silica gel chromatography (ethyl acetate:methanol=100:0 to 95:5, volume ratio) to give pale yellow crystals. The crystals were recrystallized from ethyl acetate-hexane to give the title compound (150 mg, 60%) as pale yellow prisms. MS 519 (MH+). mp 131-132° C.

Example 87

2-{2-[7-(2-Methoxy-1-methylethoxy)-5-{[6-(methylsulfonyl)pyridin-3-yl]oxy}-1H-indol-2-yl]-4,5-dihydro-1,3-thiazol-5-yl}-N-methylacetamide

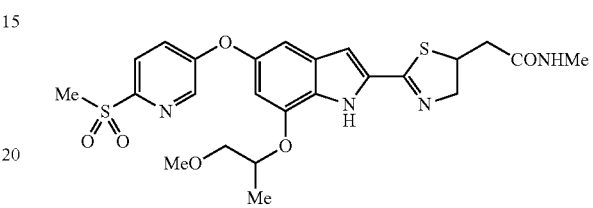

A mixture of {2-[7-(2-methoxy-1-methylethoxy)-5-{[6-(methylsulfonyl)pyridin-3-yl]oxy}-1H-indol-2-yl]-4,5-dihydro-1,3-thiazol-5-yl}acetic acid (250 mg), 1-ethyl-3-(3-dimethylaminopropyl)carbodiimide hydrochloride (140 mg), 1-hydroxybenzotriazole (100 mg), methylamine hydrochloride (100 mg), triethylamine (120 mg) and N,N-dimethylformamide (3 mL) was stirred at room temperature for 15 h. Water was added to the mixture and the resultant was extracted with ethyl acetate. The organic layer was washed successively with saturated aqueous sodium hydrogen carbonate solution and brine, dried (MgSO₄), filtered, and concentrated in vacuo. The residue was purified by silica gel chromatography (ethyl acetate:methanol=100:0 to 95:5, volume ratio) to give pale yellow crystals. The crystals were recrystallized from ethyl acetate-hexane to give the title compound (160 mg, 62%) as pale yellow prisms. MS 533 (MH+). mp 107-109° C.

Example 88

2-[5-(Dimethoxymethyl)-4,5-dihydro-1,3-thiazol-2-yl]-7-(2-methoxy-1-methylethoxy)-5-[4-(methylsulfonyl)phenoxy]-1H-indole

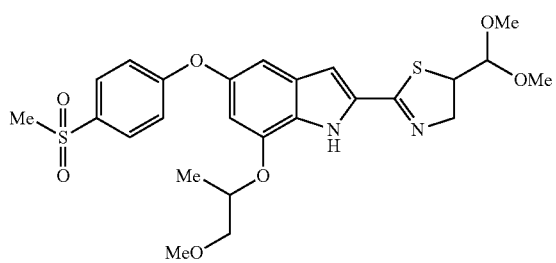 [SMILES: COCC(C)Oc1cc(Oc2ccc(S(C)(=O)=O)cc2)cc2cc(C3=NCC(C(OC)OC)S3)[nH]c12]

To an ice-cooled and stirred solution of triphenylphosphine oxide (0.43 g) in acetonitrile (8 mL) was added trifluoromethanesulfonic anhydride (0.13 mL), and the mixture was stirred at 4° C. for 30 min, followed by an addition of a solution of N-[2-(benzylsulfanyl)-3,3-dimethoxypropyl]-7-(2-methoxy-1-methylethoxy)-5-[4-(methylsulfonyl)phenoxy]-1H-indole-2-carboxamide (0.25 g) and thioanisole (0.093 mL) in acetonitrile (5 mL). After stirring at 4° C. for 30 min, the reaction mixture was partitioned between ethyl acetate and aqueous sodium hydrogen carbonate solution, and the organic layer was washed with brine, dried (MgSO₄), filtered, and concentrated. The resulting precipitate was removed by filtration and washed with ethyl acetate-hexane. The combined filtrate and washings were concentrated and the residue was purified by basic silica gel chromatography (ethyl acetate:hexane=25:75 to 35:65, volume ratio) and then by silica gel chromatography (ethyl acetate:hexane=25:75 to 80:20) to give a colorless oil, which was crystallized from diethyl ether-hexane to give the title compound (21 mg, 10%) as colorless crystals. MS 535 (MH⁺). mp 109-112° C.

Example 89

Ethyl {2-[6-fluoro-7-(2-methoxyethoxy)-5-{[6-(methylsulfonyl)pyridin-3-yl]oxy}-1H-indol-2-yl]-4,5-dihydro-1,3-thiazol-5-yl}acetate

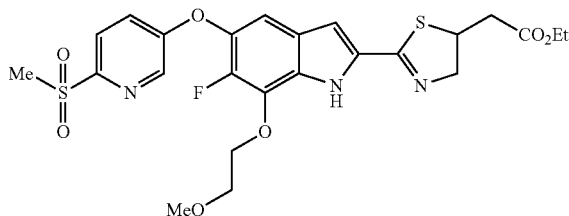 [SMILES: CCOC(=O)CC1CN=C(c2cc3cc(Oc4ccc(S(C)(=O)=O)nc4)c(F)c(OCCOC)c3[nH]2)S1]

To a stirred solution of 6-fluoro-7-(2-methoxyethoxy)-5-{[6-(methylsulfonyl)pyridin-3-yl]oxy}-1H-indole-2-carbothioamide (0.58 g), ethyl 2-butynoate (0.31 mL), tetrahydrofuran (10 mL) and toluene (15 mL) was added tributylphosphine (0.40 mL) at room temperature under argon atmosphere. After stirring at 40° C. for 3 h, the reaction mixture was concentrated to give a light brown oil, which was purified by silica gel chromatography (ethyl acetate:hexane=35:65 to 100:0, volume ratio) to give the title compound (525 mg, 72%) as a pale yellow oil. MS 552 (MH⁺).

¹H NMR (CDCl₃) δ 1.28 (3H, t, J=7.2 Hz), 2.72 (2H, d, J=7.2 Hz), 3.20 (3H, s), 3.59 (3H, s), 3.76-3.82 (2H, m), 4.18 (2H, q, J=7.2 Hz), 4.24-4.48 (5H, m), 6.83 (1H, d, J=2.1 Hz), 7.17 (1H, d, J=6.6 Hz), 7.31 (1H, dd, J=2.7, 8.7 Hz), 7.99 (1H, d, J=8.7 Hz), 8.45 (1H, d, J=2.7 Hz), 10.69 (1H, brs).

Example 90

2-{2-[6-Fluoro-7-(2-methoxyethoxy)-5-{[6-(methylsulfonyl)pyridin-3-yl]oxy}-1H-indol-2-yl]-4,5-dihydro-1,3-thiazol-5-yl}ethanol

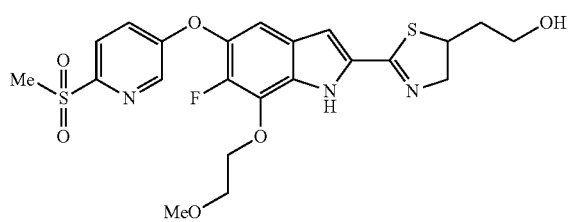 [SMILES: COCCOc1c(F)c(Oc2ccc(S(C)(=O)=O)nc2)cc2cc(C3=NCC(CCO)S3)[nH]c12]

To an ice-cooled and stirred solution of ethyl {2-[6-fluoro-7-(2-methoxyethoxy)-5-{[6-(methylsulfonyl)pyridin-3-yl] oxy}-1H-indol-2-yl]-4,5-dihydro-1,3-thiazol-5-yl}acetate (200 mg) in tetrahydrofuran (8 mL)-methanol (6 mL) was added lithium borohydride (40 mg), and the mixture was stirred at room temperature for 2.5 h, followed by an addition of lithium borohydride (40 mg). After the mixture was stirred at room temperature for 2 h, lithium borohydride (40 mg) was further added thereto. After stirring at room temperature for 2 h, the reaction mixture was partitioned between ethyl acetate and aqueous citric acid solution. The organic layer was washed with brine, dried (MgSO₄), filtered, and concentrated. The residue was purified by silica gel chromatography (ethyl acetate:hexane=60:40 to 100:0, volume ratio) to give colorless crystals, which were recrystallized from tetrahydrofuran-ethyl acetate-hexane to give the title compound (76 mg, 41%) as colorless crystals. MS 510 (MH⁺). mp 160-161° C.

Example 91

{2-[6-Fluoro-7-(2-methoxyethoxy)-5-{[6-(methylsulfonyl)pyridin-3-yl]oxy}-1H-indol-2-yl]-4,5-dihydro-1,3-thiazol-5-yl}acetic acid

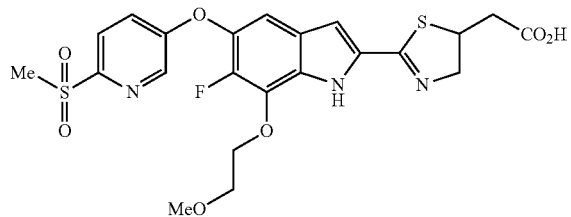 [SMILES: COCCOc1c(F)c(Oc2ccc(S(C)(=O)=O)nc2)cc2cc(C3=NCC(CC(=O)O)S3)[nH]c12]

To a mixture of ethyl {2-[6-fluoro-7-(2-methoxyethoxy)-5-{[6-(methylsulfonyl)pyridin-3-yl]oxy}-1H-indol-2-yl]-4,5-dihydro-1,3-thiazol-5-yl}acetate (0.30 g), tetrahydrofuran (12 mL) and methanol (12 mL) was added a solution of potassium hydroxide (85%, 0.18 g) in water (10 mL). The mixture was stirred at room temperature for 15 h and then partitioned between ethyl acetate and aqueous citric acid solution. The organic layer was washed with brine, dried (MgSO₄), filtered, and concentrated to give a light yellow oil, which was crystallized from ethyl acetate-hexane to give the title compound (267 mg, 94%) as pale yellow crystals. MS 524 (MH⁺).

¹H NMR (CDCl₃) δ 2.80 (2H, d, J=6.9 Hz), 3.21 (3H, s), 3.57 (3H, s), 3.78-3.84 (2H, m), 4.30-4.50 (5H, m), 6.85 (1H, d, J=1.8 Hz), 7.17 (1H, d, J=6.6 Hz), 7.31 (1H, dd, J=2.7, 8.7 Hz), 8.00 (1H, d, J=8.7 Hz), 8.46 (1H, d, J=2.7 Hz), 10.77 (1H, brs).

Example 92

2-{2-[6-Fluoro-7-(2-methoxyethoxy)-5-{[6-(methylsulfonyl)pyridin-3-yl]oxy}-1H-indol-2-yl]-4,5-dihydro-1,3-thiazol-5-yl}-N-methylacetamide

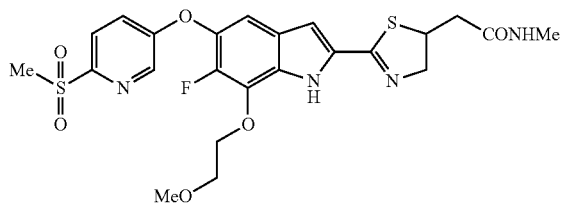

To an ice-cooled and stirred mixture of methylamine hydrochloride (35 mg) and triethylamine (0.072 mL) in N,N-dimethylformamide (7 mL) were added {2-[6-fluoro-7-(2-methoxyethoxy)-5-{[6-(methylsulfonyl)pyridin-3-yl]oxy}-1H-indol-2-yl]-4,5-dihydro-1,3-thiazol-5-yl}acetic acid (135 mg), 1-hydroxybenzotriazole (70 mg) and 1-ethyl-3-(3-dimethylaminopropyl)carbodiimide hydrochloride (100 mg). After stirring at 4° C. to room temperature for 15 h, the reaction mixture was partitioned between ethyl acetate and water. The organic layer was washed successively with aqueous sodium hydrogen carbonate solution and brine, dried (MgSO$_4$), filtered, and concentrated to give colorless crystals, which were recrystallized from tetrahydrofuran-ethyl acetate to give the title compound (109 mg, 79%) as colorless crystals. MS 537 (MH$^+$). mp 151-152° C.

Example 93

2-{2-[6-Fluoro-7-(2-methoxyethoxy)-5-{[6-(methylsulfonyl)pyridin-3-yl]oxy}-1H-indol-2-yl]-4,5-dihydro-1,3-thiazol-5-yl}acetamide

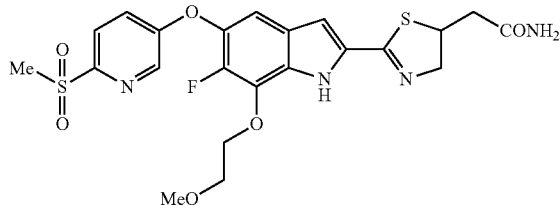 [SMILES: COCCOc1c(F)c(Oc2ccc(S(C)(=O)=O)nc2)cc2cc(C3=NCC(CC(N)=O)S3)[nH]c12]

To an ice-cooled and stirred mixture of {2-[6-fluoro-7-(2-methoxyethoxy)-5-{[6-(methylsulfonyl)pyridin-3-yl]oxy}-1H-indol-2-yl]-4,5-dihydro-1,3-thiazol-5-yl}acetic acid (135 mg) in N,N-dimethylformamide (7 mL) were added 1-hydroxybenzotriazole (70 mg) and 1-ethyl-3-(3-dimethylaminopropyl)carbodiimide hydrochloride (100 mg). After stirring at 4° C. to room temperature for 15 h, the reaction mixture was cooled on an ice bath and 10% aqueous ammonia solution (1.0 mL) was added thereto. The mixture was stirred at room temperature for 5 h and partitioned between ethyl acetate and water. The organic layer was washed with aqueous sodium hydrogen carbonate solution and brine, dried (MgSO$_4$), filtered, and concentrated to give light yellow crystals, which were recrystallized from tetrahydrofuran-ethyl acetate to give the title compound (84 mg) as pale yellow crystals. MS 523 (MH$^+$). mp 143-144° C.

Example 94

Ethyl [2-(7-ethoxy-5-{[6-(methylsulfonyl)pyridin-3-yl]oxy}-1H-indol-2-yl)-4,5-dihydro-1,3-thiazol-5-yl]acetate

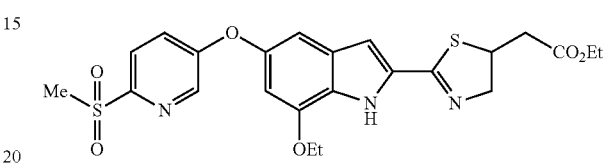

To a stirred solution of 7-ethoxy-5-{[6-(methylsulfonyl)pyridin-3-yl]oxy}-1H-indole-2-carbothioamide (0.41 g), ethyl 2-butynoate (0.25 mL), tetrahydrofuran (10 mL) and toluene (15 mL) was added tributylphosphine (0.31 mL) at room temperature under argon atmosphere. After stirring at 40° C. for 3 h, the reaction mixture was concentrated to give a light brown oil, which was purified by silica gel chromatography (ethyl acetate:hexane=30:70 to 50:50, volume ratio) to give the title compound (350 mg, 66%) as a light yellow oil. MS 504 (MH$^+$).

$^1$H NMR (CDCl$_3$) δ 1.28 (3H, t, J=7.2 Hz), 1.47 (3H, t, J=7.2 Hz), 2.70-2.80 (2H, m), 3.20 (3H, s), 4.08-4.48 (7H, m), 6.42 (1H, d, J=1.8 Hz), 6.84 (1H, d, J=2.1 Hz), 6.93 (1H, d, J=1.8 Hz), 7.32 (1H, dd, J=2.7, 8.7 Hz), 7.98 (1H, d, J=8.7 Hz), 8.44 (1H, d, J=2.7 Hz), 9.36 (1H, brs).

Example 95

2-[2-(7-Ethoxy-5-{[6-(methylsulfonyl)pyridin-3-yl]oxy}-1H-indol-2-yl)-4,5-dihydro-1,3-thiazol-5-yl]ethanol

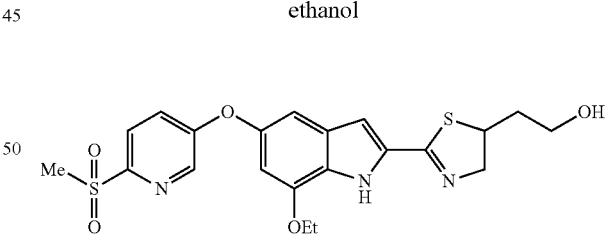

To an ice-cooled and stirred solution of ethyl [2-(7-ethoxy-5-{[6-(methylsulfonyl)pyridin-3-yl]oxy}-1H-indol-2-yl)-4,5-dihydro-1,3-thiazol-5-yl]acetate (110 mg) in tetrahydrofuran (8 mL)-methanol (2 mL) was added lithium borohydride (25 mg), and the mixture was stirred at room temperature for 4 h, followed by an addition of lithium borohydride (25 mg). After stirring at room temperature for 3 h, the reaction mixture was partitioned between ethyl acetate and aqueous citric acid solution. The organic layer was washed with brine, dried (MgSO$_4$), filtered, and concentrated. The residue was purified by silica gel chromatography (ethyl acetate:hexane=50:50 to 100:0, volume ratio) to give a colorless oil, which was crystallized from ethyl acetate-hexane to give the title compound (54 mg, 54%) as colorless crystals. MS 462 (MH$^+$). mp 147-148° C.

Example 96

[2-(7-Ethoxy-5-{[6-(methylsulfonyl)pyridin-3-yl]oxy}-1H-indol-2-yl)-4,5-dihydro-1,3-thiazol-5-yl]acetic acid

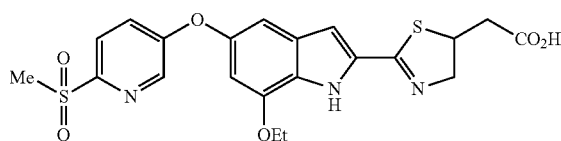 [SMILES: CCOc1cc(Oc2ccc(S(C)(=O)=O)nc2)cc2cc(C3=NCC(CC(=O)O)S3)[nH]c12]

To a mixture of ethyl [2-(7-ethoxy-5-{[6-(methylsulfonyl)pyridin-3-yl]oxy}-1H-indol-2-yl)-4,5-dihydro-1,3-thiazol-5-yl]acetate (0.22 g), tetrahydrofuran (10 mL) and methanol (10 mL) was added a solution of potassium hydroxide (85%, 0.10 g) in water (5 mL). The mixture was stirred at room temperature for 15 h and then partitioned between ethyl acetate and aqueous citric acid solution. The organic layer was washed with brine, dried (MgSO$_4$), filtered, and concentrated to give a light yellow amorphous solid, which was crystallized from ethyl acetate-hexane to give the title compound (186 mg, 90%) as light yellow crystals. MS 476 (MH$^+$). mp 208-210° C.

Example 97

2-[2-(7-Ethoxy-5-{[6-(methylsulfonyl)pyridin-3-yl]oxy}-1H-indol-2-yl)-4,5-dihydro-1,3-thiazol-5-yl]-N-methylacetamide

To an ice-cooled and stirred mixture of methylamine hydrochloride (26 mg) and triethylamine (0.053 mL) in N,N-dimethylformamide (5 mL) were added [2-(7-ethoxy-5-{[6-(methylsulfonyl)pyridin-3-yl]oxy}-1H-indol-2-yl)-4,5-dihydro-1,3-thiazol-5-yl]acetic acid (90 mg), 1-hydroxybenzotriazole (52 mg) and 1-ethyl-3-(3-dimethylaminopropyl)carbodiimide hydrochloride (73 mg). After stirring at 4° C. to room temperature for 15 h, the reaction mixture was partitioned between ethyl acetate and water. The organic layer was washed successively with aqueous sodium hydrogen carbonate solution and brine, dried (MgSO$_4$), filtered, and concentrated to give a pale yellow amorphous solid, which was crystallized from ethyl acetate-hexane to give the title compound (91 mg, 99%) as pale yellow crystals. MS 489 (MH$^+$). mp 233-235° C.

Example 98

2-[2-(7-Ethoxy-5-{[6-(methylsulfonyl)pyridin-3-yl]oxy}-1H-indol-2-yl)-4,5-dihydro-1,3-thiazol-5-yl]-N-methylacetamide

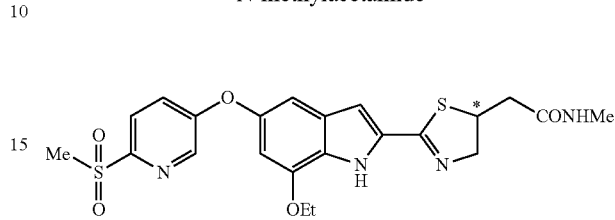

A solution of 2-[2-(7-ethoxy-5-{[6-(methylsulfonyl)pyridin-3-yl]oxy}-1H-indol-2-yl)-4,5-dihydro-1,3-thiazol-5-yl]-N-methylacetamide (360 mg) in methanol-acetonitrile (500:500, 360 mL) was resolved by preparative supercritical fluid chromatography (SFC), using CHIRALPAK AS-H (2 cm i.d.×25 cm, Daicel Chemical Industries, Ltd.) and supercritical CO$_2$/methanol/acetonitrile (70/15/15) as the mobile phase with the flow rate of 50 mL/min at 10 MPa and 30° C. The fractions containing a single enantiomer, eluted at a retention time of 7.4 min, were collected and concentrated to give the title compound (155 mg). Recrystallization from ethyl acetate-hexane gave the title compound (140 mg) as white crystals. MS 501 (MH$^+$). mp 224-225° C.

Example 99

2-[2-(7-Ethoxy-5-{[6-(methylsulfonyl)pyridin-3-yl]oxy}-1H-indol-2-yl)-4,5-dihydro-1,3-thiazol-5-yl]-N-methylacetamide A solution of 2-[2-(7-ethoxy-5-{[6-(methylsulfonyl)pyridin-3-yl]oxy}-1H-indol-2-yl)-4,5-dihydro-1,3-thiazol-5-yl]-N-methylacetamide (360 mg) in methanol-acetonitrile (500:500, 360 mL) was resolved by preparative supercritical fluid chromatography (SFC), using CHIRALPAK AS-H (2 cm i.d.×25 cm, Daicel Chemical Industries, Ltd.) and supercritical CO$_2$/methanol/acetonitrile (70/15/15) as the mobile phase with the flow rate of 50 mL/min at 10 MPa and 30° C. The fractions containing a single enantiomer, eluted at a retention time of 9.0 min, were collected and concentrated to give the title compound (150 mg). Recrystallization from ethyl acetate-hexane gave the title compound (137 mg) as white crystals. MS 501 (MH+). mp 225-226° C.

Example 100

2-[2-(7-Ethoxy-5-{[6-(methylsulfonyl)pyridin-3-yl]oxy}-1H-indol-2-yl)-4,5-dihydro-1,3-thiazol-5-yl]acetamide

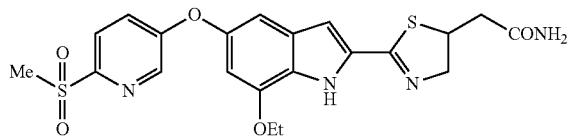 [SMILES: CCOc1cc(Oc2ccc(S(C)(=O)=O)nc2)cc2cc(C3=NCC(CC(N)=O)S3)[nH]c12]

To an ice-cooled and stirred mixture of [2-(7-ethoxy-5-{[6-(methylsulfonyl)pyridin-3-yl]oxy}-1H-indol-2-yl)-4,5-dihydro-1,3-thiazol-5-yl]acetic acid (95 mg) in N,N-dimethylformamide (5 mL) were added 1-hydroxybenzotriazole ammonium salt (61 mg) and 1-ethyl-3-(3-dimethylaminopropyl)carbodiimide hydrochloride (77 mg). After stirring at 4° C. to room temperature for 15 h, the reaction mixture was partitioned between ethyl acetate and water. The organic layer was washed successively with aqueous sodium hydrogen carbonate solution and brine, dried (MgSO4), filtered, and concentrated to give a pale yellow amorphous solid, which was crystallized from ethyl acetate-hexane to give the title compound (84 mg) as colorless crystals. Recrystallization from ethyl acetate-hexane gave the title compound (71 mg, 76%) as colorless crystals. MS 475 (MH+). mp 195-196° C.

Example 101

Ethyl (2-{7-methoxy-5-[4-(methylsulfonyl)phenoxy]-1H-indol-2-yl}-4,5-dihydro-1,3-thiazol-5-yl)acetate

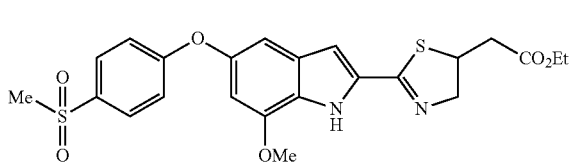 [SMILES: CCOC(=O)CC1CN=C(c2cc3cc(Oc4ccc(S(C)(=O)=O)cc4)cc(OC)c3[nH]2)S1]

To a stirred solution of 7-methoxy-5-[4-(methylsulfonyl)phenoxy]-1H-indole-2-carbothioamide (0.69 g), ethyl 2-butynoate (0.43 mL), tetrahydrofuran (15 mL) and toluene (25 mL) was added tributylphosphine (0.54 mL) at room temperature under argon atmosphere. After the mixture was stirred at 40° C. for 4 h, ethyl 2-butynoate (0.22 mL) and tributylphosphine (0.27 mL) were added thereto. After stirring at 40° C. for 2 h, the reaction mixture was concentrated to give a light brown oil, which was purified by silica gel chromatography (ethyl acetate:hexane=30:70 to 75:25, volume ratio) to give the title compound (684 mg, 72%) as a light yellow oil. MS 489 (MH+).

$^1$H NMR (CDCl$_3$) δ 1.28 (3H, t, J=7.2 Hz), 2.74-2.84 (2H, m), 3.04 (3H, s), 3.91 (3H, s), 4.18 (2H, q, J=7.2 Hz), 4.24- 4.46 (3H, m), 6.45 (1H, d, J=2.1 Hz), 6.83 (1H, d, J=2.1 Hz), 6.93 (1H, d, J=2.1 Hz), 7.05 (2H, d, J=9.0 Hz), 7.84 (2H, d, J=9.0 Hz), 9.27 (1H, brs).

Example 102

(2-{7-Methoxy-5-[4-(methylsulfonyl)phenoxy]-1H-indol-2-yl}-4,5-dihydro-1,3-thiazol-5-yl)acetic acid

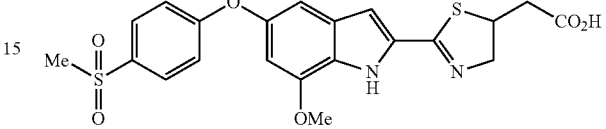

To a mixture of ethyl (2-{7-methoxy-5-[4-(methylsulfonyl)phenoxy]-1H-indol-2-yl}-4,5-dihydro-1,3-thiazol-5-yl)acetate (0.42 g), tetrahydrofuran (8 mL) and methanol (8 mL) was added a solution of potassium hydroxide (85%, 0.25 g) in water (5 mL). The mixture was stirred at room temperature for 15 h and concentrated. The residue was partitioned between ethyl acetate and water. The organic layer was washed with brine, dried (MgSO4), filtered, and concentrated to give a light amorphous solid, which was crystallized from ethyl acetate-hexane to give the title compound (340 mg, 86%) as pale yellow crystals. MS 461 (MH+). mp 144-145° C.

Example 103

2-(2-{7-Methoxy-5-[4-(methylsulfonyl)phenoxy]-1H-indol-2-yl}-4,5-dihydro-1,3-thiazol-5-yl)-N-methylacetamide

To an ice-cooled and stirred mixture of methylamine hydrochloride (48 mg) and triethylamine (0.10 mL) in N,N-dimethylformamide (10 mL) were added (2-{7-methoxy-5-[4-(methylsulfonyl)phenoxy]-1H-indol-2-yl}-4,5-dihydro-1,3-thiazol-5-yl)acetic acid (0.16 g), 1-hydroxybenzotriazole (94 mg) and 1-ethyl-3-(3-dimethylaminopropyl)carbodiimide hydrochloride (134 mg). After stirring at 4° C. to room temperature for 7 h, the reaction mixture was partitioned between ethyl acetate and water. The organic layer was washed successively with aqueous sodium hydrogen carbonate solution and brine, dried (MgSO4), filtered, and concentrated to give a pale yellow oil, which was purified by silica gel chromatography (ethyl acetate:methanol=100:0 to 90:10, volume ratio) to give a colorless oil. The oil was crystallized

Example 104

2-(2-{7-Methoxy-5-[4-(methylsulfonyl)phenoxy]-1H-indol-2-yl}-4,5-dihydro-1,3-thiazol-5-yl)acetamide

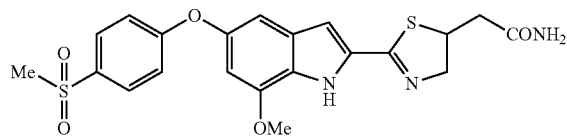 [SMILES: COc1cc(Oc2ccc(S(C)(=O)=O)cc2)cc2cc(C3=NCC(CC(N)=O)S3)[nH]c12]

To an ice-cooled and stirred mixture of (2-{7-methoxy-5-[4-(methylsulfonyl)phenoxy]-1H-indol-2-yl}-4,5-dihydro-1,3-thiazol-5-yl)acetic acid (80 mg) in N,N-dimethylformamide (10 mL) were added 1-hydroxybenzotriazole ammonium salt (53 mg) and 1-ethyl-3-(3-dimethylaminopropyl)carbodiimide hydrochloride (67 mg). After stirring at 4° C. to room temperature for 15 h, the reaction mixture was partitioned between ethyl acetate and water. The organic layer was washed successively with aqueous sodium hydrogen carbonate solution and brine, dried (MgSO$_4$), filtered, and concentrated to give a pale yellow oil, which was crystallized from ethyl acetate-hexane to give the title compound (72 mg, 91%) as colorless crystals. MS 460 (MH$^+$). mp 169-170° C.

Reference Example 1A

Construction of Glucokinase (GK) Expression Vector

Plasmid DNA to be used for the expression of a protein (GST-hLGK1) containing GST (Glutathione S-transferase) added to the amino terminal of human liver GK in *Escherichia coli* was prepared as follows.

First, PCR was performed using human liver cDNA (Marathon Ready cDNA, Clontech Laboratories, Inc.) as a template and two kinds of synthetic DNAs (5'-CAGCTCTCCATC-CAAGCAGCCGTTGCT-3' (SEQ ID NO: 1) and 5'-GGCG-GCCTGGGTCCTGACAAG-3' (SEQ ID NO: 2)), and the obtained DNA fragment was closed using a TOPO TA Cloning Kit (Invitrogen Corporation). PCR was performed using the obtained plasmid DNA as a template and a synthetic DNA (5'-GGATCCATGCCAGACCAAGATC-CCAACTCCCACAACCCAACTCCCAGGTA-GAGCAGATCCTGG CAGAG-3' (SEQ ID NO: 3)) with a BamHI site added to immediately before the initiation codon, and a synthetic DNA (5'-GAATTCCTGGCCCAGCATA-CAGGC-3' (SEQ ID NO: 4)) with an EcoRI site added to immediately after the stop codon. The obtained DNA fragment was subcloned to pGEX6P-2 (Amersham Biosciences K.K.) cleaved with BamHI and EcoRI to give a plasmid (pGEX6P-2/hLGK1) for expression of human liver GK.

Reference Example 2A

Expression and Purification of GST-hLGK1

BL21 strain (Stratagene) transformed with pGEX6P-2/hLGK1 obtained in Reference Example 1A was cultured with shaking at 37° C. for 14 hr in a 200 ml Erlenmeyer flask containing 50 ml of 100 μg/ml ampicillin-containing LB medium. The culture medium (25 ml) was diluted with 225 ml of 100 μg/ml ampicillin-containing LB medium, and further cultured with shaking at 37° C. for 1 hr in a 1 L Erlenmeyer flask. After culture, the Erlenmeyer flask was cooled on ice, 125 μL of 100 mM isopropyl-thio-β-D-galactopyranoside (IPTG) was added (final concentration 50 μM), and cultured at 17° C. for 20 hr. The culture medium was centrifuged, and the obtained fungus was disrupted by ultrasonication. The object protein (GST-hLGK1) was purified from the supernatant using Glutathione Sepharose 4B (Amersham Biosciences K.K.).

Experimental Example 1

Measurement of GK Activation Value

GK enzyme reactions were performed in 50 mmol/L HEPES pH 7.4, 200 mmol/L KCl, 5 mmol/L MgCl$_2$, 2 mmol/L DTT, containing 50 μmol/L 2'-(or -3')-O—(N-methylanthraniloyl)adenosine 5'-triphosphate (Mant-ATP) (Jena Bioscience GmbH), 5 mmol/L D-glucose, 5% DMSO and 6 μg/mL GST-hLGK1 obtained in Reference Example 2A in a total volume 50 μL. The reactions were performed in 384 well black plates (Nalge Nunc International K.K.). Prior to the reaction, the enzyme and test compound were incubated for 10 min at 37° C., and 25 mM D-glucose solution (10 μL) was added to start the reaction.

After the incubation for 60 min at 37° C., the reaction was quenched by adding 25 μL of a quenching solution (containing 200 mM HEPES (pH 7.4), 20 mM MgCl$_2$, 200 mM EDTA, 0.03% Triton-X 100, 0.3% Coating 3 reagent (Caliper Life Sciences, Inc.)).

Mant-ATP (substrate, 2'- (or -3')-O—(N-methylanthraniloyl) adenosine 5'-triphosphate) and Mant-ADP (reaction resultant product) were separated from each well after the reaction by a microchip type capillary electrophoresis apparatus 250 HTS (Caliper Life Sciences, Inc.). The reaction rate [(reaction resultant product peak height)/(reaction resultant product peak height+substrate peak height)×100(%)] was calculated from the ratio of the substrate peak height and reaction resultant product peak height obtained by fluorescence detection (excitation wavelength 355 nm, measurement wavelength 460 nm) and used as the index of GK activity.

As a control group, the reaction rate was calculated in the same manner as above without the test compounds.

The percentage obtained by dividing the reaction rate of the well added with each concentration of the test compound (test compound addition group) by the reaction rate of the control group was taken as the GK activity value, and the concentration of the test compound at the midpoint between the maximum activity value of the test compound addition group and the control group activity value is shown as EC$_{50}$ value. The results are shown in Table 1.

TABLE 1

| Test compound (Example No.) | EC$_{50}$ value (μM) |
|---|---|
| 3 | 0.055 |
| 7 | 0.042 |
| 11 | 0.052 |
| 16 | 0.033 |
| 17 | 0.048 |
| 19 | 0.044 |

TABLE 1-continued

| Test compound (Example No.) | EC$_{50}$ value (μM) |
| --- | --- |
| 31 | 0.028 |
| 57 | 0.017 |
| 58 | 0.015 |
| 65 | 0.059 |
| 74 | 0.028 |
| 78 | 0.037 |
| 79 | 0.035 |
| 80 | 0.037 |
| 81 | 0.038 |
| 82 | 0.042 |
| 98 | 0.020 |

As is clear from Table 1, the compound of the present invention has a superior glucokinase activation action.

Formulation Example 1

Production of Capsule

| | |
| --- | --- |
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablet

| | |
| --- | --- |
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3), and 30 g of 4) are kneaded with water, vacuum dried and sized. The sized powder is mixed with 14 g of 4) and 1 g of 5), and the mixture is punched by a tabletting machine. In this way, 1000 tablets containing 30 mg of the compound of Example 1 per tablet are obtained.

Industrial Applicability

The compound of the present invention has a superior glucokinase activating action, and is useful as a pharmaceutical agent such as an agent for the prophylaxis or treatment of diabetes, obesity and the like, and the like.

This application is based on patent application No. 102691/2008 filed in Japan, the contents of which are hereby incorporated by reference.

The invention claimed is:

1. A compound represented by the formula (I):

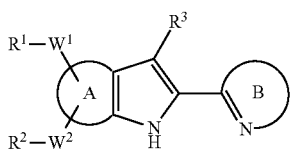

wherein
ring A is a benzene optionally substituted by, besides —$W^1$—$R^1$ and —$W^2$—$R^2$, 1 to 3 halogen atoms;
ring B is a 4,5-dihydro-1,3-thiazole optionally substituted by 1 to 3 substituents selected from the group consisting of
(1) a $C_{1-6}$ alkyl group optionally substituted by 1 to 3 substituents selected from the group consisting of
 (a) a hydroxy group,
 (b) a carbamoyl group optionally mono- or di-substituted by substituent(s) selected from the group consisting of
  (i) a $C_{1-6}$ alkyl group optionally substituted by 1 to 3 substituents selected from the group consisting of a hydroxy group and a $C_{1-6}$ alkoxy group, and
  (ii) a $C_{3-10}$ cycloalkyl group,
 (c) a $C_{1-6}$ alkoxy group,
 (d) a carboxy group, and
 (e) a $C_{1-6}$ alkoxy-carbonyl group, and
(2) a $C_{1-6}$ alkoxy-carbonyl group;
$W^1$ and $W^2$ are independently O, S, SO or $SO_2$;
$R^1$ is a pyridyl optionally substituted by 1 to 3 substituents selected from the group consisting of
(1) a $C_{1-6}$ alkylsulfonyl group, and
(2) a $C_{1-6}$ alkyl group optionally substituted by 1 to 3 $C_{1-6}$ alkoxy groups;
$R^2$ is a $C_{1-6}$ alkyl group optionally substituted by 1 to 3 substituents selected from the group consisting of
(1) a $C_{6-14}$ aryl group,
(2) a hydroxy group,
(3) a $C_{1-6}$ alkoxy group, and
(4) a di-tert-butylphenylsilyloxy group,
or a $C_{3-10}$ cycloalkyl group; and
$R^3$ is a hydrogen atom or a halogen atom,
or a salt thereof.

2. The compound or salt of claim 1, wherein $W^1$ and $W^2$ are both O.

3. The compound or salt of claim 1, wherein $R^2$ is a $C_{1-6}$ alkyl group optionally substituted by 1 to 3 substituents selected from the group consisting of
(1) a $C_{6-14}$ aryl group,
(2) a hydroxy group,
(3) a $C_{1-6}$ alkoxy group, and
(4) a di-tert-butylphenylsilyloxy group.

4. The compound or salt of claim 1, wherein $R^3$ is a hydrogen atom.

5. The compound or salt of claim 1, wherein
ring A is benzene,
$W^1$ and $W^2$ are both O,
$R^2$ is a $C_{1-6}$ alkyl group optionally substituted by 1 to 3 substituents selected from the group consisting of
(1) a $C_{6-14}$ aryl group,
(2) a hydroxy group,
(3) a $C_{1-6}$ alkoxy group, and
(4) a di-tert-butylphenylsilyloxy group, and
$R^3$ is a hydrogen atom.

6. A compound represented by the formula (II):

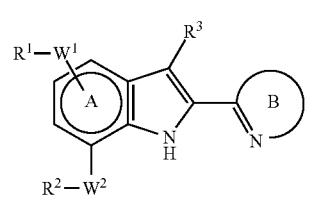

wherein
ring A is a benzene optionally substituted by, besides —$W^1$—$R^1$ and —$W^2$—$R^2$, 1 to 3 halogen atoms;
ring B is a 4,5-dihydro-1,3-thiazole optionally substituted by 1 to 3 substituents selected from the group consisting of
(1) a $C_{1-6}$ alkyl group optionally substituted by 1 to 3 substituents selected from the group consisting of
 (a) a hydroxy group,
 (b) a carbamoyl group optionally mono- or di-substituted by substituent(s) selected from the group consisting of
  (i) a $C_{1-6}$ alkyl group optionally substituted by 1 to 3 substituents selected from the group consisting of a hydroxy group and a $C_{1-6}$ alkoxy group, and
  (ii) a $C_{3-10}$ cycloalkyl group,
 (c) a $C_{1-6}$ alkoxy group,
 (d) a carboxy group, and
 (e) a $C_{1-6}$ alkoxy-carbonyl group, and (2) a $C_{1-6}$ alkoxy-carbonyl group;

$W^1$ and $W^2$ are independently O, S, SO or $SO_2$;

$R^1$ is a pyridyl optionally substituted by 1 to 3 substituents selected from the group consisting of
(1) a $C_{1-6}$ alkylsulfonyl group, and
(2) a $C_{1-6}$ alkyl group optionally substituted by 1 to 3 $C_{1-6}$ alkoxy groups;

$R^2$ is a $C_{1-6}$ alkyl group optionally substituted by 1 to 3 substituents selected from the group consisting of
(1) a $C_{6-14}$ aryl group,
(2) a hydroxy group,
(3) a $C_{1-6}$ alkoxy group, and
(4) a di-tert-butylphenylsilyloxy group,
or a $C_{3-10}$ cycloalkyl group; and $R^3$ is a hydrogen atom or a halogen atom,
or a salt thereof.

7. 2-[2-(7-Methoxy-5-{[6-(methylsulfonyl)pyridin-3-yl]oxy}-1H-indol-2-yl)-4,5-dihydro-1,3-thiazol-5-yl]-N-methylacetamide or a salt thereof.

8. 2-Methyl-1-{2-[7-(1-methylethoxy)-5-{[5-(methylsulfonyl)pyridin-2-yl]oxy}-1H-indol-2-yl]-4,5-dihydro-1,3-thiazol-5-yl}propan-2-ol or a salt thereof.

9. N-(2-Hydroxy-2-methylpropyl)-2-[2-(7-methoxy-5-{[6-(methylsulfonyl)pyridin-3-yl]oxy}-1H-indol-2-yl)-4,5-dihydro-1,3-thiazol-5-yl]acetamide or a salt thereof.

10. 2-[2-(7-Ethoxy-5-{[6-(methylsulfonyl)pyridin-3-yl]oxy}-1H-indol-2-yl)-4,5-dihydro-1,3-thiazol-5-yl]-N-methylacetamide or a salt thereof.

11. N-[2-Hydroxypropyl]-2-[2-(7-methoxy-5-{[6-(methylsulfonyl)pyridin-3-yl]oxy}-1H-indol-2-yl)-4,5-dihydro-1,3-thiazol-5-yl]acetamide or a salt thereof.

12. A pharmaceutical composition comprising the compound or salt of claim 1, and a pharmacologically acceptable carrier.

13. The compound or salt of claim 6, wherein
ring A is a benzene substituted by —$W^1$—$R^1$ and —$W^2$—$R^2$, and optionally substituted by 1 to 3 halogen atoms;
ring B is a 4,5-dihydro-1,3-thiazole optionally substituted by 1 to 3 substituents selected from the group consisting of
(1) a $C_{1-6}$ alkyl group optionally substituted by 1 to 3 substituents selected from the group consisting of
  (a) a hydroxy group,
  (b) a carbamoyl group optionally mono- or di-substituted by substituent(s) selected from the group consisting of
    (i) a $C_{1-6}$ alkyl group optionally substituted by 1 to 3 substituents selected from the group consisting of a hydroxy group and a $C_{1-6}$ alkoxy group, and
    (ii) a $C_{3-10}$ cycloalkyl group,
  (c) a $C_{1-6}$ alkoxy group,
  (d) a carboxy group, and
  (e) a $C_{1-6}$ alkoxy-carbonyl group, and
(2) a $C_{1-6}$ alkoxy-carbonyl group;

$W^1$ and $W^2$ are both O;

$R^1$ is a pyridyl optionally substituted by 1 to 3 substituents selected from the group consisting of
(1) a $C_{1-6}$ alkylsulfonyl group, and
(2) a $C_{1-6}$ alkyl group optionally substituted by 1 to 3 $C_{1-6}$ alkoxy groups;

$R^2$ is a $C_{1-6}$ alkyl group optionally substituted by 1 to 3 substituents selected from the group consisting of
(1) a $C_{6-14}$ aryl group,
(2) a hydroxyl group,
(3) a $C_{1-6}$ alkoxy group, and
(4) a di-tert-butylphenylsilyloxy group; and $R^3$ is a hydrogen atom.

* * * * *

```
                        SEQUENCE LISTING

<160> NUMBER OF SEQ ID NOS: 4

<210> SEQ ID NO 1
<211> LENGTH: 27
<212> TYPE: DNA
<213> ORGANISM: Artificial sequence
<220> FEATURE:
<223> OTHER INFORMATION: Synthetic construct; primer for cloning
      glucokinase

<400> SEQUENCE: 1
cagctctcca tccaagcagc cgttgct                                         27

<210> SEQ ID NO 2
<211> LENGTH: 21
<212> TYPE: DNA
<213> ORGANISM: Artificial sequence
<220> FEATURE:
<223> OTHER INFORMATION: Synthetic construct; primer for cloning
      glucokinase

<400> SEQUENCE: 2
ggcggcctgg gtcctgacaa g                                               21

<210> SEQ ID NO 3
<211> LENGTH: 69
<212> TYPE: DNA
<213> ORGANISM: Artificial sequence
<220> FEATURE:
<223> OTHER INFORMATION: Synthetic construct; primer for cloning
      glucokinase

<400> SEQUENCE: 3
```

```
ggatccatgc ccagaccaag atcccaactc ccacaaccca actcccaggt agagcagatc        60
ctggcagag                                                                69

<210> SEQ ID NO 4
<211> LENGTH: 24
<212> TYPE: DNA
<213> ORGANISM: Artificial sequence
<220> FEATURE:
<223> OTHER INFORMATION: Synthetic construct; primer for cloning
      glucokinase

<400> SEQUENCE: 4
gaattcctgg cccagcatac aggc                                               24
```